US009840738B2

(12) United States Patent
Ward et al.

(10) Patent No.: US 9,840,738 B2
(45) **Date of Patent: *Dec. 12, 2017**

(54) METHOD OF TESTING FOR ENDOMETRIOSIS AND TREATMENT THEREFOR

(71) Applicant: Juneau Biosciences, LLC, Salt Lake City, UT (US)

(72) Inventors: Kenneth Ward, Salt Lake City, UT (US); Rakesh N. Chettier, West Jordan, UT (US); Hans Albertsen, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,266

(22) Filed: Jan. 12, 2015

(65) Prior Publication Data

US 2015/0133382 A1 May 14, 2015

Related U.S. Application Data

(63) Continuation of application No. 13/788,913, filed on Mar. 7, 2013, now Pat. No. 8,932,993, which is a continuation-in-part of application No. 12/056,754, filed on Mar. 27, 2008, now abandoned, application No. 14/594,266, which is a continuation of application No. 13/788,913, which is a continuation-in-part of application No. 12/120,322, filed on May 14, 2008, now abandoned, application No. 14/594,266, which is a continuation-in-part of application No. 12/765,643, filed on Apr. 22, 2010, and a continuation-in-part of application No. 13/159,132, filed on Jun. 13, 2011, which is a continuation-in-part of application No. 13/071,598, filed on Mar. 25, 2011, now abandoned, application No. 14/594,266, which is a continuation of application No. 13/788,913, which is a continuation-in-part of application No. 13/681,575, filed on Nov. 20, 2012, now abandoned, which is a continuation of application No. 13/602,409, filed on Sep. 4, 2012, now abandoned, application No. 14/594,266, which is a continuation-in-part of application No. 13/603,284, filed on Sep. 4, 2012, now abandoned, and a continuation of application No. 13/788,913, which is a continuation-in-part of application No. 13/680,414, filed on Nov. 19, 2012, now abandoned, which is a continuation of application No. 13/603,297, filed on Sep. 4, 2012, now abandoned, application No. 14/594,266, which is a continuation of application No. 13/788,913, which is a continuation-in-part of application No. 13/735,828, filed on Jan. 7, 2013, now abandoned, which is a continuation of application No. 13/652,018, filed on Oct. 15, 2012, now abandoned.

(60) Provisional application No. 60/943,193, filed on Jun. 11, 2007, provisional application No. 61/171,717, filed on Apr. 22, 2009, provisional application No. 61/245,808, filed on Sep. 25, 2009, provisional application No. 61/318,145, filed on Mar. 26, 2010, provisional application No. 61/530,944, filed on Sep. 3, 2011, provisional application No. 61/530,948, filed on Sep. 3, 2011, provisional application No. 61/530,945, filed on Sep. 3, 2011, provisional application No. 61/530,947, filed on Sep. 3, 2011, provisional application No. 61/547,624, filed on Oct. 14, 2011, provisional application No. 61/717,048, filed on Oct. 22, 2012, provisional application No. 61/717,053, filed on Oct. 22, 2012, provisional application No. 61/721,219, filed on Nov. 1, 2012.

(51) Int. Cl.
*C12Q 1/68* (2006.01)

(52) U.S. Cl.
CPC ..... *C12Q 1/6883* (2013.01); *C12Q 2600/106* (2013.01); *C12Q 2600/156* (2013.01); *C12Q 2600/172* (2013.01)

(58) Field of Classification Search
CPC .................. G01N 33/6893; G01N 2333/4725
USPC ........................................... 435/7.1; 436/518
See application file for complete search history.

(56) References Cited

U.S. PATENT DOCUMENTS

| | | | | |
|---|---|---|---|---|
| 6,525,187 | B1 | 2/2003 | El Shami et al. | 536/23.5 |
| 6,540,980 | B1 | 4/2003 | Blumenthal et al. | 424/9.43 |
| 6,586,569 | B1 | 7/2003 | Starzinski-Powitz et al. | 530/300 |
| 7,268,117 | B2 | 9/2007 | Messer et al. | 514/12 |
| 7,368,533 | B2 | 5/2008 | El Shami et al. | 530/350 |
| 7,399,598 | B2 | 7/2008 | Yang et al. | 435/7.1 |

(Continued)

FOREIGN PATENT DOCUMENTS

| | | | |
|---|---|---|---|
| CA | 2329527 | 5/1999 | C12Q 1/68 |
| CA | 2399259 | 8/2001 | C12Q 1/68 |

(Continued)

OTHER PUBLICATIONS

May et al (Science (1988) vol. 241, p. 1441).*

(Continued)

*Primary Examiner* — Janet L Epps-Smith
(74) *Attorney, Agent, or Firm* — Michael R. Schramm

(57) ABSTRACT

The present invention relates to novel genetic markers associated with endometriosis and risk of developing endometriosis, and methods and materials for determining whether a human subject has endometriosis or is at risk of developing endometriosis and the use of such risk information in selectively administering a treatment that at least partially prevents or compensates for an endometriosis related symptom.

29 Claims, 2 Drawing Sheets

(56) References Cited

U.S. PATENT DOCUMENTS

| | | | | |
|---|---|---|---|---|
| 8,932,993 | B1 * | 1/2015 | Ward | C12Q 1/6883 435/6.11 |
| 2002/0127555 | A1 | 9/2002 | Baban et al. | 435/6 |
| 2002/0147155 | A1 | 10/2002 | Foster et al. | 514/23 |
| 2002/0192647 | A1 | 12/2002 | Smith | 435/6 |
| 2003/0077589 | A1 | 4/2003 | Hess-Stumpp et al. | 435/6 |
| 2003/0109018 | A1 | 6/2003 | Starzinski-Powitz et al. | 435/195 |
| 2003/0124551 | A1 | 7/2003 | Pappa et al. | 435/6 |
| 2003/0166014 | A1 | 9/2003 | Timms | 435/7.2 |
| 2003/0219835 | A1 | 11/2003 | Gosselin et al. | 435/7.2 |
| 2004/0048919 | A1 | 3/2004 | Dreon et al. | 514/458 |
| 2004/0052787 | A1 | 3/2004 | King et al. | 424/144.1 |
| 2004/0091912 | A1 | 5/2004 | Smith | 435/6 |
| 2004/0210400 | A1 * | 10/2004 | Konvicka | G06F 19/24 702/20 |
| 2005/0130182 | A1 | 6/2005 | Messer et al. | 435/6 |
| 2005/0142580 | A1 | 6/2005 | Tay et al. | 435/6 |
| 2005/0214836 | A1 | 9/2005 | Nakamura et al. | 435/6 |
| 2006/0014166 | A1 | 1/2006 | Cohen et al. | 435/6 |
| 2006/0057584 | A1 | 3/2006 | Baban et al. | 435/6 |
| 2007/0015160 | A1 | 1/2007 | Kuroda et al. | 435/6 |
| 2007/0087386 | A1 | 4/2007 | Yang et al. | 435/7.1 |
| 2007/0092484 | A1 | 4/2007 | Levine et al. | 424/85.1 |
| 2007/0264270 | A1 | 11/2007 | Barnhart et al. | 424/184.1 |
| 2007/0287676 | A1 | 12/2007 | Guo et al. | 514/43 |
| 2008/0008650 | A1 | 1/2008 | Fukuda et al. | 424/9.1 |
| 2008/0187527 | A1 | 8/2008 | Starzinski-Powitz et al. | 424/130 |
| 2008/0241852 | A1 | 10/2008 | Messer et al. | 435/7.1 |
| 2008/0318237 | A1 | 12/2008 | Giudice | 435/6 |
| 2013/0022593 | A1 | 1/2013 | Giudice | 424/130.1 |

FOREIGN PATENT DOCUMENTS

| | | | |
|---|---|---|---|
| CA | 2497132 | 3/2004 | C12Q 1/68 |
| CA | 2596932 | 8/2006 | C12Q 1/68 |
| CA | 2607341 | 11/2006 | C12Q 1/68 |
| CA | 2681933 | 11/2007 | G01N 33/68 |
| CA | 2676415 | 10/2008 | C40B 40/06 |
| CN | 101334410 | 12/2008 | G01N 33/68 |
| JP | 2009168646 | 7/2009 | G01N 27/62 |
| WO | WO9963079 | 12/1999 | C12Q 1/68 |
| WO | WO0132920 | 5/2001 | C12Q 1/68 |
| WO | WO0162959 | 8/2001 | C12Q 1/68 |
| WO | WO2004024952 | 3/2004 | C12Q 1/68 |
| WO | WO2006091254 | 8/2006 | C12Q 1/68 |
| WO | WO2006116873 | 11/2006 | C12Q 1/68 |
| WO | WO2007126982 | 11/2007 | G01N 33/68 |
| WO | WO2008049175 | 5/2008 | G01N 33/68 |
| WO | W02008103812 | 8/2008 | C07K 14/745 |
| WO | WO2008123901 | 10/2008 | C12Q 1/68 |
| WO | WO2009068254 | 6/2009 | G01N 33/68 |
| WO | WO2010010951 | 1/2010 | C12Q 1/68 |

OTHER PUBLICATIONS

Colette (Exper Opin Investig Drugs (2011) vol. 20, pates 917-931).*
Hegele (Arterioscler Thromb Vasc Biol. 2002;22:1058-1061).*
Lucentini J. (The Scientist (Dec. 20, 2004), p. 20).*
Benner et al (Trends in Genetics (2001) vol. 17, pp. 414-418).*
Weiser (Fertility and Sterility (2002) vol. 77, pp. 309-312).*
dbSNP ss13045391 (http://www.ncbi.nlm.nih.gov/projects/SNP/snp_ss.cgi?subsnp_id=13045391, submitted Oct. 22, 2003.*
Kennedy et al (Human reproduction (2005) vol. 20, pp. 2698-2704).*
Pennisi (E. Science (1998) vol. 281, No. 5384, pp. 1787-1789).*
U.S. Appl. No. 60/948,565, filed Jul. 9, 2007, Belouchi et al.
U.S. Appl. No. 60/899,615, filed Feb. 6, 2007, Belouchi et al.
U.S. Appl. No. 60/875,527, filed Jun. 6, 2007, Goldman et al.
U.S. Appl. No. 60/788,058, filed Apr. 3, 2006, Goldman et al.
Albertsen et al, Genome-Wide Association Study Link Novel Loci to Endometriosis, PLOS One, Mar. 5, 2013, vol. 8, Issue 3, e58257 p. 1-8.
Altinkaya SO, et al. Vascular endothelial growth factor +405 C/G polymorphism is highly associated with an increased risk of endometriosis in Turkish women. *Arch Gynecol Obstet.* Dec. 30, 2009.
Ammendola M, et al. Acid phosphatase locus 1 genetic polymorphism, endometriosis, and allergy. *Fertil Steril.* Oct. 2008; 90(4):1203-1205.
Arvanitis DA, et al. CYP1A1, CYP19, and GSTM1 polymorphisms increase the risk of endometriosis, Fertility and Sterility, Mar. 2003, 79 Suppl 1, p. 702-709.
Asghar T, et al. The tumor necrosis factor-alpha promoter—1031C polymorphism is associated with decreased risk of endometriosis in a Japanese population. Hum Reprod. Nov. 2004;19(11):2509-2514.
Babu KA, et al. GSTM1, GSTT1 and CYP1A1 detoxification gene polymorphisms and their relationship with advanced stages of endometriosis in South Indian women. Pharmacogenet Genomics. Mar. 2005;15(3):167-172.
Baranova et al, Gluthione S-transferase M1 gene polymorphism and susceptibility to endometriosis in a French population, MHR, 1997, vol. 3, No. 9, pp. 775-780.
Bedaiwy MA, et al. Genetic polymorphism in the fibrinolytic system and endometriosis. Obstet Gynecol. Jul. 2006;108(1):162-168.
Benner et al, Evolution, Language and analogy in function genomics, Trends in Genetics, Jul. 2001, vol. 17, No. 7, p. 414-418.
Bhanoori M, et al. The G2964A 3'-untranslated region polymorphism of the signal transducer and activator of transcription 6 gene is associated with endometriosis in South Indian women. *Hum Reprod.* Apr. 2007;22(4):1026-1030.
Bhanoori M, et al. The vascular endothelial growth factor (VEGF) +405G>C 5'-untranslated region polymorphism and increased risk of endometriosis in South Indian women: a case control study. Hum Reprod. Jul. 2005; 20(7):1844-1849.
Bianco B, et al. +1730 G/A polymorphism of the estrogen receptor beta gene (ERbeta) may be an important genetic factor predisposing to endometriosis. *Acta Obstet Gynecol Scand.* 2009;88(12):1397-1401.
Borghese B, et al. Genetic polymorphisms of matrix metalloproteinase 12 and 13 genes are implicated in endometriosis progression. *Hum Reprod.* May 2008;23(5):1207-1213.
Caballero V, et al. Preliminary molecular genetic analysis of the Receptor Interacting Protein 140 (RIP140) in women affected by endometriosis. J Exp Clin Assist Reprod. Aug. 30, 2005;2:11.
Cayan F, et al. Association of G1057D variant of insulin receptor substrate-2 with endometriosis. *Fertil Steril.* Oct. 28, 2009.
Chae SJ, et al. Tumor necrosis factor (TNF)—TNF receptor gene polymorphisms and their serum levels in Korean women with endometriosis. *Am J Reprod Immunol.* Nov. 2008;60(5):432-439.
Chang CC, et al. The proline form of p53 codon 72 polymorphism is associated with endometriosis. Fertil Steril. Jan. 2002;77(1):43-45.
Chettier et al, Endometriosis Is Associated with Rare Copy Number Variants, PLOS One, Aug. 2014, vol. 9, Issue 8, e103968 p. 1-11.
Colette et al, Are aromatase inhibitors effect in endometriosis treatment, Expert Opinion, 2011, p. 917-931.
dbSNP, SNP ss13045391, NCBI, Oct. 22, 2003, p. 1-8.
Dun et al, Advances in the genetics of endometriosis, Genome Medicine, 2010, vol. 2, No. 75 p. 1-6.
Ertunc D, et al. Glutathione-S-transferase P1 gene polymorphism and susceptibility to endometriosis. Hum Reprod. Aug. 2005;20(8):2157-2161.
Gentilini D, et al. Progesterone receptor +331G/A polymorphism in endometriosis and deep-infiltrating endometriosis. *Fertil Steril.* Oct. 2008;90(4):1243-1245.
Gimenes et al, The progins progesterone receptor gene polymorphism is not related to endometriosis-associated infertility or to idiopathic infertility, Clinical Science, 2010, vol. 65, No. 11, p. 1073-1076.
Gomes FM, et al. PTPN22 C1858T polymorphism in women with endometriosis. *Am J Reprod Immunol.* Mar. 1, 2010; 63(3):227-232.

(56) References Cited

OTHER PUBLICATIONS

Govindan et al, Association of progesterone receptor gene polymorphism (PROGINS) with endometriosis, uterine fibroids and breast cancer, Cancer Biomarkers, May 21, 2007, vol. 3. No. 2, p. 73-78.
Govindan S, et al. Estrogen receptor-alpha gene (T/C) Pvu II polymorphism in endometriosis and uterine fibroids. *Dis Markers.* 2009;26(4):149-154.
Han YJ, et al. Haplotype analysis of the matrix metalloproteinase-9 gene associated with advanced-stage endometriosis. *Fertil Steril.* Jun. 2009;91(6):2324-2330.
Hegele, Robert, SNP Judgments and Freedom of Association, ATVB, Mar. 21, 2008, vol. 22, p. 1058-1061.
Hsieh YY, et al. Angiotensin I-converting enzyme ACE 2350*G and ACE-240*T-related genotypes and alleles are associated with higher susceptibility to endometriosis. Mol Hum Reprod. Jan. 2005; 11(1):11-14.
Hsieh YY, et al. Angiotensin I-converting enzyme insertion-related genotypes and allele are associated with higher susceptibility of endometriosis and leiomyoma. Mol Reprod Dev. Jul. 2007;74(7):808-814.
Hsieh YY, et al. Estrogen receptor alpha dinucleotide repeat and cytochrome P450c17alpha gene polymorphisms are associated with susceptibility to endometriosis. Fertil Steril. Mar. 2005; 83(3):567-572.
Hsieh YY, et al. Glutathione S-transferase M1 *null genotype but not myeloperoxidase promoter G-463A polymorphism is associated with higher susceptibility to endometriosis. Mol Hum Reprod. Oct. 2004; 10(10):713-717.
Hsieh YY, et al. Interleukin-2 receptor beta (IL-2R beta)-627*C homozygote but not IL-12R beta 1 codon 378 or IL-18 105 polymorphism is associated with higher susceptibility to endometriosis. Fertil Steril. Aug. 2005;84(2):510-512.
Hsieh YY, et al. T homozygote and allele of epidermal growth factor receptor 2073 gene polymorphism are associated with higher susceptibility to endometriosis and leiomyomas. Fertil Steril. Mar. 2005;83(3):796-799.
Ivashchenko TE, et al. Analysis of the polymorphic alleles of genes encoding phase 1 and phase 2 detoxication enzymes in patients with endometriosis. Genetika. Apr. 2003;39(4):427-430.
Kado et al, Association of the CYP17 gene and CYP19 gene polymorphisms with risk of endometriosis in Japanese women, Human Reproduction, 2002, vol. 17, No. 4, pp. 897-902.
Kennedy et al, ESHRE guideline for the diagnosis and treatment of endometriosis, Hum Repro, Jun. 24, 2005, vol. 20, No. 10, p. 2698-2704.
Kim JG, et al. Association between human alpha 2-Heremans Schmidt glycoprotein (AHSG) polymorphism and endometriosis in Korean women. Fertil Steril. Dec. 2004;82(6):1497-1500.
Kim SH, et al. Association between susceptibility to advanced stage endometriosis and the genetic polymorphisms of aryl hydrocarbon receptor repressor and glutathione-S-transferase T1 genes, Hum Reprod. May 18, 2007; 22(7):1866-1870.
Kim SH, et al. Vascular endothelial growth factor gene +405 C/G polymorphism is associated with susceptibility to advanced stage endometriosis. Hum Reprod. Oct. 2005; 20(10):2904-2908.
Kitawaki J, et al. Association of HLA class I and class II alleles with susceptibility to endometriosis. Hum Immunol. Nov. 2002; 63(11):1033-1038.
Kitawaki J, et al. Genetic contribution of the interleukin-10 promoter polymorphism in endometriosis susceptibility. Am J Reprod Immunol. Jan. 2002; 47(1):12-18.
Kitawaki J, et al. Interferon-gamma gene dinucleotide (CA) repeat and interleukin-4 promoter region (−590C/T) polymorphisms in Japanese patients with endometriosis. Hum Reprod. Aug. 2004; 19(8):1765-1769.
Kitawaki J, et al. Synergistic effect of interleukin-6 promoter (IL6 −634C/G) and intercellular adhesion molecule -1 (ICAM-1 469K/E) gene polymorphisms on the risk of endometriosis in Japanese women. Am J Reprod Immunol. Oct. 2006; 56(4):267-274.
Kiyomizu M, et al. Association of two polymorphisms in the peroxisome proliferator-activated receptor-gamma gene with adenomyosis, endometriosis, and leiomyomata in Japanese women. J Soc Gynecol Investig. Jul. 2006; 13(5):372-377.
Lattuada D, et al. Analysis of the codon 72 polymorphism of the TP53 gene in patients with endometriosis. Mol Hum Reprod. Sep. 2004; 10(9):651-654.
Lattuada D, et al. Genetics of endometriosis: a role for the progesterone receptor gene polymorphism PROGINS? Clin Endocrinol (Oxf). Aug. 2004; 61(2):190-194.
Lee GH, et al. Association of tumor necrosis factor-{alpha} gene polymorphisms with advanced stage endometriosis. *Hum Reprod.* Apr. 2008; 23(4):977-981.
Liu Q, et al. Association of polymorphisms −1154G/A and -2578C/A in the vascular endothelial growth factor gene with decreased risk of endometriosis in Chinese women. *Hum Reprod.* Jun. 16, 2009.
Lucentini Jack, Gene Association Studies Typically Wrong, The Scientist, Dec. 20, 2004, p. 20.
May Robert, How Many Species Are There on Earth, Science. Sep. 16, 1998, vol. 241, p. 1441-1449.
Nishida et al, Evaluating the performance of Affymetrix SNP Array 6.0 platform with 400 Japanese individuals, BMC Genomics, Sep. 22, 2008, pp. 1-10.
Nnoaham et al, Developing Symptom-based Predictive Models of Endometriosis as a Clinical Screening Tool: Results from a Multicenter Study, Fertility and Sterility, Sep. 2012, vol. 98, No. 3, p. 692-701e5.
Pennisi Elizabeth, A Closer Look at SNPs Suggests Difficulties, Science, Sep. 18, 1998, vol. 281, p. 1787-1789.
Petrozza et al, A polymorphism in the biliary glycoprotein gene in women with endometriosis, FS, 2002, vol. 78, pp. s198-s199.
Rahmioglu et al, Genetic variants underlying risk of endometriosis: insights from meta-analysis of eight genome-wide association and replication datasets, Hum Repro, Mar. 27, 2014, vol. 0, No. 0, p. 1-15.
Setakis et al, Logistic regression protects against population structure in genetic association studies, Genome Research, 2006, vol. 16, pp. 290-296.
Shan K, et al. Association of three single nucleotide polymorphisms of the E-cadherin gene with endometriosis in a Chinese population. Reproduction. Aug. 2007; 134(2):373-378.
Shan K, et al. The function of the SNP in the MMP1 and MMP3 promoter in susceptibility to endometriosis in China. Mol Hum Reprod. Jun. 2005; 11(6):423-427.
Sotos et al, The Transitivity Misconception of Pearson's Correlation Coefficient, IASE, Nov. 2009, p. 33-55.
Teramoto M, et al. Genetic contribution of tumor necrosis factor (TNF)-alpha gene promoter (-1031, -863 and -857) and TNF receptor 2 gene polymorphisms in endometriosis susceptibility. Am J Reprod Immunol. May 2004; 51(5):352-357.
Terwilliger et al, An utter refutation of the Fundamental Theorem of the HapMap, EJHG, 2006, p. 426-437.
Tsuchiya M, et al. Analysis of the AhR, ARNT, and AhRR gene polymorphisms: genetic contribution to endometriosis susceptibility and severity. Fertil Steril. Aug. 2005; 84(2):454-458.
Tsuchiya M, et al. Association between endometriosis and genetic polymorphisms of the estradiol-synthesizing enzyme genes HSD17B1 and CYP19. Hum Reprod. Apr. 2005; 20(4):974-978.
Vigano, et al. Intercellular adhesion molecule-1 (ICAM-1) gene polymorphisms in endometriosis. Mol Hum Reprod. Jan. 2003; 9(1):47-52.
Vijaya Lakshmi K, et al. Tumor necrosis factor alpha-C850T polymorphism is significantly associated with endometriosis in Asian Indian women. *Fertil Steril.* Apr. 24, 2009.
Wall et al, Haplotype Blocks and Linkage Disequilibrium in the Human Genome, Nat Rev Gen, Aug. 2003, vol. 4, p. 587-597.
Wang Z, et al. Polymorphisms in the estrogen receptor beta gene but not estrogen receptor alpha gene affect the risk of developing endometriosis in a Japanese population. Fertil Steril. Jun. 2004; 81(6):1650-1656.

(56) References Cited

OTHER PUBLICATIONS

Wieser et al, PROGINS receptor gene polymorphism is associated with endometriosis, Fertility and Sterility, Feb. 2002, vol. 77, No. 2, p. 309-312.
Wu YL, et al. Sensitive and real-time polymerase chain reaction assays to accurately determine copy number variations (CNVs) of human complement C4A, C4B, C4-long, C4-short, and RCCX modules: elucidation of C4 CNVs in 50 consanguineous subjects with defined HLA genotypes. J Immunol. Sep. 1, 2007; 179(5):3012-3025.
Zervou S, et al. The Glu298→Asp polymorphism of the endothelial nitric oxide synthase gene is associated with endometriosis. Fertil Steril. Dec. 2003; 80(6):1524-1525.
Zhang X, et al. Interleukin-10 gene promoter polymorphisms and their protein production in peritoneal fluid in patients with endometriosis. *Mol Hum Reprod.* Feb. 2007; 13(2):135-140.
Zill et al, SNP and haplotype analysis of a novel tryptophan hydroxylase isoform (TPH2) gene provide evidence for association with major depression, Mole Psyc, 2004, p. 1030-1036.

* cited by examiner

Three Endometriosis Related Clinical Questions:

| | Odds Ratio |
|---|---|
| 1) Menarche after age 14? (Y/N) | 0.3 (0.1 – 0.6) |
| 2) Dysmenorrhea? (Y/N) | 2.6 (1.1 – 6.2) |
| 3) Previous pregnancy? (Y/N) | 0.65 (0.49 – 0.87) |

FIG. 1

SEQUENCE LISTING

<160> NUMBER OF SEQ ID NOS: 1398

<210> SEQ ID NO 1
<211> LENGTH: 33
<212> TYPE: DNA
<213> ORGANISM: Homo Sapiens

<400> SEQUENCE: 1
aaggatcatc ttggctrgag gagggatccc aac 33

<210> SEQ ID NO 2
<211> LENGTH: 33
<212> TYPE: DNA
<213> ORGANISM: Homo Sapiens

<400> SEQUENCE: 2
cctcgcctta caactarttc ctgcctttcg tcc 33

<210> SEQ ID NO 3
<211> LENGTH: 33
<212> TYPE: DNA
<213> ORGANISM: Homo Sapiens

<400> SEQUENCE: 3
gagaattgag ttgaaamttt aaagaaggag ttg 33

<210> SEQ ID NO 4
<211> LENGTH: 33
<212> TYPE: DNA
<213> ORGANISM: Homo Sapiens

<400> SEQUENCE: 4
gccaaaaccc agaggcrata gtgttggttt ttc 33

<210> SEQ ID NO 5
<211> LENGTH: 33
<212> TYPE: DNA
<213> ORGANISM: Homo Sapiens

<400> SEQUENCE: 5
ccatttaatc catagtmctc ctctctccta tct 33

<210> SEQ ID NO 6
<211> LENGTH: 33
<212> TYPE: DNA
<213> ORGANISM: Homo Sapiens

<400> SEQUENCE: 6
gcacatgaaa gtttaartag cactactacc aga 33

<210> SEQ ID NO 7
<211> LENGTH: 33
<212> TYPE: DNA
<213> ORGANISM: Homo Sapiens

<400> SEQUENCE: 7
tcatgaacta tgtaggraag gaagtgaaat ttg 33

<210> SEQ ID NO 8
<211> LENGTH: 33
<212> TYPE: DNA
<213> ORGANISM: Homo Sapiens

<400> SEQUENCE: 8
gaaacaactg ctcaggrcat tttgcaaatt tac 33

<210> SEQ ID NO 9
<211> LENGTH: 33
<212> TYPE: DNA
<213> ORGANISM: Homo Sapiens

<400> SEQUENCE: 9
atcctttctc agcaggrccc attatttctc att 33

<210> SEQ ID NO 10
<211> LENGTH: 33
<212> TYPE: DNA
<213> ORGANISM: Homo Sapiens

<400> SEQUENCE: 10
acagatagtt cctatgrgct agacttggtc aga 33

<210> SEQ ID NO 11
<211> LENGTH: 33
<212> TYPE: DNA
<213> ORGANISM: Homo Sapiens

<400> SEQUENCE: 11
gaactgcata gtcccarctt acaaagaatc agc 33

<210> SEQ ID NO 12
<211> LENGTH: 33
<212> TYPE: DNA
<213> ORGANISM: Homo Sapiens

<400> SEQUENCE: 12
agagcttagt agcttcraca gaaaccacat gtg 33

<210> SEQ ID NO 13
<211> LENGTH: 33
<212> TYPE: DNA
<213> ORGANISM: Homo Sapiens

<400> SEQUENCE: 13
agtaatagac atttacrttt cctccaggtt ttt 33

<210> SEQ ID NO 14
<211> LENGTH: 33
<212> TYPE: DNA
<213> ORGANISM: Homo Sapiens

<400> SEQUENCE: 14
tctagagtta aatcctrtct ggggactctg ggc 33

<210> SEQ ID NO 15
<211> LENGTH: 33
<212> TYPE: DNA
<213> ORGANISM: Homo Sapiens

<400> SEQUENCE: 15
cactcagaag agagtarcta gagtaagaag tca 33

<210> SEQ ID NO 16
<211> LENGTH: 33
<212> TYPE: DNA
<213> ORGANISM: Homo Sapiens

<400> SEQUENCE: 16
gaaatgggaa actatcrtag ggttctttgc aga 33

<210> SEQ ID NO 17
<211> LENGTH: 33
<212> TYPE: DNA
<213> ORGANISM: Homo Sapiens

<400> SEQUENCE: 17
tgctgcaaag tgatttsgaa gttcaacctc atg 33

<210> SEQ ID NO 18
<211> LENGTH: 33
<212> TYPE: DNA
<213> ORGANISM: Homo Sapiens

<400> SEQUENCE: 18
gctgctcctg gtccctmttg taaggtcctg tga 33

<210> SEQ ID NO 19
<211> LENGTH: 33
<212> TYPE: DNA
<213> ORGANISM: Homo Sapiens

<400> SEQUENCE: 19
gatcatacga tctgtcrcaa ctgctaaatg tgc 33

<210> SEQ ID NO 20
<211> LENGTH: 33
<212> TYPE: DNA
<213> ORGANISM: Homo Sapiens

<400> SEQUENCE: 20
gagtaagaca taggagrtca aggtaggagg att 33

<210> SEQ ID NO 21
<211> LENGTH: 33
<212> TYPE: DNA
<213> ORGANISM: Homo Sapiens

<400> SEQUENCE: 21
atttatcatg ttctctrgta ggaatgctcc cca 33

<210> SEQ ID NO 22
<211> LENGTH: 33
<212> TYPE: DNA
<213> ORGANISM: Homo Sapiens

<400> SEQUENCE: 22
aaaatctcag ctccacmtca gccccaatta tct 33

<210> SEQ ID NO 23
<211> LENGTH: 33
<212> TYPE: DNA
<213> ORGANISM: Homo Sapiens

<400> SEQUENCE: 23
tatacagaaa cacaaamccc atcttggatc act 33

<210> SEQ ID NO 24
<211> LENGTH: 33
<212> TYPE: DNA
<213> ORGANISM: Homo Sapiens

<400> SEQUENCE: 24
tattaatctt tttcacmtca gcacagcaga act 33

<210> SEQ ID NO 25
<211> LENGTH: 33
<212> TYPE: DNA
<213> ORGANISM: Homo Sapiens

<400> SEQUENCE: 25
ttcgtaacta cgatgamttt ctcggttaag agt 33

<210> SEQ ID NO 26
<211> LENGTH: 33
<212> TYPE: DNA
<213> ORGANISM: Homo Sapiens

<400> SEQUENCE: 26
agttttgttt cacaggrcta aagcctgaac aga 33

<210> SEQ ID NO 27
<211> LENGTH: 33
<212> TYPE: DNA
<213> ORGANISM: Homo Sapiens

<400> SEQUENCE: 27
cgggcggcgc ggacccmaag tccgagaagc agt 33

<210> SEQ ID NO 28
<211> LENGTH: 33
<212> TYPE: DNA
<213> ORGANISM: Homo Sapiens

<400> SEQUENCE: 28
aaaaagaatc agaaatrtct ggtgcatgga gcc 33

<210> SEQ ID NO 29
<211> LENGTH: 33
<212> TYPE: DNA
<213> ORGANISM: Homo Sapiens

<400> SEQUENCE: 29
gacctccagc aggggcrtgg ccagtgggtg cca 33

<210> SEQ ID NO 30
<211> LENGTH: 33
<212> TYPE: DNA
<213> ORGANISM: Homo Sapiens

<400> SEQUENCE: 30
tagtttccct ggaaacrtat atctttgtac act 33

<210> SEQ ID NO 31
<211> LENGTH: 33
<212> TYPE: DNA
<213> ORGANISM: Homo Sapiens

<400> SEQUENCE: 31
gtgcaatgta tgaggtrtaa attaatgcag cct 33

<210> SEQ ID NO 32
<211> LENGTH: 33
<212> TYPE: DNA

<213> ORGANISM: Homo Sapiens

<400> SEQUENCE: 32
ttattttgga gtcacaraga cacttggctt ttt 33

<210> SEQ ID NO 33
<211> LENGTH: 33
<212> TYPE: DNA
<213> ORGANISM: Homo Sapiens

<400> SEQUENCE: 33
gtgctctagc tgcaagrcag gtggaaaaag tgt 33

<210> SEQ ID NO 34
<211> LENGTH: 33
<212> TYPE: DNA
<213> ORGANISM: Homo Sapiens

<400> SEQUENCE: 34
agccagcacc acctggrtgg ggtcattggc gag 33

<210> SEQ ID NO 35
<211> LENGTH: 33
<212> TYPE: DNA
<213> ORGANISM: Homo Sapiens

<400> SEQUENCE: 35
gtttgctctc actcttmata caatcgccaa aat 33

<210> SEQ ID NO 36
<211> LENGTH: 33
<212> TYPE: DNA
<213> ORGANISM: Homo Sapiens

<400> SEQUENCE: 36
taggggatct cattgcmcag taaaataggc gac 33

<210> SEQ ID NO 37
<211> LENGTH: 33
<212> TYPE: DNA
<213> ORGANISM: Homo Sapiens

<400> SEQUENCE: 37
gttccatttt gtagccragg atataaaagc tca 33

<210> SEQ ID NO 38
<211> LENGTH: 33
<212> TYPE: DNA
<213> ORGANISM: Homo Sapiens

<400> SEQUENCE: 38
agagacttgg gtacacmgag aggggatgtc tat 33

<210> SEQ ID NO 39
<211> LENGTH: 33
<212> TYPE: DNA
<213> ORGANISM: Homo Sapiens

<400> SEQUENCE: 39
gggcggaggg gaggcgrgag atttctgagc tcc 33

<210> SEQ ID NO 40
<211> LENGTH: 33

<212> TYPE: DNA
<213> ORGANISM: Homo Sapiens

<400> SEQUENCE: 40
cactgcttct accccamatt gacatccatc ttt 33

<210> SEQ ID NO 41
<211> LENGTH: 33
<212> TYPE: DNA
<213> ORGANISM: Homo Sapiens

<400> SEQUENCE: 41
tgagagaata tgacacmttc ttcctttaga gga 33

<210> SEQ ID NO 42
<211> LENGTH: 33
<212> TYPE: DNA
<213> ORGANISM: Homo Sapiens

<400> SEQUENCE: 42
gctatacctc ccaatcrtca acctgtagaa cat 33

<210> SEQ ID NO 43
<211> LENGTH: 33
<212> TYPE: DNA
<213> ORGANISM: Homo Sapiens

<400> SEQUENCE: 43
tgctggtcag gatggartat gttatcagag ccc 33

<210> SEQ ID NO 44
<211> LENGTH: 33
<212> TYPE: DNA
<213> ORGANISM: Homo Sapiens

<400> SEQUENCE: 44
agaaccaggt agagaargct ggaggagccg cca 33

<210> SEQ ID NO 45
<211> LENGTH: 33
<212> TYPE: DNA
<213> ORGANISM: Homo Sapiens

<400> SEQUENCE: 45
acagcgtctc ctcatcragg ataagaccac aga 33

<210> SEQ ID NO 46
<211> LENGTH: 33
<212> TYPE: DNA
<213> ORGANISM: Homo Sapiens

<400> SEQUENCE: 46
tgctgcccca ccccatmctc caatttttat act 33

<210> SEQ ID NO 47
<211> LENGTH: 33
<212> TYPE: DNA
<213> ORGANISM: Homo Sapiens

<400> SEQUENCE: 47
aggtcaaggg caccagrttc atttcagccc tta 33

<210> SEQ ID NO 48

<211> LENGTH: 33
<212> TYPE: DNA
<213> ORGANISM: Homo Sapiens

<400> SEQUENCE: 48
aattcttaat gagaaartct cttggaggaa atg 33

<210> SEQ ID NO 49
<211> LENGTH: 33
<212> TYPE: DNA
<213> ORGANISM: Homo Sapiens

<400> SEQUENCE: 49
atgcacacag aagcccrgcc ggtatcccca cag 33

<210> SEQ ID NO 50
<211> LENGTH: 33
<212> TYPE: DNA
<213> ORGANISM: Homo Sapiens

<400> SEQUENCE: 50
ccctgatgat atggttrtca gaatgtattt tca 33

<210> SEQ ID NO 51
<211> LENGTH: 33
<212> TYPE: DNA
<213> ORGANISM: Homo Sapiens

<400> SEQUENCE: 51
ggttctccga gaggtcrctc ctggatgtag ggg 33

<210> SEQ ID NO 52
<211> LENGTH: 33
<212> TYPE: DNA
<213> ORGANISM: Homo Sapiens

<400> SEQUENCE: 52
actggctcat tattcgrcgt ctgtaactct ggg 33

<210> SEQ ID NO 53
<211> LENGTH: 33
<212> TYPE: DNA
<213> ORGANISM: Homo Sapiens

<400> SEQUENCE: 53
aatgagtgtt cttagargct gggtcggatt cct 33

<210> SEQ ID NO 54
<211> LENGTH: 33
<212> TYPE: DNA
<213> ORGANISM: Homo Sapiens

<400> SEQUENCE: 54
tcagacctgg gagaatrtca ggtaagctga gat 33

<210> SEQ ID NO 55
<211> LENGTH: 33
<212> TYPE: DNA
<213> ORGANISM: Homo Sapiens

<400> SEQUENCE: 55
gagcgcgcac tgcaccrgcc agagtgccac aca 33

<210> SEQ ID NO 56
<211> LENGTH: 33
<212> TYPE: DNA
<213> ORGANISM: Homo Sapiens

<400> SEQUENCE: 56
cttttcttat aggtcasagg ctagtccagc acc 33

<210> SEQ ID NO 57
<211> LENGTH: 33
<212> TYPE: DNA
<213> ORGANISM: Homo Sapiens

<400> SEQUENCE: 57
ctcggctttg ccatcgsggg ggacatcctt gcc 33

<210> SEQ ID NO 58
<211> LENGTH: 33
<212> TYPE: DNA
<213> ORGANISM: Homo Sapiens

<400> SEQUENCE: 58
catgttcaag tacttcrcat cctggcggta ttt 33

<210> SEQ ID NO 59
<211> LENGTH: 33
<212> TYPE: DNA
<213> ORGANISM: Homo Sapiens

<400> SEQUENCE: 59
gttggggagt gagccarcag ttatctggag gga 33

<210> SEQ ID NO 60
<211> LENGTH: 33
<212> TYPE: DNA
<213> ORGANISM: Homo Sapiens

<400> SEQUENCE: 60
tcagcaacag ccccctmcag agcagcagcc aga 33

<210> SEQ ID NO 61
<211> LENGTH: 33
<212> TYPE: DNA
<213> ORGANISM: Homo Sapiens

<400> SEQUENCE: 61
catatcccat tcctggmcac atgaaatcca aaa 33

<210> SEQ ID NO 62
<211> LENGTH: 33
<212> TYPE: DNA
<213> ORGANISM: Homo Sapiens

<400> SEQUENCE: 62
ccaagaggct cacctgmgat ccagttgccg ggg 33

<210> SEQ ID NO 63
<211> LENGTH: 33
<212> TYPE: DNA
<213> ORGANISM: Homo Sapiens

<400> SEQUENCE: 63
aagggtcaga aaacaartaa aaggccaaga cag 33

<210> SEQ ID NO 64
<211> LENGTH: 33
<212> TYPE: DNA
<213> ORGANISM: Homo Sapiens

<400> SEQUENCE: 64
caaacctcct tgagtcrgct ttaagagttt ctt 33

<210> SEQ ID NO 65
<211> LENGTH: 33
<212> TYPE: DNA
<213> ORGANISM: Homo Sapiens

<400> SEQUENCE: 65
aactcctcaa agatctsgtg tgccctggag gcc 33

<210> SEQ ID NO 66
<211> LENGTH: 33
<212> TYPE: DNA
<213> ORGANISM: Homo Sapiens

<400> SEQUENCE: 66
gaagtttttt acaaccraaa tctatgaccg ttg 33

<210> SEQ ID NO 67
<211> LENGTH: 33
<212> TYPE: DNA
<213> ORGANISM: Homo Sapiens

<400> SEQUENCE: 67
cgcgcggcgc caaatcrtgg tcagagcccg gat 33

<210> SEQ ID NO 68
<211> LENGTH: 33
<212> TYPE: DNA
<213> ORGANISM: Homo Sapiens

<400> SEQUENCE: 68
aaggaattac caagaaragc catgcatctc aca 33

<210> SEQ ID NO 69
<211> LENGTH: 33
<212> TYPE: DNA
<213> ORGANISM: Homo Sapiens

<400> SEQUENCE: 69
ccgggaagtg cacgctrcca ccgaggagcc atc 33

<210> SEQ ID NO 70
<211> LENGTH: 33
<212> TYPE: DNA
<213> ORGANISM: Homo Sapiens

<400> SEQUENCE: 70
gatgagatcc caagtcmaag gaagatttgc cca 33

<210> SEQ ID NO 71
<211> LENGTH: 33
<212> TYPE: DNA
<213> ORGANISM: Homo Sapiens

<400> SEQUENCE: 71
cgaaacaaag cccatgraaa tccaaaggtt gga 33

<210> SEQ ID NO 72
<211> LENGTH: 33
<212> TYPE: DNA
<213> ORGANISM: Homo Sapiens

<400> SEQUENCE: 72
gcttgggggc tggagarcag aatttaacat gtt 33

<210> SEQ ID NO 73
<211> LENGTH: 33
<212> TYPE: DNA
<213> ORGANISM: Homo Sapiens

<400> SEQUENCE: 73
ttcaaggccc tttgagmtct tgatggcaca tga 33

<210> SEQ ID NO 74
<211> LENGTH: 33
<212> TYPE: DNA
<213> ORGANISM: Homo Sapiens

<400> SEQUENCE: 74
agtatattag gggattrata ttacaagcaa gaa 33

<210> SEQ ID NO 75
<211> LENGTH: 33
<212> TYPE: DNA
<213> ORGANISM: Homo Sapiens

<400> SEQUENCE: 75
gctgtatgtt ataattmtct gatagaaccc aca 33

<210> SEQ ID NO 76
<211> LENGTH: 33
<212> TYPE: DNA
<213> ORGANISM: Homo Sapiens

<400> SEQUENCE: 76
gatgaaataa tagactmcag ggatttactt ttt 33

<210> SEQ ID NO 77
<211> LENGTH: 33
<212> TYPE: DNA
<213> ORGANISM: Homo Sapiens

<400> SEQUENCE: 77
actctccaaa gtcacartat tttctggaca agc 33

<210> SEQ ID NO 78
<211> LENGTH: 33
<212> TYPE: DNA
<213> ORGANISM: Homo Sapiens

<400> SEQUENCE: 78
atcaggatca taggagsact gtctgaggat cag 33

<210> SEQ ID NO 79
<211> LENGTH: 33
<212> TYPE: DNA
<213> ORGANISM: Homo Sapiens

<400> SEQUENCE: 79
acctggctag ggatacragg ccattaacca agc 33

<210> SEQ ID NO 80
<211> LENGTH: 33
<212> TYPE: DNA
<213> ORGANISM: Homo Sapiens

<400> SEQUENCE: 80
tggttgttgc atggcayttc cagataagct gca 33

<210> SEQ ID NO 81
<211> LENGTH: 33
<212> TYPE: DNA
<213> ORGANISM: Homo Sapiens

<400> SEQUENCE: 81
aatgtttgta tttgggrttg cccttcttac atg 33

<210> SEQ ID NO 82
<211> LENGTH: 33
<212> TYPE: DNA
<213> ORGANISM: Homo Sapiens

<400> SEQUENCE: 82
caagttctac acttccrtaa ctcaaacgtg ttt 33

<210> SEQ ID NO 83
<211> LENGTH: 33
<212> TYPE: DNA
<213> ORGANISM: Homo Sapiens

<400> SEQUENCE: 83
tcaattataa tcacctrtgt ggatttttct cag 33

<210> SEQ ID NO 84
<211> LENGTH: 33
<212> TYPE: DNA
<213> ORGANISM: Homo Sapiens

<400> SEQUENCE: 84
cgaactgatc agatcgmtgc cctacacact tta 33

<210> SEQ ID NO 85
<211> LENGTH: 33
<212> TYPE: DNA
<213> ORGANISM: Homo Sapiens

<400> SEQUENCE: 85
caaatattac tgcaatragt aatatcatac aca 33

<210> SEQ ID NO 86
<211> LENGTH: 33
<212> TYPE: DNA
<213> ORGANISM: Homo Sapiens

<400> SEQUENCE: 86
aacagatgcc atggtaract agatgcctgg gtg 33

<210> SEQ ID NO 87
<211> LENGTH: 33
<212> TYPE: DNA
<213> ORGANISM: Homo Sapiens

<400> SEQUENCE: 87
tctttaaggt gggttcrgag aaaggagatg gaa 33

<210> SEQ ID NO 88
<211> LENGTH: 33
<212> TYPE: DNA
<213> ORGANISM: Homo Sapiens

<400> SEQUENCE: 88
acagacaggg tgtcatrgaa gccgcgtcat atc 33

<210> SEQ ID NO 89
<211> LENGTH: 33
<212> TYPE: DNA
<213> ORGANISM: Homo Sapiens

<400> SEQUENCE: 89
tccaccagtg aagcaartaa tctgtggcct gct 33

<210> SEQ ID NO 90
<211> LENGTH: 33
<212> TYPE: DNA
<213> ORGANISM: Homo Sapiens

<400> SEQUENCE: 90
caaaaaagaa gtatcarggt atatatgaag aga 33

<210> SEQ ID NO 91
<211> LENGTH: 33
<212> TYPE: DNA
<213> ORGANISM: Homo Sapiens

<400> SEQUENCE: 91
aacagaaaat taagatmaga ttggctaaca aga 33

<210> SEQ ID NO 92
<211> LENGTH: 33
<212> TYPE: DNA
<213> ORGANISM: Homo Sapiens

<400> SEQUENCE: 92
taaaggaatc cctgttraaa aaaaagaata agg 33

<210> SEQ ID NO 93
<211> LENGTH: 33
<212> TYPE: DNA
<213> ORGANISM: Homo Sapiens

<400> SEQUENCE: 93
tttcctttat aaaactrtgt tactctagtc tga 33

<210> SEQ ID NO 94
<211> LENGTH: 33
<212> TYPE: DNA
<213> ORGANISM: Homo Sapiens

<400> SEQUENCE: 94
ctaaatggtg gttcacrggg aattcatgaa act 33

<210> SEQ ID NO 95
<211> LENGTH: 33
<212> TYPE: DNA
<213> ORGANISM: Homo Sapiens

<400> SEQUENCE: 95
gggagctcag actcacrtgg tggaaagcct aaa 33

<210> SEQ ID NO 96
<211> LENGTH: 33
<212> TYPE: DNA
<213> ORGANISM: Homo Sapiens

<400> SEQUENCE: 96
atggcataac aatagtract caaagaggca aaa 33

<210> SEQ ID NO 97
<211> LENGTH: 33
<212> TYPE: DNA
<213> ORGANISM: Homo Sapiens

<400> SEQUENCE: 97
tttggaaatt taacacrtga atataaccat caa 33

<210> SEQ ID NO 98
<211> LENGTH: 33
<212> TYPE: DNA
<213> ORGANISM: Homo Sapiens

<400> SEQUENCE: 98
aacaggacta agtggcrtat aaattagggt aat 33

<210> SEQ ID NO 99
<211> LENGTH: 33
<212> TYPE: DNA
<213> ORGANISM: Homo Sapiens

<400> SEQUENCE: 99
tatatcatca gtgcccrgaa gagtacctga tgc 33

<210> SEQ ID NO 100
<211> LENGTH: 33
<212> TYPE: DNA
<213> ORGANISM: Homo Sapiens

<400> SEQUENCE: 100
accagtacca tccggtrtga tttgatggta tga 33

<210> SEQ ID NO 101
<211> LENGTH: 33
<212> TYPE: DNA
<213> ORGANISM: Homo Sapiens

<400> SEQUENCE: 101
tgatgaggcc ttctcgrgga agttttacga tgt 33

<210> SEQ ID NO 102
<211> LENGTH: 33
<212> TYPE: DNA
<213> ORGANISM: Homo Sapiens

<400> SEQUENCE: 102
tgcagctgca ggtcgcrgca ccactggggc aag 33

<210> SEQ ID NO 103
<211> LENGTH: 33
<212> TYPE: DNA
<213> ORGANISM: Homo Sapiens

<400> SEQUENCE: 103
actcagcccc agccccrctc actaagctca cag 33

<210> SEQ ID NO 104
<211> LENGTH: 33
<212> TYPE: DNA
<213> ORGANISM: Homo Sapiens

<400> SEQUENCE: 104
ccattgcaaa ccacagrggt gattattttt agt 33

<210> SEQ ID NO 105
<211> LENGTH: 33
<212> TYPE: DNA
<213> ORGANISM: Homo Sapiens

<400> SEQUENCE: 105
gggggaaagc gggaagrtct cttgctccag gaa 33

<210> SEQ ID NO 106
<211> LENGTH: 33
<212> TYPE: DNA
<213> ORGANISM: Homo Sapiens

<400> SEQUENCE: 106
ggatgagact ccctctrtaa taaaatcaca gtc 33

<210> SEQ ID NO 107
<211> LENGTH: 33
<212> TYPE: DNA
<213> ORGANISM: Homo Sapiens

<400> SEQUENCE: 107
ataaaattta tagtacrttt tgagcctgtg tgt 33

<210> SEQ ID NO 108
<211> LENGTH: 33
<212> TYPE: DNA
<213> ORGANISM: Homo Sapiens

<400> SEQUENCE: 108
aaacatagca tatttcrctt gattcttgtg aca 33

<210> SEQ ID NO 109
<211> LENGTH: 33
<212> TYPE: DNA
<213> ORGANISM: Homo Sapiens

<400> SEQUENCE: 109
tgcttcaaca atttccrttt gtgtatcgtt ggc 33

<210> SEQ ID NO 110
<211> LENGTH: 33
<212> TYPE: DNA
<213> ORGANISM: Homo Sapiens

<400> SEQUENCE: 110
tctgtgctgt ttttcargga aaaacatctg ggt 33

<210> SEQ ID NO 111
<211> LENGTH: 33
<212> TYPE: DNA

<213> ORGANISM: Homo Sapiens

<400> SEQUENCE: 111
cccaagacac tgtagcrttt acatagtagg tag 33

<210> SEQ ID NO 112
<211> LENGTH: 33
<212> TYPE: DNA
<213> ORGANISM: Homo Sapiens

<400> SEQUENCE: 112
atgatcatgt gattgawgta tctaaaccac agt 33

<210> SEQ ID NO 113
<211> LENGTH: 33
<212> TYPE: DNA
<213> ORGANISM: Homo Sapiens

<400> SEQUENCE: 113
gaacatatag acaatcrgga atgctaaaat aaa 33

<210> SEQ ID NO 114
<211> LENGTH: 33
<212> TYPE: DNA
<213> ORGANISM: Homo Sapiens

<400> SEQUENCE: 114
gactccttgc atttcartat aatgttagct ctg 33

<210> SEQ ID NO 115
<211> LENGTH: 33
<212> TYPE: DNA
<213> ORGANISM: Homo Sapiens

<400> SEQUENCE: 115
atgcattgat gaccttmaat atttattttg taa 33

<210> SEQ ID NO 116
<211> LENGTH: 33
<212> TYPE: DNA
<213> ORGANISM: Homo Sapiens

<400> SEQUENCE: 116
atatcattat gaactcmtag attttttaac cta 33

<210> SEQ ID NO 117
<211> LENGTH: 33
<212> TYPE: DNA
<213> ORGANISM: Homo Sapiens

<400> SEQUENCE: 117
ccagcagctc atcagaraga gggatgacag aca 33

<210> SEQ ID NO 118
<211> LENGTH: 33
<212> TYPE: DNA
<213> ORGANISM: Homo Sapiens

<400> SEQUENCE: 118
acaacgcaat actactmggg aataaaaagg aaa 33

<210> SEQ ID NO 119
<211> LENGTH: 33

<212> TYPE: DNA
<213> ORGANISM: Homo Sapiens

<400> SEQUENCE: 119
agtagtggaa cgaaatract ttggagaaaa gga 33

<210> SEQ ID NO 120
<211> LENGTH: 33
<212> TYPE: DNA
<213> ORGANISM: Homo Sapiens

<400> SEQUENCE: 120
tccctgcctc ctgtccrtat caatagatgt tgg 33

<210> SEQ ID NO 121
<211> LENGTH: 33
<212> TYPE: DNA
<213> ORGANISM: Homo Sapiens

<400> SEQUENCE: 121
actgacaaca ggcttcrcca tgtaaattgc tct 33

<210> SEQ ID NO 122
<211> LENGTH: 33
<212> TYPE: DNA
<213> ORGANISM: Homo Sapiens

<400> SEQUENCE: 122
taagatgaaa aggtctrctt tcaggggttt gtg 33

<210> SEQ ID NO 123
<211> LENGTH: 33
<212> TYPE: DNA
<213> ORGANISM: Homo Sapiens

<400> SEQUENCE: 123
aacccagcca ttaactmttg ttagatagct tta 33

<210> SEQ ID NO 124
<211> LENGTH: 33
<212> TYPE: DNA
<213> ORGANISM: Homo Sapiens

<400> SEQUENCE: 124
tccttttatt ctcctcrttt tatgtaattc tgt 33

<210> SEQ ID NO 125
<211> LENGTH: 33
<212> TYPE: DNA
<213> ORGANISM: Homo Sapiens

<400> SEQUENCE: 125
actttttgct tagtctraat taaaaaaagt ctt 33

<210> SEQ ID NO 126
<211> LENGTH: 33
<212> TYPE: DNA
<213> ORGANISM: Homo Sapiens

<400> SEQUENCE: 126
ttacaagatt ttctttrgtt tatagaccta ctt 33

<210> SEQ ID NO 127

<211> LENGTH: 33
<212> TYPE: DNA
<213> ORGANISM: Homo Sapiens

<400> SEQUENCE: 127
cttgtttggg gacacamttt caaatacaaa atg 33

<210> SEQ ID NO 128
<211> LENGTH: 33
<212> TYPE: DNA
<213> ORGANISM: Homo Sapiens

<400> SEQUENCE: 128
tttttagtat cgtagasctc tgctttgtca cag 33

<210> SEQ ID NO 129
<211> LENGTH: 33
<212> TYPE: DNA
<213> ORGANISM: Homo Sapiens

<400> SEQUENCE: 129
gactcaggtt tgaggcrttt tgcatctggt ggc 33

<210> SEQ ID NO 130
<211> LENGTH: 33
<212> TYPE: DNA
<213> ORGANISM: Homo Sapiens

<400> SEQUENCE: 130
gggaacaaat taatatrtaa actatagcct tga 33

<210> SEQ ID NO 131
<211> LENGTH: 33
<212> TYPE: DNA
<213> ORGANISM: Homo Sapiens

<400> SEQUENCE: 131
tccctgcatc ccctgcrgat aagaaaactg gca 33

<210> SEQ ID NO 132
<211> LENGTH: 33
<212> TYPE: DNA
<213> ORGANISM: Homo Sapiens

<400> SEQUENCE: 132
atagtatgtg ttcattraag atgatttggg ttt 33

<210> SEQ ID NO 133
<211> LENGTH: 33
<212> TYPE: DNA
<213> ORGANISM: Homo Sapiens

<400> SEQUENCE: 133
agatggctac cagcaaraat ggtgcaatgg cgt 33

<210> SEQ ID NO 134
<211> LENGTH: 33
<212> TYPE: DNA
<213> ORGANISM: Homo Sapiens

<400> SEQUENCE: 134
tcatttattg cttgatrgac acctctaatg tat 33

-continued

<210> SEQ ID NO 135
<211> LENGTH: 33
<212> TYPE: DNA
<213> ORGANISM: Homo Sapiens

<400> SEQUENCE: 135
aaaagtgtgt aattcartgc attaaataca ttc 33

<210> SEQ ID NO 136
<211> LENGTH: 33
<212> TYPE: DNA
<213> ORGANISM: Homo Sapiens

<400> SEQUENCE: 136
gccttcccgc taaaatraga ataaggttaa gta 33

<210> SEQ ID NO 137
<211> LENGTH: 33
<212> TYPE: DNA
<213> ORGANISM: Homo Sapiens

<400> SEQUENCE: 137
tgtcggtagg actactrgat agccacaggc aaa 33

<210> SEQ ID NO 138
<211> LENGTH: 33
<212> TYPE: DNA
<213> ORGANISM: Homo Sapiens

<400> SEQUENCE: 138
ttgtggtctg tgtttargat aatgtggaag cta 33

<210> SEQ ID NO 139
<211> LENGTH: 33
<212> TYPE: DNA
<213> ORGANISM: Homo Sapiens

<400> SEQUENCE: 139
ggagtggggg gaatgcrgga gatgcccttt atg 33

<210> SEQ ID NO 140
<211> LENGTH: 33
<212> TYPE: DNA
<213> ORGANISM: Homo Sapiens

<400> SEQUENCE: 140
atgatgctga gaatctrtga aatgacggaa gaa 33

<210> SEQ ID NO 141
<211> LENGTH: 33
<212> TYPE: DNA
<213> ORGANISM: Homo Sapiens

<400> SEQUENCE: 141
tttattcctt ctatctract gaaattctgt att 33

<210> SEQ ID NO 142
<211> LENGTH: 33
<212> TYPE: DNA
<213> ORGANISM: Homo Sapiens

<400> SEQUENCE: 142
acctcctgag ctcagamcaa gagtgcagcc ttt 33

<210> SEQ ID NO 143
<211> LENGTH: 33
<212> TYPE: DNA
<213> ORGANISM: Homo Sapiens

<400> SEQUENCE: 143
gtttaatcat acatccrtgg aggaacatgt tgg 33

<210> SEQ ID NO 144
<211> LENGTH: 33
<212> TYPE: DNA
<213> ORGANISM: Homo Sapiens

<400> SEQUENCE: 144
ctctcagggt tatgggraat tggatattaa ctg 33

<210> SEQ ID NO 145
<211> LENGTH: 33
<212> TYPE: DNA
<213> ORGANISM: Homo Sapiens

<400> SEQUENCE: 145
actaatagtg tatgagrgtt tcattttctc tac 33

<210> SEQ ID NO 146
<211> LENGTH: 33
<212> TYPE: DNA
<213> ORGANISM: Homo Sapiens

<400> SEQUENCE: 146
ctaactgaca ttcaacrcac tttcaaagac acc 33

<210> SEQ ID NO 147
<211> LENGTH: 33
<212> TYPE: DNA
<213> ORGANISM: Homo Sapiens

<400> SEQUENCE: 147
ttctgcagca ccatgcrgaa ggtcccgatg agc 33

<210> SEQ ID NO 148
<211> LENGTH: 33
<212> TYPE: DNA
<213> ORGANISM: Homo Sapiens

<400> SEQUENCE: 148
gcgaaagaac aaacaarcca tgtaatacat atg 33

<210> SEQ ID NO 149
<211> LENGTH: 33
<212> TYPE: DNA
<213> ORGANISM: Homo Sapiens

<400> SEQUENCE: 149
gccaggtcta ggcattrttt tggtaagtga ctg 33

<210> SEQ ID NO 150
<211> LENGTH: 33
<212> TYPE: DNA
<213> ORGANISM: Homo Sapiens

<400> SEQUENCE: 150
tttaactgct cggcccrtgt acttgatcat gga 33

<210> SEQ ID NO 151
<211> LENGTH: 33
<212> TYPE: DNA
<213> ORGANISM: Homo Sapiens

<400> SEQUENCE: 151
acatgttgca taggttmtcc ctccattccc tgt 33

<210> SEQ ID NO 152
<211> LENGTH: 33
<212> TYPE: DNA
<213> ORGANISM: Homo Sapiens

<400> SEQUENCE: 152
atagctatag caccgcraat tgccacatct gta 33

<210> SEQ ID NO 153
<211> LENGTH: 33
<212> TYPE: DNA
<213> ORGANISM: Homo Sapiens

<400> SEQUENCE: 153
ttattgccat tcttgtrgaa gtaaggtggt atc 33

<210> SEQ ID NO 154
<211> LENGTH: 33
<212> TYPE: DNA
<213> ORGANISM: Homo Sapiens

<400> SEQUENCE: 154
cataagtggt ggaatcrttg ttcagaaaca tta 33

<210> SEQ ID NO 155
<211> LENGTH: 33
<212> TYPE: DNA
<213> ORGANISM: Homo Sapiens

<400> SEQUENCE: 155
tctagaaact tagtacmtcc tgttgcattg gta 33

<210> SEQ ID NO 156
<211> LENGTH: 33
<212> TYPE: DNA
<213> ORGANISM: Homo Sapiens

<400> SEQUENCE: 156
tttacatact tttcctrttg acttctccat att 33

<210> SEQ ID NO 157
<211> LENGTH: 33
<212> TYPE: DNA
<213> ORGANISM: Homo Sapiens

<400> SEQUENCE: 157
attccttctg ggatctmtta agggataaaa ccg 33

<210> SEQ ID NO 158
<211> LENGTH: 33
<212> TYPE: DNA
<213> ORGANISM: Homo Sapiens

<400> SEQUENCE: 158
caccacattc tctctcrtca gcttctcaga cat 33

<210> SEQ ID NO 159
<211> LENGTH: 33
<212> TYPE: DNA
<213> ORGANISM: Homo Sapiens

<400> SEQUENCE: 159
aaaaattcct ccatgartct tacccagatg gag 33

<210> SEQ ID NO 160
<211> LENGTH: 33
<212> TYPE: DNA
<213> ORGANISM: Homo Sapiens

<400> SEQUENCE: 160
gggaggttca gcagccrcca ctgcgaggag tgg 33

<210> SEQ ID NO 161
<211> LENGTH: 33
<212> TYPE: DNA
<213> ORGANISM: Homo Sapiens

<400> SEQUENCE: 161
ccagtgcttg accctcrcca acgaccgcac tct 33

<210> SEQ ID NO 162
<211> LENGTH: 33
<212> TYPE: DNA
<213> ORGANISM: Homo Sapiens

<400> SEQUENCE: 162
ctcctgggaa cttatamgag taaaagtctg cag 33

<210> SEQ ID NO 163
<211> LENGTH: 33
<212> TYPE: DNA
<213> ORGANISM: Homo Sapiens

<400> SEQUENCE: 163
gcaactaaaa ttaaccrtac ttctgattgt gtc 33

<210> SEQ ID NO 164
<211> LENGTH: 33
<212> TYPE: DNA
<213> ORGANISM: Homo Sapiens

<400> SEQUENCE: 164
tcccatccag cttaagrcat ttaaaataca att 33

<210> SEQ ID NO 165
<211> LENGTH: 33
<212> TYPE: DNA
<213> ORGANISM: Homo Sapiens

<400> SEQUENCE: 165
aaatgcctcc ttggtcmgtt tctcccgcgt ttt 33

<210> SEQ ID NO 166
<211> LENGTH: 33
<212> TYPE: DNA
<213> ORGANISM: Homo Sapiens

<400> SEQUENCE: 166
agcaatttat actgggraaa tatcagaagg tgt 33

<210> SEQ ID NO 167
<211> LENGTH: 33
<212> TYPE: DNA
<213> ORGANISM: Homo Sapiens

<400> SEQUENCE: 167
ggacagtaaa taagaaraaa agaactggag caa 33

<210> SEQ ID NO 168
<211> LENGTH: 33
<212> TYPE: DNA
<213> ORGANISM: Homo Sapiens

<400> SEQUENCE: 168
ttcttatggc tattttmgtg tgtactccta ctt 33

<210> SEQ ID NO 169
<211> LENGTH: 33
<212> TYPE: DNA
<213> ORGANISM: Homo Sapiens

<400> SEQUENCE: 169
taagaatcac agagagrcgg agtaatcaga ccg 33

<210> SEQ ID NO 170
<211> LENGTH: 33
<212> TYPE: DNA
<213> ORGANISM: Homo Sapiens

<400> SEQUENCE: 170
tattttgcat cccttcmata aatacaaaaa tgc 33

<210> SEQ ID NO 171
<211> LENGTH: 33
<212> TYPE: DNA
<213> ORGANISM: Homo Sapiens

<400> SEQUENCE: 171
actctgccac agacacmttc cctggagccc tcc 33

<210> SEQ ID NO 172
<211> LENGTH: 33
<212> TYPE: DNA
<213> ORGANISM: Homo Sapiens

<400> SEQUENCE: 172
tgggagaaag ggcttcract gtggtttcag aca 33

<210> SEQ ID NO 173
<211> LENGTH: 33
<212> TYPE: DNA
<213> ORGANISM: Homo Sapiens

<400> SEQUENCE: 173
ctcttcctat aaggatrcac tgttggatct agg 33

<210> SEQ ID NO 174
<211> LENGTH: 33
<212> TYPE: DNA
<213> ORGANISM: Homo Sapiens

<400> SEQUENCE: 174
gtcatgtaat tttgatracc atcaaaagga ttt 33

<210> SEQ ID NO 175
<211> LENGTH: 33
<212> TYPE: DNA
<213> ORGANISM: Homo Sapiens

<400> SEQUENCE: 175
ttgatatgaa gtgagcmtgc ataaatttca gtt 33

<210> SEQ ID NO 176
<211> LENGTH: 33
<212> TYPE: DNA
<213> ORGANISM: Homo Sapiens

<400> SEQUENCE: 176
ttatgaagat ctacttmtat tttgtcaata gta 33

<210> SEQ ID NO 177
<211> LENGTH: 33
<212> TYPE: DNA
<213> ORGANISM: Homo Sapiens

<400> SEQUENCE: 177
atttccaaat tctttarccc ttgactttgc tga 33

<210> SEQ ID NO 178
<211> LENGTH: 33
<212> TYPE: DNA
<213> ORGANISM: Homo Sapiens

<400> SEQUENCE: 178
aagaatggag attacartga ggtgatgaag acg 33

<210> SEQ ID NO 179
<211> LENGTH: 33
<212> TYPE: DNA
<213> ORGANISM: Homo Sapiens

<400> SEQUENCE: 179
gttggatctg tgacccrtgc tttctacaga gaa 33

<210> SEQ ID NO 180
<211> LENGTH: 33
<212> TYPE: DNA
<213> ORGANISM: Homo Sapiens

<400> SEQUENCE: 180
gaggtccttt ggggagygat accattaatt tgt 33

<210> SEQ ID NO 181
<211> LENGTH: 33
<212> TYPE: DNA
<213> ORGANISM: Homo Sapiens

<400> SEQUENCE: 181
tcactcaaga aaaaacraga acagacaata ata 33

<210> SEQ ID NO 182
<211> LENGTH: 33
<212> TYPE: DNA
<213> ORGANISM: Homo Sapiens

<400> SEQUENCE: 182
atgtttcact aaagtarcag atgtgaaata gga 33

<210> SEQ ID NO 183
<211> LENGTH: 33
<212> TYPE: DNA
<213> ORGANISM: Homo Sapiens

<400> SEQUENCE: 183
agctgtgtgt gatagcrtgt gcctatagtt tca 33

<210> SEQ ID NO 184
<211> LENGTH: 33
<212> TYPE: DNA
<213> ORGANISM: Homo Sapiens

<400> SEQUENCE: 184
ttagaacatc acctatrctg attactccca tgc 33

<210> SEQ ID NO 185
<211> LENGTH: 33
<212> TYPE: DNA
<213> ORGANISM: Homo Sapiens

<400> SEQUENCE: 185
gagtgatttg cccatcrtgt aatggagact ggt 33

<210> SEQ ID NO 186
<211> LENGTH: 33
<212> TYPE: DNA
<213> ORGANISM: Homo Sapiens

<400> SEQUENCE: 186
ctcctcctta acatgarttg agttcacttt acc 33

<210> SEQ ID NO 187
<211> LENGTH: 33
<212> TYPE: DNA
<213> ORGANISM: Homo Sapiens

<400> SEQUENCE: 187
tgaaagagac ggttacmtag taccctgttt ctg 33

<210> SEQ ID NO 188
<211> LENGTH: 33
<212> TYPE: DNA
<213> ORGANISM: Homo Sapiens

<400> SEQUENCE: 188
caggatcccg tttaggract ttcaacaccc ttg 33

<210> SEQ ID NO 189
<211> LENGTH: 33
<212> TYPE: DNA
<213> ORGANISM: Homo Sapiens

<400> SEQUENCE: 189
ctctgtgttg atgcttmctt ccatattttg cac 33

<210> SEQ ID NO 190
<211> LENGTH: 33
<212> TYPE: DNA

```
<213> ORGANISM: Homo Sapiens

<400> SEQUENCE: 190

atgagagaac atcactrtag ataatttaga ctt                                33

<210> SEQ ID NO 191
<211> LENGTH: 33
<212> TYPE: DNA
<213> ORGANISM: Homo Sapiens

<400> SEQUENCE: 191

aaacatttta aaatgtragt gggataaaac atg                                33

<210> SEQ ID NO 192
<211> LENGTH: 33
<212> TYPE: DNA
<213> ORGANISM: Homo Sapiens

<400> SEQUENCE: 192

tcctgccttt gtataarcat gctatttatt cca                                33

<210> SEQ ID NO 193
<211> LENGTH: 33
<212> TYPE: DNA
<213> ORGANISM: Homo Sapiens

<400> SEQUENCE: 193

atgatgtctt gtgacarata ataaagctat ggg                                33

<210> SEQ ID NO 194
<211> LENGTH: 33
<212> TYPE: DNA
<213> ORGANISM: Homo Sapiens

<400> SEQUENCE: 194

cagtcagtgc tgtaacrtca caaatcacta atc                                33

<210> SEQ ID NO 195
<211> LENGTH: 33
<212> TYPE: DNA
<213> ORGANISM: Homo Sapiens

<400> SEQUENCE: 195

ttgtatatga gaaaaaraga ggcaattttt taa                                33

<210> SEQ ID NO 196
<211> LENGTH: 33
<212> TYPE: DNA
<213> ORGANISM: Homo Sapiens

<400> SEQUENCE: 196

atgtctattg aagcccrcct ttgacattta tga                                33

<210> SEQ ID NO 197
<211> LENGTH: 33
<212> TYPE: DNA
<213> ORGANISM: Homo Sapiens

<400> SEQUENCE: 197

cttttttctt ttcccarttg cttcagtgat agc                                33

<210> SEQ ID NO 198
<211> LENGTH: 33
```

```
<212> TYPE: DNA
<213> ORGANISM: Homo Sapiens

<400> SEQUENCE: 198

aaagcaaaag gtgaagragt tatttattat cca                                   33

<210> SEQ ID NO 199
<211> LENGTH: 33
<212> TYPE: DNA
<213> ORGANISM: Homo Sapiens

<400> SEQUENCE: 199

aataattttc agatttmttt gaacttactt tct                                   33

<210> SEQ ID NO 200
<211> LENGTH: 33
<212> TYPE: DNA
<213> ORGANISM: Homo Sapiens

<400> SEQUENCE: 200

tcattgactt tgaaaaraat tccagtcatt atc                                   33

<210> SEQ ID NO 201
<211> LENGTH: 33
<212> TYPE: DNA
<213> ORGANISM: Homo Sapiens

<400> SEQUENCE: 201

tgaagagtta gacaatmatt tatttgagca tga                                   33

<210> SEQ ID NO 202
<211> LENGTH: 33
<212> TYPE: DNA
<213> ORGANISM: Homo Sapiens

<400> SEQUENCE: 202

acagaaagaa aatgccrtct tgtagtaatc cac                                   33

<210> SEQ ID NO 203
<211> LENGTH: 33
<212> TYPE: DNA
<213> ORGANISM: Homo Sapiens

<400> SEQUENCE: 203

cttgggaagg aacacartgg attttccctg gaa                                   33

<210> SEQ ID NO 204
<211> LENGTH: 33
<212> TYPE: DNA
<213> ORGANISM: Homo Sapiens

<400> SEQUENCE: 204

gcctccttgc ctacaartca aatagtagga ttt                                   33

<210> SEQ ID NO 205
<211> LENGTH: 33
<212> TYPE: DNA
<213> ORGANISM: Homo Sapiens

<400> SEQUENCE: 205

cagtggggtg ataggtrtgt catggaaata ata                                   33

<210> SEQ ID NO 206
```

<211> LENGTH: 33
<212> TYPE: DNA
<213> ORGANISM: Homo Sapiens

<400> SEQUENCE: 206
acaaacctta gcgaggmata gtggtgtgat gaa 33

<210> SEQ ID NO 207
<211> LENGTH: 33
<212> TYPE: DNA
<213> ORGANISM: Homo Sapiens

<400> SEQUENCE: 207
gaatatgaaa tccaccrcac tggctgtcaa taa 33

<210> SEQ ID NO 208
<211> LENGTH: 33
<212> TYPE: DNA
<213> ORGANISM: Homo Sapiens

<400> SEQUENCE: 208
agatagagat acatatraag ctactgctgt cct 33

<210> SEQ ID NO 209
<211> LENGTH: 33
<212> TYPE: DNA
<213> ORGANISM: Homo Sapiens

<400> SEQUENCE: 209
aaaagcatac tagcaamata tattacaaag aac 33

<210> SEQ ID NO 210
<211> LENGTH: 33
<212> TYPE: DNA
<213> ORGANISM: Homo Sapiens

<400> SEQUENCE: 210
cttaatatga tacagaraag aacccaacat cac 33

<210> SEQ ID NO 211
<211> LENGTH: 33
<212> TYPE: DNA
<213> ORGANISM: Homo Sapiens

<400> SEQUENCE: 211
cgaaattgac tcaagcrttt tgtcttcaca ggt 33

<210> SEQ ID NO 212
<211> LENGTH: 33
<212> TYPE: DNA
<213> ORGANISM: Homo Sapiens

<400> SEQUENCE: 212
tgagagtcaa agaagarggg aaaactccag gaa 33

<210> SEQ ID NO 213
<211> LENGTH: 33
<212> TYPE: DNA
<213> ORGANISM: Homo Sapiens

<400> SEQUENCE: 213
gaatgtgaaa gatctgrtgt gcaaatacac gtg 33

<210> SEQ ID NO 214
<211> LENGTH: 33
<212> TYPE: DNA
<213> ORGANISM: Homo Sapiens

<400> SEQUENCE: 214
ccaatccttt gggttarctg atttagtagg taa 33

<210> SEQ ID NO 215
<211> LENGTH: 33
<212> TYPE: DNA
<213> ORGANISM: Homo Sapiens

<400> SEQUENCE: 215
gttttgattt ctctggrata aatgtccaag tat 33

<210> SEQ ID NO 216
<211> LENGTH: 33
<212> TYPE: DNA
<213> ORGANISM: Homo Sapiens

<400> SEQUENCE: 216
tgctgattct ttcaacrctt tagccagaat cat 33

<210> SEQ ID NO 217
<211> LENGTH: 33
<212> TYPE: DNA
<213> ORGANISM: Homo Sapiens

<400> SEQUENCE: 217
gaaatgattc cataaascct gaatttatct tat 33

<210> SEQ ID NO 218
<211> LENGTH: 33
<212> TYPE: DNA
<213> ORGANISM: Homo Sapiens

<400> SEQUENCE: 218
ctgatgtttc tgtccartct gtggctgatc aac 33

<210> SEQ ID NO 219
<211> LENGTH: 33
<212> TYPE: DNA
<213> ORGANISM: Homo Sapiens

<400> SEQUENCE: 219
ttggatcctt ccgaagrctg gcttctttgt gag 33

<210> SEQ ID NO 220
<211> LENGTH: 33
<212> TYPE: DNA
<213> ORGANISM: Homo Sapiens

<400> SEQUENCE: 220
tacaataaaa atctacrcaa aatactgaac aag 33

<210> SEQ ID NO 221
<211> LENGTH: 33
<212> TYPE: DNA
<213> ORGANISM: Homo Sapiens

<400> SEQUENCE: 221
agagagaaca gttcctrtaa ttcaagtaat taa 33

<210> SEQ ID NO 222
<211> LENGTH: 33
<212> TYPE: DNA
<213> ORGANISM: Homo Sapiens

<400> SEQUENCE: 222
tacagacagt ttttgtrtat ttcaacttgc cat 33

<210> SEQ ID NO 223
<211> LENGTH: 33
<212> TYPE: DNA
<213> ORGANISM: Homo Sapiens

<400> SEQUENCE: 223
ctgggatgat aagaccrtgc attggaggac gag 33

<210> SEQ ID NO 224
<211> LENGTH: 33
<212> TYPE: DNA
<213> ORGANISM: Homo Sapiens

<400> SEQUENCE: 224
aaacacgtgt gtgtgcrcgt gcattctcat gcg 33

<210> SEQ ID NO 225
<211> LENGTH: 33
<212> TYPE: DNA
<213> ORGANISM: Homo Sapiens

<400> SEQUENCE: 225
tactgggtct gaaggarcat gtggaggagg cag 33

<210> SEQ ID NO 226
<211> LENGTH: 33
<212> TYPE: DNA
<213> ORGANISM: Homo Sapiens

<400> SEQUENCE: 226
ccattcagca tttacartgg taccccaata gga 33

<210> SEQ ID NO 227
<211> LENGTH: 33
<212> TYPE: DNA
<213> ORGANISM: Homo Sapiens

<400> SEQUENCE: 227
ttgtccccaa gttttcrtgt ttagcacaat ata 33

<210> SEQ ID NO 228
<211> LENGTH: 33
<212> TYPE: DNA
<213> ORGANISM: Homo Sapiens

<400> SEQUENCE: 228
attcaaactc caatatrgtc ccaagtttaa aac 33

<210> SEQ ID NO 229
<211> LENGTH: 33
<212> TYPE: DNA
<213> ORGANISM: Homo Sapiens

<400> SEQUENCE: 229
tctacattgc ttttctrtct gctatcaccc ctc 33

<210> SEQ ID NO 230
<211> LENGTH: 33
<212> TYPE: DNA
<213> ORGANISM: Homo Sapiens

<400> SEQUENCE: 230
tttgtgcccc acggcgrttc tggacgcacc tgt 33

<210> SEQ ID NO 231
<211> LENGTH: 33
<212> TYPE: DNA
<213> ORGANISM: Homo Sapiens

<400> SEQUENCE: 231
cattaccaat agtaatrtca gaaatgaaac acc 33

<210> SEQ ID NO 232
<211> LENGTH: 33
<212> TYPE: DNA
<213> ORGANISM: Homo Sapiens

<400> SEQUENCE: 232
gtatttcact ccaggartgg aactgataga tct 33

<210> SEQ ID NO 233
<211> LENGTH: 33
<212> TYPE: DNA
<213> ORGANISM: Homo Sapiens

<400> SEQUENCE: 233
aggaggtcct catcccrtga gtcccccact cct 33

<210> SEQ ID NO 234
<211> LENGTH: 33
<212> TYPE: DNA
<213> ORGANISM: Homo Sapiens

<400> SEQUENCE: 234
ctacccattt tccttgragt tacgtccctt ggt 33

<210> SEQ ID NO 235
<211> LENGTH: 33
<212> TYPE: DNA
<213> ORGANISM: Homo Sapiens

<400> SEQUENCE: 235
gacaaggagc tggtggscca ggccaaggcg ctg 33

<210> SEQ ID NO 236
<211> LENGTH: 33
<212> TYPE: DNA
<213> ORGANISM: Homo Sapiens

<400> SEQUENCE: 236
cccacatcta agatacmcaa aggtcagtga cgc 33

<210> SEQ ID NO 237
<211> LENGTH: 33
<212> TYPE: DNA
<213> ORGANISM: Homo Sapiens

<400> SEQUENCE: 237
tgagcgttta actcctmcct ccccttactc aca 33

<210> SEQ ID NO 238
<211> LENGTH: 33
<212> TYPE: DNA
<213> ORGANISM: Homo Sapiens

<400> SEQUENCE: 238
aggccttaag gacactrgta gactgaagga ggt 33

<210> SEQ ID NO 239
<211> LENGTH: 33
<212> TYPE: DNA
<213> ORGANISM: Homo Sapiens

<400> SEQUENCE: 239
atccacatat ccatccrtcc ctctattctg aca 33

<210> SEQ ID NO 240
<211> LENGTH: 33
<212> TYPE: DNA
<213> ORGANISM: Homo Sapiens

<400> SEQUENCE: 240
gctctccctt ttccccrgca cccacctcac tcc 33

<210> SEQ ID NO 241
<211> LENGTH: 33
<212> TYPE: DNA
<213> ORGANISM: Homo Sapiens

<400> SEQUENCE: 241
ctgaactaca cggaggrgga tgacacgggg gct 33

<210> SEQ ID NO 242
<211> LENGTH: 33
<212> TYPE: DNA
<213> ORGANISM: Homo Sapiens

<400> SEQUENCE: 242
ggcaagccat cccggamgga cgtcagatcc tgg 33

<210> SEQ ID NO 243
<211> LENGTH: 33
<212> TYPE: DNA
<213> ORGANISM: Homo Sapiens

<400> SEQUENCE: 243
ctgggcacgt gcttcartaa gaacagctgc tca 33

<210> SEQ ID NO 244
<211> LENGTH: 33
<212> TYPE: DNA
<213> ORGANISM: Homo Sapiens

<400> SEQUENCE: 244
tgtgtcgggg ggtgcgmgga gagggacgag gac 33

<210> SEQ ID NO 245
<211> LENGTH: 33
<212> TYPE: DNA
<213> ORGANISM: Homo Sapiens

<400> SEQUENCE: 245
ataaatccca cttggtmatg atgaatgctc ttt 33

<210> SEQ ID NO 246
<211> LENGTH: 33
<212> TYPE: DNA
<213> ORGANISM: Homo Sapiens

<400> SEQUENCE: 246
cttgaatttg tggatgrttt gtgaaatgta ata 33

<210> SEQ ID NO 247
<211> LENGTH: 33
<212> TYPE: DNA
<213> ORGANISM: Homo Sapiens

<400> SEQUENCE: 247
ttattttatg gacatartgt gtgggagctt gaa 33

<210> SEQ ID NO 248
<211> LENGTH: 33
<212> TYPE: DNA
<213> ORGANISM: Homo Sapiens

<400> SEQUENCE: 248
gaagcgcgca tgcaatrgat ccagggtgta tgc 33

<210> SEQ ID NO 249
<211> LENGTH: 33
<212> TYPE: DNA
<213> ORGANISM: Homo Sapiens

<400> SEQUENCE: 249
taacaaatag gcagaarttt tgagcaacat taa 33

<210> SEQ ID NO 250
<211> LENGTH: 33
<212> TYPE: DNA
<213> ORGANISM: Homo Sapiens

<400> SEQUENCE: 250
atattgtact ttgtatrcag aatttcaact tgg 33

<210> SEQ ID NO 251
<211> LENGTH: 33
<212> TYPE: DNA
<213> ORGANISM: Homo Sapiens

<400> SEQUENCE: 251
tttctttatc tagtggrcac ttttaggtcg att 33

<210> SEQ ID NO 252
<211> LENGTH: 33
<212> TYPE: DNA
<213> ORGANISM: Homo Sapiens

<400> SEQUENCE: 252
tttttgtgtg tatgtcrttc ttgaatacag tga 33

<210> SEQ ID NO 253
<211> LENGTH: 33
<212> TYPE: DNA
<213> ORGANISM: Homo Sapiens

<400> SEQUENCE: 253
aaggaggtaa agttaaragt taggagcaga ggg 33

<210> SEQ ID NO 254
<211> LENGTH: 33
<212> TYPE: DNA
<213> ORGANISM: Homo Sapiens

<400> SEQUENCE: 254
tgagggcacc gcccccrgcc actttccaca ctg 33

<210> SEQ ID NO 255
<211> LENGTH: 33
<212> TYPE: DNA
<213> ORGANISM: Homo Sapiens

<400> SEQUENCE: 255
ctgcctccct ggtgatrtac tccaggttaa cca 33

<210> SEQ ID NO 256
<211> LENGTH: 33
<212> TYPE: DNA
<213> ORGANISM: Homo Sapiens

<400> SEQUENCE: 256
tcacctgctc cgtgaaracc tccttgcccc tcc 33

<210> SEQ ID NO 257
<211> LENGTH: 33
<212> TYPE: DNA
<213> ORGANISM: Homo Sapiens

<400> SEQUENCE: 257
gccaggagct ggggatrtaa ggaaggggga tgt 33

<210> SEQ ID NO 258
<211> LENGTH: 33
<212> TYPE: DNA
<213> ORGANISM: Homo Sapiens

<400> SEQUENCE: 258
ccagagcagc tgcgtcrctt ggcgccgggt atg 33

<210> SEQ ID NO 259
<211> LENGTH: 33
<212> TYPE: DNA
<213> ORGANISM: Homo Sapiens

<400> SEQUENCE: 259
ttacatggct ttgcgcmtcc tacctggaag gcg 33

<210> SEQ ID NO 260
<211> LENGTH: 33
<212> TYPE: DNA
<213> ORGANISM: Homo Sapiens

<400> SEQUENCE: 260
cagcgtctct ttcacargat gctctccgtg agc 33

<210> SEQ ID NO 261
<211> LENGTH: 33
<212> TYPE: DNA
<213> ORGANISM: Homo Sapiens

<400> SEQUENCE: 261
tgcaccatcc gacccamcca taacttttct ttt 33

<210> SEQ ID NO 262
<211> LENGTH: 33
<212> TYPE: DNA
<213> ORGANISM: Homo Sapiens

<400> SEQUENCE: 262
gagttccttt gcccctrtta cgacaagagg gtt 33

<210> SEQ ID NO 263
<211> LENGTH: 33
<212> TYPE: DNA
<213> ORGANISM: Homo Sapiens

<400> SEQUENCE: 263
gtgtatcaat tgtgtcratt tgtgcagtga gta 33

<210> SEQ ID NO 264
<211> LENGTH: 33
<212> TYPE: DNA
<213> ORGANISM: Homo Sapiens

<400> SEQUENCE: 264
aaacaatgaa gccaagraca gaagtgactg gac 33

<210> SEQ ID NO 265
<211> LENGTH: 33
<212> TYPE: DNA
<213> ORGANISM: Homo Sapiens

<400> SEQUENCE: 265
gtttttatgt cagctcracc tttgctttta agt 33

<210> SEQ ID NO 266
<211> LENGTH: 33
<212> TYPE: DNA
<213> ORGANISM: Homo Sapiens

<400> SEQUENCE: 266
taccagaagc acgaaarggc ctgggtctgc tgc 33

<210> SEQ ID NO 267
<211> LENGTH: 33
<212> TYPE: DNA
<213> ORGANISM: Homo Sapiens

<400> SEQUENCE: 267
tcttttgacc acacgcrcac acacacacac aca 33

<210> SEQ ID NO 268
<211> LENGTH: 33
<212> TYPE: DNA
<213> ORGANISM: Homo Sapiens

<400> SEQUENCE: 268
atggatatgc agttagraaa atgagtcatc act 33

<210> SEQ ID NO 269
<211> LENGTH: 33
<212> TYPE: DNA

<213> ORGANISM: Homo Sapiens

<400> SEQUENCE: 269
gtcgtaactt aaaatcrtat tcaaagctgt gat 33

<210> SEQ ID NO 270
<211> LENGTH: 33
<212> TYPE: DNA
<213> ORGANISM: Homo Sapiens

<400> SEQUENCE: 270
ttcataattc tactttrctg gaatcagctg aga 33

<210> SEQ ID NO 271
<211> LENGTH: 33
<212> TYPE: DNA
<213> ORGANISM: Homo Sapiens

<400> SEQUENCE: 271
aagcaaagca agcaaarcat catctgtatt tat 33

<210> SEQ ID NO 272
<211> LENGTH: 33
<212> TYPE: DNA
<213> ORGANISM: Homo Sapiens

<400> SEQUENCE: 272
attagtggag tgaactrctt ctccctgcaa tta 33

<210> SEQ ID NO 273
<211> LENGTH: 33
<212> TYPE: DNA
<213> ORGANISM: Homo Sapiens

<400> SEQUENCE: 273
aactaactgt ggctctrctt actcacgaag ttg 33

<210> SEQ ID NO 274
<211> LENGTH: 33
<212> TYPE: DNA
<213> ORGANISM: Homo Sapiens

<400> SEQUENCE: 274
tgtgaggtgt ggcacaragg taaggaatag cca 33

<210> SEQ ID NO 275
<211> LENGTH: 33
<212> TYPE: DNA
<213> ORGANISM: Homo Sapiens

<400> SEQUENCE: 275
cccagagcta cctcaarccc cctccccaag cca 33

<210> SEQ ID NO 276
<211> LENGTH: 33
<212> TYPE: DNA
<213> ORGANISM: Homo Sapiens

<400> SEQUENCE: 276
gggtaaagat gaggcamaat caagtccatc gaa 33

<210> SEQ ID NO 277
<211> LENGTH: 33

<212> TYPE: DNA
<213> ORGANISM: Homo Sapiens

<400> SEQUENCE: 277
gatgcaatta gagatargct ttaggaagat ctt 33

<210> SEQ ID NO 278
<211> LENGTH: 33
<212> TYPE: DNA
<213> ORGANISM: Homo Sapiens

<400> SEQUENCE: 278
accaaagggg agagaarcaa aagaaaatta tgg 33

<210> SEQ ID NO 279
<211> LENGTH: 33
<212> TYPE: DNA
<213> ORGANISM: Homo Sapiens

<400> SEQUENCE: 279
attttcctct taatgcrgta ctaatatatg ttg 33

<210> SEQ ID NO 280
<211> LENGTH: 33
<212> TYPE: DNA
<213> ORGANISM: Homo Sapiens

<400> SEQUENCE: 280
gacttcacat agtgccrcct agttcttcca atg 33

<210> SEQ ID NO 281
<211> LENGTH: 33
<212> TYPE: DNA
<213> ORGANISM: Homo Sapiens

<400> SEQUENCE: 281
cctctacccc caggctraaa aggcctgaca caa 33

<210> SEQ ID NO 282
<211> LENGTH: 33
<212> TYPE: DNA
<213> ORGANISM: Homo Sapiens

<400> SEQUENCE: 282
ctgtgtagct atttgamgat atgctggcct gta 33

<210> SEQ ID NO 283
<211> LENGTH: 33
<212> TYPE: DNA
<213> ORGANISM: Homo Sapiens

<400> SEQUENCE: 283
aaaaaaaaaa ataagtmctc ttaaagctag cac 33

<210> SEQ ID NO 284
<211> LENGTH: 33
<212> TYPE: DNA
<213> ORGANISM: Homo Sapiens

<400> SEQUENCE: 284
ttctaaaaaa gcaactmctc atgagaagct gta 33

<210> SEQ ID NO 285

<211> LENGTH: 33
<212> TYPE: DNA
<213> ORGANISM: Homo Sapiens

<400> SEQUENCE: 285
gttgagtcct tctcagrctt ggaatctcta aga 33

<210> SEQ ID NO 286
<211> LENGTH: 33
<212> TYPE: DNA
<213> ORGANISM: Homo Sapiens

<400> SEQUENCE: 286
tctcctccct ttggttraat ctttgtagct gtt 33

<210> SEQ ID NO 287
<211> LENGTH: 33
<212> TYPE: DNA
<213> ORGANISM: Homo Sapiens

<400> SEQUENCE: 287
ttgtttcagg tactgtrcta gttatagttt att 33

<210> SEQ ID NO 288
<211> LENGTH: 33
<212> TYPE: DNA
<213> ORGANISM: Homo Sapiens

<400> SEQUENCE: 288
ccagccagga tattcaragg accgaaccct ctt 33

<210> SEQ ID NO 289
<211> LENGTH: 33
<212> TYPE: DNA
<213> ORGANISM: Homo Sapiens

<400> SEQUENCE: 289
ttgagtgtga aagaatrtaa cagtaaaaat aaa 33

<210> SEQ ID NO 290
<211> LENGTH: 33
<212> TYPE: DNA
<213> ORGANISM: Homo Sapiens

<400> SEQUENCE: 290
ctacatgaga aacctgrgag ctatcttcaa atc 33

<210> SEQ ID NO 291
<211> LENGTH: 33
<212> TYPE: DNA
<213> ORGANISM: Homo Sapiens

<400> SEQUENCE: 291
taatgctagc cttcctrgag tctagtattt cag 33

<210> SEQ ID NO 292
<211> LENGTH: 33
<212> TYPE: DNA
<213> ORGANISM: Homo Sapiens

<400> SEQUENCE: 292
ctagcacgtt ttattgrcca tcattctttt cat 33

<210> SEQ ID NO 293
<211> LENGTH: 33
<212> TYPE: DNA
<213> ORGANISM: Homo Sapiens

<400> SEQUENCE: 293
gggtctcggt ggccatrttc ccgcctgtcc atg 33

<210> SEQ ID NO 294
<211> LENGTH: 33
<212> TYPE: DNA
<213> ORGANISM: Homo Sapiens

<400> SEQUENCE: 294
ttcaaaggtc aggcaarttg attttgaaaa gaa 33

<210> SEQ ID NO 295
<211> LENGTH: 33
<212> TYPE: DNA
<213> ORGANISM: Homo Sapiens

<400> SEQUENCE: 295
ctgcatagtg agactgmatg tttttcagga gtt 33

<210> SEQ ID NO 296
<211> LENGTH: 33
<212> TYPE: DNA
<213> ORGANISM: Homo Sapiens

<400> SEQUENCE: 296
tgtggaagaa aaacacrtat tagttcaata aat 33

<210> SEQ ID NO 297
<211> LENGTH: 33
<212> TYPE: DNA
<213> ORGANISM: Homo Sapiens

<400> SEQUENCE: 297
tgatgaatga taattarctt ttcctctaga gca 33

<210> SEQ ID NO 298
<211> LENGTH: 33
<212> TYPE: DNA
<213> ORGANISM: Homo Sapiens

<400> SEQUENCE: 298
tacacttagt ctatccraaa tgacaaaaat agt 33

<210> SEQ ID NO 299
<211> LENGTH: 33
<212> TYPE: DNA
<213> ORGANISM: Homo Sapiens

<400> SEQUENCE: 299
ttgagctttt gaagcamgtc agattggaac ttg 33

<210> SEQ ID NO 300
<211> LENGTH: 33
<212> TYPE: DNA
<213> ORGANISM: Homo Sapiens

<400> SEQUENCE: 300
aaactgaggc tgtgaamggc tgaaaggttt cag 33

<210> SEQ ID NO 301
<211> LENGTH: 33
<212> TYPE: DNA
<213> ORGANISM: Homo Sapiens

<400> SEQUENCE: 301
gaaccagagc ataagcrgca ttgttcatat ggt 33

<210> SEQ ID NO 302
<211> LENGTH: 33
<212> TYPE: DNA
<213> ORGANISM: Homo Sapiens

<400> SEQUENCE: 302
attaatgttc tctcccrtat gagtcactct tca 33

<210> SEQ ID NO 303
<211> LENGTH: 33
<212> TYPE: DNA
<213> ORGANISM: Homo Sapiens

<400> SEQUENCE: 303
aggatgaagc ttaactragg aaggtagaac caa 33

<210> SEQ ID NO 304
<211> LENGTH: 33
<212> TYPE: DNA
<213> ORGANISM: Homo Sapiens

<400> SEQUENCE: 304
caaaagcctg aggaagrgtg aaaagaacaa agc 33

<210> SEQ ID NO 305
<211> LENGTH: 33
<212> TYPE: DNA
<213> ORGANISM: Homo Sapiens

<400> SEQUENCE: 305
ttggaagaga aaggaaraaa attttatgtg gct 33

<210> SEQ ID NO 306
<211> LENGTH: 33
<212> TYPE: DNA
<213> ORGANISM: Homo Sapiens

<400> SEQUENCE: 306
cagcccagaa aatattraaa agataatgag caa 33

<210> SEQ ID NO 307
<211> LENGTH: 33
<212> TYPE: DNA
<213> ORGANISM: Homo Sapiens

<400> SEQUENCE: 307
aaagtaacat cagggargtc tggaaataaa atg 33

<210> SEQ ID NO 308
<211> LENGTH: 33
<212> TYPE: DNA
<213> ORGANISM: Homo Sapiens

<400> SEQUENCE: 308
gaaaagaaag cttacaraaa agccaaggag cgg 33

<210> SEQ ID NO 309
<211> LENGTH: 33
<212> TYPE: DNA
<213> ORGANISM: Homo Sapiens

<400> SEQUENCE: 309
ggtcttgcca tctctcrcac acatgcatac cta 33

<210> SEQ ID NO 310
<211> LENGTH: 33
<212> TYPE: DNA
<213> ORGANISM: Homo Sapiens

<400> SEQUENCE: 310
actcactgga gtgcccraac tgctgtccac atc 33

<210> SEQ ID NO 311
<211> LENGTH: 33
<212> TYPE: DNA
<213> ORGANISM: Homo Sapiens

<400> SEQUENCE: 311
agaaaactgt actgacmgct acgaagtttg agc 33

<210> SEQ ID NO 312
<211> LENGTH: 33
<212> TYPE: DNA
<213> ORGANISM: Homo Sapiens

<400> SEQUENCE: 312
cccaagccaa ctcaacrcct gcagatggct ctt 33

<210> SEQ ID NO 313
<211> LENGTH: 33
<212> TYPE: DNA
<213> ORGANISM: Homo Sapiens

<400> SEQUENCE: 313
gcttcactgt tcttccrgtg tctagtggca aac 33

<210> SEQ ID NO 314
<211> LENGTH: 33
<212> TYPE: DNA
<213> ORGANISM: Homo Sapiens

<400> SEQUENCE: 314
gacagttgcc ttatacrgag ggctcattaa aca 33

<210> SEQ ID NO 315
<211> LENGTH: 33
<212> TYPE: DNA
<213> ORGANISM: Homo Sapiens

<400> SEQUENCE: 315
ggaagagtga agaagargag aagatgccca agc 33

<210> SEQ ID NO 316
<211> LENGTH: 33
<212> TYPE: DNA
<213> ORGANISM: Homo Sapiens

<400> SEQUENCE: 316
tagtgacctt ataagargag atgtcagaaa att 33

<210> SEQ ID NO 317
<211> LENGTH: 33
<212> TYPE: DNA
<213> ORGANISM: Homo Sapiens

<400> SEQUENCE: 317
catcatgaag ttcatgragc cgagaccacc agt 33

<210> SEQ ID NO 318
<211> LENGTH: 33
<212> TYPE: DNA
<213> ORGANISM: Homo Sapiens

<400> SEQUENCE: 318
gaaatgatgt gtgactraac aaagagacat gca 33

<210> SEQ ID NO 319
<211> LENGTH: 33
<212> TYPE: DNA
<213> ORGANISM: Homo Sapiens

<400> SEQUENCE: 319
ggcaaagtga ttacctraga cattagataa ctc 33

<210> SEQ ID NO 320
<211> LENGTH: 33
<212> TYPE: DNA
<213> ORGANISM: Homo Sapiens

<400> SEQUENCE: 320
cttcccacat gacttamttt cacaggttgg aga 33

<210> SEQ ID NO 321
<211> LENGTH: 33
<212> TYPE: DNA
<213> ORGANISM: Homo Sapiens

<400> SEQUENCE: 321
agactcctta cctctamtga aatcatccca aac 33

<210> SEQ ID NO 322
<211> LENGTH: 33
<212> TYPE: DNA
<213> ORGANISM: Homo Sapiens

<400> SEQUENCE: 322
attgctccaa taatagrcgt gtatttctca tgt 33

<210> SEQ ID NO 323
<211> LENGTH: 33
<212> TYPE: DNA
<213> ORGANISM: Homo Sapiens

<400> SEQUENCE: 323
tgcaatattt cctctcrctc cttatgtcta ctc 33

<210> SEQ ID NO 324
<211> LENGTH: 33
<212> TYPE: DNA
<213> ORGANISM: Homo Sapiens

<400> SEQUENCE: 324
taggcctcag ccccccrttt aaacagaggg taa 33

<210> SEQ ID NO 325
<211> LENGTH: 33
<212> TYPE: DNA
<213> ORGANISM: Homo Sapiens

<400> SEQUENCE: 325
cacactgtta gagtgtrttt gagcatgtgg gag 33

<210> SEQ ID NO 326
<211> LENGTH: 33
<212> TYPE: DNA
<213> ORGANISM: Homo Sapiens

<400> SEQUENCE: 326
tcctgcatag gtgtccytct taaaaaataa ttg 33

<210> SEQ ID NO 327
<211> LENGTH: 33
<212> TYPE: DNA
<213> ORGANISM: Homo Sapiens

<400> SEQUENCE: 327
gatatctctt ttaacgragg ccaggtatct gta 33

<210> SEQ ID NO 328
<211> LENGTH: 33
<212> TYPE: DNA
<213> ORGANISM: Homo Sapiens

<400> SEQUENCE: 328
aaggtctcct tggccartaa gagtctgttc agt 33

<210> SEQ ID NO 329
<211> LENGTH: 33
<212> TYPE: DNA
<213> ORGANISM: Homo Sapiens

<400> SEQUENCE: 329
agatttttat gtgcctratg atagtctcaa aat 33

<210> SEQ ID NO 330
<211> LENGTH: 33
<212> TYPE: DNA
<213> ORGANISM: Homo Sapiens

<400> SEQUENCE: 330
ccccactaca ctcatargca gctgatttgc aca 33

<210> SEQ ID NO 331
<211> LENGTH: 33
<212> TYPE: DNA
<213> ORGANISM: Homo Sapiens

<400> SEQUENCE: 331
tgaagataga atggcarata ccctatccta tcc 33

<210> SEQ ID NO 332
<211> LENGTH: 33
<212> TYPE: DNA
<213> ORGANISM: Homo Sapiens

<400> SEQUENCE: 332
gattctatcc gtctgcracc ccccaccctt gca 33

<210> SEQ ID NO 333
<211> LENGTH: 33
<212> TYPE: DNA
<213> ORGANISM: Homo Sapiens

<400> SEQUENCE: 333
ggcaattgtg gtccttrtat ttcagacaca agc 33

<210> SEQ ID NO 334
<211> LENGTH: 33
<212> TYPE: DNA
<213> ORGANISM: Homo Sapiens

<400> SEQUENCE: 334
gcgggcccac cacatcmccg aggaccctgg cca 33

<210> SEQ ID NO 335
<211> LENGTH: 33
<212> TYPE: DNA
<213> ORGANISM: Homo Sapiens

<400> SEQUENCE: 335
aaggcctgag gcagaayaac cggggtcaag agg 33

<210> SEQ ID NO 336
<211> LENGTH: 33
<212> TYPE: DNA
<213> ORGANISM: Homo Sapiens

<400> SEQUENCE: 336
accatcagcc tctcacratt tttgagtagt tcc 33

<210> SEQ ID NO 337
<211> LENGTH: 33
<212> TYPE: DNA
<213> ORGANISM: Homo Sapiens

<400> SEQUENCE: 337
tggggctgaa gaatacmttt ctggtgtgac tca 33

<210> SEQ ID NO 338
<211> LENGTH: 33
<212> TYPE: DNA
<213> ORGANISM: Homo Sapiens

<400> SEQUENCE: 338
caggctggag gagcggrggc ggcaggagga gga 33

<210> SEQ ID NO 339
<211> LENGTH: 33
<212> TYPE: DNA
<213> ORGANISM: Homo Sapiens

<400> SEQUENCE: 339
aatgaatcaa gtcagasgca ttttttttcta ctc 33

<210> SEQ ID NO 340
<211> LENGTH: 33
<212> TYPE: DNA
<213> ORGANISM: Homo Sapiens

<400> SEQUENCE: 340
ttgtaaataa gtacatraga gttcttagca gga 33

<210> SEQ ID NO 341
<211> LENGTH: 33
<212> TYPE: DNA
<213> ORGANISM: Homo Sapiens

<400> SEQUENCE: 341
tctcatccta aaatgtrgat tctggaatat aag 33

<210> SEQ ID NO 342
<211> LENGTH: 33
<212> TYPE: DNA
<213> ORGANISM: Homo Sapiens

<400> SEQUENCE: 342
taaaagcact ttacatraat aattttatgt cag 33

<210> SEQ ID NO 343
<211> LENGTH: 33
<212> TYPE: DNA
<213> ORGANISM: Homo Sapiens

<400> SEQUENCE: 343
tgtcacttgt taatgamctt ccaatcttct aag 33

<210> SEQ ID NO 344
<211> LENGTH: 33
<212> TYPE: DNA
<213> ORGANISM: Homo Sapiens

<400> SEQUENCE: 344
aaagaaaata aaggacracg atgcctaaat ccc 33

<210> SEQ ID NO 345
<211> LENGTH: 33
<212> TYPE: DNA
<213> ORGANISM: Homo Sapiens

<400> SEQUENCE: 345
cagctggggg agaaatmatc caaaatgcaa tat 33

<210> SEQ ID NO 346
<211> LENGTH: 33
<212> TYPE: DNA
<213> ORGANISM: Homo Sapiens

<400> SEQUENCE: 346
atttttattc agttggratg gggtggctgc aaa 33

<210> SEQ ID NO 347
<211> LENGTH: 33
<212> TYPE: DNA
<213> ORGANISM: Homo Sapiens

<400> SEQUENCE: 347
ttgtgctcag gcaagtrtgt tgattggata aat 33

<210> SEQ ID NO 348
<211> LENGTH: 33
<212> TYPE: DNA

<213> ORGANISM: Homo Sapiens

<400> SEQUENCE: 348
tcatttatta aaacacrgca tgattagacc act 33

<210> SEQ ID NO 349
<211> LENGTH: 33
<212> TYPE: DNA
<213> ORGANISM: Homo Sapiens

<400> SEQUENCE: 349
gtctctacct ttttctrccc tgctttgctc cct 33

<210> SEQ ID NO 350
<211> LENGTH: 33
<212> TYPE: DNA
<213> ORGANISM: Homo Sapiens

<400> SEQUENCE: 350
agggagtgga aagaaaragt gctgcaattt ttt 33

<210> SEQ ID NO 351
<211> LENGTH: 33
<212> TYPE: DNA
<213> ORGANISM: Homo Sapiens

<400> SEQUENCE: 351
tagtacagat ttttatrttg caatcaaatc cta 33

<210> SEQ ID NO 352
<211> LENGTH: 33
<212> TYPE: DNA
<213> ORGANISM: Homo Sapiens

<400> SEQUENCE: 352
tgttaccaac tgattarggt acaagtttta gga 33

<210> SEQ ID NO 353
<211> LENGTH: 33
<212> TYPE: DNA
<213> ORGANISM: Homo Sapiens

<400> SEQUENCE: 353
ccagaagtga aactgtrgga actgtgttct taa 33

<210> SEQ ID NO 354
<211> LENGTH: 33
<212> TYPE: DNA
<213> ORGANISM: Homo Sapiens

<400> SEQUENCE: 354
taggactcat tcacatrgtg atccagggtt cct 33

<210> SEQ ID NO 355
<211> LENGTH: 33
<212> TYPE: DNA
<213> ORGANISM: Homo Sapiens

<400> SEQUENCE: 355
gttgtttggg ctatccrtct tctcaactgt tta 33

<210> SEQ ID NO 356
<211> LENGTH: 33

<212> TYPE: DNA
<213> ORGANISM: Homo Sapiens

<400> SEQUENCE: 356
atttagtata taataamagt aacactacag cac 33

<210> SEQ ID NO 357
<211> LENGTH: 33
<212> TYPE: DNA
<213> ORGANISM: Homo Sapiens

<400> SEQUENCE: 357 gggcccttc cttgctracc tgcagtagca tgt 33

<210> SEQ ID NO 358
<211> LENGTH: 33
<212> TYPE: DNA
<213> ORGANISM: Homo Sapiens

<400> SEQUENCE: 358
caaagggaag tataccrcta aataaggaag gca 33

<210> SEQ ID NO 359
<211> LENGTH: 33
<212> TYPE: DNA
<213> ORGANISM: Homo Sapiens

<400> SEQUENCE: 359
cgtggctcca ggactgrtct cagcctttgc ata 33

<210> SEQ ID NO 360
<211> LENGTH: 33
<212> TYPE: DNA
<213> ORGANISM: Homo Sapiens

<400> SEQUENCE: 360
tatctcagat tcatgaratg gtaacttcta tgt 33

<210> SEQ ID NO 361
<211> LENGTH: 33
<212> TYPE: DNA
<213> ORGANISM: Homo Sapiens

<400> SEQUENCE: 361
tctcaccaag gtcaccmgtg acttctagct gag 33

<210> SEQ ID NO 362
<211> LENGTH: 33
<212> TYPE: DNA
<213> ORGANISM: Homo Sapiens

<400> SEQUENCE: 362
ctaaagagta ctgtaargtt aaagggatca tgt 33

<210> SEQ ID NO 363
<211> LENGTH: 33
<212> TYPE: DNA
<213> ORGANISM: Homo Sapiens

<400> SEQUENCE: 363
acaatgactt aacaatmcct ttcctttctg att 33

<210> SEQ ID NO 364

<211> LENGTH: 33
<212> TYPE: DNA
<213> ORGANISM: Homo Sapiens

<400> SEQUENCE: 364
taaccttgat cactggrctg aagtagtgtt tgt 33

<210> SEQ ID NO 365
<211> LENGTH: 33
<212> TYPE: DNA
<213> ORGANISM: Homo Sapiens

<400> SEQUENCE: 365
cttaagaagg atacacraaa tatgtatgta tat 33

<210> SEQ ID NO 366
<211> LENGTH: 33
<212> TYPE: DNA
<213> ORGANISM: Homo Sapiens

<400> SEQUENCE: 366
ccctggcaac caaagargga gcttttacac cag 33

<210> SEQ ID NO 367
<211> LENGTH: 33
<212> TYPE: DNA
<213> ORGANISM: Homo Sapiens

<400> SEQUENCE: 367
ctgccttctc agagttraac ctgacataat tta 33

<210> SEQ ID NO 368
<211> LENGTH: 33
<212> TYPE: DNA
<213> ORGANISM: Homo Sapiens

<400> SEQUENCE: 368
gcaaatgaga ataatcrttt tttgtctttt cca 33

<210> SEQ ID NO 369
<211> LENGTH: 33
<212> TYPE: DNA
<213> ORGANISM: Homo Sapiens

<400> SEQUENCE: 369
ggaatgaact tctaaamtgc tgtaatctct tga 33

<210> SEQ ID NO 370
<211> LENGTH: 33
<212> TYPE: DNA
<213> ORGANISM: Homo Sapiens

<400> SEQUENCE: 370
tgaggtcaca tgtgctrcgg tgtgtgcgga gct 33

<210> SEQ ID NO 371
<211> LENGTH: 33
<212> TYPE: DNA
<213> ORGANISM: Homo Sapiens

<400> SEQUENCE: 371
tagtcaaatt cattcartgt ggctcagata tga 33

<210> SEQ ID NO 372
<211> LENGTH: 33
<212> TYPE: DNA
<213> ORGANISM: Homo Sapiens

<400> SEQUENCE: 372
atgtgaacat ttttttrgac aagtttattg cta 33

<210> SEQ ID NO 373
<211> LENGTH: 33
<212> TYPE: DNA
<213> ORGANISM: Homo Sapiens

<400> SEQUENCE: 373
aacacagcca acatcartta agcctaattt aca 33

<210> SEQ ID NO 374
<211> LENGTH: 33
<212> TYPE: DNA
<213> ORGANISM: Homo Sapiens

<400> SEQUENCE: 374
ggaaaagtgg aatgccraga acagaaacta aga 33

<210> SEQ ID NO 375
<211> LENGTH: 33
<212> TYPE: DNA
<213> ORGANISM: Homo Sapiens

<400> SEQUENCE: 375
ctctctagag tttactrtca tctggcattc atg 33

<210> SEQ ID NO 376
<211> LENGTH: 33
<212> TYPE: DNA
<213> ORGANISM: Homo Sapiens

<400> SEQUENCE: 376
ctacatggaa aattgamgta gcaaggtagg tca 33

<210> SEQ ID NO 377
<211> LENGTH: 33
<212> TYPE: DNA
<213> ORGANISM: Homo Sapiens

<400> SEQUENCE: 377
agcctgtctc ctctggragt cttatctctc agt 33

<210> SEQ ID NO 378
<211> LENGTH: 33
<212> TYPE: DNA
<213> ORGANISM: Homo Sapiens

<400> SEQUENCE: 378
ttccatatcc tcgtccrcaa ttagtacgca cag 33

<210> SEQ ID NO 379
<211> LENGTH: 33
<212> TYPE: DNA
<213> ORGANISM: Homo Sapiens

<400> SEQUENCE: 379
catgtttact atctctrtag gtttgccttt ttg 33

<210> SEQ ID NO 380
<211> LENGTH: 33
<212> TYPE: DNA
<213> ORGANISM: Homo Sapiens

<400> SEQUENCE: 380
taccaaattg tatggtrtca gtgatggcag cag 33

<210> SEQ ID NO 381
<211> LENGTH: 33
<212> TYPE: DNA
<213> ORGANISM: Homo Sapiens

<400> SEQUENCE: 381
cagaactgaa ataattmtcc ataggatcct tag 33

<210> SEQ ID NO 382
<211> LENGTH: 33
<212> TYPE: DNA
<213> ORGANISM: Homo Sapiens

<400> SEQUENCE: 382
ttttaatgaa gcccctrtag gctagttgtc aag 33

<210> SEQ ID NO 383
<211> LENGTH: 33
<212> TYPE: DNA
<213> ORGANISM: Homo Sapiens

<400> SEQUENCE: 383
catctcaaac catgcarttc ctggaaatca cta 33

<210> SEQ ID NO 384
<211> LENGTH: 33
<212> TYPE: DNA
<213> ORGANISM: Homo Sapiens

<400> SEQUENCE: 384
tgcaaggaaa ccatttrcca gcctcctgca att 33

<210> SEQ ID NO 385
<211> LENGTH: 33
<212> TYPE: DNA
<213> ORGANISM: Homo Sapiens

<400> SEQUENCE: 385
ctgaaaataa gttcccrcat atatattgta gaa 33

<210> SEQ ID NO 386
<211> LENGTH: 33
<212> TYPE: DNA
<213> ORGANISM: Homo Sapiens

<400> SEQUENCE: 386
tgatgctata attcctrgat tttgtttgat ttc 33

<210> SEQ ID NO 387
<211> LENGTH: 33
<212> TYPE: DNA
<213> ORGANISM: Homo Sapiens

<400> SEQUENCE: 387
ctagagaaga tgaaggratg tgcattccag gca 33

<210> SEQ ID NO 388
<211> LENGTH: 33
<212> TYPE: DNA
<213> ORGANISM: Homo Sapiens

<400> SEQUENCE: 388
tgctcaagag cagaccrgat gagccacaca tgg 33

<210> SEQ ID NO 389
<211> LENGTH: 33
<212> TYPE: DNA
<213> ORGANISM: Homo Sapiens

<400> SEQUENCE: 389
agggatcaat tcttacrata aaattttaaa acc 33

<210> SEQ ID NO 390
<211> LENGTH: 33
<212> TYPE: DNA
<213> ORGANISM: Homo Sapiens

<400> SEQUENCE: 390
tgaaactgag taaaccrtta agaatgaatt att 33

<210> SEQ ID NO 391
<211> LENGTH: 33
<212> TYPE: DNA
<213> ORGANISM: Homo Sapiens

<400> SEQUENCE: 391
ctgcataagc cctggcrtgc taccacagcc caa 33

<210> SEQ ID NO 392
<211> LENGTH: 33
<212> TYPE: DNA
<213> ORGANISM: Homo Sapiens

<400> SEQUENCE: 392
gtgtgtccca tgtggcraga gctcaaacaa ggc 33

<210> SEQ ID NO 393
<211> LENGTH: 33
<212> TYPE: DNA
<213> ORGANISM: Homo Sapiens

<400> SEQUENCE: 393
atctaagtta aggtagraat gatgaggtca aaa 33

<210> SEQ ID NO 394
<211> LENGTH: 33
<212> TYPE: DNA
<213> ORGANISM: Homo Sapiens

<400> SEQUENCE: 394
acttcatggt gatccamtgt ctacctccag caa 33

<210> SEQ ID NO 395
<211> LENGTH: 33
<212> TYPE: DNA
<213> ORGANISM: Homo Sapiens

<400> SEQUENCE: 395
gtgactataa aagatgrggc cttcggcagc tcc 33

<210> SEQ ID NO 396
<211> LENGTH: 33
<212> TYPE: DNA
<213> ORGANISM: Homo Sapiens

<400> SEQUENCE: 396
atattaatac gtggctmaga ttaatgacag caa 33

<210> SEQ ID NO 397
<211> LENGTH: 33
<212> TYPE: DNA
<213> ORGANISM: Homo Sapiens

<400> SEQUENCE: 397
ggcaactcac agaaaargag agtttgagga tct 33

<210> SEQ ID NO 398
<211> LENGTH: 33
<212> TYPE: DNA
<213> ORGANISM: Homo Sapiens

<400> SEQUENCE: 398
aaacaatgct gaggagrctt tatctttaca gtt 33

<210> SEQ ID NO 399
<211> LENGTH: 33
<212> TYPE: DNA
<213> ORGANISM: Homo Sapiens

<400> SEQUENCE: 399
tcatgatgag gacgccrgaa gagatgggga gat 33

<210> SEQ ID NO 400
<211> LENGTH: 33
<212> TYPE: DNA
<213> ORGANISM: Homo Sapiens

<400> SEQUENCE: 400
tggcatgctg aactgaraag acctggcttg gaa 33

<210> SEQ ID NO 401
<211> LENGTH: 33
<212> TYPE: DNA
<213> ORGANISM: Homo Sapiens

<400> SEQUENCE: 401
tccctccaat tgaaggrcag gcagggactc caa 33

<210> SEQ ID NO 402
<211> LENGTH: 33
<212> TYPE: DNA
<213> ORGANISM: Homo Sapiens

<400> SEQUENCE: 402
tcttgctcac ggggtcrgtg atggggaccg agt 33

<210> SEQ ID NO 403
<211> LENGTH: 33
<212> TYPE: DNA
<213> ORGANISM: Homo Sapiens

<400> SEQUENCE: 403
agtgtttcaa ataattrtct cacttccagc tca 33

<210> SEQ ID NO 404
<211> LENGTH: 33
<212> TYPE: DNA
<213> ORGANISM: Homo Sapiens

<400> SEQUENCE: 404
acctggagag aggggcmcag ctcagagctt tcc 33

<210> SEQ ID NO 405
<211> LENGTH: 33
<212> TYPE: DNA
<213> ORGANISM: Homo Sapiens

<400> SEQUENCE: 405
catctgtgga tatggcmgtt ttaccctcct ggc 33

<210> SEQ ID NO 406
<211> LENGTH: 33
<212> TYPE: DNA
<213> ORGANISM: Homo Sapiens

<400> SEQUENCE: 406
gttttgaccc cttggaraca ctcatgaaca acc 33

<210> SEQ ID NO 407
<211> LENGTH: 33
<212> TYPE: DNA
<213> ORGANISM: Homo Sapiens

<400> SEQUENCE: 407
tgtaccccat ggttttrgca tcattgacta tta 33

<210> SEQ ID NO 408
<211> LENGTH: 33
<212> TYPE: DNA
<213> ORGANISM: Homo Sapiens

<400> SEQUENCE: 408
aagaaaagta ttgattmctc cctttgtgcc ttt 33

<210> SEQ ID NO 409
<211> LENGTH: 33
<212> TYPE: DNA
<213> ORGANISM: Homo Sapiens

<400> SEQUENCE: 409
aagaggatag ggaaacrttg agagaatcgg ttg 33

<210> SEQ ID NO 410
<211> LENGTH: 33
<212> TYPE: DNA
<213> ORGANISM: Homo Sapiens

<400> SEQUENCE: 410
atgtgcccaa agccggrttc cttgaggctg ggg 33

<210> SEQ ID NO 411
<211> LENGTH: 33
<212> TYPE: DNA
<213> ORGANISM: Homo Sapiens

<400> SEQUENCE: 411
ttttctgtgc cttcacrtgt acttacacgc aca 33

<210> SEQ ID NO 412
<211> LENGTH: 33
<212> TYPE: DNA
<213> ORGANISM: Homo Sapiens

<400> SEQUENCE: 412
gattagtgca cttacarggg gatgaagaga cca 33

<210> SEQ ID NO 413
<211> LENGTH: 33
<212> TYPE: DNA
<213> ORGANISM: Homo Sapiens

<400> SEQUENCE: 413
atgaataagc taacttragc cgaaatgtta aca 33

<210> SEQ ID NO 414
<211> LENGTH: 33
<212> TYPE: DNA
<213> ORGANISM: Homo Sapiens

<400> SEQUENCE: 414
cactgcaaca ttttcaract tgaatctcac aga 33

<210> SEQ ID NO 415
<211> LENGTH: 33
<212> TYPE: DNA
<213> ORGANISM: Homo Sapiens

<400> SEQUENCE: 415
tgccagctga ggctccrgca gacacaggtt tgc 33

<210> SEQ ID NO 416
<211> LENGTH: 33
<212> TYPE: DNA
<213> ORGANISM: Homo Sapiens

<400> SEQUENCE: 416
agaaatggga tgtagcrtga gttgtgagtt gtt 33

<210> SEQ ID NO 417
<211> LENGTH: 33
<212> TYPE: DNA
<213> ORGANISM: Homo Sapiens

<400> SEQUENCE: 417
gctcgcagcg ggcagtrcgt cttgaggagc acc 33

<210> SEQ ID NO 418
<211> LENGTH: 33
<212> TYPE: DNA
<213> ORGANISM: Homo Sapiens

<400> SEQUENCE: 418
catatgtttg tgtgagmaga tctttgtaag ttt 33

<210> SEQ ID NO 419
<211> LENGTH: 33
<212> TYPE: DNA
<213> ORGANISM: Homo Sapiens

<400> SEQUENCE: 419
agagtcgagt agatgargtg tgcttcaggt ttt 33

<210> SEQ ID NO 420
<211> LENGTH: 33
<212> TYPE: DNA
<213> ORGANISM: Homo Sapiens

<400> SEQUENCE: 420
aaaatctcac aaatgcratt caagtaagtt gaa 33

<210> SEQ ID NO 421
<211> LENGTH: 33
<212> TYPE: DNA
<213> ORGANISM: Homo Sapiens

<400> SEQUENCE: 421
tacagcagac cgaaacmatg tattttagaa tta 33

<210> SEQ ID NO 422
<211> LENGTH: 33
<212> TYPE: DNA
<213> ORGANISM: Homo Sapiens

<400> SEQUENCE: 422
aatcactcta aacaacrcat ttaataggtt cca 33

<210> SEQ ID NO 423
<211> LENGTH: 33
<212> TYPE: DNA
<213> ORGANISM: Homo Sapiens

<400> SEQUENCE: 423
aataaacgag agacatmtgg agaaaggaga cct 33

<210> SEQ ID NO 424
<211> LENGTH: 33
<212> TYPE: DNA
<213> ORGANISM: Homo Sapiens

<400> SEQUENCE: 424
atctgagaaa attctcrgtc actgtcactt caa 33

<210> SEQ ID NO 425
<211> LENGTH: 33
<212> TYPE: DNA
<213> ORGANISM: Homo Sapiens

<400> SEQUENCE: 425
cactgattag ctgatgrgac tctaccctat ata 33

<210> SEQ ID NO 426
<211> LENGTH: 33
<212> TYPE: DNA
<213> ORGANISM: Homo Sapiens

<400> SEQUENCE: 426
ggacaggcca cacccaragg aaaacctgga gtc 33

<210> SEQ ID NO 427
<211> LENGTH: 33
<212> TYPE: DNA

<213> ORGANISM: Homo Sapiens

<400> SEQUENCE: 427
gaacctaaac tgttgtratt ttataccaag tat 33

<210> SEQ ID NO 428
<211> LENGTH: 33
<212> TYPE: DNA
<213> ORGANISM: Homo Sapiens

<400> SEQUENCE: 428
tttggtgaga ggagacrgct gacggagtaa gta 33

<210> SEQ ID NO 429
<211> LENGTH: 33
<212> TYPE: DNA
<213> ORGANISM: Homo Sapiens

<400> SEQUENCE: 429
actttttgtt gtttcaraag agtggttctc ttg 33

<210> SEQ ID NO 430
<211> LENGTH: 33
<212> TYPE: DNA
<213> ORGANISM: Homo Sapiens

<400> SEQUENCE: 430
cactttggta ttaatcrttg atcttgcagt tag 33

<210> SEQ ID NO 431
<211> LENGTH: 33
<212> TYPE: DNA
<213> ORGANISM: Homo Sapiens

<400> SEQUENCE: 431
gacactcctt gagactrcaa accacatacc tgg 33

<210> SEQ ID NO 432
<211> LENGTH: 33
<212> TYPE: DNA
<213> ORGANISM: Homo Sapiens

<400> SEQUENCE: 432
aaacctaaaa gatcaarttg gctaaacacg tac 33

<210> SEQ ID NO 433
<211> LENGTH: 33
<212> TYPE: DNA
<213> ORGANISM: Homo Sapiens

<400> SEQUENCE: 433
tccgggcatt tcttggmtat ttctttaata atg 33

<210> SEQ ID NO 434
<211> LENGTH: 33
<212> TYPE: DNA
<213> ORGANISM: Homo Sapiens

<400> SEQUENCE: 434
agaaactgag cagtgtrttg tgcagaattg gtg 33

<210> SEQ ID NO 435
<211> LENGTH: 33

<212> TYPE: DNA
<213> ORGANISM: Homo Sapiens

<400> SEQUENCE: 435
cagcagaata gagaacracc aaatcaaaca aca 33

<210> SEQ ID NO 436
<211> LENGTH: 33
<212> TYPE: DNA
<213> ORGANISM: Homo Sapiens

<400> SEQUENCE: 436
atggcctgtg acatagmtag catttaataa aca 33

<210> SEQ ID NO 437
<211> LENGTH: 33
<212> TYPE: DNA
<213> ORGANISM: Homo Sapiens

<400> SEQUENCE: 437
acccataaac cattctragg gccagattaa aac 33

<210> SEQ ID NO 438
<211> LENGTH: 33
<212> TYPE: DNA
<213> ORGANISM: Homo Sapiens

<400> SEQUENCE: 438
aaatatgtta tatttamtgg cagttatctt tct 33

<210> SEQ ID NO 439
<211> LENGTH: 33
<212> TYPE: DNA
<213> ORGANISM: Homo Sapiens

<400> SEQUENCE: 439
taaagtaaac gtactcrtct tagcttagac aca 33

<210> SEQ ID NO 440
<211> LENGTH: 33
<212> TYPE: DNA
<213> ORGANISM: Homo Sapiens

<400> SEQUENCE: 440
agaaaatcaa atttttrtaa gacttaccaa aaa 33

<210> SEQ ID NO 441
<211> LENGTH: 33
<212> TYPE: DNA
<213> ORGANISM: Homo Sapiens

<400> SEQUENCE: 441
tagatggtaa ccaggcrtga agagacagct gac 33

<210> SEQ ID NO 442
<211> LENGTH: 33
<212> TYPE: DNA
<213> ORGANISM: Homo Sapiens

<400> SEQUENCE: 442
agacaagcag cgcctcrttt atgtgatgta ttt 33

<210> SEQ ID NO 443

-continued

<211> LENGTH: 33
<212> TYPE: DNA
<213> ORGANISM: Homo Sapiens

<400> SEQUENCE: 443
ggttaagagc tcaggayttc ccggagtcac aca 33

<210> SEQ ID NO 444
<211> LENGTH: 33
<212> TYPE: DNA
<213> ORGANISM: Homo Sapiens

<400> SEQUENCE: 444
atttcagagg ctgcagract tctgcctgaa cct 33

<210> SEQ ID NO 445
<211> LENGTH: 33
<212> TYPE: DNA
<213> ORGANISM: Homo Sapiens

<400> SEQUENCE: 445
atgagactga atccccrgag acctacactt gaa 33

<210> SEQ ID NO 446
<211> LENGTH: 33
<212> TYPE: DNA
<213> ORGANISM: Homo Sapiens

<400> SEQUENCE: 446
caaacttatc acagtartca catttttaag gag 33

<210> SEQ ID NO 447
<211> LENGTH: 33
<212> TYPE: DNA
<213> ORGANISM: Homo Sapiens

<400> SEQUENCE: 447
agtgtgttaa gctttcmtgc tcagaaatga cag 33

<210> SEQ ID NO 448
<211> LENGTH: 33
<212> TYPE: DNA
<213> ORGANISM: Homo Sapiens

<400> SEQUENCE: 448
ccagtaccac cctttgragc tttacttgtt ttg 33

<210> SEQ ID NO 449
<211> LENGTH: 33
<212> TYPE: DNA
<213> ORGANISM: Homo Sapiens

<400> SEQUENCE: 449
tccaacactt agggtargta agtagctagt tac 33

<210> SEQ ID NO 450
<211> LENGTH: 33
<212> TYPE: DNA
<213> ORGANISM: Homo Sapiens

<400> SEQUENCE: 450
cacgatgtca tgtgttratt gagttgtata ctt 33

<210> SEQ ID NO 451
<211> LENGTH: 33
<212> TYPE: DNA
<213> ORGANISM: Homo Sapiens

<400> SEQUENCE: 451
atgcttcacc gtctacrtcc cctaattcta acc 33

<210> SEQ ID NO 452
<211> LENGTH: 33
<212> TYPE: DNA
<213> ORGANISM: Homo Sapiens

<400> SEQUENCE: 452
gagagctctg tgtgccmcgt gcggcgttct cgg 33

<210> SEQ ID NO 453
<211> LENGTH: 33
<212> TYPE: DNA
<213> ORGANISM: Homo Sapiens

<400> SEQUENCE: 453
aaacgccctt ttatcartct tactgctggt caa 33

<210> SEQ ID NO 454
<211> LENGTH: 33
<212> TYPE: DNA
<213> ORGANISM: Homo Sapiens

<400> SEQUENCE: 454
cccaagcaaa tgatagmtat tgccaattaa act 33

<210> SEQ ID NO 455
<211> LENGTH: 33
<212> TYPE: DNA
<213> ORGANISM: Homo Sapiens

<400> SEQUENCE: 455
ccagtgactg ccaaccrtgg ccacacataa gca 33

<210> SEQ ID NO 456
<211> LENGTH: 33
<212> TYPE: DNA
<213> ORGANISM: Homo Sapiens

<400> SEQUENCE: 456
ctctctatac taccccrtca gtgactcgct tta 33

<210> SEQ ID NO 457
<211> LENGTH: 33
<212> TYPE: DNA
<213> ORGANISM: Homo Sapiens

<400> SEQUENCE: 457
tgagtctctt cactgaragg tgagctttgc tac 33

<210> SEQ ID NO 458
<211> LENGTH: 33
<212> TYPE: DNA
<213> ORGANISM: Homo Sapiens

<400> SEQUENCE: 458
cttacaactg tgccacrcat atctagaatc ctc 33

<210> SEQ ID NO 459
<211> LENGTH: 33
<212> TYPE: DNA
<213> ORGANISM: Homo Sapiens

<400> SEQUENCE: 459
accaccagga gaggttmtct ctcttcttgg agc 33

<210> SEQ ID NO 460
<211> LENGTH: 33
<212> TYPE: DNA
<213> ORGANISM: Homo Sapiens

<400> SEQUENCE: 460
cctcctccaa ctcaccrtct ccagccacag ccg 33

<210> SEQ ID NO 461
<211> LENGTH: 33
<212> TYPE: DNA
<213> ORGANISM: Homo Sapiens

<400> SEQUENCE: 461
gtagtatgaa caaaagmgcc ctgggcttgg agt 33

<210> SEQ ID NO 462
<211> LENGTH: 33
<212> TYPE: DNA
<213> ORGANISM: Homo Sapiens

<400> SEQUENCE: 462
tgtgataaat ttaatcrtag tctgtccaaa cca 33

<210> SEQ ID NO 463
<211> LENGTH: 33
<212> TYPE: DNA
<213> ORGANISM: Homo Sapiens

<400> SEQUENCE: 463
cagagtcttc cccccartct gactcttctc cat 33

<210> SEQ ID NO 464
<211> LENGTH: 33
<212> TYPE: DNA
<213> ORGANISM: Homo Sapiens

<400> SEQUENCE: 464
tttaaataca ggagacrgga gcccaacaca taa 33

<210> SEQ ID NO 465
<211> LENGTH: 33
<212> TYPE: DNA
<213> ORGANISM: Homo Sapiens

<400> SEQUENCE: 465
tgagcctgac ctccaamacc tcagcagcag cat 33

<210> SEQ ID NO 466
<211> LENGTH: 33
<212> TYPE: DNA
<213> ORGANISM: Homo Sapiens

<400> SEQUENCE: 466
atgagggttt tagaatrtat ttgaatgctg aca 33

<210> SEQ ID NO 467
<211> LENGTH: 33
<212> TYPE: DNA
<213> ORGANISM: Homo Sapiens

<400> SEQUENCE: 467
taactccaag ttaaagrcta tttctaccac atc 33

<210> SEQ ID NO 468
<211> LENGTH: 33
<212> TYPE: DNA
<213> ORGANISM: Homo Sapiens

<400> SEQUENCE: 468
tgacactgct gacagargaa gaccccacct cca 33

<210> SEQ ID NO 469
<211> LENGTH: 33
<212> TYPE: DNA
<213> ORGANISM: Homo Sapiens

<400> SEQUENCE: 469
tctactgtgg aaacagrata gagtaacagc aaa 33

<210> SEQ ID NO 470
<211> LENGTH: 33
<212> TYPE: DNA
<213> ORGANISM: Homo Sapiens

<400> SEQUENCE: 470
atgtgattta ttttaarcct caccatttga agt 33

<210> SEQ ID NO 471
<211> LENGTH: 33
<212> TYPE: DNA
<213> ORGANISM: Homo Sapiens

<400> SEQUENCE: 471
cagaaacttc ttcaccrtgg gcaggttgct gat 33

<210> SEQ ID NO 472
<211> LENGTH: 33
<212> TYPE: DNA
<213> ORGANISM: Homo Sapiens

<400> SEQUENCE: 472
taagttgttg aaccacragc atgacagtct tta 33

<210> SEQ ID NO 473
<211> LENGTH: 33
<212> TYPE: DNA
<213> ORGANISM: Homo Sapiens

<400> SEQUENCE: 473
gaaaaccttg acaaacrgag ctggaaaacc atg 33

<210> SEQ ID NO 474
<211> LENGTH: 33
<212> TYPE: DNA
<213> ORGANISM: Homo Sapiens

<400> SEQUENCE: 474
cagaggatgc cagtttrctt gaatgccaaa att 33

<210> SEQ ID NO 475
<211> LENGTH: 33
<212> TYPE: DNA
<213> ORGANISM: Homo Sapiens

<400> SEQUENCE: 475
tcattttgat cactctrtgg catttgacac ttt 33

<210> SEQ ID NO 476
<211> LENGTH: 33
<212> TYPE: DNA
<213> ORGANISM: Homo Sapiens

<400> SEQUENCE: 476
gctggtgaga gggcacrctt actctgtgac tgg 33

<210> SEQ ID NO 477
<211> LENGTH: 33
<212> TYPE: DNA
<213> ORGANISM: Homo Sapiens

<400> SEQUENCE: 477
aaaggaacag agccccrtta gaggaaccat agc 33

<210> SEQ ID NO 478
<211> LENGTH: 33
<212> TYPE: DNA
<213> ORGANISM: Homo Sapiens

<400> SEQUENCE: 478
cattggagcc tacaccrctt gtgcttttct cac 33

<210> SEQ ID NO 479
<211> LENGTH: 33
<212> TYPE: DNA
<213> ORGANISM: Homo Sapiens

<400> SEQUENCE: 479
ggtctgttcc ttccccrcga tgccgcaggc ccc 33

<210> SEQ ID NO 480
<211> LENGTH: 33
<212> TYPE: DNA
<213> ORGANISM: Homo Sapiens

<400> SEQUENCE: 480
aatgaataca actgtamaaa ctggaaccaa acc 33

<210> SEQ ID NO 481
<211> LENGTH: 33
<212> TYPE: DNA
<213> ORGANISM: Homo Sapiens

<400> SEQUENCE: 481
agttgagaga agccagrgtg aaattcctcc tgc 33

<210> SEQ ID NO 482
<211> LENGTH: 33
<212> TYPE: DNA
<213> ORGANISM: Homo Sapiens

<400> SEQUENCE: 482
tagggataaa aataccrtga agctcatagg gat 33

<210> SEQ ID NO 483
<211> LENGTH: 33
<212> TYPE: DNA
<213> ORGANISM: Homo Sapiens

<400> SEQUENCE: 483
tcgtgtcctt cccaacrgct ccctcttcct tcc 33

<210> SEQ ID NO 484
<211> LENGTH: 33
<212> TYPE: DNA
<213> ORGANISM: Homo Sapiens

<400> SEQUENCE: 484
agaagagaga gagtaartgt attccaccaa gaa 33

<210> SEQ ID NO 485
<211> LENGTH: 33
<212> TYPE: DNA
<213> ORGANISM: Homo Sapiens

<400> SEQUENCE: 485
tcctgctgat ctgagcrtgt gggtcctaga ggc 33

<210> SEQ ID NO 486
<211> LENGTH: 33
<212> TYPE: DNA
<213> ORGANISM: Homo Sapiens

<400> SEQUENCE: 486
tttatcaaga gacattrtct atcatatagc aat 33

<210> SEQ ID NO 487
<211> LENGTH: 33
<212> TYPE: DNA
<213> ORGANISM: Homo Sapiens

<400> SEQUENCE: 487
ctgcaacatc agcagargct tcctgtgggt tcc 33

<210> SEQ ID NO 488
<211> LENGTH: 33
<212> TYPE: DNA
<213> ORGANISM: Homo Sapiens

<400> SEQUENCE: 488
ctaaggggag gtgactrgta agtttcaggt ggc 33

<210> SEQ ID NO 489
<211> LENGTH: 33
<212> TYPE: DNA
<213> ORGANISM: Homo Sapiens

<400> SEQUENCE: 489
tcagagagag atcaagrtaa aacgaaaaac tca 33

<210> SEQ ID NO 490
<211> LENGTH: 33
<212> TYPE: DNA
<213> ORGANISM: Homo Sapiens

<400> SEQUENCE: 490
tacaaagatt aatgatrtac aatctctggc ctt 33

<210> SEQ ID NO 491
<211> LENGTH: 33
<212> TYPE: DNA
<213> ORGANISM: Homo Sapiens

<400> SEQUENCE: 491
tatttcttga tgaaatrtgt aagcctccct tta 33

<210> SEQ ID NO 492
<211> LENGTH: 33
<212> TYPE: DNA
<213> ORGANISM: Homo Sapiens

<400> SEQUENCE: 492
tttggtgcct tcctacmgtt atggaaggaa gct 33

<210> SEQ ID NO 493
<211> LENGTH: 33
<212> TYPE: DNA
<213> ORGANISM: Homo Sapiens

<400> SEQUENCE: 493
cctatagtca agtaagmctg taataataaa tat 33

<210> SEQ ID NO 494
<211> LENGTH: 33
<212> TYPE: DNA
<213> ORGANISM: Homo Sapiens

<400> SEQUENCE: 494
gggagatctc ttacacrtga tgtttctttc aga 33

<210> SEQ ID NO 495
<211> LENGTH: 33
<212> TYPE: DNA
<213> ORGANISM: Homo Sapiens

<400> SEQUENCE: 495
agaaatccac ttagatrtct accctacttc ccc 33

<210> SEQ ID NO 496
<211> LENGTH: 33
<212> TYPE: DNA
<213> ORGANISM: Homo Sapiens

<400> SEQUENCE: 496
tttcttaaca cagcagmaaa attgttttat gtc 33

<210> SEQ ID NO 497
<211> LENGTH: 33
<212> TYPE: DNA
<213> ORGANISM: Homo Sapiens

<400> SEQUENCE: 497
gtagattcta atcttargcc ctttgccata gac 33

<210> SEQ ID NO 498
<211> LENGTH: 33
<212> TYPE: DNA
<213> ORGANISM: Homo Sapiens

<400> SEQUENCE: 498
agaaaataaa aactatrtaa tcttagatgg cac 33

<210> SEQ ID NO 499
<211> LENGTH: 33
<212> TYPE: DNA
<213> ORGANISM: Homo Sapiens

<400> SEQUENCE: 499
ataacactga tgatatrgat ttgaggtgag aga 33

<210> SEQ ID NO 500
<211> LENGTH: 33
<212> TYPE: DNA
<213> ORGANISM: Homo Sapiens

<400> SEQUENCE: 500
gggggtcaag agtggaract gcaccgaggc aag 33

<210> SEQ ID NO 501
<211> LENGTH: 33
<212> TYPE: DNA
<213> ORGANISM: Homo Sapiens

<400> SEQUENCE: 501
agagactttg gtctgcrccc tggggttgtc tgt 33

<210> SEQ ID NO 502
<211> LENGTH: 33
<212> TYPE: DNA
<213> ORGANISM: Homo Sapiens

<400> SEQUENCE: 502
ctgcacttac cgggagrgtc tctgccctca gcc 33

<210> SEQ ID NO 503
<211> LENGTH: 33
<212> TYPE: DNA
<213> ORGANISM: Homo Sapiens

<400> SEQUENCE: 503
agaatcaagg aataagraaa ataatgtgag ctg 33

<210> SEQ ID NO 504
<211> LENGTH: 33
<212> TYPE: DNA
<213> ORGANISM: Homo Sapiens

<400> SEQUENCE: 504
catcttcttc aggaagrtgt ccctaacttc tcc 33

<210> SEQ ID NO 505
<211> LENGTH: 33
<212> TYPE: DNA
<213> ORGANISM: Homo Sapiens

<400> SEQUENCE: 505
ttcgccctgg gatttartgc tcttctttct gct 33

<210> SEQ ID NO 506
<211> LENGTH: 33
<212> TYPE: DNA

<213> ORGANISM: Homo Sapiens

<400> SEQUENCE: 506
tgatgcagtg tgtgacrtct aatctccccc ata 33

<210> SEQ ID NO 507
<211> LENGTH: 33
<212> TYPE: DNA
<213> ORGANISM: Homo Sapiens

<400> SEQUENCE: 507
tatatgatat tttattrttt ttagataggg tct 33

<210> SEQ ID NO 508
<211> LENGTH: 33
<212> TYPE: DNA
<213> ORGANISM: Homo Sapiens

<400> SEQUENCE: 508
ggagcattct gggttgrcct gagcaaaggc tgc 33

<210> SEQ ID NO 509
<211> LENGTH: 33
<212> TYPE: DNA
<213> ORGANISM: Homo Sapiens

<400> SEQUENCE: 509
tctgcttatc tttcaaract catctcagcc atc 33

<210> SEQ ID NO 510
<211> LENGTH: 33
<212> TYPE: DNA
<213> ORGANISM: Homo Sapiens

<400> SEQUENCE: 510
tccagctaca ctcaacrcat ttcaccccac ccc 33

<210> SEQ ID NO 511
<211> LENGTH: 33
<212> TYPE: DNA
<213> ORGANISM: Homo Sapiens

<400> SEQUENCE: 511
tattaattgc cccagaratc tatcctcaca tcc 33

<210> SEQ ID NO 512
<211> LENGTH: 33
<212> TYPE: DNA
<213> ORGANISM: Homo Sapiens

<400> SEQUENCE: 512
tctggctccg cagcagraca cgaagtttgc att 33

<210> SEQ ID NO 513
<211> LENGTH: 33
<212> TYPE: DNA
<213> ORGANISM: Homo Sapiens

<400> SEQUENCE: 513
ggagcccttt gctgggrtgg ggatgagggt agt 33

<210> SEQ ID NO 514
<211> LENGTH: 33

<212> TYPE: DNA
<213> ORGANISM: Homo Sapiens

<400> SEQUENCE: 514
ctggtggcca aagtggmttt ctcccttcag ggg 33

<210> SEQ ID NO 515
<211> LENGTH: 33
<212> TYPE: DNA
<213> ORGANISM: Homo Sapiens

<400> SEQUENCE: 515
aagtctggaa tcagcaraaa tgtattacat tga 33

<210> SEQ ID NO 516
<211> LENGTH: 33
<212> TYPE: DNA
<213> ORGANISM: Homo Sapiens

<400> SEQUENCE: 516
atagaaataa gtgctaract gggagttggg aga 33

<210> SEQ ID NO 517
<211> LENGTH: 33
<212> TYPE: DNA
<213> ORGANISM: Homo Sapiens

<400> SEQUENCE: 517
gtgagagccc aggctgrggt caggaatgga aac 33

<210> SEQ ID NO 518
<211> LENGTH: 33
<212> TYPE: DNA
<213> ORGANISM: Homo Sapiens

<400> SEQUENCE: 518
gctaaaacgg gccccarttg gaccgtcacc ttc 33

<210> SEQ ID NO 519
<211> LENGTH: 33
<212> TYPE: DNA
<213> ORGANISM: Homo Sapiens

<400> SEQUENCE: 519
cacttaaagc ccaaagrtgg ccggctgtgg tgg 33

<210> SEQ ID NO 520
<211> LENGTH: 33
<212> TYPE: DNA
<213> ORGANISM: Homo Sapiens

<400> SEQUENCE: 520
tgtggatctt cagcacrtct acaactccct cca 33

<210> SEQ ID NO 521
<211> LENGTH: 33
<212> TYPE: DNA
<213> ORGANISM: Homo Sapiens

<400> SEQUENCE: 521
acaaaccttc ttggaargtg gaaagttttg caa 33

<210> SEQ ID NO 522

<211> LENGTH: 33
<212> TYPE: DNA
<213> ORGANISM: Homo Sapiens

<400> SEQUENCE: 522
acaaaagcta ccagatraaa acactcacta tgg 33

<210> SEQ ID NO 523
<211> LENGTH: 33
<212> TYPE: DNA
<213> ORGANISM: Homo Sapiens

<400> SEQUENCE: 523
cctgagagat ctgagtratc aagacccagt gtt 33

<210> SEQ ID NO 524
<211> LENGTH: 33
<212> TYPE: DNA
<213> ORGANISM: Homo Sapiens

<400> SEQUENCE: 524
attcggtatt taatacmttt tgtgtgactg cct 33

<210> SEQ ID NO 525
<211> LENGTH: 33
<212> TYPE: DNA
<213> ORGANISM: Homo Sapiens

<400> SEQUENCE: 525
ctttcattta ttgaacrcct tagatatgag cta 33

<210> SEQ ID NO 526
<211> LENGTH: 33
<212> TYPE: DNA
<213> ORGANISM: Homo Sapiens

<400> SEQUENCE: 526
ttacagctca acaaaarcta ccagataaaa aca 33

<210> SEQ ID NO 527
<211> LENGTH: 33
<212> TYPE: DNA
<213> ORGANISM: Homo Sapiens

<400> SEQUENCE: 527
ggaggaagtg tggggtrtgg gtagactcct cct 33

<210> SEQ ID NO 528
<211> LENGTH: 33
<212> TYPE: DNA
<213> ORGANISM: Homo Sapiens

<400> SEQUENCE: 528
gtgtgtgatg cagtatrggg tagaaccagg aga 33

<210> SEQ ID NO 529
<211> LENGTH: 33
<212> TYPE: DNA
<213> ORGANISM: Homo Sapiens

<400> SEQUENCE: 529
ttcacacatg gaaaatragg tggaaaagga gaa 33

<210> SEQ ID NO 530
<211> LENGTH: 33
<212> TYPE: DNA
<213> ORGANISM: Homo Sapiens

<400> SEQUENCE: 530
gtttgtgata aggagcrttg gggaggagat ttg 33

<210> SEQ ID NO 531
<211> LENGTH: 33
<212> TYPE: DNA
<213> ORGANISM: Homo Sapiens

<400> SEQUENCE: 531
tttaaggagg ctaactrctt ccacattaga tca 33

<210> SEQ ID NO 532
<211> LENGTH: 33
<212> TYPE: DNA
<213> ORGANISM: Homo Sapiens

<400> SEQUENCE: 532
cttttttgtc ttccccrtgc attcgccccc aca 33

<210> SEQ ID NO 533
<211> LENGTH: 33
<212> TYPE: DNA
<213> ORGANISM: Homo Sapiens

<400> SEQUENCE: 533
gacccaacag taagacrttt ctccttttgg taa 33

<210> SEQ ID NO 534
<211> LENGTH: 33
<212> TYPE: DNA
<213> ORGANISM: Homo Sapiens

<400> SEQUENCE: 534
cgttgaagaa tcagtamaat ttggagactt tga 33

<210> SEQ ID NO 535
<211> LENGTH: 33
<212> TYPE: DNA
<213> ORGANISM: Homo Sapiens

<400> SEQUENCE: 535
atcctgcacc ttttccmgtc aaatccccat tcc 33

<210> SEQ ID NO 536
<211> LENGTH: 33
<212> TYPE: DNA
<213> ORGANISM: Homo Sapiens

<400> SEQUENCE: 536
taagagaaga ctcaccrttc tgaggctgtc tga 33

<210> SEQ ID NO 537
<211> LENGTH: 33
<212> TYPE: DNA
<213> ORGANISM: Homo Sapiens

<400> SEQUENCE: 537
tccttcccag aaaaccrcct cagggctcac ccc 33

<210> SEQ ID NO 538
<211> LENGTH: 33
<212> TYPE: DNA
<213> ORGANISM: Homo Sapiens

<400> SEQUENCE: 538
gaactggaat gagaaartaa cctctaactg cta 33

<210> SEQ ID NO 539
<211> LENGTH: 33
<212> TYPE: DNA
<213> ORGANISM: Homo Sapiens

<400> SEQUENCE: 539
agctcctact cagatarcag aactcacaaa ctt 33

<210> SEQ ID NO 540
<211> LENGTH: 33
<212> TYPE: DNA
<213> ORGANISM: Homo Sapiens

<400> SEQUENCE: 540
ggtcaaatag taatttrttg ggtgaatgac agt 33

<210> SEQ ID NO 541
<211> LENGTH: 33
<212> TYPE: DNA
<213> ORGANISM: Homo Sapiens

<400> SEQUENCE: 541
atttaccaga tcaaccrttc tcaatgctct tta 33

<210> SEQ ID NO 542
<211> LENGTH: 33
<212> TYPE: DNA
<213> ORGANISM: Homo Sapiens

<400> SEQUENCE: 542
tggaagaatg tgtccargct gtgcttcccc ttt 33

<210> SEQ ID NO 543
<211> LENGTH: 33
<212> TYPE: DNA
<213> ORGANISM: Homo Sapiens

<400> SEQUENCE: 543
ccatcacccc cggaccrtgg gctccatgcc agt 33

<210> SEQ ID NO 544
<211> LENGTH: 33
<212> TYPE: DNA
<213> ORGANISM: Homo Sapiens

<400> SEQUENCE: 544
tcctctcctg tagaccrctg gctcatgaaa taa 33

<210> SEQ ID NO 545
<211> LENGTH: 33
<212> TYPE: DNA
<213> ORGANISM: Homo Sapiens

<400> SEQUENCE: 545
cagactgctg gctctgrgca tctgagcagc gcc 33

<210> SEQ ID NO 546
<211> LENGTH: 33
<212> TYPE: DNA
<213> ORGANISM: Homo Sapiens

<400> SEQUENCE: 546
agggttttct tgaatgrcat ttctcattgc taa 33

<210> SEQ ID NO 547
<211> LENGTH: 33
<212> TYPE: DNA
<213> ORGANISM: Homo Sapiens

<400> SEQUENCE: 547
agaatagacg tgttagraac caggttagcc tgg 33

<210> SEQ ID NO 548
<211> LENGTH: 33
<212> TYPE: DNA
<213> ORGANISM: Homo Sapiens

<400> SEQUENCE: 548
tcttgggggt cttttgrggg aacagagaac aat 33

<210> SEQ ID NO 549
<211> LENGTH: 33
<212> TYPE: DNA
<213> ORGANISM: Homo Sapiens

<400> SEQUENCE: 549
ttgatgatgg tgatatrgaa tgattaataa cca 33

<210> SEQ ID NO 550
<211> LENGTH: 33
<212> TYPE: DNA
<213> ORGANISM: Homo Sapiens

<400> SEQUENCE: 550
tgatgggaga gaaatargaa ttcaacttgt agc 33

<210> SEQ ID NO 551
<211> LENGTH: 33
<212> TYPE: DNA
<213> ORGANISM: Homo Sapiens

<400> SEQUENCE: 551
tttttccctg aaactcrgcc aaaagttttt cct 33

<210> SEQ ID NO 552
<211> LENGTH: 33
<212> TYPE: DNA
<213> ORGANISM: Homo Sapiens

<400> SEQUENCE: 552
gctatattaa aagaaartag acttcaaagc aaa 33

<210> SEQ ID NO 553
<211> LENGTH: 33
<212> TYPE: DNA
<213> ORGANISM: Homo Sapiens

<400> SEQUENCE: 553
aggggcctaa gcccagrtgt cagaggcaca gta 33

<210> SEQ ID NO 554
<211> LENGTH: 33
<212> TYPE: DNA
<213> ORGANISM: Homo Sapiens

<400> SEQUENCE: 554
gtttccagcc acctctrttt ccattccctt aaa 33

<210> SEQ ID NO 555
<211> LENGTH: 33
<212> TYPE: DNA
<213> ORGANISM: Homo Sapiens

<400> SEQUENCE: 555
gacgcagtct gtaggcrctt ggcaagtgtt tgc 33

<210> SEQ ID NO 556
<211> LENGTH: 33
<212> TYPE: DNA
<213> ORGANISM: Homo Sapiens

<400> SEQUENCE: 556
tcccctgcca ctccctrttt aatgcctttg taa 33

<210> SEQ ID NO 557
<211> LENGTH: 33
<212> TYPE: DNA
<213> ORGANISM: Homo Sapiens

<400> SEQUENCE: 557
gtgtgaggga ctcctcrtaa ctcctgggca agg 33

<210> SEQ ID NO 558
<211> LENGTH: 33
<212> TYPE: DNA
<213> ORGANISM: Homo Sapiens

<400> SEQUENCE: 558
gttgtcatga gttaccrtga ttaaagtggt gga 33

<210> SEQ ID NO 559
<211> LENGTH: 33
<212> TYPE: DNA
<213> ORGANISM: Homo Sapiens

<400> SEQUENCE: 559
tataatcttt gtctcartag tcaaatactt aga 33

<210> SEQ ID NO 560
<211> LENGTH: 33
<212> TYPE: DNA
<213> ORGANISM: Homo Sapiens

<400> SEQUENCE: 560
tccccatagc tatccarttg agccagaacc att 33

<210> SEQ ID NO 561
<211> LENGTH: 33
<212> TYPE: DNA
<213> ORGANISM: Homo Sapiens

<400> SEQUENCE: 561
tgcgatcacc tggattratg gcaactaatg ctc 33

<210> SEQ ID NO 562
<211> LENGTH: 33
<212> TYPE: DNA
<213> ORGANISM: Homo Sapiens

<400> SEQUENCE: 562
tctggaggtg gagtctragg atactgctct tag 33

<210> SEQ ID NO 563
<211> LENGTH: 33
<212> TYPE: DNA
<213> ORGANISM: Homo Sapiens

<400> SEQUENCE: 563
agtctagcca ggctccrtag aaactggagt gcc 33

<210> SEQ ID NO 564
<211> LENGTH: 33
<212> TYPE: DNA
<213> ORGANISM: Homo Sapiens

<400> SEQUENCE: 564
gaattttgga attcagrtat cagaaaaaag ctg 33

<210> SEQ ID NO 565
<211> LENGTH: 33
<212> TYPE: DNA
<213> ORGANISM: Homo Sapiens

<400> SEQUENCE: 565
agttatgtaa acaggargtg cagcatagtg tct 33

<210> SEQ ID NO 566
<211> LENGTH: 33
<212> TYPE: DNA
<213> ORGANISM: Homo Sapiens

<400> SEQUENCE: 566
ttctttcatc cttatgrcct ttcttgtata ggt 33

<210> SEQ ID NO 567
<211> LENGTH: 33
<212> TYPE: DNA
<213> ORGANISM: Homo Sapiens

<400> SEQUENCE: 567
atatatcatt ttatttratt tcccagtcac ctt 33

<210> SEQ ID NO 568
<211> LENGTH: 33
<212> TYPE: DNA
<213> ORGANISM: Homo Sapiens

<400> SEQUENCE: 568
cgtacccatg tgtcacragt acacatgctt ttc 33

<210> SEQ ID NO 569
<211> LENGTH: 33
<212> TYPE: DNA
<213> ORGANISM: Homo Sapiens

<400> SEQUENCE: 569
aatcattttt tcaaaartgt agtcttttgt gag    33

<210> SEQ ID NO 570
<211> LENGTH: 33
<212> TYPE: DNA
<213> ORGANISM: Homo Sapiens

<400> SEQUENCE: 570
aggaggtgat tagatcrtag aggttgttcc cac    33

<210> SEQ ID NO 571
<211> LENGTH: 33
<212> TYPE: DNA
<213> ORGANISM: Homo Sapiens

<400> SEQUENCE: 571
ctttgaagtc cttctgraaa atacctaaat tag    33

<210> SEQ ID NO 572
<211> LENGTH: 33
<212> TYPE: DNA
<213> ORGANISM: Homo Sapiens

<400> SEQUENCE: 572
aacccactcc actaagrcct tcagtctgtg ctc    33

<210> SEQ ID NO 573
<211> LENGTH: 33
<212> TYPE: DNA
<213> ORGANISM: Homo Sapiens

<400> SEQUENCE: 573
ctccgctgcc accgccrcca ctgctcctcc tgc    33

<210> SEQ ID NO 574
<211> LENGTH: 33
<212> TYPE: DNA
<213> ORGANISM: Homo Sapiens

<400> SEQUENCE: 574
tttgccatac taatttrgta actttagcta ggt    33

<210> SEQ ID NO 575
<211> LENGTH: 33
<212> TYPE: DNA
<213> ORGANISM: Homo Sapiens

<400> SEQUENCE: 575
gcctctagtc actaagraaa gtctaagtat ctt    33

<210> SEQ ID NO 576
<211> LENGTH: 33
<212> TYPE: DNA
<213> ORGANISM: Homo Sapiens

<400> SEQUENCE: 576
ttcaggatta gatgctraga cttcaaatca gtc    33

<210> SEQ ID NO 577
<211> LENGTH: 33
<212> TYPE: DNA
<213> ORGANISM: Homo Sapiens

<400> SEQUENCE: 577
acttgtttac aaaagcrtct ctataggtct gtg 33

<210> SEQ ID NO 578
<211> LENGTH: 33
<212> TYPE: DNA
<213> ORGANISM: Homo Sapiens

<400> SEQUENCE: 578
aagataaata agacaartaa cacattaaaa agc 33

<210> SEQ ID NO 579
<211> LENGTH: 33
<212> TYPE: DNA
<213> ORGANISM: Homo Sapiens

<400> SEQUENCE: 579
atgggcaaac ttctctmatg ctaacagtga tga 33

<210> SEQ ID NO 580
<211> LENGTH: 33
<212> TYPE: DNA
<213> ORGANISM: Homo Sapiens

<400> SEQUENCE: 580
ctgtcttcat tcctccrgct actatcccta ccc 33

<210> SEQ ID NO 581
<211> LENGTH: 33
<212> TYPE: DNA
<213> ORGANISM: Homo Sapiens

<400> SEQUENCE: 581
tactgccaaa cctccamtca aaatagctag ggc 33

<210> SEQ ID NO 582
<211> LENGTH: 33
<212> TYPE: DNA
<213> ORGANISM: Homo Sapiens

<400> SEQUENCE: 582
ctgtctgcta ggagtarcat caggaagtgt ctg 33

<210> SEQ ID NO 583
<211> LENGTH: 33
<212> TYPE: DNA
<213> ORGANISM: Homo Sapiens

<400> SEQUENCE: 583
accctagatc tttctcmttc tcttcataca cat 33

<210> SEQ ID NO 584
<211> LENGTH: 33
<212> TYPE: DNA
<213> ORGANISM: Homo Sapiens

<400> SEQUENCE: 584
attgctagca tttattmagt gaatgaataa atg 33

<210> SEQ ID NO 585
<211> LENGTH: 33
<212> TYPE: DNA

<213> ORGANISM: Homo Sapiens

<400> SEQUENCE: 585
agcctcaaag gtagcarcct ttagaaagaa aaa 33

<210> SEQ ID NO 586
<211> LENGTH: 33
<212> TYPE: DNA
<213> ORGANISM: Homo Sapiens

<400> SEQUENCE: 586
aaaaactctg tagctartat catgcttaat gat 33

<210> SEQ ID NO 587
<211> LENGTH: 33
<212> TYPE: DNA
<213> ORGANISM: Homo Sapiens

<400> SEQUENCE: 587
tttctgatgg catccartcc agagcaaatc cct 33

<210> SEQ ID NO 588
<211> LENGTH: 33
<212> TYPE: DNA
<213> ORGANISM: Homo Sapiens

<400> SEQUENCE: 588
tagtttgaaa ccctatratg ttctttgaaa cct 33

<210> SEQ ID NO 589
<211> LENGTH: 33
<212> TYPE: DNA
<213> ORGANISM: Homo Sapiens

<400> SEQUENCE: 589
agagcatcct aaatccract cttaggggaa gac 33

<210> SEQ ID NO 590
<211> LENGTH: 33
<212> TYPE: DNA
<213> ORGANISM: Homo Sapiens

<400> SEQUENCE: 590
ctgtgctgct taccatrtat ggatgagggg ttg 33

<210> SEQ ID NO 591
<211> LENGTH: 33
<212> TYPE: DNA
<213> ORGANISM: Homo Sapiens

<400> SEQUENCE: 591
aaaagactgg aggaagrcaa ttgtagctag ggc 33

<210> SEQ ID NO 592
<211> LENGTH: 33
<212> TYPE: DNA
<213> ORGANISM: Homo Sapiens

<400> SEQUENCE: 592
ggtatatggt taagatratc atacgacttg gtt 33

<210> SEQ ID NO 593
<211> LENGTH: 33

<212> TYPE: DNA
<213> ORGANISM: Homo Sapiens

<400> SEQUENCE: 593
tcaattgttc atttggrcaa gagtttgggt ttg 33

<210> SEQ ID NO 594
<211> LENGTH: 33
<212> TYPE: DNA
<213> ORGANISM: Homo Sapiens

<400> SEQUENCE: 594
tccagatttt tactatrtgt ggctgtaaaa atg 33

<210> SEQ ID NO 595
<211> LENGTH: 33
<212> TYPE: DNA
<213> ORGANISM: Homo Sapiens

<400> SEQUENCE: 595
taaacttaga catgaartag agaaaggagg tta 33

<210> SEQ ID NO 596
<211> LENGTH: 33
<212> TYPE: DNA
<213> ORGANISM: Homo Sapiens

<400> SEQUENCE: 596
ataaaggaag gtaaaarctc agaaggccaa agg 33

<210> SEQ ID NO 597
<211> LENGTH: 33
<212> TYPE: DNA
<213> ORGANISM: Homo Sapiens

<400> SEQUENCE: 597
catgattaaa agtatcrtct tcagacatct gct 33

<210> SEQ ID NO 598
<211> LENGTH: 33
<212> TYPE: DNA
<213> ORGANISM: Homo Sapiens

<400> SEQUENCE: 598
gcctggtatt ccatggrtca tgtcaaaaaa cct 33

<210> SEQ ID NO 599
<211> LENGTH: 33
<212> TYPE: DNA
<213> ORGANISM: Homo Sapiens

<400> SEQUENCE: 599
acactttaaa taacgtrtcc aagaaagtgg aaa 33

<210> SEQ ID NO 600
<211> LENGTH: 33
<212> TYPE: DNA
<213> ORGANISM: Homo Sapiens

<400> SEQUENCE: 600
tggtcattcg accttcrccc cataaatagt ggt 33

<210> SEQ ID NO 601

<211> LENGTH: 33
<212> TYPE: DNA
<213> ORGANISM: Homo Sapiens

<400> SEQUENCE: 601
ggccaatcta acacaarcat gactagtggg ttc 33

<210> SEQ ID NO 602
<211> LENGTH: 33
<212> TYPE: DNA
<213> ORGANISM: Homo Sapiens

<400> SEQUENCE: 602
tatggtctgc tgagtcrata atctatgttt tta 33

<210> SEQ ID NO 603
<211> LENGTH: 33
<212> TYPE: DNA
<213> ORGANISM: Homo Sapiens

<400> SEQUENCE: 603
ctgtgtataa ttcaaarcat ctccttttt gtt 33

<210> SEQ ID NO 604
<211> LENGTH: 33
<212> TYPE: DNA
<213> ORGANISM: Homo Sapiens

<400> SEQUENCE: 604
aacaatcaca attttcrttg atttatctcc cca 33

<210> SEQ ID NO 605
<211> LENGTH: 33
<212> TYPE: DNA
<213> ORGANISM: Homo Sapiens

<400> SEQUENCE: 605
gataccttat gtgaccrtag ttagtcggtg atc 33

<210> SEQ ID NO 606
<211> LENGTH: 33
<212> TYPE: DNA
<213> ORGANISM: Homo Sapiens

<400> SEQUENCE: 606
ttaaatatct aaatgtrtaa aacagacctg atc 33

<210> SEQ ID NO 607
<211> LENGTH: 33
<212> TYPE: DNA
<213> ORGANISM: Homo Sapiens

<400> SEQUENCE: 607
cgacaaggct gggatcrgtg ctctccttcc agc 33

<210> SEQ ID NO 608
<211> LENGTH: 33
<212> TYPE: DNA
<213> ORGANISM: Homo Sapiens

<400> SEQUENCE: 608
caattcattc tgtgccract cacccctggg gtc 33

<210> SEQ ID NO 609
<211> LENGTH: 33
<212> TYPE: DNA
<213> ORGANISM: Homo Sapiens

<400> SEQUENCE: 609
gtctagcaat ccttgtrtat gctttaatca cag 33

<210> SEQ ID NO 610
<211> LENGTH: 33
<212> TYPE: DNA
<213> ORGANISM: Homo Sapiens

<400> SEQUENCE: 610
caggtttagt ttgagarcca gcaaactgaa aag 33

<210> SEQ ID NO 611
<211> LENGTH: 33
<212> TYPE: DNA
<213> ORGANISM: Homo Sapiens

<400> SEQUENCE: 611
ggaagtcaat taaaaartct aaatataaat ttg 33

<210> SEQ ID NO 612
<211> LENGTH: 33
<212> TYPE: DNA
<213> ORGANISM: Homo Sapiens

<400> SEQUENCE: 612
gaatttaaaa atatcartac aagaaagtca tta 33

<210> SEQ ID NO 613
<211> LENGTH: 33
<212> TYPE: DNA
<213> ORGANISM: Homo Sapiens

<400> SEQUENCE: 613
ttagcatgag ccacagraaa ggtttttgag cca 33

<210> SEQ ID NO 614
<211> LENGTH: 33
<212> TYPE: DNA
<213> ORGANISM: Homo Sapiens

<400> SEQUENCE: 614
agtttctgtg ttttaamgga atagcctgct gtg 33

<210> SEQ ID NO 615
<211> LENGTH: 33
<212> TYPE: DNA
<213> ORGANISM: Homo Sapiens

<400> SEQUENCE: 615
gtccggccct gctaccrcca acctttgcgt aat 33

<210> SEQ ID NO 616
<211> LENGTH: 33
<212> TYPE: DNA
<213> ORGANISM: Homo Sapiens

<400> SEQUENCE: 616
aagtaaattg cccaagrtgg cccagctagt aaa 33

<210> SEQ ID NO 617
<211> LENGTH: 33
<212> TYPE: DNA
<213> ORGANISM: Homo Sapiens

<400> SEQUENCE: 617
tgtctgtctc taaatcrtgt gctgttaaaa aat 33

<210> SEQ ID NO 618
<211> LENGTH: 33
<212> TYPE: DNA
<213> ORGANISM: Homo Sapiens

<400> SEQUENCE: 618
gctccttttt aactcartat tacctgtggt ttt 33

<210> SEQ ID NO 619
<211> LENGTH: 33
<212> TYPE: DNA
<213> ORGANISM: Homo Sapiens

<400> SEQUENCE: 619
tggggggtcc atgtggraaa gactgtgagt ggc 33

<210> SEQ ID NO 620
<211> LENGTH: 33
<212> TYPE: DNA
<213> ORGANISM: Homo Sapiens

<400> SEQUENCE: 620
tgttttatct gtggacrcta cctcgtgaga ttg 33

<210> SEQ ID NO 621
<211> LENGTH: 33
<212> TYPE: DNA
<213> ORGANISM: Homo Sapiens

<400> SEQUENCE: 621
ttccttgctt cttttgrccc aacattttag cgc 33

<210> SEQ ID NO 622
<211> LENGTH: 33
<212> TYPE: DNA
<213> ORGANISM: Homo Sapiens

<400> SEQUENCE: 622
ttctgaagta tctctaraaa gtgtctctat aaa 33

<210> SEQ ID NO 623
<211> LENGTH: 33
<212> TYPE: DNA
<213> ORGANISM: Homo Sapiens

<400> SEQUENCE: 623
gactgcccta gctgagrgta tgggagggag ggg 33

<210> SEQ ID NO 624
<211> LENGTH: 33
<212> TYPE: DNA
<213> ORGANISM: Homo Sapiens

<400> SEQUENCE: 624
tgattacccc tgttctmgga gtcgctgctt tct 33

<210> SEQ ID NO 625
<211> LENGTH: 33
<212> TYPE: DNA
<213> ORGANISM: Homo Sapiens

<400> SEQUENCE: 625
gaattgacta ctgcaamtgt gcatgatttt atc 33

<210> SEQ ID NO 626
<211> LENGTH: 33
<212> TYPE: DNA
<213> ORGANISM: Homo Sapiens

<400> SEQUENCE: 626
ccgaggttag gcgaagrgtc ggggcttctc tga 33

<210> SEQ ID NO 627
<211> LENGTH: 33
<212> TYPE: DNA
<213> ORGANISM: Homo Sapiens

<400> SEQUENCE: 627
gatggcaagc atacatrgtt ttgagtgttc cat 33

<210> SEQ ID NO 628
<211> LENGTH: 33
<212> TYPE: DNA
<213> ORGANISM: Homo Sapiens

<400> SEQUENCE: 628
gtagttgaat atttgcract tatatcaacc tat 33

<210> SEQ ID NO 629
<211> LENGTH: 33
<212> TYPE: DNA
<213> ORGANISM: Homo Sapiens

<400> SEQUENCE: 629
tgatttcggg gctttcrctt tcattatgct gtc 33

<210> SEQ ID NO 630
<211> LENGTH: 33
<212> TYPE: DNA
<213> ORGANISM: Homo Sapiens

<400> SEQUENCE: 630
tgagtcaaca tgaagtragg gaaatgaaaa ggg 33

<210> SEQ ID NO 631
<211> LENGTH: 33
<212> TYPE: DNA
<213> ORGANISM: Homo Sapiens

<400> SEQUENCE: 631
ctactgctta cttctgmctc catgtagaat aaa 33

<210> SEQ ID NO 632
<211> LENGTH: 33
<212> TYPE: DNA
<213> ORGANISM: Homo Sapiens

<400> SEQUENCE: 632
aaaggagcat tcacacmgct tctcttgtca tga 33

<210> SEQ ID NO 633
<211> LENGTH: 33
<212> TYPE: DNA
<213> ORGANISM: Homo Sapiens

<400> SEQUENCE: 633
ggcagaactt ttattgrcta ggagtttctt ttt 33

<210> SEQ ID NO 634
<211> LENGTH: 33
<212> TYPE: DNA
<213> ORGANISM: Homo Sapiens

<400> SEQUENCE: 634
gtgagcacat gcctctrtaa gtgattttaa aat 33

<210> SEQ ID NO 635
<211> LENGTH: 33
<212> TYPE: DNA
<213> ORGANISM: Homo Sapiens

<400> SEQUENCE: 635
aagagccagg gttgacrgct ctcagagaga aga 33

<210> SEQ ID NO 636
<211> LENGTH: 33
<212> TYPE: DNA
<213> ORGANISM: Homo Sapiens

<400> SEQUENCE: 636
gaatgtttga acatctrtag taatattgaa cca 33

<210> SEQ ID NO 637
<211> LENGTH: 33
<212> TYPE: DNA
<213> ORGANISM: Homo Sapiens

<400> SEQUENCE: 637
ttctacagaa atacaarctg tcttatgagt aaa 33

<210> SEQ ID NO 638
<211> LENGTH: 33
<212> TYPE: DNA
<213> ORGANISM: Homo Sapiens

<400> SEQUENCE: 638
agaagtaaaa cagttcrtat aaaagtgaat ttt 33

<210> SEQ ID NO 639
<211> LENGTH: 33
<212> TYPE: DNA
<213> ORGANISM: Homo Sapiens

<400> SEQUENCE: 639
gaaaggagga atttctrttt caagcgacac cgt 33

<210> SEQ ID NO 640
<211> LENGTH: 33
<212> TYPE: DNA
<213> ORGANISM: Homo Sapiens

<400> SEQUENCE: 640

-continued ttagtatatt gtatccrgtg aatttcgcta aat          33

<210> SEQ ID NO 641
<211> LENGTH: 33
<212> TYPE: DNA
<213> ORGANISM: Homo Sapiens

<400> SEQUENCE: 641
ctgggattac aagcatragc caccaggcct agc          33

<210> SEQ ID NO 642
<211> LENGTH: 33
<212> TYPE: DNA
<213> ORGANISM: Homo Sapiens

<400> SEQUENCE: 642
actttggaag tgtcaargtc atggaagaca aag          33

<210> SEQ ID NO 643
<211> LENGTH: 33
<212> TYPE: DNA
<213> ORGANISM: Homo Sapiens

<400> SEQUENCE: 643
tttaattaca gtcattrcct ttgttttttc tca          33

<210> SEQ ID NO 644
<211> LENGTH: 33
<212> TYPE: DNA
<213> ORGANISM: Homo Sapiens

<400> SEQUENCE: 644
atgaaaataa aaaaacmatg taaacatttg gga          33

<210> SEQ ID NO 645
<211> LENGTH: 33
<212> TYPE: DNA
<213> ORGANISM: Homo Sapiens

<400> SEQUENCE: 645
tgataactac tggcccrtct caaggcaaga tga          33

<210> SEQ ID NO 646
<211> LENGTH: 33
<212> TYPE: DNA
<213> ORGANISM: Homo Sapiens

<400> SEQUENCE: 646
tgagtcccaa gccaggmaca tggcatcccc tga          33

<210> SEQ ID NO 647
<211> LENGTH: 33
<212> TYPE: DNA
<213> ORGANISM: Homo Sapiens

<400> SEQUENCE: 647
atgctgctga ggccctrggc ttctatggta gat          33

<210> SEQ ID NO 648
<211> LENGTH: 33
<212> TYPE: DNA
<213> ORGANISM: Homo Sapiens

<400> SEQUENCE: 648
tctcgctttt gctctcrctc tcactctgta gcc 33

<210> SEQ ID NO 649
<211> LENGTH: 33
<212> TYPE: DNA
<213> ORGANISM: Homo Sapiens

<400> SEQUENCE: 649
atttaagttt cccctcrcct atcactatgt gct 33

<210> SEQ ID NO 650
<211> LENGTH: 33
<212> TYPE: DNA
<213> ORGANISM: Homo Sapiens

<400> SEQUENCE: 650
tagtaaatgg tattggrtga actgagtagc cat 33

<210> SEQ ID NO 651
<211> LENGTH: 33
<212> TYPE: DNA
<213> ORGANISM: Homo Sapiens

<400> SEQUENCE: 651
ttcatttacc aatcacrtac cttttttgtc att 33

<210> SEQ ID NO 652
<211> LENGTH: 33
<212> TYPE: DNA
<213> ORGANISM: Homo Sapiens

<400> SEQUENCE: 652
tattggttca gccctgmaac acaggccatc ttg 33

<210> SEQ ID NO 653
<211> LENGTH: 33
<212> TYPE: DNA
<213> ORGANISM: Homo Sapiens

<400> SEQUENCE: 653
ggaaagaaac tagtttrtct caactctgta ttc 33

<210> SEQ ID NO 654
<211> LENGTH: 33
<212> TYPE: DNA
<213> ORGANISM: Homo Sapiens

<400> SEQUENCE: 654
gatcttctct accttgrtat aaaaatcacc tca 33

<210> SEQ ID NO 655
<211> LENGTH: 33
<212> TYPE: DNA
<213> ORGANISM: Homo Sapiens

<400> SEQUENCE: 655
ttggttaatt tgaactmttc cctctgatat att 33

<210> SEQ ID NO 656
<211> LENGTH: 33
<212> TYPE: DNA
<213> ORGANISM: Homo Sapiens

<400> SEQUENCE: 656
ataccaggcc atacttrgcc atcaaaagtt tga 33

<210> SEQ ID NO 657
<211> LENGTH: 33
<212> TYPE: DNA
<213> ORGANISM: Homo Sapiens

<400> SEQUENCE: 657
tgctaatctg ttccttrtaa attttcacac aaa 33

<210> SEQ ID NO 658
<211> LENGTH: 33
<212> TYPE: DNA
<213> ORGANISM: Homo Sapiens

<400> SEQUENCE: 658
gcggccggcc gccaatrgaa tcttgctcct act 33

<210> SEQ ID NO 659
<211> LENGTH: 33
<212> TYPE: DNA
<213> ORGANISM: Homo Sapiens

<400> SEQUENCE: 659
tattttcaac aaacagrata ggactatttt cac 33

<210> SEQ ID NO 660
<211> LENGTH: 33
<212> TYPE: DNA
<213> ORGANISM: Homo Sapiens

<400> SEQUENCE: 660
agagagtcta ggtgagrcac ttcatcacaa cca 33

<210> SEQ ID NO 661
<211> LENGTH: 33
<212> TYPE: DNA
<213> ORGANISM: Homo Sapiens

<400> SEQUENCE: 661
tctctctcaa aatcatrcac ttctttccac tac 33

<210> SEQ ID NO 662
<211> LENGTH: 33
<212> TYPE: DNA
<213> ORGANISM: Homo Sapiens

<400> SEQUENCE: 662
atctgatgtg caggtargaa atgtcacagg agg 33

<210> SEQ ID NO 663
<211> LENGTH: 33
<212> TYPE: DNA
<213> ORGANISM: Homo Sapiens

<400> SEQUENCE: 663
tgagggggaa agcaacrtag atactgggaa caa 33

<210> SEQ ID NO 664
<211> LENGTH: 33
<212> TYPE: DNA

<213> ORGANISM: Homo Sapiens

<400> SEQUENCE: 664
ttctggtcaa tgtgctrtat gtacatgaca aat 33

<210> SEQ ID NO 665
<211> LENGTH: 33
<212> TYPE: DNA
<213> ORGANISM: Homo Sapiens

<400> SEQUENCE: 665
ggaggaacaa aaaccarcca gtctctggac tgt 33

<210> SEQ ID NO 666
<211> LENGTH: 33
<212> TYPE: DNA
<213> ORGANISM: Homo Sapiens

<400> SEQUENCE: 666
caatttcatt tccttcrgac atatacccgg agt 33

<210> SEQ ID NO 667
<211> LENGTH: 33
<212> TYPE: DNA
<213> ORGANISM: Homo Sapiens

<400> SEQUENCE: 667
taagaaaagg aatgagraaa cttgattggt gta 33

<210> SEQ ID NO 668
<211> LENGTH: 33
<212> TYPE: DNA
<213> ORGANISM: Homo Sapiens

<400> SEQUENCE: 668
ccatgccaac aacattraga agaacaaggt tgg 33

<210> SEQ ID NO 669
<211> LENGTH: 33
<212> TYPE: DNA
<213> ORGANISM: Homo Sapiens

<400> SEQUENCE: 669
ttagagaaga aatactrtat gacacagatg agg 33

<210> SEQ ID NO 670
<211> LENGTH: 33
<212> TYPE: DNA
<213> ORGANISM: Homo Sapiens

<400> SEQUENCE: 670
gcaattccac ttctggrtat atgccacaaa gta 33

<210> SEQ ID NO 671
<211> LENGTH: 33
<212> TYPE: DNA
<213> ORGANISM: Homo Sapiens

<400> SEQUENCE: 671
cagttcagca cgggggrcag taagcgtcca gcc 33

<210> SEQ ID NO 672
<211> LENGTH: 33

<212> TYPE: DNA
<213> ORGANISM: Homo Sapiens

<400> SEQUENCE: 672
gaatctgtta ctctggraca cagatgcagg gtt 33

<210> SEQ ID NO 673
<211> LENGTH: 33
<212> TYPE: DNA
<213> ORGANISM: Homo Sapiens

<400> SEQUENCE: 673
cccagcagct tacaccrcac ctccctgtta cat 33

<210> SEQ ID NO 674
<211> LENGTH: 33
<212> TYPE: DNA
<213> ORGANISM: Homo Sapiens

<400> SEQUENCE: 674
aatgaagatt caggacracg aagcagtggt aac 33

<210> SEQ ID NO 675
<211> LENGTH: 33
<212> TYPE: DNA
<213> ORGANISM: Homo Sapiens

<400> SEQUENCE: 675
gtaatactcc ttctacratc ctaagatggg tct 33

<210> SEQ ID NO 676
<211> LENGTH: 33
<212> TYPE: DNA
<213> ORGANISM: Homo Sapiens

<400> SEQUENCE: 676
gaatgtctat tctctgratg agcaggggag gag 33

<210> SEQ ID NO 677
<211> LENGTH: 33
<212> TYPE: DNA
<213> ORGANISM: Homo Sapiens

<400> SEQUENCE: 677
atggtcagct ggctttrctg ttcacaacat gtt 33

<210> SEQ ID NO 678
<211> LENGTH: 33
<212> TYPE: DNA
<213> ORGANISM: Homo Sapiens

<400> SEQUENCE: 678
tttccagtct tatttcmggg gctggcggtg gta 33

<210> SEQ ID NO 679
<211> LENGTH: 33
<212> TYPE: DNA
<213> ORGANISM: Homo Sapiens

<400> SEQUENCE: 679
ctttcttgtg agcttgmttt tctccacaat ttg 33

<210> SEQ ID NO 680

-continued

```
<211> LENGTH: 33
<212> TYPE: DNA
<213> ORGANISM: Homo Sapiens

<400> SEQUENCE: 680

tcctgaaaag gtctcarttc tcatcagcca gcg                                  33

<210> SEQ ID NO 681
<211> LENGTH: 33
<212> TYPE: DNA
<213> ORGANISM: Homo Sapiens

<400> SEQUENCE: 681

accaaacttc aagaccraac atagggaacc caa                                  33

<210> SEQ ID NO 682
<211> LENGTH: 33
<212> TYPE: DNA
<213> ORGANISM: Homo Sapiens

<400> SEQUENCE: 682

ctatttgcaa gggagargaa gggcacctaa tat                                  33

<210> SEQ ID NO 683
<211> LENGTH: 33
<212> TYPE: DNA
<213> ORGANISM: Homo Sapiens

<400> SEQUENCE: 683

gaagagcacc acttagrcac ttcagagacc cat                                  33

<210> SEQ ID NO 684
<211> LENGTH: 33
<212> TYPE: DNA
<213> ORGANISM: Homo Sapiens

<400> SEQUENCE: 684

tgaaccagga aactgarggc tcttgtggtc cag                                  33

<210> SEQ ID NO 685
<211> LENGTH: 33
<212> TYPE: DNA
<213> ORGANISM: Homo Sapiens

<400> SEQUENCE: 685

ctaccccttc aacagcratt tactacttga tcc                                  33

<210> SEQ ID NO 686
<211> LENGTH: 33
<212> TYPE: DNA
<213> ORGANISM: Homo Sapiens

<400> SEQUENCE: 686

cttgaattct ttagaartca tagaaattat cct                                  33

<210> SEQ ID NO 687
<211> LENGTH: 33
<212> TYPE: DNA
<213> ORGANISM: Homo Sapiens

<400> SEQUENCE: 687

ggctccctgt cctttcrccc ctcggttcct tcc                                  33
```

<210> SEQ ID NO 688
<211> LENGTH: 33
<212> TYPE: DNA
<213> ORGANISM: Homo Sapiens

<400> SEQUENCE: 688
gagagattac ggagacrgaa gacaggcagc tgg 33

<210> SEQ ID NO 689
<211> LENGTH: 33
<212> TYPE: DNA
<213> ORGANISM: Homo Sapiens

<400> SEQUENCE: 689
atgaaagatg aggggaraga gagatgtgca aaa 33

<210> SEQ ID NO 690
<211> LENGTH: 33
<212> TYPE: DNA
<213> ORGANISM: Homo Sapiens

<400> SEQUENCE: 690
tgcaattcat ccacacmctg aaagatcctg tta 33

<210> SEQ ID NO 691
<211> LENGTH: 33
<212> TYPE: DNA
<213> ORGANISM: Homo Sapiens

<400> SEQUENCE: 691
tgcacctttg ttaaaaraca aatgactgta tgt 33

<210> SEQ ID NO 692
<211> LENGTH: 33
<212> TYPE: DNA
<213> ORGANISM: Homo Sapiens

<400> SEQUENCE: 692
catgctgccc ttttctrctg tctcaaactt gat 33

<210> SEQ ID NO 693
<211> LENGTH: 33
<212> TYPE: DNA
<213> ORGANISM: Homo Sapiens

<400> SEQUENCE: 693
cctgaacatt ataaacraga caagtataaa cag 33

<210> SEQ ID NO 694
<211> LENGTH: 33
<212> TYPE: DNA
<213> ORGANISM: Homo Sapiens

<400> SEQUENCE: 694
tcactgtctt ccatcaraaa aacaaatgat tta 33

<210> SEQ ID NO 695
<211> LENGTH: 33
<212> TYPE: DNA
<213> ORGANISM: Homo Sapiens

<400> SEQUENCE: 695
agggttctat tctttcraac tactccagca gtc 33

<210> SEQ ID NO 696
<211> LENGTH: 33
<212> TYPE: DNA
<213> ORGANISM: Homo Sapiens

<400> SEQUENCE: 696
aatcttttgc tagaatraag tcctttgcat ttt 33

<210> SEQ ID NO 697
<211> LENGTH: 33
<212> TYPE: DNA
<213> ORGANISM: Homo Sapiens

<400> SEQUENCE: 697
tgccttcagc cgaagarttg gttttcactt tgg 33

<210> SEQ ID NO 698
<211> LENGTH: 33
<212> TYPE: DNA
<213> ORGANISM: Homo Sapiens

<400> SEQUENCE: 698
gaatgccctt ttttcartcc tccgtgtgat tgg 33

<210> SEQ ID NO 699
<211> LENGTH: 33
<212> TYPE: DNA
<213> ORGANISM: Homo Sapiens

<400> SEQUENCE: 699
ctgttgttaa acacatrtgc taatttcaaa ata 33

<210> SEQ ID NO 700
<211> LENGTH: 33
<212> TYPE: DNA
<213> ORGANISM: Homo Sapiens

<400> SEQUENCE: 700
aggaggtttg tctttgrttc gcctgcacct tcc 33

<210> SEQ ID NO 701
<211> LENGTH: 33
<212> TYPE: DNA
<213> ORGANISM: Homo Sapiens

<400> SEQUENCE: 701
gtggactagt gcctctrttt tctctaatgc ttt 33

<210> SEQ ID NO 702
<211> LENGTH: 33
<212> TYPE: DNA
<213> ORGANISM: Homo Sapiens

<400> SEQUENCE: 702
tttctcagaa acctctraaa gccatcttct gct 33

<210> SEQ ID NO 703
<211> LENGTH: 33
<212> TYPE: DNA
<213> ORGANISM: Homo Sapiens

<400> SEQUENCE: 703
gtcttctttc atccagsgct cctcggcctt cct 33

<210> SEQ ID NO 704
<211> LENGTH: 33
<212> TYPE: DNA
<213> ORGANISM: Homo Sapiens

<400> SEQUENCE: 704
tccctcttct tcatacrcag ccactgaata gga 33

<210> SEQ ID NO 705
<211> LENGTH: 33
<212> TYPE: DNA
<213> ORGANISM: Homo Sapiens

<400> SEQUENCE: 705
tccctccgtc atgtaamgta ggatggcagt tac 33

<210> SEQ ID NO 706
<211> LENGTH: 33
<212> TYPE: DNA
<213> ORGANISM: Homo Sapiens

<400> SEQUENCE: 706
catgagtcca ctggagrtgt tttgtagact tac 33

<210> SEQ ID NO 707
<211> LENGTH: 33
<212> TYPE: DNA
<213> ORGANISM: Homo Sapiens

<400> SEQUENCE: 707
tacaggacct tggaaamcat gcttgaactt ctt 33

<210> SEQ ID NO 708
<211> LENGTH: 33
<212> TYPE: DNA
<213> ORGANISM: Homo Sapiens

<400> SEQUENCE: 708
aaatgagtga ggaccamagc tgttatgttt ttt 33

<210> SEQ ID NO 709
<211> LENGTH: 33
<212> TYPE: DNA
<213> ORGANISM: Homo Sapiens

<400> SEQUENCE: 709
gcaggatacc cccttgraac aagcagcgaa gat 33

<210> SEQ ID NO 710
<211> LENGTH: 33
<212> TYPE: DNA
<213> ORGANISM: Homo Sapiens

<400> SEQUENCE: 710
cacctgtgtg tatccarcag caagaagact gaa 33

<210> SEQ ID NO 711
<211> LENGTH: 33
<212> TYPE: DNA
<213> ORGANISM: Homo Sapiens

<400> SEQUENCE: 711
ggtttagagt aattcarttt agctgtcatt taa 33

<210> SEQ ID NO 712
<211> LENGTH: 33
<212> TYPE: DNA
<213> ORGANISM: Homo Sapiens

<400> SEQUENCE: 712
atttttgttt tgtaggmgtg aactgctttc ttt 33

<210> SEQ ID NO 713
<211> LENGTH: 33
<212> TYPE: DNA
<213> ORGANISM: Homo Sapiens

<400> SEQUENCE: 713
gtcctggtgg tcaaaarggc ctggacaggc atc 33

<210> SEQ ID NO 714
<211> LENGTH: 33
<212> TYPE: DNA
<213> ORGANISM: Homo Sapiens

<400> SEQUENCE: 714
aaaagacttc ttcaaamgaa actgtgaagt ctc 33

<210> SEQ ID NO 715
<211> LENGTH: 33
<212> TYPE: DNA
<213> ORGANISM: Homo Sapiens

<400> SEQUENCE: 715
gaagaaagtt tagtagrgct gaagtgtgca ttt 33

<210> SEQ ID NO 716
<211> LENGTH: 33
<212> TYPE: DNA
<213> ORGANISM: Homo Sapiens

<400> SEQUENCE: 716
gtaggtagca cacaagrtaa tcatgtcagg atg 33

<210> SEQ ID NO 717
<211> LENGTH: 33
<212> TYPE: DNA
<213> ORGANISM: Homo Sapiens

<400> SEQUENCE: 717
taatagacaa atgttgmaca atagtcaaat tct 33

<210> SEQ ID NO 718
<211> LENGTH: 33
<212> TYPE: DNA
<213> ORGANISM: Homo Sapiens

<400> SEQUENCE: 718
tgcacatcaa tctctcrtat tttgcattta aac 33

<210> SEQ ID NO 719
<211> LENGTH: 33
<212> TYPE: DNA
<213> ORGANISM: Homo Sapiens

<400> SEQUENCE: 719
acctcaggaa aggatcrtgg aacagggagg cct 33

<210> SEQ ID NO 720
<211> LENGTH: 33
<212> TYPE: DNA
<213> ORGANISM: Homo Sapiens

<400> SEQUENCE: 720
caagtttgtt gctttartac taccttgagt ctg 33

<210> SEQ ID NO 721
<211> LENGTH: 33
<212> TYPE: DNA
<213> ORGANISM: Homo Sapiens

<400> SEQUENCE: 721
gtttcctagc ttgaaamacg aagagaagaa aag 33

<210> SEQ ID NO 722
<211> LENGTH: 33
<212> TYPE: DNA
<213> ORGANISM: Homo Sapiens

<400> SEQUENCE: 722
tgactcacca tcaggargga tctgctgcac tgg 33

<210> SEQ ID NO 723
<211> LENGTH: 33
<212> TYPE: DNA
<213> ORGANISM: Homo Sapiens

<400> SEQUENCE: 723
tactgaaaaa gagaatraac aacataacag tca 33

<210> SEQ ID NO 724
<211> LENGTH: 33
<212> TYPE: DNA
<213> ORGANISM: Homo Sapiens

<400> SEQUENCE: 724
cttacttacc tagaggrcat atgtctgcta ctg 33

<210> SEQ ID NO 725
<211> LENGTH: 33
<212> TYPE: DNA
<213> ORGANISM: Homo Sapiens

<400> SEQUENCE: 725
tataattaag gttaatrgtg agattgtttg gct 33

<210> SEQ ID NO 726
<211> LENGTH: 33
<212> TYPE: DNA
<213> ORGANISM: Homo Sapiens

<400> SEQUENCE: 726
ttgacttatc tatggarttt ttgactattt ctg 33

<210> SEQ ID NO 727
<211> LENGTH: 33
<212> TYPE: DNA
<213> ORGANISM: Homo Sapiens

<400> SEQUENCE: 727
taacataata gaaattract gacatatgta tgg 33

<210> SEQ ID NO 728
<211> LENGTH: 33
<212> TYPE: DNA
<213> ORGANISM: Homo Sapiens

<400> SEQUENCE: 728
atccatagaa acagacrtta attaaataac aca 33

<210> SEQ ID NO 729
<211> LENGTH: 33
<212> TYPE: DNA
<213> ORGANISM: Homo Sapiens

<400> SEQUENCE: 729
tttcatatca gaggcarcct ctcaaccaga tgt 33

<210> SEQ ID NO 730
<211> LENGTH: 33
<212> TYPE: DNA
<213> ORGANISM: Homo Sapiens

<400> SEQUENCE: 730
tggccagaaa gagagamaga gagacagaga cag 33

<210> SEQ ID NO 731
<211> LENGTH: 33
<212> TYPE: DNA
<213> ORGANISM: Homo Sapiens

<400> SEQUENCE: 731
aaataggacc cttgacrcac aaaggaattt tgg 33

<210> SEQ ID NO 732
<211> LENGTH: 33
<212> TYPE: DNA
<213> ORGANISM: Homo Sapiens

<400> SEQUENCE: 732
tggaagggcg tgctgcrgcc cggcacggcc ctg 33

<210> SEQ ID NO 733
<211> LENGTH: 33
<212> TYPE: DNA
<213> ORGANISM: Homo Sapiens

<400> SEQUENCE: 733
acacttggta cccttgrtac atttaatagt aaa 33

<210> SEQ ID NO 734
<211> LENGTH: 33
<212> TYPE: DNA
<213> ORGANISM: Homo Sapiens

<400> SEQUENCE: 734
ccacctgtgc gccaggrcat acactggctg cac 33

<210> SEQ ID NO 735
<211> LENGTH: 33
<212> TYPE: DNA
<213> ORGANISM: Homo Sapiens

<400> SEQUENCE: 735
ctatcattat cgattcyacc cagcaatttc tct 33

<210> SEQ ID NO 736
<211> LENGTH: 33
<212> TYPE: DNA
<213> ORGANISM: Homo Sapiens

<400> SEQUENCE: 736
atctgctata caacatmctc agtccccctc atc 33

<210> SEQ ID NO 737
<211> LENGTH: 33
<212> TYPE: DNA
<213> ORGANISM: Homo Sapiens

<400> SEQUENCE: 737
gttgaaggat ccaggartat tttcttcttg ggt 33

<210> SEQ ID NO 738
<211> LENGTH: 33
<212> TYPE: DNA
<213> ORGANISM: Homo Sapiens

<400> SEQUENCE: 738
tgtcactttc agtatarata aaactcttta gaa 33

<210> SEQ ID NO 739
<211> LENGTH: 33
<212> TYPE: DNA
<213> ORGANISM: Homo Sapiens

<400> SEQUENCE: 739
ctacattata aattatrctt gataccagac atc 33

<210> SEQ ID NO 740
<211> LENGTH: 33
<212> TYPE: DNA
<213> ORGANISM: Homo Sapiens

<400> SEQUENCE: 740
actgatatca ttccctmcct gaaatatccc atg 33

<210> SEQ ID NO 741
<211> LENGTH: 33
<212> TYPE: DNA
<213> ORGANISM: Homo Sapiens

<400> SEQUENCE: 741
ggcaaggaga gcaccartttt aggaaatgtt aga 33

<210> SEQ ID NO 742
<211> LENGTH: 33
<212> TYPE: DNA
<213> ORGANISM: Homo Sapiens

<400> SEQUENCE: 742
gaataagaat actaacrttt atcccctgca ttt 33

<210> SEQ ID NO 743
<211> LENGTH: 33
<212> TYPE: DNA

<213> ORGANISM: Homo Sapiens

<400> SEQUENCE: 743
caatgggatt tggtaamtat tttcttatct ttg 33

<210> SEQ ID NO 744
<211> LENGTH: 33
<212> TYPE: DNA
<213> ORGANISM: Homo Sapiens

<400> SEQUENCE: 744
aaaaaagtac taattcrgaa aagatataaa agt 33

<210> SEQ ID NO 745
<211> LENGTH: 33
<212> TYPE: DNA
<213> ORGANISM: Homo Sapiens

<400> SEQUENCE: 745
atcagagtat atgccamagc gggtttcgta tcc 33

<210> SEQ ID NO 746
<211> LENGTH: 33
<212> TYPE: DNA
<213> ORGANISM: Homo Sapiens

<400> SEQUENCE: 746
tactaagcat tattctrtag atggaatata taa 33

<210> SEQ ID NO 747
<211> LENGTH: 33
<212> TYPE: DNA
<213> ORGANISM: Homo Sapiens

<400> SEQUENCE: 747
gagacttcac tctgacrtct ttctcttttt gga 33

<210> SEQ ID NO 748
<211> LENGTH: 33
<212> TYPE: DNA
<213> ORGANISM: Homo Sapiens

<400> SEQUENCE: 748
caagtgctct ctcaacrtgt tcaatattac taa 33

<210> SEQ ID NO 749
<211> LENGTH: 33
<212> TYPE: DNA
<213> ORGANISM: Homo Sapiens

<400> SEQUENCE: 749
gtttctaaat atgtcaragt agatattaaa gaa 33

<210> SEQ ID NO 750
<211> LENGTH: 33
<212> TYPE: DNA
<213> ORGANISM: Homo Sapiens

<400> SEQUENCE: 750
gcggggccgc tggacascgc ggggagttcg acg 33

<210> SEQ ID NO 751
<211> LENGTH: 33

<212> TYPE: DNA
<213> ORGANISM: Homo Sapiens

<400> SEQUENCE: 751
ggtgttgaga ctcatartaa ctcagtaaca cct 33

<210> SEQ ID NO 752
<211> LENGTH: 33
<212> TYPE: DNA
<213> ORGANISM: Homo Sapiens

<400> SEQUENCE: 752
tggaaactaa aggggamtac ttatttatga ctt 33

<210> SEQ ID NO 753
<211> LENGTH: 33
<212> TYPE: DNA
<213> ORGANISM: Homo Sapiens

<400> SEQUENCE: 753
ctttgacccc agtggartgc tctctcctgc aaa 33

<210> SEQ ID NO 754
<211> LENGTH: 33
<212> TYPE: DNA
<213> ORGANISM: Homo Sapiens

<400> SEQUENCE: 754
ttagcatgtg tggaatrttt tccatattat gta 33

<210> SEQ ID NO 755
<211> LENGTH: 33
<212> TYPE: DNA
<213> ORGANISM: Homo Sapiens

<400> SEQUENCE: 755
accatgggat tccaatmcat tgcaagtatt tca 33

<210> SEQ ID NO 756
<211> LENGTH: 33
<212> TYPE: DNA
<213> ORGANISM: Homo Sapiens

<400> SEQUENCE: 756
gcagtctctc ccttgamaca tccttcccct tcc 33

<210> SEQ ID NO 757
<211> LENGTH: 33
<212> TYPE: DNA
<213> ORGANISM: Homo Sapiens

<400> SEQUENCE: 757
tccagacaca agtcacragt tcaggggttc aca 33

<210> SEQ ID NO 758
<211> LENGTH: 33
<212> TYPE: DNA
<213> ORGANISM: Homo Sapiens

<400> SEQUENCE: 758
cccccaataa caggaargag attcctttgt tcc 33

<210> SEQ ID NO 759

<211> LENGTH: 33
<212> TYPE: DNA
<213> ORGANISM: Homo Sapiens

<400> SEQUENCE: 759
cttctttggc ttctcartgc actctgaatg aaa 33

<210> SEQ ID NO 760
<211> LENGTH: 33
<212> TYPE: DNA
<213> ORGANISM: Homo Sapiens

<400> SEQUENCE: 760
cactgcctga gatagamgtt tgcatcttat tgg 33

<210> SEQ ID NO 761
<211> LENGTH: 33
<212> TYPE: DNA
<213> ORGANISM: Homo Sapiens

<400> SEQUENCE: 761
tttttcttat tgattcmtag gagttcttta cat 33

<210> SEQ ID NO 762
<211> LENGTH: 33
<212> TYPE: DNA
<213> ORGANISM: Homo Sapiens

<400> SEQUENCE: 762
tttattgata gtttacrctg ctggaaatat aat 33

<210> SEQ ID NO 763
<211> LENGTH: 33
<212> TYPE: DNA
<213> ORGANISM: Homo Sapiens

<400> SEQUENCE: 763
agacctgaag agcaggracc ctggtggatt ttt 33

<210> SEQ ID NO 764
<211> LENGTH: 33
<212> TYPE: DNA
<213> ORGANISM: Homo Sapiens

<400> SEQUENCE: 764
tcaagtttcc ttttgtrtcc ctggcgaact tta 33

<210> SEQ ID NO 765
<211> LENGTH: 33
<212> TYPE: DNA
<213> ORGANISM: Homo Sapiens

<400> SEQUENCE: 765
tatggttttt ggatttmgca tttagttaat gac 33

<210> SEQ ID NO 766
<211> LENGTH: 33
<212> TYPE: DNA
<213> ORGANISM: Homo Sapiens

<400> SEQUENCE: 766
tcctgtacag gtgcatrtgg atgtgctatg tgt 33

<210> SEQ ID NO 767
<211> LENGTH: 33
<212> TYPE: DNA
<213> ORGANISM: Homo Sapiens

<400> SEQUENCE: 767
aaattctatg ccaagcrctt tcatatacaa tat 33

<210> SEQ ID NO 768
<211> LENGTH: 33
<212> TYPE: DNA
<213> ORGANISM: Homo Sapiens

<400> SEQUENCE: 768
gccattcttt ctattcrgtc aatatgaaag aca 33

<210> SEQ ID NO 769
<211> LENGTH: 33
<212> TYPE: DNA
<213> ORGANISM: Homo Sapiens

<400> SEQUENCE: 769
cctgttgtta attcccratc aatagtcccg aga 33

<210> SEQ ID NO 770
<211> LENGTH: 33
<212> TYPE: DNA
<213> ORGANISM: Homo Sapiens

<400> SEQUENCE: 770
gctccagggc tgggacmctt tctgagcctc ctc 33

<210> SEQ ID NO 771
<211> LENGTH: 33
<212> TYPE: DNA
<213> ORGANISM: Homo Sapiens

<400> SEQUENCE: 771
gatgtaggta accatcrtta tgggacccca gag 33

<210> SEQ ID NO 772
<211> LENGTH: 33
<212> TYPE: DNA
<213> ORGANISM: Homo Sapiens

<400> SEQUENCE: 772
gcaacagggg tactagrgca tcatgaaatt cac 33

<210> SEQ ID NO 773
<211> LENGTH: 33
<212> TYPE: DNA
<213> ORGANISM: Homo Sapiens

<400> SEQUENCE: 773
ctacacagtc gtgtgarcca atccctccaa ata 33

<210> SEQ ID NO 774
<211> LENGTH: 33
<212> TYPE: DNA
<213> ORGANISM: Homo Sapiens

<400> SEQUENCE: 774
aggctctgtg atgggcrcag gaacacactg agg 33

<210> SEQ ID NO 775
<211> LENGTH: 33
<212> TYPE: DNA
<213> ORGANISM: Homo Sapiens

<400> SEQUENCE: 775
ttgtgccgtt attaatkcca tttgttattt cat 33

<210> SEQ ID NO 776
<211> LENGTH: 33
<212> TYPE: DNA
<213> ORGANISM: Homo Sapiens

<400> SEQUENCE: 776
gcttgcagta gcgcgamatg gttagctacc ttc 33

<210> SEQ ID NO 777
<211> LENGTH: 33
<212> TYPE: DNA
<213> ORGANISM: Homo Sapiens

<400> SEQUENCE: 777
gccttgcgga ccaccartgg gaaagcagac tcc 33

<210> SEQ ID NO 778
<211> LENGTH: 33
<212> TYPE: DNA
<213> ORGANISM: Homo Sapiens

<400> SEQUENCE: 778
cttgatgtgt caggacmatt ttgttgctgt agg 33

<210> SEQ ID NO 779
<211> LENGTH: 33
<212> TYPE: DNA
<213> ORGANISM: Homo Sapiens

<400> SEQUENCE: 779
ctcgctactg atggacrttc acatttaaat ttt 33

<210> SEQ ID NO 780
<211> LENGTH: 33
<212> TYPE: DNA
<213> ORGANISM: Homo Sapiens

<400> SEQUENCE: 780
actgaaatat agccagmaat aaataatcat gct 33

<210> SEQ ID NO 781
<211> LENGTH: 33
<212> TYPE: DNA
<213> ORGANISM: Homo Sapiens

<400> SEQUENCE: 781
ctcctatatt caacagraca gcaaatgaag act 33

<210> SEQ ID NO 782
<211> LENGTH: 33
<212> TYPE: DNA
<213> ORGANISM: Homo Sapiens

<400> SEQUENCE: 782
atgaaaatat aaaatcratt gtggtgatgg ttt 33

<210> SEQ ID NO 783
<211> LENGTH: 33
<212> TYPE: DNA
<213> ORGANISM: Homo Sapiens

<400> SEQUENCE: 783
agctcagaaa atctcaytgg aacccttgaa gta 33

<210> SEQ ID NO 784
<211> LENGTH: 33
<212> TYPE: DNA
<213> ORGANISM: Homo Sapiens

<400> SEQUENCE: 784
cggggtttaa gaggacraca ggtgtctgta ttg 33

<210> SEQ ID NO 785
<211> LENGTH: 33
<212> TYPE: DNA
<213> ORGANISM: Homo Sapiens

<400> SEQUENCE: 785
atcagagcca agacccrgcc ctcaagtcct cct 33

<210> SEQ ID NO 786
<211> LENGTH: 33
<212> TYPE: DNA
<213> ORGANISM: Homo Sapiens

<400> SEQUENCE: 786
tgtggaaggg gaggtcmgtc agccagcatt aag 33

<210> SEQ ID NO 787
<211> LENGTH: 33
<212> TYPE: DNA
<213> ORGANISM: Homo Sapiens

<400> SEQUENCE: 787
gatttttctc tcctctraaa gagcaatttt ctc 33

<210> SEQ ID NO 788
<211> LENGTH: 33
<212> TYPE: DNA
<213> ORGANISM: Homo Sapiens

<400> SEQUENCE: 788
acaggaaact tcaaccmagt atcaagttac taa 33

<210> SEQ ID NO 789
<211> LENGTH: 33
<212> TYPE: DNA
<213> ORGANISM: Homo Sapiens

<400> SEQUENCE: 789
cctcttcaga gggaatrtgg tcctgtggac acc 33

<210> SEQ ID NO 790
<211> LENGTH: 33
<212> TYPE: DNA
<213> ORGANISM: Homo Sapiens

<400> SEQUENCE: 790
ggacccaggg aatctcrccc tggctcttcc tcc 33

<210> SEQ ID NO 791
<211> LENGTH: 33
<212> TYPE: DNA
<213> ORGANISM: Homo Sapiens

<400> SEQUENCE: 791
cactgatatc gaatgtrtct tggagtgaga aag 33

<210> SEQ ID NO 792
<211> LENGTH: 33
<212> TYPE: DNA
<213> ORGANISM: Homo Sapiens

<400> SEQUENCE: 792
ggaattaaca gccacartgc aagcttcttg ctg 33

<210> SEQ ID NO 793
<211> LENGTH: 33
<212> TYPE: DNA
<213> ORGANISM: Homo Sapiens

<400> SEQUENCE: 793
ggatccatgg cctggcratt ccaggtctgg gtt 33

<210> SEQ ID NO 794
<211> LENGTH: 33
<212> TYPE: DNA
<213> ORGANISM: Homo Sapiens

<400> SEQUENCE: 794
tgttctaggg ccaaccrggg gatcggagga gtc 33

<210> SEQ ID NO 795
<211> LENGTH: 33
<212> TYPE: DNA
<213> ORGANISM: Homo Sapiens

<400> SEQUENCE: 795
gggcagagta cttatcrtat gtgcatacta tat 33

<210> SEQ ID NO 796
<211> LENGTH: 33
<212> TYPE: DNA
<213> ORGANISM: Homo Sapiens

<400> SEQUENCE: 796
ctcataacat tttcccrcta gaaataatgt gtg 33

<210> SEQ ID NO 797
<211> LENGTH: 33
<212> TYPE: DNA
<213> ORGANISM: Homo Sapiens

<400> SEQUENCE: 797
cttctatttt gctgttrctg ttttgcattt gag 33

<210> SEQ ID NO 798
<211> LENGTH: 33
<212> TYPE: DNA
<213> ORGANISM: Homo Sapiens

<400> SEQUENCE: 798
atccagtggg aaagtcrgtt gcatcctatg ttt 33

<210> SEQ ID NO 799
<211> LENGTH: 33
<212> TYPE: DNA
<213> ORGANISM: Homo Sapiens

<400> SEQUENCE: 799
tatgtttgtg gtccttrtaa ctgacttctg ctt 33

<210> SEQ ID NO 800
<211> LENGTH: 33
<212> TYPE: DNA
<213> ORGANISM: Homo Sapiens

<400> SEQUENCE: 800
tatggaaatg atatggrata cataggaatg gcg 33

<210> SEQ ID NO 801
<211> LENGTH: 33
<212> TYPE: DNA
<213> ORGANISM: Homo Sapiens

<400> SEQUENCE: 801
aatacatagc agttgcrata tccattttgg gta 33

<210> SEQ ID NO 802
<211> LENGTH: 33
<212> TYPE: DNA
<213> ORGANISM: Homo Sapiens

<400> SEQUENCE: 802
tgcttagcag ggcactrgga aatgcacttc agt 33

<210> SEQ ID NO 803
<211> LENGTH: 33
<212> TYPE: DNA
<213> ORGANISM: Homo Sapiens

<400> SEQUENCE: 803
ttaatttgca ttttcaraaa gactaccttg gct 33

<210> SEQ ID NO 804
<211> LENGTH: 33
<212> TYPE: DNA
<213> ORGANISM: Homo Sapiens

<400> SEQUENCE: 804
tgcctctaag atattgkaca cacaaatgaa gca 33

<210> SEQ ID NO 805
<211> LENGTH: 33
<212> TYPE: DNA
<213> ORGANISM: Homo Sapiens

<400> SEQUENCE: 805
actaactcca aacaagmatc aacagtaaaa tta 33

<210> SEQ ID NO 806
<211> LENGTH: 33
<212> TYPE: DNA
<213> ORGANISM: Homo Sapiens

<400> SEQUENCE: 806
tcacatatga tagattmggc aattgagtta tat 33

<210> SEQ ID NO 807
<211> LENGTH: 33
<212> TYPE: DNA
<213> ORGANISM: Homo Sapiens

<400> SEQUENCE: 807
gctgtttaaa tgtttamttg atgatggaat gtg 33

<210> SEQ ID NO 808
<211> LENGTH: 33
<212> TYPE: DNA
<213> ORGANISM: Homo Sapiens

<400> SEQUENCE: 808
gtgtgtgtga acaagcrcaa agtccatatc cag 33

<210> SEQ ID NO 809
<211> LENGTH: 33
<212> TYPE: DNA
<213> ORGANISM: Homo Sapiens

<400> SEQUENCE: 809
agtaatgcca actacaratt atgaaatatt tca 33

<210> SEQ ID NO 810
<211> LENGTH: 33
<212> TYPE: DNA
<213> ORGANISM: Homo Sapiens

<400> SEQUENCE: 810
ggagtttccc tatcccrggc tgcagtgcaa tgg 33

<210> SEQ ID NO 811
<211> LENGTH: 33
<212> TYPE: DNA
<213> ORGANISM: Homo Sapiens

<400> SEQUENCE: 811
atggggctca ctgcctrtaa cttcaaggaa gca 33

<210> SEQ ID NO 812
<211> LENGTH: 33
<212> TYPE: DNA
<213> ORGANISM: Homo Sapiens

<400> SEQUENCE: 812
ataagaaaat atccagmact gagtgtatgt tta 33

<210> SEQ ID NO 813
<211> LENGTH: 33
<212> TYPE: DNA
<213> ORGANISM: Homo Sapiens

<400> SEQUENCE: 813
tcaagtcatc agattgmatc tccccacctg cca 33

<210> SEQ ID NO 814
<211> LENGTH: 33
<212> TYPE: DNA
<213> ORGANISM: Homo Sapiens

<400> SEQUENCE: 814
cgcccaccac tgtgccrgaa tgtgatgcac aca 33

<210> SEQ ID NO 815
<211> LENGTH: 33
<212> TYPE: DNA
<213> ORGANISM: Homo Sapiens

<400> SEQUENCE: 815
agagatcaca ccccgamctc cagctcccac gtg 33

<210> SEQ ID NO 816
<211> LENGTH: 33
<212> TYPE: DNA
<213> ORGANISM: Homo Sapiens

<400> SEQUENCE: 816
gcacaccctg aaccaargaa aacacagaag aaa 33

<210> SEQ ID NO 817
<211> LENGTH: 33
<212> TYPE: DNA
<213> ORGANISM: Homo Sapiens

<400> SEQUENCE: 817
ggtccaaaaa tatcacrgta cttcgagaga cca 33

<210> SEQ ID NO 818
<211> LENGTH: 33
<212> TYPE: DNA
<213> ORGANISM: Homo Sapiens

<400> SEQUENCE: 818
cacctcccca tctgtgrccc tctgtgacac acg 33

<210> SEQ ID NO 819
<211> LENGTH: 33
<212> TYPE: DNA
<213> ORGANISM: Homo Sapiens

<400> SEQUENCE: 819
acctaccatg tttatcrgaa atctcagcct aaa 33

<210> SEQ ID NO 820
<211> LENGTH: 33
<212> TYPE: DNA
<213> ORGANISM: Homo Sapiens

<400> SEQUENCE: 820
aatgactggc tctaaarctg ggtctctgtt cac 33

<210> SEQ ID NO 821
<211> LENGTH: 33
<212> TYPE: DNA
<213> ORGANISM: Homo Sapiens

<400> SEQUENCE: 821
gcaatgttta aaaacarcat tttgggctgg gcg 33

<210> SEQ ID NO 822
<211> LENGTH: 33
<212> TYPE: DNA

<213> ORGANISM: Homo Sapiens

<400> SEQUENCE: 822
ggtgggtgct gatgagrgaa ggcaggagat gca 33

<210> SEQ ID NO 823
<211> LENGTH: 33
<212> TYPE: DNA
<213> ORGANISM: Homo Sapiens

<400> SEQUENCE: 823
tttatctaat ctgatgrtct ctgctctttt tat 33

<210> SEQ ID NO 824
<211> LENGTH: 33
<212> TYPE: DNA
<213> ORGANISM: Homo Sapiens

<400> SEQUENCE: 824
cctgccgcct agggagrttg tgctctgccc ctc 33

<210> SEQ ID NO 825
<211> LENGTH: 33
<212> TYPE: DNA
<213> ORGANISM: Homo Sapiens

<400> SEQUENCE: 825
ccactaaaat tctacartca gaatgcttgg caa 33

<210> SEQ ID NO 826
<211> LENGTH: 33
<212> TYPE: DNA
<213> ORGANISM: Homo Sapiens

<400> SEQUENCE: 826
ctagaagccg aggacartga gatctcttct tct 33

<210> SEQ ID NO 827
<211> LENGTH: 33
<212> TYPE: DNA
<213> ORGANISM: Homo Sapiens

<400> SEQUENCE: 827
ccctcccttt agtcagrgat tattctgggg acc 33

<210> SEQ ID NO 828
<211> LENGTH: 33
<212> TYPE: DNA
<213> ORGANISM: Homo Sapiens

<400> SEQUENCE: 828
tgctaacagc tctaccrtga tgacaaggcc att 33

<210> SEQ ID NO 829
<211> LENGTH: 33
<212> TYPE: DNA
<213> ORGANISM: Homo Sapiens

<400> SEQUENCE: 829
gggttactat ggtgatragg attaggataa tgg 33

<210> SEQ ID NO 830
<211> LENGTH: 33

<212> TYPE: DNA
<213> ORGANISM: Homo Sapiens

<400> SEQUENCE: 830
tgcccccacc acaaccragg acagtgtctt gcc 33

<210> SEQ ID NO 831
<211> LENGTH: 33
<212> TYPE: DNA
<213> ORGANISM: Homo Sapiens

<400> SEQUENCE: 831
ggacccagta tcttcarggt agcatttttg aac 33

<210> SEQ ID NO 832
<211> LENGTH: 33
<212> TYPE: DNA
<213> ORGANISM: Homo Sapiens

<400> SEQUENCE: 832
ctgacagaag gactgcrgct gaatttcaca ttt 33

<210> SEQ ID NO 833
<211> LENGTH: 33
<212> TYPE: DNA
<213> ORGANISM: Homo Sapiens

<400> SEQUENCE: 833
tggcctccag cactggrtcg cgccttgggg cca 33

<210> SEQ ID NO 834
<211> LENGTH: 33
<212> TYPE: DNA
<213> ORGANISM: Homo Sapiens

<400> SEQUENCE: 834 tttttcaat gctgacrcag agtgatttaa aaa 33

<210> SEQ ID NO 835
<211> LENGTH: 33
<212> TYPE: DNA
<213> ORGANISM: Homo Sapiens

<400> SEQUENCE: 835
ccttgggtag ctatcargta catgcctaac ttg 33

<210> SEQ ID NO 836
<211> LENGTH: 33
<212> TYPE: DNA
<213> ORGANISM: Homo Sapiens

<400> SEQUENCE: 836
gtgtgaccag agcagcrgtg actgctggtg tgt 33

<210> SEQ ID NO 837
<211> LENGTH: 33
<212> TYPE: DNA
<213> ORGANISM: Homo Sapiens

<400> SEQUENCE: 837
tagggcacgg gagaagraca tcgaggccgc agg 33

<210> SEQ ID NO 838

<211> LENGTH: 33
<212> TYPE: DNA
<213> ORGANISM: Homo Sapiens

<400> SEQUENCE: 838
ggcagctagg gactgargca gcgtagcata aca 33

<210> SEQ ID NO 839
<211> LENGTH: 33
<212> TYPE: DNA
<213> ORGANISM: Homo Sapiens

<400> SEQUENCE: 839
gttcgactgc aggaaarccc tacaggttgc tgg 33

<210> SEQ ID NO 840
<211> LENGTH: 33
<212> TYPE: DNA
<213> ORGANISM: Homo Sapiens

<400> SEQUENCE: 840
ctttcctggg gatgctmatt gaggttggaa aga 33

<210> SEQ ID NO 841
<211> LENGTH: 33
<212> TYPE: DNA
<213> ORGANISM: Homo Sapiens

<400> SEQUENCE: 841
ctggttttcc taatcaraga aagcttcaaa gaa 33

<210> SEQ ID NO 842
<211> LENGTH: 33
<212> TYPE: DNA
<213> ORGANISM: Homo Sapiens

<400> SEQUENCE: 842
tattagcaga ctcaccrcaa aaggatatgc cag 33

<210> SEQ ID NO 843
<211> LENGTH: 33
<212> TYPE: DNA
<213> ORGANISM: Homo Sapiens

<400> SEQUENCE: 843
acagcacaag aggatgrtga gtgggtatat agt 33

<210> SEQ ID NO 844
<211> LENGTH: 33
<212> TYPE: DNA
<213> ORGANISM: Homo Sapiens

<400> SEQUENCE: 844
gaagcccagg atgaaamagg gttgttcaat gtc 33

<210> SEQ ID NO 845
<211> LENGTH: 33
<212> TYPE: DNA
<213> ORGANISM: Homo Sapiens

<400> SEQUENCE: 845
cacagacatg caaattrgga tgtggaacca ctt 33

<210> SEQ ID NO 846
<211> LENGTH: 33
<212> TYPE: DNA
<213> ORGANISM: Homo Sapiens

<400> SEQUENCE: 846
gggaatagat gcagaaytgg caaagaagca aga 33

<210> SEQ ID NO 847
<211> LENGTH: 33
<212> TYPE: DNA
<213> ORGANISM: Homo Sapiens

<400> SEQUENCE: 847
gcaggctttc atgtgtrtta actattaagg ctc 33

<210> SEQ ID NO 848
<211> LENGTH: 33
<212> TYPE: DNA
<213> ORGANISM: Homo Sapiens

<400> SEQUENCE: 848
aacaaattcc atatgtratt aggatgtaca tgc 33

<210> SEQ ID NO 849
<211> LENGTH: 33
<212> TYPE: DNA
<213> ORGANISM: Homo Sapiens

<400> SEQUENCE: 849
tccccctacc attcatmcat cattgatttt agg 33

<210> SEQ ID NO 850
<211> LENGTH: 33
<212> TYPE: DNA
<213> ORGANISM: Homo Sapiens

<400> SEQUENCE: 850
ttgtggtata tatacartaa tatcctccaa tgc 33

<210> SEQ ID NO 851
<211> LENGTH: 33
<212> TYPE: DNA
<213> ORGANISM: Homo Sapiens

<400> SEQUENCE: 851
tggtagggga ggaagtrgta ggcagaaacc agt 33

<210> SEQ ID NO 852
<211> LENGTH: 33
<212> TYPE: DNA
<213> ORGANISM: Homo Sapiens

<400> SEQUENCE: 852
atataaatcc catagartga agtcttttct ata 33

<210> SEQ ID NO 853
<211> LENGTH: 33
<212> TYPE: DNA
<213> ORGANISM: Homo Sapiens

<400> SEQUENCE: 853
ccttggtcct ttactcrtgc ctctctgtac tca 33

<210> SEQ ID NO 854
<211> LENGTH: 33
<212> TYPE: DNA
<213> ORGANISM: Homo Sapiens

<400> SEQUENCE: 854
aagatggtat aagtcartga tttttctgcc ttc 33

<210> SEQ ID NO 855
<211> LENGTH: 33
<212> TYPE: DNA
<213> ORGANISM: Homo Sapiens

<400> SEQUENCE: 855
gcaccctgag aattgamttg aagttctcct ctt 33

<210> SEQ ID NO 856
<211> LENGTH: 33
<212> TYPE: DNA
<213> ORGANISM: Homo Sapiens

<400> SEQUENCE: 856
acagcctaca ttgagcmaaa caaaacttga ttt 33

<210> SEQ ID NO 857
<211> LENGTH: 33
<212> TYPE: DNA
<213> ORGANISM: Homo Sapiens

<400> SEQUENCE: 857
tccagcctaa ataaatmccc acccggtttg ggg 33

<210> SEQ ID NO 858
<211> LENGTH: 33
<212> TYPE: DNA
<213> ORGANISM: Homo Sapiens

<400> SEQUENCE: 858
ggggacacaa gaggccrggg agctctcttc ccg 33

<210> SEQ ID NO 859
<211> LENGTH: 33
<212> TYPE: DNA
<213> ORGANISM: Homo Sapiens

<400> SEQUENCE: 859
agatatacgc tcaagcmcct ccaagccttt act 33

<210> SEQ ID NO 860
<211> LENGTH: 33
<212> TYPE: DNA
<213> ORGANISM: Homo Sapiens

<400> SEQUENCE: 860
ctagaaacct gcctcaratg gggaaagatt agg 33

<210> SEQ ID NO 861
<211> LENGTH: 33
<212> TYPE: DNA
<213> ORGANISM: Homo Sapiens

<400> SEQUENCE: 861
caacactgtg cctagamctt ggggccagtc tgg 33

<210> SEQ ID NO 862
<211> LENGTH: 33
<212> TYPE: DNA
<213> ORGANISM: Homo Sapiens

<400> SEQUENCE: 862
ggtgcttgag ccagtarctc agaggtaacc cct 33

<210> SEQ ID NO 863
<211> LENGTH: 33
<212> TYPE: DNA
<213> ORGANISM: Homo Sapiens

<400> SEQUENCE: 863
gtgattgtta ggggtgrcat cagcaaggac tgt 33

<210> SEQ ID NO 864
<211> LENGTH: 33
<212> TYPE: DNA
<213> ORGANISM: Homo Sapiens

<400> SEQUENCE: 864
gctgtaggca aacagtraat ccaatttcct cca 33

<210> SEQ ID NO 865
<211> LENGTH: 33
<212> TYPE: DNA
<213> ORGANISM: Homo Sapiens

<400> SEQUENCE: 865
ctgtgctcta acactgmaca ttcatgtagc ttt 33

<210> SEQ ID NO 866
<211> LENGTH: 33
<212> TYPE: DNA
<213> ORGANISM: Homo Sapiens

<400> SEQUENCE: 866
tccaggaatt cagcacmttc cagccctgga gac 33

<210> SEQ ID NO 867
<211> LENGTH: 33
<212> TYPE: DNA
<213> ORGANISM: Homo Sapiens

<400> SEQUENCE: 867
agagaggagg ggagagrtaa ctgatacatg cta 33

<210> SEQ ID NO 868
<211> LENGTH: 33
<212> TYPE: DNA
<213> ORGANISM: Homo Sapiens

<400> SEQUENCE: 868
cactgtccct gaatgcraaa taagggtgac ctt 33

<210> SEQ ID NO 869
<211> LENGTH: 33
<212> TYPE: DNA
<213> ORGANISM: Homo Sapiens

<400> SEQUENCE: 869
aagcaaacca attggaragg tgttccctgt att 33

<210> SEQ ID NO 870
<211> LENGTH: 33
<212> TYPE: DNA
<213> ORGANISM: Homo Sapiens

<400> SEQUENCE: 870
ccgatagttg gtgactrttt tatttctttg ttg 33

<210> SEQ ID NO 871
<211> LENGTH: 33
<212> TYPE: DNA
<213> ORGANISM: Homo Sapiens

<400> SEQUENCE: 871
cagaggaaaa cctgccraga ggggcaaatg gat 33

<210> SEQ ID NO 872
<211> LENGTH: 33
<212> TYPE: DNA
<213> ORGANISM: Homo Sapiens

<400> SEQUENCE: 872
tctcctttaa gatacargaa gcttggaagc gga 33

<210> SEQ ID NO 873
<211> LENGTH: 33
<212> TYPE: DNA
<213> ORGANISM: Homo Sapiens

<400> SEQUENCE: 873
cccatctgta aaatggrcac ctaccattga ttc 33

<210> SEQ ID NO 874
<211> LENGTH: 33
<212> TYPE: DNA
<213> ORGANISM: Homo Sapiens

<400> SEQUENCE: 874
gagggaatgg ccattargta aatgctcttt aga 33

<210> SEQ ID NO 875
<211> LENGTH: 33
<212> TYPE: DNA
<213> ORGANISM: Homo Sapiens

<400> SEQUENCE: 875
caggtcccac gataccrtca ggaatgtccg ttt 33

<210> SEQ ID NO 876
<211> LENGTH: 33
<212> TYPE: DNA
<213> ORGANISM: Homo Sapiens

<400> SEQUENCE: 876
agttaagaaa agtgtcrcag gctaaggaac tgg 33

<210> SEQ ID NO 877
<211> LENGTH: 33
<212> TYPE: DNA
<213> ORGANISM: Homo Sapiens

<400> SEQUENCE: 877
attgtagact tgcacgmggg gctgtatggg ctc 33

<210> SEQ ID NO 878
<211> LENGTH: 33
<212> TYPE: DNA
<213> ORGANISM: Homo Sapiens

<400> SEQUENCE: 878
ggggacccct gctcccrgag tgacagggga gga 33

<210> SEQ ID NO 879
<211> LENGTH: 33
<212> TYPE: DNA
<213> ORGANISM: Homo Sapiens

<400> SEQUENCE: 879
cgcaaccgcg tgaggcraca gaaccgacgg gca 33

<210> SEQ ID NO 880
<211> LENGTH: 33
<212> TYPE: DNA
<213> ORGANISM: Homo Sapiens

<400> SEQUENCE: 880
tttattaccc acagtcmccc tcggtctgaa aat 33

<210> SEQ ID NO 881
<211> LENGTH: 33
<212> TYPE: DNA
<213> ORGANISM: Homo Sapiens

<400> SEQUENCE: 881
tcaattttcg tccagcrttc tctgctacac tgc 33

<210> SEQ ID NO 882
<211> LENGTH: 33
<212> TYPE: DNA
<213> ORGANISM: Homo Sapiens

<400> SEQUENCE: 882
cacgcctggc caacctmttc accctcaatc taa 33

<210> SEQ ID NO 883
<211> LENGTH: 33
<212> TYPE: DNA
<213> ORGANISM: Homo Sapiens

<400> SEQUENCE: 883
tcagcatcac taataamaga aacacagcgt agt 33

<210> SEQ ID NO 884
<211> LENGTH: 33
<212> TYPE: DNA
<213> ORGANISM: Homo Sapiens

<400> SEQUENCE: 884
gaaaatgaga tagagaragg aaagaaataa tat 33

<210> SEQ ID NO 885
<211> LENGTH: 33
<212> TYPE: DNA
<213> ORGANISM: Homo Sapiens

<400> SEQUENCE: 885
ccctattggg ctattartag attggcattt aaa 33

<210> SEQ ID NO 886
<211> LENGTH: 33
<212> TYPE: DNA
<213> ORGANISM: Homo Sapiens

<400> SEQUENCE: 886
attgaaaaaa gcctgtrggg gtgctttgtg cag 33

<210> SEQ ID NO 887
<211> LENGTH: 33
<212> TYPE: DNA
<213> ORGANISM: Homo Sapiens

<400> SEQUENCE: 887
ctgttgattc taccctrtga acagctgggc tta 33

<210> SEQ ID NO 888
<211> LENGTH: 33
<212> TYPE: DNA
<213> ORGANISM: Homo Sapiens

<400> SEQUENCE: 888
tcaagaccct gaattcmatt tttttgaata tat 33

<210> SEQ ID NO 889
<211> LENGTH: 33
<212> TYPE: DNA
<213> ORGANISM: Homo Sapiens

<400> SEQUENCE: 889
tccagttttt atggaarcta ccatttactc tgt 33

<210> SEQ ID NO 890
<211> LENGTH: 33
<212> TYPE: DNA
<213> ORGANISM: Homo Sapiens

<400> SEQUENCE: 890
agactcatat caaaacrcaa taagtgtgtg gca 33

<210> SEQ ID NO 891
<211> LENGTH: 33
<212> TYPE: DNA
<213> ORGANISM: Homo Sapiens

<400> SEQUENCE: 891
tgcttctagt tagcttrtct atagcttccc tgt 33

<210> SEQ ID NO 892
<211> LENGTH: 33
<212> TYPE: DNA
<213> ORGANISM: Homo Sapiens

<400> SEQUENCE: 892
accctacata cacatarcta aatttttttt tct 33

<210> SEQ ID NO 893
<211> LENGTH: 33
<212> TYPE: DNA
<213> ORGANISM: Homo Sapiens

<400> SEQUENCE: 893
tgtggctcgc agatttraaa taaagcagag gtc 33

<210> SEQ ID NO 894
<211> LENGTH: 33
<212> TYPE: DNA
<213> ORGANISM: Homo Sapiens

<400> SEQUENCE: 894
gagagtcaca ggaaggrccc ctttacgtcg gat 33

<210> SEQ ID NO 895
<211> LENGTH: 33
<212> TYPE: DNA
<213> ORGANISM: Homo Sapiens

<400> SEQUENCE: 895
agtagatagt ggtccargcc tagtattttt aac 33

<210> SEQ ID NO 896
<211> LENGTH: 33
<212> TYPE: DNA
<213> ORGANISM: Homo Sapiens

<400> SEQUENCE: 896
tcccccagag gtgtgtrtgg ctagttagct cac 33

<210> SEQ ID NO 897
<211> LENGTH: 33
<212> TYPE: DNA
<213> ORGANISM: Homo Sapiens

<400> SEQUENCE: 897
attagtgtgc agttacrtag cttgggccca gac 33

<210> SEQ ID NO 898
<211> LENGTH: 33
<212> TYPE: DNA
<213> ORGANISM: Homo Sapiens

<400> SEQUENCE: 898
cagcacatga atatggmggc ctgctgtgtg cca 33

<210> SEQ ID NO 899
<211> LENGTH: 33
<212> TYPE: DNA
<213> ORGANISM: Homo Sapiens

<400> SEQUENCE: 899
ctagcctata cttaacrcat aagtttcatc cat 33

<210> SEQ ID NO 900
<211> LENGTH: 33
<212> TYPE: DNA
<213> ORGANISM: Homo Sapiens

<400> SEQUENCE: 900
aaaagattgg gctgaargga aagagatgag atg 33

<210> SEQ ID NO 901
<211> LENGTH: 33
<212> TYPE: DNA

<213> ORGANISM: Homo Sapiens

<400> SEQUENCE: 901
ccctcctgct gccctcrgtt tagggtttac aag 33

<210> SEQ ID NO 902
<211> LENGTH: 33
<212> TYPE: DNA
<213> ORGANISM: Homo Sapiens

<400> SEQUENCE: 902
ctcagtgaaa atggctragg ggaggagctt ttc 33

<210> SEQ ID NO 903
<211> LENGTH: 33
<212> TYPE: DNA
<213> ORGANISM: Homo Sapiens

<400> SEQUENCE: 903
tctcctcttt caccccmaca tgcaattcaa ctt 33

<210> SEQ ID NO 904
<211> LENGTH: 33
<212> TYPE: DNA
<213> ORGANISM: Homo Sapiens

<400> SEQUENCE: 904
tatatctcca tgatatrtaa tccaagatat ata 33

<210> SEQ ID NO 905
<211> LENGTH: 33
<212> TYPE: DNA
<213> ORGANISM: Homo Sapiens

<400> SEQUENCE: 905
cttatttgtg agagaasaga aacctccagg gtg 33

<210> SEQ ID NO 906
<211> LENGTH: 33
<212> TYPE: DNA
<213> ORGANISM: Homo Sapiens

<400> SEQUENCE: 906
cggtgctcca gtcgtcmtgc tgggccagca cag 33

<210> SEQ ID NO 907
<211> LENGTH: 33
<212> TYPE: DNA
<213> ORGANISM: Homo Sapiens

<400> SEQUENCE: 907
ggaggaagcg gctgtcrcag tggctgggct tag 33

<210> SEQ ID NO 908
<211> LENGTH: 33
<212> TYPE: DNA
<213> ORGANISM: Homo Sapiens

<400> SEQUENCE: 908
cttactaaag aactcartgt atgcagggaa cag 33

<210> SEQ ID NO 909
<211> LENGTH: 33

<212> TYPE: DNA
<213> ORGANISM: Homo Sapiens

<400> SEQUENCE: 909
ttgcatttgt tttgggract gtctgaggtt aga 33

<210> SEQ ID NO 910
<211> LENGTH: 33
<212> TYPE: DNA
<213> ORGANISM: Homo Sapiens

<400> SEQUENCE: 910
tggcagcagt ggagatrgac agagcagaga gat 33

<210> SEQ ID NO 911
<211> LENGTH: 33
<212> TYPE: DNA
<213> ORGANISM: Homo Sapiens

<400> SEQUENCE: 911
tgaccagtac agctgcrccc tgactggccc tgt 33

<210> SEQ ID NO 912
<211> LENGTH: 33
<212> TYPE: DNA
<213> ORGANISM: Homo Sapiens

<400> SEQUENCE: 912
aataagcaat aataaaratg tgacttttac agc 33

<210> SEQ ID NO 913
<211> LENGTH: 33
<212> TYPE: DNA
<213> ORGANISM: Homo Sapiens

<400> SEQUENCE: 913
tcatataact tagctargtc attgtgaaat ttt 33

<210> SEQ ID NO 914
<211> LENGTH: 33
<212> TYPE: DNA
<213> ORGANISM: Homo Sapiens

<400> SEQUENCE: 914
catggagaac aggtgtracc taagtgcaga gcc 33

<210> SEQ ID NO 915
<211> LENGTH: 33
<212> TYPE: DNA
<213> ORGANISM: Homo Sapiens

<400> SEQUENCE: 915
tctaccaaac atacaaraaa gagctgatat caa 33

<210> SEQ ID NO 916
<211> LENGTH: 33
<212> TYPE: DNA
<213> ORGANISM: Homo Sapiens

<400> SEQUENCE: 916
aaatcctggt gaacacmtgt gccttttcac aga 33

<210> SEQ ID NO 917

<211> LENGTH: 33
<212> TYPE: DNA
<213> ORGANISM: Homo Sapiens

<400> SEQUENCE: 917
atggtgcttt tttcaamcat acccatgacc aat 33

<210> SEQ ID NO 918
<211> LENGTH: 33
<212> TYPE: DNA
<213> ORGANISM: Homo Sapiens

<400> SEQUENCE: 918
ctcacattta aactgamgga atcataaagt aac 33

<210> SEQ ID NO 919
<211> LENGTH: 33
<212> TYPE: DNA
<213> ORGANISM: Homo Sapiens

<400> SEQUENCE: 919
aaaagaaatt ctgggtrtct ccagagaggg aat 33

<210> SEQ ID NO 920
<211> LENGTH: 33
<212> TYPE: DNA
<213> ORGANISM: Homo Sapiens

<400> SEQUENCE: 920
aaaagaagac ctttaasgct caacaacatg cat 33

<210> SEQ ID NO 921
<211> LENGTH: 33
<212> TYPE: DNA
<213> ORGANISM: Homo Sapiens

<400> SEQUENCE: 921
aatgccatct agaaagrtct tgatcagcaa ctt 33

<210> SEQ ID NO 922
<211> LENGTH: 33
<212> TYPE: DNA
<213> ORGANISM: Homo Sapiens

<400> SEQUENCE: 922
ccagccaatg ggagagrtga atgctagagg gtt 33

<210> SEQ ID NO 923
<211> LENGTH: 33
<212> TYPE: DNA
<213> ORGANISM: Homo Sapiens

<400> SEQUENCE: 923
agagctccct tcatgcratt aaagtatgac tga 33

<210> SEQ ID NO 924
<211> LENGTH: 33
<212> TYPE: DNA
<213> ORGANISM: Homo Sapiens

<400> SEQUENCE: 924
gataatctca atatagrcct cgcatggagt aag 33

<210> SEQ ID NO 925
<211> LENGTH: 33
<212> TYPE: DNA
<213> ORGANISM: Homo Sapiens

<400> SEQUENCE: 925
gttttcacca tgggagraag aaaacacaaa taa 33

<210> SEQ ID NO 926
<211> LENGTH: 33
<212> TYPE: DNA
<213> ORGANISM: Homo Sapiens

<400> SEQUENCE: 926
ggaggagggt gagcacrcct atgatacgct gag 33

<210> SEQ ID NO 927
<211> LENGTH: 33
<212> TYPE: DNA
<213> ORGANISM: Homo Sapiens

<400> SEQUENCE: 927
ctaacagata gcgcccrggt tggaggcaaa gca 33

<210> SEQ ID NO 928
<211> LENGTH: 33
<212> TYPE: DNA
<213> ORGANISM: Homo Sapiens

<400> SEQUENCE: 928
cctcttcata ttttcarctt tgtgcagtga aaa 33

<210> SEQ ID NO 929
<211> LENGTH: 33
<212> TYPE: DNA
<213> ORGANISM: Homo Sapiens

<400> SEQUENCE: 929
gtgttcactc ctttgtrtaa ttccctcccc tca 33

<210> SEQ ID NO 930
<211> LENGTH: 33
<212> TYPE: DNA
<213> ORGANISM: Homo Sapiens

<400> SEQUENCE: 930
tatctgagat gaggccrtca gtgaggacct cct 33

<210> SEQ ID NO 931
<211> LENGTH: 33
<212> TYPE: DNA
<213> ORGANISM: Homo Sapiens

<400> SEQUENCE: 931
cgacgcgctc cacctgrgcg ccgccatctt aca 33

<210> SEQ ID NO 932
<211> LENGTH: 33
<212> TYPE: DNA
<213> ORGANISM: Homo Sapiens

<400> SEQUENCE: 932
ctgaggtttc cgggatragg agagggtgtg gcg 33

<210> SEQ ID NO 933
<211> LENGTH: 33
<212> TYPE: DNA
<213> ORGANISM: Homo Sapiens

<400> SEQUENCE: 933
acaaggctgc actttcrtag ggttccatca taa 33

<210> SEQ ID NO 934
<211> LENGTH: 33
<212> TYPE: DNA
<213> ORGANISM: Homo Sapiens

<400> SEQUENCE: 934
ccagacccta tacatamgaa taaaatgtta cat 33

<210> SEQ ID NO 935
<211> LENGTH: 33
<212> TYPE: DNA
<213> ORGANISM: Homo Sapiens

<400> SEQUENCE: 935
ggcagtgaaa gtcatgmttg taccgcaatc aat 33

<210> SEQ ID NO 936
<211> LENGTH: 33
<212> TYPE: DNA
<213> ORGANISM: Homo Sapiens

<400> SEQUENCE: 936
atagggactc agaaaargca tcattccctt cat 33

<210> SEQ ID NO 937
<211> LENGTH: 33
<212> TYPE: DNA
<213> ORGANISM: Homo Sapiens

<400> SEQUENCE: 937
ccctaataaa caaactrctt aattgaacag ccc 33

<210> SEQ ID NO 938
<211> LENGTH: 33
<212> TYPE: DNA
<213> ORGANISM: Homo Sapiens

<400> SEQUENCE: 938
gtctcaatcc cagccargag tgaataatag atg 33

<210> SEQ ID NO 939
<211> LENGTH: 33
<212> TYPE: DNA
<213> ORGANISM: Homo Sapiens

<400> SEQUENCE: 939
tagaaatttg tcgaacrtgt ttgataaaat gga 33

<210> SEQ ID NO 940
<211> LENGTH: 33
<212> TYPE: DNA
<213> ORGANISM: Homo Sapiens

<400> SEQUENCE: 940
gtctcctgga ttgggcrtga ggagggcttt ggg 33

<210> SEQ ID NO 941
<211> LENGTH: 33
<212> TYPE: DNA
<213> ORGANISM: Homo Sapiens

<400> SEQUENCE: 941
aaaaaaaaat gattctrcct tatctgggat ttt 33

<210> SEQ ID NO 942
<211> LENGTH: 33
<212> TYPE: DNA
<213> ORGANISM: Homo Sapiens

<400> SEQUENCE: 942
tgcagatata ttctgargct gaactgtgtt aca 33

<210> SEQ ID NO 943
<211> LENGTH: 33
<212> TYPE: DNA
<213> ORGANISM: Homo Sapiens

<400> SEQUENCE: 943
cacttccctt tctgacrtat cccctgatgt aag 33

<210> SEQ ID NO 944
<211> LENGTH: 33
<212> TYPE: DNA
<213> ORGANISM: Homo Sapiens

<400> SEQUENCE: 944
catccacctt atctgtrggt gactcctgct ggg 33

<210> SEQ ID NO 945
<211> LENGTH: 33
<212> TYPE: DNA
<213> ORGANISM: Homo Sapiens

<400> SEQUENCE: 945
tggaagggca gacaccrtag tccccagcta cct 33

<210> SEQ ID NO 946
<211> LENGTH: 33
<212> TYPE: DNA
<213> ORGANISM: Homo Sapiens

<400> SEQUENCE: 946
ctgcttgggc tgggtcraag gctctgctga ctg 33

<210> SEQ ID NO 947
<211> LENGTH: 33
<212> TYPE: DNA
<213> ORGANISM: Homo Sapiens

<400> SEQUENCE: 947
ttatgtcccc aaacccrcct ggggcaaggg ggt 33

<210> SEQ ID NO 948
<211> LENGTH: 33
<212> TYPE: DNA
<213> ORGANISM: Homo Sapiens

<400> SEQUENCE: 948
tccccggtgc tgccccrggg gagccgccca gcc 33

<210> SEQ ID NO 949
<211> LENGTH: 33
<212> TYPE: DNA
<213> ORGANISM: Homo Sapiens

<400> SEQUENCE: 949
ttcatcctta tttggcrtta aagttaacac aaa 33

<210> SEQ ID NO 950
<211> LENGTH: 33
<212> TYPE: DNA
<213> ORGANISM: Homo Sapiens

<400> SEQUENCE: 950
atttcaactt gaacaaraaa acaaaggcgt tag 33

<210> SEQ ID NO 951
<211> LENGTH: 33
<212> TYPE: DNA
<213> ORGANISM: Homo Sapiens

<400> SEQUENCE: 951
tgcacaggag gctgagrtgg gagagagaaa aag 33

<210> SEQ ID NO 952
<211> LENGTH: 33
<212> TYPE: DNA
<213> ORGANISM: Homo Sapiens

<400> SEQUENCE: 952
taatatttgg caaagcrttg ccacttaccc act 33

<210> SEQ ID NO 953
<211> LENGTH: 33
<212> TYPE: DNA
<213> ORGANISM: Homo Sapiens

<400> SEQUENCE: 953
ctgttatagt ttccacrtca caactaactg ttt 33

<210> SEQ ID NO 954
<211> LENGTH: 33
<212> TYPE: DNA
<213> ORGANISM: Homo Sapiens

<400> SEQUENCE: 954
aaaggggatg aggagcrgat gggctgggga cac 33

<210> SEQ ID NO 955
<211> LENGTH: 33
<212> TYPE: DNA
<213> ORGANISM: Homo Sapiens

<400> SEQUENCE: 955
gttcgacatt ttgcaartct ctttaatgtc tgg 33

<210> SEQ ID NO 956
<211> LENGTH: 33
<212> TYPE: DNA
<213> ORGANISM: Homo Sapiens

<400> SEQUENCE: 956
cctttccttc caggtcrttt gagtcaagtt gaa 33

<210> SEQ ID NO 957
<211> LENGTH: 33
<212> TYPE: DNA
<213> ORGANISM: Homo Sapiens

<400> SEQUENCE: 957
ggctgctgta agtgacmagt tgtagttgcc tgt 33

<210> SEQ ID NO 958
<211> LENGTH: 33
<212> TYPE: DNA
<213> ORGANISM: Homo Sapiens

<400> SEQUENCE: 958
tagactaaaa ttaatamaga taagagttga aac 33

<210> SEQ ID NO 959
<211> LENGTH: 33
<212> TYPE: DNA
<213> ORGANISM: Homo Sapiens

<400> SEQUENCE: 959
attatcattt cttcttmatt tattcctagt ctg 33

<210> SEQ ID NO 960
<211> LENGTH: 33
<212> TYPE: DNA
<213> ORGANISM: Homo Sapiens

<400> SEQUENCE: 960
tccctataaa ggaagargta gtcagtgtgg tga 33

<210> SEQ ID NO 961
<211> LENGTH: 33
<212> TYPE: DNA
<213> ORGANISM: Homo Sapiens

<400> SEQUENCE: 961
tgggctgcta tttctcrtgg accaataaca aga 33

<210> SEQ ID NO 962
<211> LENGTH: 33
<212> TYPE: DNA
<213> ORGANISM: Homo Sapiens

<400> SEQUENCE: 962
attagtcttg ggtccaratt aatttcatga tca 33

<210> SEQ ID NO 963
<211> LENGTH: 33
<212> TYPE: DNA
<213> ORGANISM: Homo Sapiens

<400> SEQUENCE: 963
ctaataatct ccctagrttt tgtcctttgt cta 33

<210> SEQ ID NO 964
<211> LENGTH: 33
<212> TYPE: DNA
<213> ORGANISM: Homo Sapiens

<400> SEQUENCE: 964
gaattcttga ctgcctrtgt gttactcttc ttc         33

<210> SEQ ID NO 965
<211> LENGTH: 33
<212> TYPE: DNA
<213> ORGANISM: Homo Sapiens

<400> SEQUENCE: 965
gtaaagattg ggaaaarctt gcactaactt cca         33

<210> SEQ ID NO 966
<211> LENGTH: 33
<212> TYPE: DNA
<213> ORGANISM: Homo Sapiens

<400> SEQUENCE: 966
ctggatgttg gggagartta acttgagttc aga         33

<210> SEQ ID NO 967
<211> LENGTH: 33
<212> TYPE: DNA
<213> ORGANISM: Homo Sapiens

<400> SEQUENCE: 967
ctcttctctg cttctgraat ggttagcagt gct         33

<210> SEQ ID NO 968
<211> LENGTH: 33
<212> TYPE: DNA
<213> ORGANISM: Homo Sapiens

<400> SEQUENCE: 968
aagtaaagga attataract agctgctgct tca         33

<210> SEQ ID NO 969
<211> LENGTH: 33
<212> TYPE: DNA
<213> ORGANISM: Homo Sapiens

<400> SEQUENCE: 969
gccaaagctg tcagaaraca tcctacaatg cac         33

<210> SEQ ID NO 970
<211> LENGTH: 33
<212> TYPE: DNA
<213> ORGANISM: Homo Sapiens

<400> SEQUENCE: 970
accccttgtt gagcacrtgg atacctttga ggt         33

<210> SEQ ID NO 971
<211> LENGTH: 33
<212> TYPE: DNA
<213> ORGANISM: Homo Sapiens

<400> SEQUENCE: 971
tatttttagt aaaatamtaa atacacacct tgt         33

<210> SEQ ID NO 972
<211> LENGTH: 33
<212> TYPE: DNA
<213> ORGANISM: Homo Sapiens

<400> SEQUENCE: 972
tgtctcctca acccacrttt gaaaggggct cca 33

<210> SEQ ID NO 973
<211> LENGTH: 33
<212> TYPE: DNA
<213> ORGANISM: Homo Sapiens

<400> SEQUENCE: 973
ctggagttgc ttttggrgtc tgcattttaa caa 33

<210> SEQ ID NO 974
<211> LENGTH: 33
<212> TYPE: DNA
<213> ORGANISM: Homo Sapiens

<400> SEQUENCE: 974
ttttgacaga tagttgrcaa cagacatgta cag 33

<210> SEQ ID NO 975
<211> LENGTH: 33
<212> TYPE: DNA
<213> ORGANISM: Homo Sapiens

<400> SEQUENCE: 975
gctacaggtg tgcctgraat gtttctttac ttt 33

<210> SEQ ID NO 976
<211> LENGTH: 33
<212> TYPE: DNA
<213> ORGANISM: Homo Sapiens

<400> SEQUENCE: 976
aatacaacta gagagarata tatagatact taa 33

<210> SEQ ID NO 977
<211> LENGTH: 33
<212> TYPE: DNA
<213> ORGANISM: Homo Sapiens

<400> SEQUENCE: 977
taaaattgac cattttrcag acataatggc aag 33

<210> SEQ ID NO 978
<211> LENGTH: 33
<212> TYPE: DNA
<213> ORGANISM: Homo Sapiens

<400> SEQUENCE: 978
gaatgaatca tccccarttt gtttcttgct aca 33

<210> SEQ ID NO 979
<211> LENGTH: 33
<212> TYPE: DNA
<213> ORGANISM: Homo Sapiens

<400> SEQUENCE: 979
acctgatggg agagacrcgg ctaagtagga aag 33

<210> SEQ ID NO 980
<211> LENGTH: 33
<212> TYPE: DNA

<213> ORGANISM: Homo Sapiens

<400> SEQUENCE: 980
tcctctgaca tggatgrttg tggcattagt aac 33

<210> SEQ ID NO 981
<211> LENGTH: 33
<212> TYPE: DNA
<213> ORGANISM: Homo Sapiens

<400> SEQUENCE: 981
atgcttcata gcttacmaag ttatttcaga gat 33

<210> SEQ ID NO 982
<211> LENGTH: 33
<212> TYPE: DNA
<213> ORGANISM: Homo Sapiens

<400> SEQUENCE: 982
ataggactga acaacaraga attgctgata tct 33

<210> SEQ ID NO 983
<211> LENGTH: 33
<212> TYPE: DNA
<213> ORGANISM: Homo Sapiens

<400> SEQUENCE: 983
cgcaataact gctattrtaa ctgacttaac agg 33

<210> SEQ ID NO 984
<211> LENGTH: 33
<212> TYPE: DNA
<213> ORGANISM: Homo Sapiens

<400> SEQUENCE: 984
gaacagactt ttggtgrtga ggaggaagaa caa 33

<210> SEQ ID NO 985
<211> LENGTH: 33
<212> TYPE: DNA
<213> ORGANISM: Homo Sapiens

<400> SEQUENCE: 985
gaagtcagtg gttctcrgtt gtattagtgg ggt 33

<210> SEQ ID NO 986
<211> LENGTH: 33
<212> TYPE: DNA
<213> ORGANISM: Homo Sapiens

<400> SEQUENCE: 986
cctctggttt ggtgatrtca gtggaggctg ata 33

<210> SEQ ID NO 987
<211> LENGTH: 33
<212> TYPE: DNA
<213> ORGANISM: Homo Sapiens

<400> SEQUENCE: 987
aatgcaaatg aaaacartat gagaagccac tac 33

<210> SEQ ID NO 988
<211> LENGTH: 33

<212> TYPE: DNA
<213> ORGANISM: Homo Sapiens

<400> SEQUENCE: 988
tgtgctgcac aaggacract gaaacaaaag aat 33

<210> SEQ ID NO 989
<211> LENGTH: 33
<212> TYPE: DNA
<213> ORGANISM: Homo Sapiens

<400> SEQUENCE: 989
taacaagaat gacccartct atatgatcaa ctt 33

<210> SEQ ID NO 990
<211> LENGTH: 33
<212> TYPE: DNA
<213> ORGANISM: Homo Sapiens

<400> SEQUENCE: 990
catgaaagtg tcactaraaa actctaccta ctg 33

<210> SEQ ID NO 991
<211> LENGTH: 33
<212> TYPE: DNA
<213> ORGANISM: Homo Sapiens

<400> SEQUENCE: 991
ggagagagaa atatctrtca gtggaacaac tgt 33

<210> SEQ ID NO 992
<211> LENGTH: 33
<212> TYPE: DNA
<213> ORGANISM: Homo Sapiens

<400> SEQUENCE: 992
atagacactg gcccacrgtg ttgttgaaaa gaa 33

<210> SEQ ID NO 993
<211> LENGTH: 33
<212> TYPE: DNA
<213> ORGANISM: Homo Sapiens

<400> SEQUENCE: 993
cctatgatct ggtggarcac cctccctcct gaa 33

<210> SEQ ID NO 994
<211> LENGTH: 33
<212> TYPE: DNA
<213> ORGANISM: Homo Sapiens

<400> SEQUENCE: 994
tgtctgttca tacaccrgaa tatcattcag ccc 33

<210> SEQ ID NO 995
<211> LENGTH: 33
<212> TYPE: DNA
<213> ORGANISM: Homo Sapiens

<400> SEQUENCE: 995
gtgagagtag gtcactrttg aggcccccat aca 33

<210> SEQ ID NO 996

<211> LENGTH: 33
<212> TYPE: DNA
<213> ORGANISM: Homo Sapiens

<400> SEQUENCE: 996
tgccgctgga ggatccrgaa agagtttccg aag 33

<210> SEQ ID NO 997
<211> LENGTH: 33
<212> TYPE: DNA
<213> ORGANISM: Homo Sapiens

<400> SEQUENCE: 997
atcacaaagc catactrcag gtacagggtc tga 33

<210> SEQ ID NO 998
<211> LENGTH: 33
<212> TYPE: DNA
<213> ORGANISM: Homo Sapiens

<400> SEQUENCE: 998
ctcctgggtt gcccccrtcc ttgagccaat gta 33

<210> SEQ ID NO 999
<211> LENGTH: 33
<212> TYPE: DNA
<213> ORGANISM: Homo Sapiens

<400> SEQUENCE: 999
catgtctctg aggagcsgcg ggcggcggcg cgc 33

<210> SEQ ID NO 1000
<211> LENGTH: 33
<212> TYPE: DNA
<213> ORGANISM: Homo Sapiens

<400> SEQUENCE: 1000
cacatattgc aagctasgat attattcaat ttt 33

<210> SEQ ID NO 1001
<211> LENGTH: 33
<212> TYPE: DNA
<213> ORGANISM: Homo Sapiens

<400> SEQUENCE: 1001
tgtcctccca gagtctrtca tctatcagga agt 33

<210> SEQ ID NO 1002
<211> LENGTH: 33
<212> TYPE: DNA
<213> ORGANISM: Homo Sapiens

<400> SEQUENCE: 1002
aattaagaat attgggrcac ggccaggcgt ggt 33

<210> SEQ ID NO 1003
<211> LENGTH: 33
<212> TYPE: DNA
<213> ORGANISM: Homo Sapiens

<400> SEQUENCE: 1003
ttaagtcact gcataartat ctgtcacaca aat 33

<210> SEQ ID NO 1004
<211> LENGTH: 33
<212> TYPE: DNA
<213> ORGANISM: Homo Sapiens

<400> SEQUENCE: 1004
ccaaagctcc ctccacrgca gccaacacac cct 33

<210> SEQ ID NO 1005
<211> LENGTH: 33
<212> TYPE: DNA
<213> ORGANISM: Homo Sapiens

<400> SEQUENCE: 1005
tctgaacaaa gatgacmgga ggagctgcct tgg 33

<210> SEQ ID NO 1006
<211> LENGTH: 33
<212> TYPE: DNA
<213> ORGANISM: Homo Sapiens

<400> SEQUENCE: 1006
tgtgctttgg agtttgrgcg gcagaaccgc gta 33

<210> SEQ ID NO 1007
<211> LENGTH: 33
<212> TYPE: DNA
<213> ORGANISM: Homo Sapiens

<400> SEQUENCE: 1007
tatttccccc gaataaragc cttatataat gtt 33

<210> SEQ ID NO 1008
<211> LENGTH: 33
<212> TYPE: DNA
<213> ORGANISM: Homo Sapiens

<400> SEQUENCE: 1008
actgagtagt catcagrata tttggttgtg ttg 33

<210> SEQ ID NO 1009
<211> LENGTH: 33
<212> TYPE: DNA
<213> ORGANISM: Homo Sapiens

<400> SEQUENCE: 1009
caagtactca ataaatrtaa acaaacctgt cat 33

<210> SEQ ID NO 1010
<211> LENGTH: 33
<212> TYPE: DNA
<213> ORGANISM: Homo Sapiens

<400> SEQUENCE: 1010
atgaaatagt aaatacmagc cttacacttt gaa 33

<210> SEQ ID NO 1011
<211> LENGTH: 33
<212> TYPE: DNA
<213> ORGANISM: Homo Sapiens

<400> SEQUENCE: 1011
gagctgggtt tatatgmatt gacatgaaaa gtt 33

<210> SEQ ID NO 1012
<211> LENGTH: 33
<212> TYPE: DNA
<213> ORGANISM: Homo Sapiens

<400> SEQUENCE: 1012
aactggttat ttcctaragc tgagattgtg agg 33

<210> SEQ ID NO 1013
<211> LENGTH: 33
<212> TYPE: DNA
<213> ORGANISM: Homo Sapiens

<400> SEQUENCE: 1013
attacaagtc agcagtmcaa gaaaggaaca ggg 33

<210> SEQ ID NO 1014
<211> LENGTH: 33
<212> TYPE: DNA
<213> ORGANISM: Homo Sapiens

<400> SEQUENCE: 1014
acaaagaata taaacaragt acacagaaga agt 33

<210> SEQ ID NO 1015
<211> LENGTH: 33
<212> TYPE: DNA
<213> ORGANISM: Homo Sapiens

<400> SEQUENCE: 1015
agtctgtctt tgcatawacc cactttccat gtc 33

<210> SEQ ID NO 1016
<211> LENGTH: 33
<212> TYPE: DNA
<213> ORGANISM: Homo Sapiens

<400> SEQUENCE: 1016
ggcacagtca cacgccmacg aggccagccc tgc 33

<210> SEQ ID NO 1017
<211> LENGTH: 33
<212> TYPE: DNA
<213> ORGANISM: Homo Sapiens

<400> SEQUENCE: 1017
ccttcagttt ctccctrggg cttcattatg gct 33

<210> SEQ ID NO 1018
<211> LENGTH: 33
<212> TYPE: DNA
<213> ORGANISM: Homo Sapiens

<400> SEQUENCE: 1018
taattttaat tgatccrtca cctctactgt ttg 33

<210> SEQ ID NO 1019
<211> LENGTH: 33
<212> TYPE: DNA
<213> ORGANISM: Homo Sapiens

<400> SEQUENCE: 1019
gtaattatta aattacrtgg aagttccttg ccc 33

<210> SEQ ID NO 1020
<211> LENGTH: 33
<212> TYPE: DNA
<213> ORGANISM: Homo Sapiens

<400> SEQUENCE: 1020
tttacttacc tcttacrtag tcctaagcac aat 33

<210> SEQ ID NO 1021
<211> LENGTH: 33
<212> TYPE: DNA
<213> ORGANISM: Homo Sapiens

<400> SEQUENCE: 1021
gaggagagct agtgaamtaa aagcctaagt ata 33

<210> SEQ ID NO 1022
<211> LENGTH: 33
<212> TYPE: DNA
<213> ORGANISM: Homo Sapiens

<400> SEQUENCE: 1022
tttggggata tagcctrgaa atgtgtactt tta 33

<210> SEQ ID NO 1023
<211> LENGTH: 33
<212> TYPE: DNA
<213> ORGANISM: Homo Sapiens

<400> SEQUENCE: 1023
ctgtattaca cattatmcat aatctagaaa tga 33

<210> SEQ ID NO 1024
<211> LENGTH: 33
<212> TYPE: DNA
<213> ORGANISM: Homo Sapiens

<400> SEQUENCE: 1024
aaagctgttt gtttttraga agttctatgc tca 33

<210> SEQ ID NO 1025
<211> LENGTH: 33
<212> TYPE: DNA
<213> ORGANISM: Homo Sapiens

<400> SEQUENCE: 1025
aacttctgtt tttactrttt tctaggcaat gtc 33

<210> SEQ ID NO 1026
<211> LENGTH: 33
<212> TYPE: DNA
<213> ORGANISM: Homo Sapiens

<400> SEQUENCE: 1026
tggtgtctag aactgcmtct agcaagtggg agg 33

<210> SEQ ID NO 1027
<211> LENGTH: 33
<212> TYPE: DNA
<213> ORGANISM: Homo Sapiens

<400> SEQUENCE: 1027
tgctggacaa gtgtaargaa tctggggttt aga 33

<210> SEQ ID NO 1028
<211> LENGTH: 33
<212> TYPE: DNA
<213> ORGANISM: Homo Sapiens

<400> SEQUENCE: 1028
gagggtttgg ctttagrctt tgttagggca agt 33

<210> SEQ ID NO 1029
<211> LENGTH: 33
<212> TYPE: DNA
<213> ORGANISM: Homo Sapiens

<400> SEQUENCE: 1029
tagaagcaca cctagcrtat ttaaaacttg gag 33

<210> SEQ ID NO 1030
<211> LENGTH: 33
<212> TYPE: DNA
<213> ORGANISM: Homo Sapiens

<400> SEQUENCE: 1030
acggatgaat caaaacrtta agctctctaa aag 33

<210> SEQ ID NO 1031
<211> LENGTH: 33
<212> TYPE: DNA
<213> ORGANISM: Homo Sapiens

<400> SEQUENCE: 1031
aaataatcct tgatacrgta ctgaatattt tgt 33

<210> SEQ ID NO 1032
<211> LENGTH: 33
<212> TYPE: DNA
<213> ORGANISM: Homo Sapiens

<400> SEQUENCE: 1032
ttatctcaaa aaaaatmtgt aggtataaat ttg 33

<210> SEQ ID NO 1033
<211> LENGTH: 33
<212> TYPE: DNA
<213> ORGANISM: Homo Sapiens

<400> SEQUENCE: 1033
aatccatttg aaattgrcag tgtttttata ttt 33

<210> SEQ ID NO 1034
<211> LENGTH: 33
<212> TYPE: DNA
<213> ORGANISM: Homo Sapiens

<400> SEQUENCE: 1034
cttcagtctt cgtacaraaa cacttacttt ata 33

<210> SEQ ID NO 1035
<211> LENGTH: 33
<212> TYPE: DNA
<213> ORGANISM: Homo Sapiens

<400> SEQUENCE: 1035
cctggtaatt tgatcartca ttaagctatc ctt 33

<210> SEQ ID NO 1036
<211> LENGTH: 33
<212> TYPE: DNA
<213> ORGANISM: Homo Sapiens

<400> SEQUENCE: 1036
tgaagaattt actcacrtgg ggaaataaag gcc 33

<210> SEQ ID NO 1037
<211> LENGTH: 33
<212> TYPE: DNA
<213> ORGANISM: Homo Sapiens

<400> SEQUENCE: 1037
tgtattctct agtcagrttc tctttccagc ttg 33

<210> SEQ ID NO 1038
<211> LENGTH: 33
<212> TYPE: DNA
<213> ORGANISM: Homo Sapiens

<400> SEQUENCE: 1038
tagtatttta ggtaacratg agtaaatctt aag 33

<210> SEQ ID NO 1039
<211> LENGTH: 33
<212> TYPE: DNA
<213> ORGANISM: Homo Sapiens

<400> SEQUENCE: 1039
acagagtctg gaaatargac cgatgaaacc agg 33

<210> SEQ ID NO 1040
<211> LENGTH: 33
<212> TYPE: DNA
<213> ORGANISM: Homo Sapiens

<400> SEQUENCE: 1040
agcacaaact tttgctraat agcatgtcat cta 33

<210> SEQ ID NO 1041
<211> LENGTH: 33
<212> TYPE: DNA
<213> ORGANISM: Homo Sapiens

<400> SEQUENCE: 1041
atatcggttc tgctatrtct atgagttcct ttc 33

<210> SEQ ID NO 1042
<211> LENGTH: 33
<212> TYPE: DNA
<213> ORGANISM: Homo Sapiens

<400> SEQUENCE: 1042
aatagatgag gaagttraag tccaaaaata gtc 33

<210> SEQ ID NO 1043
<211> LENGTH: 33
<212> TYPE: DNA
<213> ORGANISM: Homo Sapiens

<400> SEQUENCE: 1043
aaagtgaatg agaacartac tgataataat agc 33

<210> SEQ ID NO 1044
<211> LENGTH: 33
<212> TYPE: DNA
<213> ORGANISM: Homo Sapiens

<400> SEQUENCE: 1044
tgcctgtgac acaataktga aatcttactt aaa 33

<210> SEQ ID NO 1045
<211> LENGTH: 33
<212> TYPE: DNA
<213> ORGANISM: Homo Sapiens

<400> SEQUENCE: 1045
atgttgaaag ggtgccrgtg ccttggtgat caa 33

<210> SEQ ID NO 1046
<211> LENGTH: 33
<212> TYPE: DNA
<213> ORGANISM: Homo Sapiens

<400> SEQUENCE: 1046
ttgattctta atctggrggt gtttatttcc cta 33

<210> SEQ ID NO 1047
<211> LENGTH: 33
<212> TYPE: DNA
<213> ORGANISM: Homo Sapiens

<400> SEQUENCE: 1047
tggcgtagat ggatatrttg ataacataga aga 33

<210> SEQ ID NO 1048
<211> LENGTH: 33
<212> TYPE: DNA
<213> ORGANISM: Homo Sapiens

<400> SEQUENCE: 1048
tcgtcaatgt tttaaarggt aggagttgtt aca 33

<210> SEQ ID NO 1049
<211> LENGTH: 33
<212> TYPE: DNA
<213> ORGANISM: Homo Sapiens

<400> SEQUENCE: 1049
ataaccgaga ccggatmggg gagtagttac ttc 33

<210> SEQ ID NO 1050
<211> LENGTH: 33
<212> TYPE: DNA
<213> ORGANISM: Homo Sapiens

<400> SEQUENCE: 1050
agttcataat cttccargcc tccatagtct ggt 33

<210> SEQ ID NO 1051
<211> LENGTH: 33
<212> TYPE: DNA
<213> ORGANISM: Homo Sapiens

<400> SEQUENCE: 1051
tagactaatg caagcamaaa atttccattt gct 33

<210> SEQ ID NO 1052
<211> LENGTH: 33
<212> TYPE: DNA
<213> ORGANISM: Homo Sapiens

<400> SEQUENCE: 1052
ggaagtctta ttcggarcaa tcagtcaaga aaa 33

<210> SEQ ID NO 1053
<211> LENGTH: 33
<212> TYPE: DNA
<213> ORGANISM: Homo Sapiens

<400> SEQUENCE: 1053
catgcaccga aatctcytca tgatggagaa ttt 33

<210> SEQ ID NO 1054
<211> LENGTH: 33
<212> TYPE: DNA
<213> ORGANISM: Homo Sapiens

<400> SEQUENCE: 1054
ggactgcaag gtaatcrtca agggactctt aga 33

<210> SEQ ID NO 1055
<211> LENGTH: 33
<212> TYPE: DNA
<213> ORGANISM: Homo Sapiens

<400> SEQUENCE: 1055
ttcatttaat tttacamgga agagtttaaa aaa 33

<210> SEQ ID NO 1056
<211> LENGTH: 33
<212> TYPE: DNA
<213> ORGANISM: Homo Sapiens

<400> SEQUENCE: 1056
tatcattgct atttccrtgt ttggtcaagg cat 33

<210> SEQ ID NO 1057
<211> LENGTH: 33
<212> TYPE: DNA
<213> ORGANISM: Homo Sapiens

<400> SEQUENCE: 1057
aaattataac aaaagaraat tttactctta taa 33

<210> SEQ ID NO 1058
<211> LENGTH: 33
<212> TYPE: DNA
<213> ORGANISM: Homo Sapiens

<400> SEQUENCE: 1058
agtgccagca ttctgarcca taatttttgt gac 33

<210> SEQ ID NO 1059
<211> LENGTH: 33
<212> TYPE: DNA

<213> ORGANISM: Homo Sapiens

<400> SEQUENCE: 1059
gggttcaaca gtctatrttt ttagcagact gtc 33

<210> SEQ ID NO 1060
<211> LENGTH: 33
<212> TYPE: DNA
<213> ORGANISM: Homo Sapiens

<400> SEQUENCE: 1060
aggcctgcct gtgtatract gtaaatattc att 33

<210> SEQ ID NO 1061
<211> LENGTH: 33
<212> TYPE: DNA
<213> ORGANISM: Homo Sapiens

<400> SEQUENCE: 1061
tcttggcttg aactgcmaat cttaaaagtt aat 33

<210> SEQ ID NO 1062
<211> LENGTH: 33
<212> TYPE: DNA
<213> ORGANISM: Homo Sapiens

<400> SEQUENCE: 1062
tgaaatattg taaatcrgtg gttttgagtg tct 33

<210> SEQ ID NO 1063
<211> LENGTH: 33
<212> TYPE: DNA
<213> ORGANISM: Homo Sapiens

<400> SEQUENCE: 1063
aaagaaaatg agagccrctg ctcgagtgaa ggg 33

<210> SEQ ID NO 1064
<211> LENGTH: 33
<212> TYPE: DNA
<213> ORGANISM: Homo Sapiens

<400> SEQUENCE: 1064
ttttcatgat ggctttrtgg ctattttttt agg 33

<210> SEQ ID NO 1065
<211> LENGTH: 33
<212> TYPE: DNA
<213> ORGANISM: Homo Sapiens

<400> SEQUENCE: 1065
aaagtactag gccagcrttc caaagaagtg ttt 33

<210> SEQ ID NO 1066
<211> LENGTH: 33
<212> TYPE: DNA
<213> ORGANISM: Homo Sapiens

<400> SEQUENCE: 1066
tgattgggaa agagtgrctg agtgtgcaag gtg 33

<210> SEQ ID NO 1067
<211> LENGTH: 33

<212> TYPE: DNA
<213> ORGANISM: Homo Sapiens

<400> SEQUENCE: 1067
acgttactca tcaaatrtat acaatgtagc taa 33

<210> SEQ ID NO 1068
<211> LENGTH: 33
<212> TYPE: DNA
<213> ORGANISM: Homo Sapiens

<400> SEQUENCE: 1068
ttgtctatca gttgccrtct tccattggcc aag 33

<210> SEQ ID NO 1069
<211> LENGTH: 33
<212> TYPE: DNA
<213> ORGANISM: Homo Sapiens

<400> SEQUENCE: 1069
ggcagagtta cacctcrtaa acaaactatt caa 33

<210> SEQ ID NO 1070
<211> LENGTH: 33
<212> TYPE: DNA
<213> ORGANISM: Homo Sapiens

<400> SEQUENCE: 1070
agggccaagc tgccaaraac ttcttgaggt ctg 33

<210> SEQ ID NO 1071
<211> LENGTH: 33
<212> TYPE: DNA
<213> ORGANISM: Homo Sapiens

<400> SEQUENCE: 1071
ggcagcatca aagtcaratg actgacccaa ggc 33

<210> SEQ ID NO 1072
<211> LENGTH: 33
<212> TYPE: DNA
<213> ORGANISM: Homo Sapiens

<400> SEQUENCE: 1072
ctatgctctg gtttctrtat ttctagaact tgt 33

<210> SEQ ID NO 1073
<211> LENGTH: 33
<212> TYPE: DNA
<213> ORGANISM: Homo Sapiens

<400> SEQUENCE: 1073
taatctttaa attgttrcat atttagcaag tgt 33

<210> SEQ ID NO 1074
<211> LENGTH: 33
<212> TYPE: DNA
<213> ORGANISM: Homo Sapiens

<400> SEQUENCE: 1074
gctgtgctcc cagccarcag ccagaatcaa ctg 33

<210> SEQ ID NO 1075

<211> LENGTH: 33
<212> TYPE: DNA
<213> ORGANISM: Homo Sapiens

<400> SEQUENCE: 1075
taaatctgat acaaccraaa taaacacagt ata 33

<210> SEQ ID NO 1076
<211> LENGTH: 33
<212> TYPE: DNA
<213> ORGANISM: Homo Sapiens

<400> SEQUENCE: 1076
cactctagaa gaccctrcaa atcagaacca gag 33

<210> SEQ ID NO 1077
<211> LENGTH: 33
<212> TYPE: DNA
<213> ORGANISM: Homo Sapiens

<400> SEQUENCE: 1077
gcccccaagc gtagccrggg tggatgccaa aag 33

<210> SEQ ID NO 1078
<211> LENGTH: 33
<212> TYPE: DNA
<213> ORGANISM: Homo Sapiens

<400> SEQUENCE: 1078
aagcctcttc aagcaarcta ctgcccatta gtg 33

<210> SEQ ID NO 1079
<211> LENGTH: 33
<212> TYPE: DNA
<213> ORGANISM: Homo Sapiens

<400> SEQUENCE: 1079
gttgtcaatg ctaaacraga aagggtccct gga 33

<210> SEQ ID NO 1080
<211> LENGTH: 33
<212> TYPE: DNA
<213> ORGANISM: Homo Sapiens

<400> SEQUENCE: 1080
tcaaaccagc cctgccrgtg cccttgtgtc cct 33

<210> SEQ ID NO 1081
<211> LENGTH: 33
<212> TYPE: DNA
<213> ORGANISM: Homo Sapiens

<400> SEQUENCE: 1081
cactccaggg cccccamgtg gattccccca tcg 33

<210> SEQ ID NO 1082
<211> LENGTH: 33
<212> TYPE: DNA
<213> ORGANISM: Homo Sapiens

<400> SEQUENCE: 1082
cattgtggga agctctmgag atggggccat cct 33

<210> SEQ ID NO 1083
<211> LENGTH: 33
<212> TYPE: DNA
<213> ORGANISM: Homo Sapiens

<400> SEQUENCE: 1083
ctgcagtgct tattctrtct cttttgtttg ttt 33

<210> SEQ ID NO 1084
<211> LENGTH: 33
<212> TYPE: DNA
<213> ORGANISM: Homo Sapiens

<400> SEQUENCE: 1084
atcaggggaa aagcatraac tcaaaataga tga 33

<210> SEQ ID NO 1085
<211> LENGTH: 33
<212> TYPE: DNA
<213> ORGANISM: Homo Sapiens

<400> SEQUENCE: 1085
aagggcgatg aatcctrggc caggctgtgc aga 33

<210> SEQ ID NO 1086
<211> LENGTH: 33
<212> TYPE: DNA
<213> ORGANISM: Homo Sapiens

<400> SEQUENCE: 1086
cagccagggt gtcggcrccg agctgatggg gct 33

<210> SEQ ID NO 1087
<211> LENGTH: 33
<212> TYPE: DNA
<213> ORGANISM: Homo Sapiens

<400> SEQUENCE: 1087
gagggtcgca ctttcamaaa tgagtcagct ggt 33

<210> SEQ ID NO 1088
<211> LENGTH: 33
<212> TYPE: DNA
<213> ORGANISM: Homo Sapiens

<400> SEQUENCE: 1088
cagcaagagt tattgcraag agaaacaaca aag 33

<210> SEQ ID NO 1089
<211> LENGTH: 33
<212> TYPE: DNA
<213> ORGANISM: Homo Sapiens

<400> SEQUENCE: 1089
ggtcctttct aaaaatrgtc accccaatcc atc 33

<210> SEQ ID NO 1090
<211> LENGTH: 33
<212> TYPE: DNA
<213> ORGANISM: Homo Sapiens

<400> SEQUENCE: 1090
attaatattt tatgttrcat gatttagatt tat 33

<210> SEQ ID NO 1091
<211> LENGTH: 33
<212> TYPE: DNA
<213> ORGANISM: Homo Sapiens

<400> SEQUENCE: 1091
tcatggaact aaaagtragc atctcaagag act 33

<210> SEQ ID NO 1092
<211> LENGTH: 33
<212> TYPE: DNA
<213> ORGANISM: Homo Sapiens

<400> SEQUENCE: 1092
agcgtatatt atcttcraag agcattttta ttt 33

<210> SEQ ID NO 1093
<211> LENGTH: 33
<212> TYPE: DNA
<213> ORGANISM: Homo Sapiens

<400> SEQUENCE: 1093
gagcatccac atccatragg ctgctgaatt cat 33

<210> SEQ ID NO 1094
<211> LENGTH: 33
<212> TYPE: DNA
<213> ORGANISM: Homo Sapiens

<400> SEQUENCE: 1094
tctccagaag atccctragc acatgtctgg atg 33

<210> SEQ ID NO 1095
<211> LENGTH: 33
<212> TYPE: DNA
<213> ORGANISM: Homo Sapiens

<400> SEQUENCE: 1095
ttcagcacta ttcagcrcct atcactgcca gct 33

<210> SEQ ID NO 1096
<211> LENGTH: 33
<212> TYPE: DNA
<213> ORGANISM: Homo Sapiens

<400> SEQUENCE: 1096
cccagacatt ttaaccrata tggccagtat aaa 33

<210> SEQ ID NO 1097
<211> LENGTH: 33
<212> TYPE: DNA
<213> ORGANISM: Homo Sapiens

<400> SEQUENCE: 1097
cgcacggcag agggccraag ccgcggtact ctc 33

<210> SEQ ID NO 1098
<211> LENGTH: 33
<212> TYPE: DNA
<213> ORGANISM: Homo Sapiens

<400> SEQUENCE: 1098
tacaaacact tgccagrttt agaaacacct gta 33

<210> SEQ ID NO 1099
<211> LENGTH: 33
<212> TYPE: DNA
<213> ORGANISM: Homo Sapiens

<400> SEQUENCE: 1099
ttatgggccc agaatgrttc cagatcagaa ttt 33

<210> SEQ ID NO 1100
<211> LENGTH: 33
<212> TYPE: DNA
<213> ORGANISM: Homo Sapiens

<400> SEQUENCE: 1100
tattgaacat tctacaratt tttataaaaa agg 33

<210> SEQ ID NO 1101
<211> LENGTH: 33
<212> TYPE: DNA
<213> ORGANISM: Homo Sapiens

<400> SEQUENCE: 1101
ttctttgtca gctaccrttg ctataaaacc ttt 33

<210> SEQ ID NO 1102
<211> LENGTH: 33
<212> TYPE: DNA
<213> ORGANISM: Homo Sapiens

<400> SEQUENCE: 1102
tgactaatta cactggrgag tccatcaaca tct 33

<210> SEQ ID NO 1103
<211> LENGTH: 33
<212> TYPE: DNA
<213> ORGANISM: Homo Sapiens

<400> SEQUENCE: 1103
tggttggaac atagccrtga cagctagcca aca 33

<210> SEQ ID NO 1104
<211> LENGTH: 33
<212> TYPE: DNA
<213> ORGANISM: Homo Sapiens

<400> SEQUENCE: 1104
caaacaaaca gaaaaartaa ccctggctat agt 33

<210> SEQ ID NO 1105
<211> LENGTH: 33
<212> TYPE: DNA
<213> ORGANISM: Homo Sapiens

<400> SEQUENCE: 1105
gaaggcccag tgggaarccg agtagtgcta cag 33

<210> SEQ ID NO 1106
<211> LENGTH: 33
<212> TYPE: DNA
<213> ORGANISM: Homo Sapiens

<400> SEQUENCE: 1106
atccaaatca agaaaamaat ctctgaattg cca 33

<210> SEQ ID NO 1107
<211> LENGTH: 33
<212> TYPE: DNA
<213> ORGANISM: Homo Sapiens

<400> SEQUENCE: 1107
ggggtaattt attgccrccg ctcgcttcac cag 33

<210> SEQ ID NO 1108
<211> LENGTH: 33
<212> TYPE: DNA
<213> ORGANISM: Homo Sapiens

<400> SEQUENCE: 1108
attctgcaga cacacartcc tttttgccta caa 33

<210> SEQ ID NO 1109
<211> LENGTH: 33
<212> TYPE: DNA
<213> ORGANISM: Homo Sapiens

<400> SEQUENCE: 1109
cgtgcactac gagtacrtga tcatggggac caa 33

<210> SEQ ID NO 1110
<211> LENGTH: 33
<212> TYPE: DNA
<213> ORGANISM: Homo Sapiens

<400> SEQUENCE: 1110
tggtacaggg gacagtrata gccagcacac cca 33

<210> SEQ ID NO 1111
<211> LENGTH: 33
<212> TYPE: DNA
<213> ORGANISM: Homo Sapiens

<400> SEQUENCE: 1111
atctgagccc ttgggtrccc ctgcctttgg aga 33

<210> SEQ ID NO 1112
<211> LENGTH: 33
<212> TYPE: DNA
<213> ORGANISM: Homo Sapiens

<400> SEQUENCE: 1112
tgccacttgc tgccagmcct ggctgaagca ggg 33

<210> SEQ ID NO 1113
<211> LENGTH: 33
<212> TYPE: DNA
<213> ORGANISM: Homo Sapiens

<400> SEQUENCE: 1113
ttgtttttct gattacraca gaagacccaa caa 33

<210> SEQ ID NO 1114
<211> LENGTH: 33
<212> TYPE: DNA
<213> ORGANISM: Homo Sapiens

<400> SEQUENCE: 1114
gctcatcatg atagaartag tcatcatgga gct 33

<210> SEQ ID NO 1115
<211> LENGTH: 33
<212> TYPE: DNA
<213> ORGANISM: Homo Sapiens

<400> SEQUENCE: 1115
gagtctcgac gggagcrttg ggagcagcgg cag 33

<210> SEQ ID NO 1116
<211> LENGTH: 33
<212> TYPE: DNA
<213> ORGANISM: Homo Sapiens

<400> SEQUENCE: 1116
caattacaga atcatgrtgg aggtttctct gca 33

<210> SEQ ID NO 1117
<211> LENGTH: 33
<212> TYPE: DNA
<213> ORGANISM: Homo Sapiens

<400> SEQUENCE: 1117
tgataagctg gacttcrtaa aaactataca cat 33

<210> SEQ ID NO 1118
<211> LENGTH: 33
<212> TYPE: DNA
<213> ORGANISM: Homo Sapiens

<400> SEQUENCE: 1118
catggtaaaa tactttrgct atatttccat cag 33

<210> SEQ ID NO 1119
<211> LENGTH: 33
<212> TYPE: DNA
<213> ORGANISM: Homo Sapiens

<400> SEQUENCE: 1119
tgaccagacg cctggtrcag actgggcctt ctt 33

<210> SEQ ID NO 1120
<211> LENGTH: 33
<212> TYPE: DNA
<213> ORGANISM: Homo Sapiens

<400> SEQUENCE: 1120
ggatgctggt tcctccraaa acaaagagct tca 33

<210> SEQ ID NO 1121
<211> LENGTH: 33
<212> TYPE: DNA
<213> ORGANISM: Homo Sapiens

<400> SEQUENCE: 1121
accagaaagg tgaccargac agatttttta agg 33

<210> SEQ ID NO 1122
<211> LENGTH: 33
<212> TYPE: DNA
<213> ORGANISM: Homo Sapiens

<400> SEQUENCE: 1122
aacagtgacc tattctrgta aacacattac gaa 33

<210> SEQ ID NO 1123
<211> LENGTH: 33
<212> TYPE: DNA
<213> ORGANISM: Homo Sapiens

<400> SEQUENCE: 1123
agcaagatct cgtctcraca aaaaaaaagt tta 33

<210> SEQ ID NO 1124
<211> LENGTH: 33
<212> TYPE: DNA
<213> ORGANISM: Homo Sapiens

<400> SEQUENCE: 1124
atgaaccaac tatatgmtgt ctacaagaaa cac 33

<210> SEQ ID NO 1125
<211> LENGTH: 33
<212> TYPE: DNA
<213> ORGANISM: Homo Sapiens

<400> SEQUENCE: 1125
cggcctttgt ggtgctrttt ggtttcatcc cca 33

<210> SEQ ID NO 1126
<211> LENGTH: 33
<212> TYPE: DNA
<213> ORGANISM: Homo Sapiens

<400> SEQUENCE: 1126
tccttgagag acttccrggg caccgcttta atc 33

<210> SEQ ID NO 1127
<211> LENGTH: 33
<212> TYPE: DNA
<213> ORGANISM: Homo Sapiens

<400> SEQUENCE: 1127
aaggctctga ggttttrgta ccccagaaag att 33

<210> SEQ ID NO 1128
<211> LENGTH: 33
<212> TYPE: DNA
<213> ORGANISM: Homo Sapiens

<400> SEQUENCE: 1128
tattaccatg aactttrgta aaagttacaa ata 33

<210> SEQ ID NO 1129
<211> LENGTH: 33
<212> TYPE: DNA
<213> ORGANISM: Homo Sapiens

<400> SEQUENCE: 1129
ttagaaaatc tataacrgta aaaagtacat tag 33

<210> SEQ ID NO 1130
<211> LENGTH: 33
<212> TYPE: DNA
<213> ORGANISM: Homo Sapiens

<400> SEQUENCE: 1130
aaaacctctc acatgamtaa gcttacaaaa tag 33

<210> SEQ ID NO 1131
<211> LENGTH: 33
<212> TYPE: DNA
<213> ORGANISM: Homo Sapiens

<400> SEQUENCE: 1131
ttctatagca gacattrgtc tctgaacttg ggt 33

<210> SEQ ID NO 1132
<211> LENGTH: 33
<212> TYPE: DNA
<213> ORGANISM: Homo Sapiens

<400> SEQUENCE: 1132
ccgcagccgg gacgacracg tgcagtacct gac 33

<210> SEQ ID NO 1133
<211> LENGTH: 33
<212> TYPE: DNA
<213> ORGANISM: Homo Sapiens

<400> SEQUENCE: 1133
ggcaggcagg gaacagrtga ttagtaacca aag 33

<210> SEQ ID NO 1134
<211> LENGTH: 33
<212> TYPE: DNA
<213> ORGANISM: Homo Sapiens

<400> SEQUENCE: 1134
ggtgctcccg ctgaggsgcc tccgcgcctt gtg 33

<210> SEQ ID NO 1135
<211> LENGTH: 33
<212> TYPE: DNA
<213> ORGANISM: Homo Sapiens

<400> SEQUENCE: 1135
aggtgtggga gatcccrgat gggggcctga tgc 33

<210> SEQ ID NO 1136
<211> LENGTH: 33
<212> TYPE: DNA
<213> ORGANISM: Homo Sapiens

<400> SEQUENCE: 1136
cagcaaagtc tgaccartct aaagtaacca ctc 33

<210> SEQ ID NO 1137
<211> LENGTH: 33
<212> TYPE: DNA
<213> ORGANISM: Homo Sapiens

<400> SEQUENCE: 1137
agggaccctt ctaaaargtc actgtgggct ggg 33

<210> SEQ ID NO 1138
<211> LENGTH: 33
<212> TYPE: DNA

<213> ORGANISM: Homo Sapiens

<400> SEQUENCE: 1138
gagaccagcc tacgcarcat agaacctgtc tct 33

<210> SEQ ID NO 1139
<211> LENGTH: 33
<212> TYPE: DNA
<213> ORGANISM: Homo Sapiens

<400> SEQUENCE: 1139
agtaatactt cccatamgag atagttgtga aat 33

<210> SEQ ID NO 1140
<211> LENGTH: 33
<212> TYPE: DNA
<213> ORGANISM: Homo Sapiens

<400> SEQUENCE: 1140
ttctgatttc acaagcrggg ctccagggca ttt 33

<210> SEQ ID NO 1141
<211> LENGTH: 33
<212> TYPE: DNA
<213> ORGANISM: Homo Sapiens

<400> SEQUENCE: 1141
tctacaacca tgtcagraca caatctaact cct 33

<210> SEQ ID NO 1142
<211> LENGTH: 33
<212> TYPE: DNA
<213> ORGANISM: Homo Sapiens

<400> SEQUENCE: 1142
cagaggcggc ggcggcrgca gctcaaccct cct 33

<210> SEQ ID NO 1143
<211> LENGTH: 33
<212> TYPE: DNA
<213> ORGANISM: Homo Sapiens

<400> SEQUENCE: 1143
ctcccctgac ccaggtragg cagtgagtac ccc 33

<210> SEQ ID NO 1144
<211> LENGTH: 33
<212> TYPE: DNA
<213> ORGANISM: Homo Sapiens

<400> SEQUENCE: 1144
atgtcctctg gagcacrccc cacagcaagt tgg 33

<210> SEQ ID NO 1145
<211> LENGTH: 33
<212> TYPE: DNA
<213> ORGANISM: Homo Sapiens

<400> SEQUENCE: 1145
cacggcttct cggtgamcct cctggggttc tgc 33

<210> SEQ ID NO 1146
<211> LENGTH: 33

<212> TYPE: DNA
<213> ORGANISM: Homo Sapiens

<400> SEQUENCE: 1146
aggctgcagg agctgcrtgc aggtgagacc ccg 33

<210> SEQ ID NO 1147
<211> LENGTH: 33
<212> TYPE: DNA
<213> ORGANISM: Homo Sapiens

<400> SEQUENCE: 1147
atcctcctca tttttcrtct aaaagcctta gtc 33

<210> SEQ ID NO 1148
<211> LENGTH: 33
<212> TYPE: DNA
<213> ORGANISM: Homo Sapiens

<400> SEQUENCE: 1148
gcccaagagc gcccacrcgt ctcccgagaa gaa 33

<210> SEQ ID NO 1149
<211> LENGTH: 33
<212> TYPE: DNA
<213> ORGANISM: Homo Sapiens

<400> SEQUENCE: 1149
gcatgcgcgc tctcagrata aacaggccct gcc 33

<210> SEQ ID NO 1150
<211> LENGTH: 33
<212> TYPE: DNA
<213> ORGANISM: Homo Sapiens

<400> SEQUENCE: 1150
aggggcacgg ggagcasagg cccctgagca gga 33

<210> SEQ ID NO 1151
<211> LENGTH: 33
<212> TYPE: DNA
<213> ORGANISM: Homo Sapiens

<400> SEQUENCE: 1151
aaaattcaaa tttttcrtgg agggcaaaca cag 33

<210> SEQ ID NO 1152
<211> LENGTH: 33
<212> TYPE: DNA
<213> ORGANISM: Homo Sapiens

<400> SEQUENCE: 1152
cccatcccct cagcttmtat tctgagctca atg 33

<210> SEQ ID NO 1153
<211> LENGTH: 33
<212> TYPE: DNA
<213> ORGANISM: Homo Sapiens

<400> SEQUENCE: 1153
gagtcacagt gatggcracc cggtattctc agc 33

<210> SEQ ID NO 1154

<211> LENGTH: 33
<212> TYPE: DNA
<213> ORGANISM: Homo Sapiens

<400> SEQUENCE: 1154
tgcgccatca tgccctrcgc atttcattta aat 33

<210> SEQ ID NO 1155
<211> LENGTH: 33
<212> TYPE: DNA
<213> ORGANISM: Homo Sapiens

<400> SEQUENCE: 1155
atgagcatgt gatccartga tagtcaatga aat 33

<210> SEQ ID NO 1156
<211> LENGTH: 33
<212> TYPE: DNA
<213> ORGANISM: Homo Sapiens

<400> SEQUENCE: 1156
gtcaaaaaaa gcatcartaa ataagtagag agt 33

<210> SEQ ID NO 1157
<211> LENGTH: 33
<212> TYPE: DNA
<213> ORGANISM: Homo Sapiens

<400> SEQUENCE: 1157
taaatgtagt catggcmgaa agctgagtgg gtg 33

<210> SEQ ID NO 1158
<211> LENGTH: 33
<212> TYPE: DNA
<213> ORGANISM: Homo Sapiens

<400> SEQUENCE: 1158
tgatcaggtt ttgggcragg gtctgctttt ttg 33

<210> SEQ ID NO 1159
<211> LENGTH: 33
<212> TYPE: DNA
<213> ORGANISM: Homo Sapiens

<400> SEQUENCE: 1159
tgccagcttt acaagcsaca gaatcaccaa aac 33

<210> SEQ ID NO 1160
<211> LENGTH: 33
<212> TYPE: DNA
<213> ORGANISM: Homo Sapiens

<400> SEQUENCE: 1160
caacaatggc accagtmctt ctccaaatca ttt 33

<210> SEQ ID NO 1161
<211> LENGTH: 33
<212> TYPE: DNA
<213> ORGANISM: Homo Sapiens

<400> SEQUENCE: 1161
gagcaggaca tacaggragg gaaaaatgag tcc 33

<210> SEQ ID NO 1162
<211> LENGTH: 33
<212> TYPE: DNA
<213> ORGANISM: Homo Sapiens

<400> SEQUENCE: 1162
tgtgatgtga tacttgrtag tactgaagga aac 33

<210> SEQ ID NO 1163
<211> LENGTH: 33
<212> TYPE: DNA
<213> ORGANISM: Homo Sapiens

<400> SEQUENCE: 1163
tctaccctca gtcatargca ggaggaaata cca 33

<210> SEQ ID NO 1164
<211> LENGTH: 33
<212> TYPE: DNA
<213> ORGANISM: Homo Sapiens

<400> SEQUENCE: 1164
gacttcctgg aggcgtrggg ggaagcggag gag 33

<210> SEQ ID NO 1165
<211> LENGTH: 33
<212> TYPE: DNA
<213> ORGANISM: Homo Sapiens

<400> SEQUENCE: 1165
tgagatgtag agcttgrcac ctgcatataa agt 33

<210> SEQ ID NO 1166
<211> LENGTH: 33
<212> TYPE: DNA
<213> ORGANISM: Homo Sapiens

<400> SEQUENCE: 1166
ttcctagagg ttcacartaa atctaaaaag atc 33

<210> SEQ ID NO 1167
<211> LENGTH: 33
<212> TYPE: DNA
<213> ORGANISM: Homo Sapiens

<400> SEQUENCE: 1167
tccggcagtg tttacgragg gctggagata cac 33

<210> SEQ ID NO 1168
<211> LENGTH: 33
<212> TYPE: DNA
<213> ORGANISM: Homo Sapiens

<400> SEQUENCE: 1168
caggtcagcc agttggraac agagttgacg gag 33

<210> SEQ ID NO 1169
<211> LENGTH: 33
<212> TYPE: DNA
<213> ORGANISM: Homo Sapiens

<400> SEQUENCE: 1169
ttacattata catcttmggc attttttttcc ttt 33

<210> SEQ ID NO 1170
<211> LENGTH: 33
<212> TYPE: DNA
<213> ORGANISM: Homo Sapiens

<400> SEQUENCE: 1170
tttctaattt aatcttrtac atgagacagc tat 33

<210> SEQ ID NO 1171
<211> LENGTH: 33
<212> TYPE: DNA
<213> ORGANISM: Homo Sapiens

<400> SEQUENCE: 1171
gcagatagga tgatacrtgt gctctgcaac cat 33

<210> SEQ ID NO 1172
<211> LENGTH: 33
<212> TYPE: DNA
<213> ORGANISM: Homo Sapiens

<400> SEQUENCE: 1172
caccagaact gaaattrttt ccagctatgt tta 33

<210> SEQ ID NO 1173
<211> LENGTH: 33
<212> TYPE: DNA
<213> ORGANISM: Homo Sapiens

<400> SEQUENCE: 1173
gaacacagaa actgcartgg cttttggacg cta 33

<210> SEQ ID NO 1174
<211> LENGTH: 33
<212> TYPE: DNA
<213> ORGANISM: Homo Sapiens

<400> SEQUENCE: 1174
cttcttccat cagggargtt atcaggctca aag 33

<210> SEQ ID NO 1175
<211> LENGTH: 33
<212> TYPE: DNA
<213> ORGANISM: Homo Sapiens

<400> SEQUENCE: 1175
atcctctgct ctcctargtt caggcaggat aga 33

<210> SEQ ID NO 1176
<211> LENGTH: 33
<212> TYPE: DNA
<213> ORGANISM: Homo Sapiens

<400> SEQUENCE: 1176
caaaccattg catcatrttt tggactgata gtt 33

<210> SEQ ID NO 1177
<211> LENGTH: 33
<212> TYPE: DNA
<213> ORGANISM: Homo Sapiens

<400> SEQUENCE: 1177
ttccccaatt attatcmgtc actcctcctc cat 33

<210> SEQ ID NO 1178
<211> LENGTH: 33
<212> TYPE: DNA
<213> ORGANISM: Homo Sapiens

<400> SEQUENCE: 1178
tggccaatcc aactgamggg gaccccttta ttg 33

<210> SEQ ID NO 1179
<211> LENGTH: 33
<212> TYPE: DNA
<213> ORGANISM: Homo Sapiens

<400> SEQUENCE: 1179
gcagtggatc ctgaccrgcc gctgagcgcc aag 33

<210> SEQ ID NO 1180
<211> LENGTH: 33
<212> TYPE: DNA
<213> ORGANISM: Homo Sapiens

<400> SEQUENCE: 1180
gccaggagct gtgcccrgtg cctgcagcct tca 33

<210> SEQ ID NO 1181
<211> LENGTH: 33
<212> TYPE: DNA
<213> ORGANISM: Homo Sapiens

<400> SEQUENCE: 1181
ttaatcaaat atcgggrtta aagaatgtat caa 33

<210> SEQ ID NO 1182
<211> LENGTH: 33
<212> TYPE: DNA
<213> ORGANISM: Homo Sapiens

<400> SEQUENCE: 1182
gcagccccag caggaargac acgataatcg att 33

<210> SEQ ID NO 1183
<211> LENGTH: 33
<212> TYPE: DNA
<213> ORGANISM: Homo Sapiens

<400> SEQUENCE: 1183
aaggggaaac ggagccrgcc aaggacaggt gaa 33

<210> SEQ ID NO 1184
<211> LENGTH: 33
<212> TYPE: DNA
<213> ORGANISM: Homo Sapiens

<400> SEQUENCE: 1184
acatggggaa tggggtrtgg actctatggg gtg 33

<210> SEQ ID NO 1185
<211> LENGTH: 33
<212> TYPE: DNA
<213> ORGANISM: Homo Sapiens

<400> SEQUENCE: 1185
cccaaggcaa acctgcmtgg tgtcacgcag ggt 33

<210> SEQ ID NO 1186
<211> LENGTH: 33
<212> TYPE: DNA
<213> ORGANISM: Homo Sapiens

<400> SEQUENCE: 1186
tgctctctgg atcctgragg aagttgatcc act 33

<210> SEQ ID NO 1187
<211> LENGTH: 33
<212> TYPE: DNA
<213> ORGANISM: Homo Sapiens

<400> SEQUENCE: 1187
caggtcctca aaaaacraaa cagagctatt atg 33

<210> SEQ ID NO 1188
<211> LENGTH: 33
<212> TYPE: DNA
<213> ORGANISM: Homo Sapiens

<400> SEQUENCE: 1188
cacagggcct gtggacrggg gtggctatga gat 33

<210> SEQ ID NO 1189
<211> LENGTH: 33
<212> TYPE: DNA
<213> ORGANISM: Homo Sapiens

<400> SEQUENCE: 1189
gttcttttgg atgtttrctt aggagtggaa tta 33

<210> SEQ ID NO 1190
<211> LENGTH: 33
<212> TYPE: DNA
<213> ORGANISM: Homo Sapiens

<400> SEQUENCE: 1190
caggccagag ccaggartct attgcacagt taa 33

<210> SEQ ID NO 1191
<211> LENGTH: 33
<212> TYPE: DNA
<213> ORGANISM: Homo Sapiens

<400> SEQUENCE: 1191
cattcatcaa gaagtcrgat aaagggttta aac 33

<210> SEQ ID NO 1192
<211> LENGTH: 33
<212> TYPE: DNA
<213> ORGANISM: Homo Sapiens

<400> SEQUENCE: 1192
ttaactcctt tcaaacratt tcctttgtat ctt 33

<210> SEQ ID NO 1193
<211> LENGTH: 33
<212> TYPE: DNA
<213> ORGANISM: Homo Sapiens

<400> SEQUENCE: 1193
aaatagagac acagccrgag tgctggctat gac 33

<210> SEQ ID NO 1194
<211> LENGTH: 33
<212> TYPE: DNA
<213> ORGANISM: Homo Sapiens

<400> SEQUENCE: 1194
catctctgag ttcctgmacc acttatcaag tgt 33

<210> SEQ ID NO 1195
<211> LENGTH: 33
<212> TYPE: DNA
<213> ORGANISM: Homo Sapiens

<400> SEQUENCE: 1195
gggagtgtgg acacggrgct gcactgccag gct 33

<210> SEQ ID NO 1196
<211> LENGTH: 33
<212> TYPE: DNA
<213> ORGANISM: Homo Sapiens

<400> SEQUENCE: 1196
ctctctccta cctaggrtgg cggtggtggc agc 33

<210> SEQ ID NO 1197
<211> LENGTH: 33
<212> TYPE: DNA
<213> ORGANISM: Homo Sapiens

<400> SEQUENCE: 1197
aaataaaggc ctgtggrcct cagtttcctg tgt 33

<210> SEQ ID NO 1198
<211> LENGTH: 33
<212> TYPE: DNA
<213> ORGANISM: Homo Sapiens

<400> SEQUENCE: 1198
ctgaccctga ctttgaratt tcgtctgtaa aat 33

<210> SEQ ID NO 1199
<211> LENGTH: 33
<212> TYPE: DNA
<213> ORGANISM: Homo Sapiens

<400> SEQUENCE: 1199
ggagcagccc ctcttcrtct ggcccttcca cct 33

<210> SEQ ID NO 1200
<211> LENGTH: 33
<212> TYPE: DNA
<213> ORGANISM: Homo Sapiens

<400> SEQUENCE: 1200
tattgctcat ttttttrtag atgaggaaac tgc 33

<210> SEQ ID NO 1201
<211> LENGTH: 33
<212> TYPE: DNA
<213> ORGANISM: Homo Sapiens

<400> SEQUENCE: 1201
ccttgtctta gttccaracg tctccctctg tga 33

<210> SEQ ID NO 1202
<211> LENGTH: 33
<212> TYPE: DNA
<213> ORGANISM: Homo Sapiens

<400> SEQUENCE: 1202
aacaccatac agcaatragc atgaacaacc tac 33

<210> SEQ ID NO 1203
<211> LENGTH: 33
<212> TYPE: DNA
<213> ORGANISM: Homo Sapiens

<400> SEQUENCE: 1203
gcaatcttac tcctctmtga taacaaatag atc 33

<210> SEQ ID NO 1204
<211> LENGTH: 33
<212> TYPE: DNA
<213> ORGANISM: Homo Sapiens

<400> SEQUENCE: 1204
ctatgtctat aagtggraaa ggctttgttt att 33

<210> SEQ ID NO 1205
<211> LENGTH: 33
<212> TYPE: DNA
<213> ORGANISM: Homo Sapiens

<400> SEQUENCE: 1205
gaagcagatg tgtatgrttt tggagaaaca gaa 33

<210> SEQ ID NO 1206
<211> LENGTH: 33
<212> TYPE: DNA
<213> ORGANISM: Homo Sapiens

<400> SEQUENCE: 1206
gtgacttctt tcatcamcct ctggtaacca gac 33

<210> SEQ ID NO 1207
<211> LENGTH: 33
<212> TYPE: DNA
<213> ORGANISM: Homo Sapiens

<400> SEQUENCE: 1207
tctctgtttt aagggcrgtg gatagggtag ggt 33

<210> SEQ ID NO 1208
<211> LENGTH: 33
<212> TYPE: DNA
<213> ORGANISM: Homo Sapiens

<400> SEQUENCE: 1208
tccttagttg gatcagrcac agactatgaa att 33

<210> SEQ ID NO 1209
<211> LENGTH: 33
<212> TYPE: DNA
<213> ORGANISM: Homo Sapiens

<400> SEQUENCE: 1209
gatgaggtct gtgcatrctc ctttccccat caa 33

<210> SEQ ID NO 1210
<211> LENGTH: 33
<212> TYPE: DNA
<213> ORGANISM: Homo Sapiens

<400> SEQUENCE: 1210
ttaattctct tcctggmcag cctaacttct cct 33

<210> SEQ ID NO 1211
<211> LENGTH: 33
<212> TYPE: DNA
<213> ORGANISM: Homo Sapiens

<400> SEQUENCE: 1211
gtaaggactt tatccaraat cacttatgtg tct 33

<210> SEQ ID NO 1212
<211> LENGTH: 33
<212> TYPE: DNA
<213> ORGANISM: Homo Sapiens

<400> SEQUENCE: 1212
tgatagccat cacccargga gaatggtgaa aga 33

<210> SEQ ID NO 1213
<211> LENGTH: 33
<212> TYPE: DNA
<213> ORGANISM: Homo Sapiens

<400> SEQUENCE: 1213
ggatgtgtaa gaccctrtag ttaacataac act 33

<210> SEQ ID NO 1214
<211> LENGTH: 33
<212> TYPE: DNA
<213> ORGANISM: Homo Sapiens

<400> SEQUENCE: 1214
tgctgaactt tgtcctrgca tataattagt tac 33

<210> SEQ ID NO 1215
<211> LENGTH: 33
<212> TYPE: DNA
<213> ORGANISM: Homo Sapiens

<400> SEQUENCE: 1215
tagctaacac tactacmcaa gctaccagaa cag 33

<210> SEQ ID NO 1216
<211> LENGTH: 33
<212> TYPE: DNA
<213> ORGANISM: Homo Sapiens

<400> SEQUENCE: 1216
taatgactaa tcaggargca acgtaaccaa aag 33

<210> SEQ ID NO 1217
<211> LENGTH: 33
<212> TYPE: DNA

<213> ORGANISM: Homo Sapiens

<400> SEQUENCE: 1217
gacggccccc catccascct cgagctggac cac 33

<210> SEQ ID NO 1218
<211> LENGTH: 33
<212> TYPE: DNA
<213> ORGANISM: Homo Sapiens

<400> SEQUENCE: 1218
gctgagcccc ttcagcrtag tcaggcgcgg ggc 33

<210> SEQ ID NO 1219
<211> LENGTH: 33
<212> TYPE: DNA
<213> ORGANISM: Homo Sapiens

<400> SEQUENCE: 1219
tcatgtccta accaacrgaa tcaccctggt tcc 33

<210> SEQ ID NO 1220
<211> LENGTH: 33
<212> TYPE: DNA
<213> ORGANISM: Homo Sapiens

<400> SEQUENCE: 1220
gccagagtct ggggccract gttccactgg gcc 33

<210> SEQ ID NO 1221
<211> LENGTH: 33
<212> TYPE: DNA
<213> ORGANISM: Homo Sapiens

<400> SEQUENCE: 1221
ttttgaagtc aagtgcrttc ctggagatcc ggt 33

<210> SEQ ID NO 1222
<211> LENGTH: 33
<212> TYPE: DNA
<213> ORGANISM: Homo Sapiens

<400> SEQUENCE: 1222
gagagcgaag agcaggmgga ggaacaaagg cga 33

<210> SEQ ID NO 1223
<211> LENGTH: 33
<212> TYPE: DNA
<213> ORGANISM: Homo Sapiens

<400> SEQUENCE: 1223
atggcttgta ctaatgrctt ttgcccatta ata 33

<210> SEQ ID NO 1224
<211> LENGTH: 33
<212> TYPE: DNA
<213> ORGANISM: Homo Sapiens

<400> SEQUENCE: 1224
aaacaaaaag atggacrtct ttcaagatca atg 33

<210> SEQ ID NO 1225
<211> LENGTH: 33

<212> TYPE: DNA
<213> ORGANISM: Homo Sapiens

<400> SEQUENCE: 1225
ctattatgaa attctgrgtc taaagacatt gca 33

<210> SEQ ID NO 1226
<211> LENGTH: 33
<212> TYPE: DNA
<213> ORGANISM: Homo Sapiens

<400> SEQUENCE: 1226
ctaattctgt cagcctrctt actagaaacc aaa 33

<210> SEQ ID NO 1227
<211> LENGTH: 33
<212> TYPE: DNA
<213> ORGANISM: Homo Sapiens

<400> SEQUENCE: 1227
gtttttagag accacarcct gctttcttct aga 33

<210> SEQ ID NO 1228
<211> LENGTH: 33
<212> TYPE: DNA
<213> ORGANISM: Homo Sapiens

<400> SEQUENCE: 1228
tcctaaaagg tttcacrtca agcataagtt tct 33

<210> SEQ ID NO 1229
<211> LENGTH: 33
<212> TYPE: DNA
<213> ORGANISM: Homo Sapiens

<400> SEQUENCE: 1229
attatctgga gtcaggrttc ttctttagca gtg 33

<210> SEQ ID NO 1230
<211> LENGTH: 33
<212> TYPE: DNA
<213> ORGANISM: Homo Sapiens

<400> SEQUENCE: 1230
actcaccttg tcatcaraag agaaaggacc atg 33

<210> SEQ ID NO 1231
<211> LENGTH: 33
<212> TYPE: DNA
<213> ORGANISM: Homo Sapiens

<400> SEQUENCE: 1231
gggcactagg tgccacrctc accttgtcat cag 33

<210> SEQ ID NO 1232
<211> LENGTH: 33
<212> TYPE: DNA
<213> ORGANISM: Homo Sapiens

<400> SEQUENCE: 1232
cattactcag aattatrtct ggagcaaata aca 33

<210> SEQ ID NO 1233

<211> LENGTH: 33
<212> TYPE: DNA
<213> ORGANISM: Homo Sapiens

<400> SEQUENCE: 1233
cttacaccat gtttctrtca gtatcaaaca aag                33

<210> SEQ ID NO 1234
<211> LENGTH: 33
<212> TYPE: DNA
<213> ORGANISM: Homo Sapiens

<400> SEQUENCE: 1234
ggtttggagt ctgatcrctt ggattctggc agg                33

<210> SEQ ID NO 1235
<211> LENGTH: 33
<212> TYPE: DNA
<213> ORGANISM: Homo Sapiens

<400> SEQUENCE: 1235
ttcatttgaa tgaaacrggt cactttaaaa att                33

<210> SEQ ID NO 1236
<211> LENGTH: 33
<212> TYPE: DNA
<213> ORGANISM: Homo Sapiens

<400> SEQUENCE: 1236
ctgcaaagtt ccattaraaa gatggtggac aaa                33

<210> SEQ ID NO 1237
<211> LENGTH: 33
<212> TYPE: DNA
<213> ORGANISM: Homo Sapiens

<400> SEQUENCE: 1237
cctgtgcctg agatgargca ggaatctcca ggg                33

<210> SEQ ID NO 1238
<211> LENGTH: 33
<212> TYPE: DNA
<213> ORGANISM: Homo Sapiens

<400> SEQUENCE: 1238
tttacttttg gcctccrttg acccagatgg gga                33

<210> SEQ ID NO 1239
<211> LENGTH: 33
<212> TYPE: DNA
<213> ORGANISM: Homo Sapiens

<400> SEQUENCE: 1239
tttacagata ctgactrcat aaaacaacaa tcc                33

<210> SEQ ID NO 1240
<211> LENGTH: 33
<212> TYPE: DNA
<213> ORGANISM: Homo Sapiens

<400> SEQUENCE: 1240
caaaaggacg tactgcrtga tgctaattta taa                33

<210> SEQ ID NO 1241
<211> LENGTH: 33
<212> TYPE: DNA
<213> ORGANISM: Homo Sapiens

<400> SEQUENCE: 1241
acagacttaa gtgaagrccc gcattcctac ttt 33

<210> SEQ ID NO 1242
<211> LENGTH: 33
<212> TYPE: DNA
<213> ORGANISM: Homo Sapiens

<400> SEQUENCE: 1242
aagctaggag cattttraat atgtatttct gga 33

<210> SEQ ID NO 1243
<211> LENGTH: 33
<212> TYPE: DNA
<213> ORGANISM: Homo Sapiens

<400> SEQUENCE: 1243
aacactagtt gagtaartgg atacaattga ggt 33

<210> SEQ ID NO 1244
<211> LENGTH: 33
<212> TYPE: DNA
<213> ORGANISM: Homo Sapiens

<400> SEQUENCE: 1244
ctagacctac tgccatragt tttgtaagac aca 33

<210> SEQ ID NO 1245
<211> LENGTH: 33
<212> TYPE: DNA
<213> ORGANISM: Homo Sapiens

<400> SEQUENCE: 1245
caggacaggc aacacartaa cttgatacaa aag 33

<210> SEQ ID NO 1246
<211> LENGTH: 33
<212> TYPE: DNA
<213> ORGANISM: Homo Sapiens

<400> SEQUENCE: 1246
agtgaggctc atctgcmtgg gtgagaagcg aaa 33

<210> SEQ ID NO 1247
<211> LENGTH: 33
<212> TYPE: DNA
<213> ORGANISM: Homo Sapiens

<400> SEQUENCE: 1247
atgctgtagc cacttgrtaa catctttctt gaa 33

<210> SEQ ID NO 1248
<211> LENGTH: 33
<212> TYPE: DNA
<213> ORGANISM: Homo Sapiens

<400> SEQUENCE: 1248
aacgacttgg aaatagrcta taaatgtaga agg 33

<210> SEQ ID NO 1249
<211> LENGTH: 33
<212> TYPE: DNA
<213> ORGANISM: Homo Sapiens

<400> SEQUENCE: 1249
tttaatttaa aataatmaca ttctggggtg cca 33

<210> SEQ ID NO 1250
<211> LENGTH: 33
<212> TYPE: DNA
<213> ORGANISM: Homo Sapiens

<400> SEQUENCE: 1250
ccaatgacat aatatcmgac cttaaaaaaa tga 33

<210> SEQ ID NO 1251
<211> LENGTH: 33
<212> TYPE: DNA
<213> ORGANISM: Homo Sapiens

<400> SEQUENCE: 1251
caggtcttat ttcttcrttt acgttatgtg aaa 33

<210> SEQ ID NO 1252
<211> LENGTH: 33
<212> TYPE: DNA
<213> ORGANISM: Homo Sapiens

<400> SEQUENCE: 1252
gccatcccct atctctmttg aaaactgact tca 33

<210> SEQ ID NO 1253
<211> LENGTH: 33
<212> TYPE: DNA
<213> ORGANISM: Homo Sapiens

<400> SEQUENCE: 1253
cctctcccat gatccartca tctctcccca ggc 33

<210> SEQ ID NO 1254
<211> LENGTH: 33
<212> TYPE: DNA
<213> ORGANISM: Homo Sapiens

<400> SEQUENCE: 1254
gtattcaaat cttggcmaat atccaactag caa 33

<210> SEQ ID NO 1255
<211> LENGTH: 33
<212> TYPE: DNA
<213> ORGANISM: Homo Sapiens

<400> SEQUENCE: 1255
gaagaatgaa tgtcttrgga tacaattaag tga 33

<210> SEQ ID NO 1256
<211> LENGTH: 33
<212> TYPE: DNA
<213> ORGANISM: Homo Sapiens

<400> SEQUENCE: 1256
aaaccattac ataggtmtca aaatccaaat att 33

<210> SEQ ID NO 1257
<211> LENGTH: 33
<212> TYPE: DNA
<213> ORGANISM: Homo Sapiens

<400> SEQUENCE: 1257
aaacattttc cagagtmaag aaagagtaga aaa 33

<210> SEQ ID NO 1258
<211> LENGTH: 33
<212> TYPE: DNA
<213> ORGANISM: Homo Sapiens

<400> SEQUENCE: 1258
gtcattttat gagtgamaaa aagaaacaaa tgg 33

<210> SEQ ID NO 1259
<211> LENGTH: 33
<212> TYPE: DNA
<213> ORGANISM: Homo Sapiens

<400> SEQUENCE: 1259
aagcaatcct agctggrgta gagctggcat ttt 33

<210> SEQ ID NO 1260
<211> LENGTH: 33
<212> TYPE: DNA
<213> ORGANISM: Homo Sapiens

<400> SEQUENCE: 1260
aacacaatgg ggttgarcat cacctcatat tca 33

<210> SEQ ID NO 1261
<211> LENGTH: 33
<212> TYPE: DNA
<213> ORGANISM: Homo Sapiens

<400> SEQUENCE: 1261
acctgttctg tttgatrtgc agactgaggc tca 33

<210> SEQ ID NO 1262
<211> LENGTH: 33
<212> TYPE: DNA
<213> ORGANISM: Homo Sapiens

<400> SEQUENCE: 1262
atcacagatt tctgttrgtc cttttgttgg taa 33

<210> SEQ ID NO 1263
<211> LENGTH: 33
<212> TYPE: DNA
<213> ORGANISM: Homo Sapiens

<400> SEQUENCE: 1263
ttccaggtcc cctttcrctt cctgtgctgt tgc 33

<210> SEQ ID NO 1264
<211> LENGTH: 33
<212> TYPE: DNA
<213> ORGANISM: Homo Sapiens

<400> SEQUENCE: 1264
ggtcttgaca tgccagrcaa gttctctctt ggg 33

<210> SEQ ID NO 1265
<211> LENGTH: 33
<212> TYPE: DNA
<213> ORGANISM: Homo Sapiens

<400> SEQUENCE: 1265
agggaaagtg cttaacrtag cttgataaat gct 33

<210> SEQ ID NO 1266
<211> LENGTH: 33
<212> TYPE: DNA
<213> ORGANISM: Homo Sapiens

<400> SEQUENCE: 1266
cattatacta aataccragg ttaagagaat aaa 33

<210> SEQ ID NO 1267
<211> LENGTH: 33
<212> TYPE: DNA
<213> ORGANISM: Homo Sapiens

<400> SEQUENCE: 1267
agttactatg atttaamtgt ttcattgtgt tta 33

<210> SEQ ID NO 1268
<211> LENGTH: 33
<212> TYPE: DNA
<213> ORGANISM: Homo Sapiens

<400> SEQUENCE: 1268
gcttcattat atcacaraga atgagctcaa ata 33

<210> SEQ ID NO 1269
<211> LENGTH: 33
<212> TYPE: DNA
<213> ORGANISM: Homo Sapiens

<400> SEQUENCE: 1269
ctacctttaa gaaacargat aaaaaataat gat 33

<210> SEQ ID NO 1270
<211> LENGTH: 33
<212> TYPE: DNA
<213> ORGANISM: Homo Sapiens

<400> SEQUENCE: 1270
gcttttgggt acacagrccc attacataca tga 33

<210> SEQ ID NO 1271
<211> LENGTH: 33
<212> TYPE: DNA
<213> ORGANISM: Homo Sapiens

<400> SEQUENCE: 1271
ccaatttcct ttaaaaraga ggcttctgaa att 33

<210> SEQ ID NO 1272
<211> LENGTH: 33
<212> TYPE: DNA
<213> ORGANISM: Homo Sapiens

<400> SEQUENCE: 1272
atagcacctc tttctgmagc tctcgggact ctt 33

<210> SEQ ID NO 1273
<211> LENGTH: 33
<212> TYPE: DNA
<213> ORGANISM: Homo Sapiens

<400> SEQUENCE: 1273
tcctaactgt ctaactrtat gaattccaaa agt 33

<210> SEQ ID NO 1274
<211> LENGTH: 33
<212> TYPE: DNA
<213> ORGANISM: Homo Sapiens

<400> SEQUENCE: 1274
ttaaggcaga acaatcrtca tatctgttca gga 33

<210> SEQ ID NO 1275
<211> LENGTH: 33
<212> TYPE: DNA
<213> ORGANISM: Homo Sapiens

<400> SEQUENCE: 1275
tacattacag aatgaaraga aaagagggct tgg 33

<210> SEQ ID NO 1276
<211> LENGTH: 33
<212> TYPE: DNA
<213> ORGANISM: Homo Sapiens

<400> SEQUENCE: 1276
gcttgagctc tcttttragg attcatcttt gac 33

<210> SEQ ID NO 1277
<211> LENGTH: 33
<212> TYPE: DNA
<213> ORGANISM: Homo Sapiens

<400> SEQUENCE: 1277
agaggttgca agcacargta tttgacacac tgt 33

<210> SEQ ID NO 1278
<211> LENGTH: 33
<212> TYPE: DNA
<213> ORGANISM: Homo Sapiens

<400> SEQUENCE: 1278
tctctggctt taaacaraaa gatgactaaa act 33

<210> SEQ ID NO 1279
<211> LENGTH: 33
<212> TYPE: DNA
<213> ORGANISM: Homo Sapiens

<400> SEQUENCE: 1279
aaaagcaaag gaggatrgca gcaaacaagt gtc 33

<210> SEQ ID NO 1280
<211> LENGTH: 33
<212> TYPE: DNA
<213> ORGANISM: Homo Sapiens

<400> SEQUENCE: 1280
cccaccagca gtatacragg cttctcattt cac 33

<210> SEQ ID NO 1281
<211> LENGTH: 33
<212> TYPE: DNA
<213> ORGANISM: Homo Sapiens

<400> SEQUENCE: 1281
agagaaataa gtggatrtaa cagagtggat ctg 33

<210> SEQ ID NO 1282
<211> LENGTH: 33
<212> TYPE: DNA
<213> ORGANISM: Homo Sapiens

<400> SEQUENCE: 1282
agtggacttt ggggccrtcg tgccggatcc tcc 33

<210> SEQ ID NO 1283
<211> LENGTH: 33
<212> TYPE: DNA
<213> ORGANISM: Homo Sapiens

<400> SEQUENCE: 1283
cgctactcct agccccrgaa agggctcacg gtg 33

<210> SEQ ID NO 1284
<211> LENGTH: 33
<212> TYPE: DNA
<213> ORGANISM: Homo Sapiens

<400> SEQUENCE: 1284
aggaggcaag atcaagratt tttttttttc taa 33

<210> SEQ ID NO 1285
<211> LENGTH: 33
<212> TYPE: DNA
<213> ORGANISM: Homo Sapiens

<400> SEQUENCE: 1285
agcagcgcgg cctccawgcc cgccttggcc agg 33

<210> SEQ ID NO 1286
<211> LENGTH: 33
<212> TYPE: DNA
<213> ORGANISM: Homo Sapiens

<400> SEQUENCE: 1286
ctgggtgaca tcctacrcgg agctagtgtc aca 33

<210> SEQ ID NO 1287
<211> LENGTH: 33
<212> TYPE: DNA
<213> ORGANISM: Homo Sapiens

<400> SEQUENCE: 1287
ctgggcacgg ggtgccrggc tggggacgta gat 33

<210> SEQ ID NO 1288
<211> LENGTH: 33
<212> TYPE: DNA
<213> ORGANISM: Homo Sapiens

<400> SEQUENCE: 1288
ggtggggtga tgcttcraga ggctacaaga aac 33

<210> SEQ ID NO 1289
<211> LENGTH: 33
<212> TYPE: DNA
<213> ORGANISM: Homo Sapiens

<400> SEQUENCE: 1289
gcagtgcgag gaaggcrgcg ggttccacgt cgg 33

<210> SEQ ID NO 1290
<211> LENGTH: 33
<212> TYPE: DNA
<213> ORGANISM: Homo Sapiens

<400> SEQUENCE: 1290 cggggggtg gtacccrcgg tgcctactca tcc 33

<210> SEQ ID NO 1291
<211> LENGTH: 33
<212> TYPE: DNA
<213> ORGANISM: Homo Sapiens

<400> SEQUENCE: 1291
ccttttctgg tgtgtcmcca gactcttcct caa 33

<210> SEQ ID NO 1292
<211> LENGTH: 33
<212> TYPE: DNA
<213> ORGANISM: Homo Sapiens

<400> SEQUENCE: 1292
cacccatgaa agaggcrgga ggggctctgc tcc 33

<210> SEQ ID NO 1293
<211> LENGTH: 33
<212> TYPE: DNA
<213> ORGANISM: Homo Sapiens

<400> SEQUENCE: 1293
acctgacgag gcgtacrgaa caggccggaa cag 33

<210> SEQ ID NO 1294
<211> LENGTH: 33
<212> TYPE: DNA
<213> ORGANISM: Homo Sapiens

<400> SEQUENCE: 1294
ttccagtgtg aacatgrcat caaagaagag gca 33

<210> SEQ ID NO 1295
<211> LENGTH: 33
<212> TYPE: DNA
<213> ORGANISM: Homo Sapiens

<400> SEQUENCE: 1295
cccacacctc atagcargat ctcatctcta caa 33

<210> SEQ ID NO 1296
<211> LENGTH: 33
<212> TYPE: DNA

<213> ORGANISM: Homo Sapiens

<400> SEQUENCE: 1296
aaaacaagca tctaccragc accctccatg agc 33

<210> SEQ ID NO 1297
<211> LENGTH: 33
<212> TYPE: DNA
<213> ORGANISM: Homo Sapiens

<400> SEQUENCE: 1297
caagtgagag cagatamggc agcacaggga ttc 33

<210> SEQ ID NO 1298
<211> LENGTH: 33
<212> TYPE: DNA
<213> ORGANISM: Homo Sapiens

<400> SEQUENCE: 1298
cgatattcca gagggarttg cttaaggaag ggg 33

<210> SEQ ID NO 1299
<211> LENGTH: 33
<212> TYPE: DNA
<213> ORGANISM: Homo Sapiens

<400> SEQUENCE: 1299
tcggaggccg tcgagartcg cgtccgccgc cgt 33

<210> SEQ ID NO 1300
<211> LENGTH: 33
<212> TYPE: DNA
<213> ORGANISM: Homo Sapiens

<400> SEQUENCE: 1300
ctaaggggtg gttatcrtga caggaaggag gta 33

<210> SEQ ID NO 1301
<211> LENGTH: 33
<212> TYPE: DNA
<213> ORGANISM: Homo Sapiens

<400> SEQUENCE: 1301
cagtagactt tcaaggrcta gtaactcgca tgc 33

<210> SEQ ID NO 1302
<211> LENGTH: 33
<212> TYPE: DNA
<213> ORGANISM: Homo Sapiens

<400> SEQUENCE: 1302
ttcaaggcaa tgttgcmaaa ctggagaact gct 33

<210> SEQ ID NO 1303
<211> LENGTH: 33
<212> TYPE: DNA
<213> ORGANISM: Homo Sapiens

<400> SEQUENCE: 1303
aggtgtctga tcaacgmcct cagagatgac ctg 33

<210> SEQ ID NO 1304
<211> LENGTH: 33

<212> TYPE: DNA
<213> ORGANISM: Homo Sapiens

<400> SEQUENCE: 1304
gatttttaaa aaaagcrttg acattgtaac agt 33

<210> SEQ ID NO 1305
<211> LENGTH: 33
<212> TYPE: DNA
<213> ORGANISM: Homo Sapiens

<400> SEQUENCE: 1305
tctcagcact ggatccrgtg ggaaaggtaa cgc 33

<210> SEQ ID NO 1306
<211> LENGTH: 33
<212> TYPE: DNA
<213> ORGANISM: Homo Sapiens

<400> SEQUENCE: 1306
catgcccaga gtatggrtat attgggggaa tca 33

<210> SEQ ID NO 1307
<211> LENGTH: 33
<212> TYPE: DNA
<213> ORGANISM: Homo Sapiens

<400> SEQUENCE: 1307
attgaactgt aacttamaca gagcaaacat tgt 33

<210> SEQ ID NO 1308
<211> LENGTH: 33
<212> TYPE: DNA
<213> ORGANISM: Homo Sapiens

<400> SEQUENCE: 1308
gcctactaac agcaagrgcc tttattaata ttt 33

<210> SEQ ID NO 1309
<211> LENGTH: 33
<212> TYPE: DNA
<213> ORGANISM: Homo Sapiens

<400> SEQUENCE: 1309
acccatgggt tctatcratt tctgccatat cct 33

<210> SEQ ID NO 1310
<211> LENGTH: 33
<212> TYPE: DNA
<213> ORGANISM: Homo Sapiens

<400> SEQUENCE: 1310
gtgtccacct gtattaragt gttttcatgt gct 33

<210> SEQ ID NO 1311
<211> LENGTH: 33
<212> TYPE: DNA
<213> ORGANISM: Homo Sapiens

<400> SEQUENCE: 1311
cacagttttc ccataaragc tcaaatatct ttg 33

<210> SEQ ID NO 1312

<211> LENGTH: 33
<212> TYPE: DNA
<213> ORGANISM: Homo Sapiens

<400> SEQUENCE: 1312
gcctaaaggg tataatraga agagaagtaa aag 33

<210> SEQ ID NO 1313
<211> LENGTH: 33
<212> TYPE: DNA
<213> ORGANISM: Homo Sapiens

<400> SEQUENCE: 1313
ggctcacagc aaaactmtac cgttttgatc tgg 33

<210> SEQ ID NO 1314
<211> LENGTH: 33
<212> TYPE: DNA
<213> ORGANISM: Homo Sapiens

<400> SEQUENCE: 1314
gtcagatggg cctgatrtca agataaggcc tac 33

<210> SEQ ID NO 1315
<211> LENGTH: 33
<212> TYPE: DNA
<213> ORGANISM: Homo Sapiens

<400> SEQUENCE: 1315
tacttgcatc ccaaccrcct aaaagtgttg gtt 33

<210> SEQ ID NO 1316
<211> LENGTH: 33
<212> TYPE: DNA
<213> ORGANISM: Homo Sapiens

<400> SEQUENCE: 1316
tggagtccag agagaarcag cagagagagg cgc 33

<210> SEQ ID NO 1317
<211> LENGTH: 33
<212> TYPE: DNA
<213> ORGANISM: Homo Sapiens

<400> SEQUENCE: 1317
cttcaacctc atgttaratc agtacttata agc 33

<210> SEQ ID NO 1318
<211> LENGTH: 33
<212> TYPE: DNA
<213> ORGANISM: Homo Sapiens

<400> SEQUENCE: 1318
tctgcccaga tcaatarcaa tgatgacaat ggt 33

<210> SEQ ID NO 1319
<211> LENGTH: 33
<212> TYPE: DNA
<213> ORGANISM: Homo Sapiens

<400> SEQUENCE: 1319
ttggtctctg gtcaccraca tcctttgctc tgg 33

<210> SEQ ID NO 1320
<211> LENGTH: 33
<212> TYPE: DNA
<213> ORGANISM: Homo Sapiens

<400> SEQUENCE: 1320
tgagcctgcc caagcarggc ctgtctgatt act 33

<210> SEQ ID NO 1321
<211> LENGTH: 33
<212> TYPE: DNA
<213> ORGANISM: Homo Sapiens

<400> SEQUENCE: 1321
ccatacctgt acacaamcac agactccagt aaa 33

<210> SEQ ID NO 1322
<211> LENGTH: 33
<212> TYPE: DNA
<213> ORGANISM: Homo Sapiens

<400> SEQUENCE: 1322
ctaaatcaaa tgacaargag aaaagttagc ttt 33

<210> SEQ ID NO 1323
<211> LENGTH: 33
<212> TYPE: DNA
<213> ORGANISM: Homo Sapiens

<400> SEQUENCE: 1323
tctcttcccc ccacaargtc attttcttaa ttc 33

<210> SEQ ID NO 1324
<211> LENGTH: 33
<212> TYPE: DNA
<213> ORGANISM: Homo Sapiens

<400> SEQUENCE: 1324
ccaagaaaaa gtgcccrcaa gaaaaccaaa aca 33

<210> SEQ ID NO 1325
<211> LENGTH: 33
<212> TYPE: DNA
<213> ORGANISM: Homo Sapiens

<400> SEQUENCE: 1325
cacagttact caagtcraga ggcaaaaaaa aaa 33

<210> SEQ ID NO 1326
<211> LENGTH: 33
<212> TYPE: DNA
<213> ORGANISM: Homo Sapiens

<400> SEQUENCE: 1326
tgtgactaaa ccactcrtct gtttccccca ctc 33

<210> SEQ ID NO 1327
<211> LENGTH: 33
<212> TYPE: DNA
<213> ORGANISM: Homo Sapiens

<400> SEQUENCE: 1327
attaaatata tttttcrtaa taacccagct aga 33

<210> SEQ ID NO 1328
<211> LENGTH: 33
<212> TYPE: DNA
<213> ORGANISM: Homo Sapiens

<400> SEQUENCE: 1328
tattaacatt cataaamcat tcagacaatt gct 33

<210> SEQ ID NO 1329
<211> LENGTH: 33
<212> TYPE: DNA
<213> ORGANISM: Homo Sapiens

<400> SEQUENCE: 1329
tgcctatttc taaactmtgc tggggaaagc agg 33

<210> SEQ ID NO 1330
<211> LENGTH: 33
<212> TYPE: DNA
<213> ORGANISM: Homo Sapiens

<400> SEQUENCE: 1330
aggagattag ggtgttratt ttcccgttct ttc 33

<210> SEQ ID NO 1331
<211> LENGTH: 33
<212> TYPE: DNA
<213> ORGANISM: Homo Sapiens

<400> SEQUENCE: 1331
ataaacttgc cttactrtat acacacacat gca 33

<210> SEQ ID NO 1332
<211> LENGTH: 33
<212> TYPE: DNA
<213> ORGANISM: Homo Sapiens

<400> SEQUENCE: 1332
ccagggctat gaaaccrtct cattctgcag cag 33

<210> SEQ ID NO 1333
<211> LENGTH: 33
<212> TYPE: DNA
<213> ORGANISM: Homo Sapiens

<400> SEQUENCE: 1333
ttttaggggg tgtgatrtct gctatgtgga cac 33

<210> SEQ ID NO 1334
<211> LENGTH: 33
<212> TYPE: DNA
<213> ORGANISM: Homo Sapiens

<400> SEQUENCE: 1334
ggattacagg catgagmcac cacatgctgc cat 33

<210> SEQ ID NO 1335
<211> LENGTH: 33
<212> TYPE: DNA
<213> ORGANISM: Homo Sapiens

<400> SEQUENCE: 1335
atgagttgga agaggtrtta gagtccccat cgt 33

<210> SEQ ID NO 1336
<211> LENGTH: 33
<212> TYPE: DNA
<213> ORGANISM: Homo Sapiens

<400> SEQUENCE: 1336
ggttttcagg aatgcaraag tctgagaaga cac 33

<210> SEQ ID NO 1337
<211> LENGTH: 33
<212> TYPE: DNA
<213> ORGANISM: Homo Sapiens

<400> SEQUENCE: 1337
taagacaaag ataaggrtct aatttcattc ttt 33

<210> SEQ ID NO 1338
<211> LENGTH: 33
<212> TYPE: DNA
<213> ORGANISM: Homo Sapiens

<400> SEQUENCE: 1338
aatttttcct tagaagmctc aacctcagca tac 33

<210> SEQ ID NO 1339
<211> LENGTH: 33
<212> TYPE: DNA
<213> ORGANISM: Homo Sapiens

<400> SEQUENCE: 1339
ggggtccctt ccctgcrctc tcataagctc ccc 33

<210> SEQ ID NO 1340
<211> LENGTH: 33
<212> TYPE: DNA
<213> ORGANISM: Homo Sapiens

<400> SEQUENCE: 1340
tcgagggcta gagagtratg agagtgggtg ggg 33

<210> SEQ ID NO 1341
<211> LENGTH: 33
<212> TYPE: DNA
<213> ORGANISM: Homo Sapiens

<400> SEQUENCE: 1341
atgtatattt aaggtargct tttctttttc cct 33

<210> SEQ ID NO 1342
<211> LENGTH: 33
<212> TYPE: DNA
<213> ORGANISM: Homo Sapiens

<400> SEQUENCE: 1342
tgacatccct cctatcrggt ctttgaggga gaa 33

<210> SEQ ID NO 1343
<211> LENGTH: 33
<212> TYPE: DNA
<213> ORGANISM: Homo Sapiens

<400> SEQUENCE: 1343
agtggccaac actaatrtga ccttgcaggc act 33

<210> SEQ ID NO 1344
<211> LENGTH: 33
<212> TYPE: DNA
<213> ORGANISM: Homo Sapiens

<400> SEQUENCE: 1344
agcatatttg gcctccrtaa tgccgcttaa ggt 33

<210> SEQ ID NO 1345
<211> LENGTH: 33
<212> TYPE: DNA
<213> ORGANISM: Homo Sapiens

<400> SEQUENCE: 1345
taaatggcaa ttgttcrtgc aataaagaac aat 33

<210> SEQ ID NO 1346
<211> LENGTH: 33
<212> TYPE: DNA
<213> ORGANISM: Homo Sapiens

<400> SEQUENCE: 1346
ctcatctctt ctagccrgct ttccccttac agg 33

<210> SEQ ID NO 1347
<211> LENGTH: 33
<212> TYPE: DNA
<213> ORGANISM: Homo Sapiens

<400> SEQUENCE: 1347
ttccaccccc agtgatrctc agaatccagg atc 33

<210> SEQ ID NO 1348
<211> LENGTH: 33
<212> TYPE: DNA
<213> ORGANISM: Homo Sapiens

<400> SEQUENCE: 1348
ataaataacg atagccrgta acttacgttc act 33

<210> SEQ ID NO 1349
<211> LENGTH: 33
<212> TYPE: DNA
<213> ORGANISM: Homo Sapiens

<400> SEQUENCE: 1349
ctcatgctgc gctgctrtca gaggccacat ctg 33

<210> SEQ ID NO 1350
<211> LENGTH: 33
<212> TYPE: DNA
<213> ORGANISM: Homo Sapiens

<400> SEQUENCE: 1350
tgtgcgtggg cctcggyggc ctccactaga cgc 33

<210> SEQ ID NO 1351
<211> LENGTH: 33
<212> TYPE: DNA
<213> ORGANISM: Homo Sapiens

<400> SEQUENCE: 1351
actgggtttt gtggacmctt tgcagaggtc ggg 33

<210> SEQ ID NO 1352
<211> LENGTH: 33
<212> TYPE: DNA
<213> ORGANISM: Homo Sapiens

<400> SEQUENCE: 1352
gtgcctttta atatatrgac cacaagctca gag 33

<210> SEQ ID NO 1353
<211> LENGTH: 33
<212> TYPE: DNA
<213> ORGANISM: Homo Sapiens

<400> SEQUENCE: 1353
cattgacaca ctggcamact caatactgtg cac 33

<210> SEQ ID NO 1354
<211> LENGTH: 33
<212> TYPE: DNA
<213> ORGANISM: Homo Sapiens

<400> SEQUENCE: 1354
cccaaaagga aaccctraac ccaataagca gtc 33

<210> SEQ ID NO 1355
<211> LENGTH: 33
<212> TYPE: DNA
<213> ORGANISM: Homo Sapiens

<400> SEQUENCE: 1355
tgttactgag gtatgcratg ccatgatttc cac 33

<210> SEQ ID NO 1356
<211> LENGTH: 33
<212> TYPE: DNA
<213> ORGANISM: Homo Sapiens

<400> SEQUENCE: 1356
tgtaaatcac cacctcrttt tgttcctaga gct 33

<210> SEQ ID NO 1357
<211> LENGTH: 33
<212> TYPE: DNA
<213> ORGANISM: Homo Sapiens

<400> SEQUENCE: 1357
cccttgccat aaattgraat ccagagctgt aag 33

<210> SEQ ID NO 1358
<211> LENGTH: 33
<212> TYPE: DNA
<213> ORGANISM: Homo Sapiens

<400> SEQUENCE: 1358
acttctactc agcataraat gggccgttgc caa 33

<210> SEQ ID NO 1359
<211> LENGTH: 33
<212> TYPE: DNA
<213> ORGANISM: Homo Sapiens

<400> SEQUENCE: 1359
ccataaaagg ccggctrtag actcacatgt ttt 33

<210> SEQ ID NO 1360
<211> LENGTH: 33
<212> TYPE: DNA
<213> ORGANISM: Homo Sapiens

<400> SEQUENCE: 1360
gtttaaatga aataaarcat cctctgtttg cgg 33

<210> SEQ ID NO 1361
<211> LENGTH: 33
<212> TYPE: DNA
<213> ORGANISM: Homo Sapiens

<400> SEQUENCE: 1361
cgcacgccac ctcttcmcca gagacgactt tgt 33

<210> SEQ ID NO 1362
<211> LENGTH: 33
<212> TYPE: DNA
<213> ORGANISM: Homo Sapiens

<400> SEQUENCE: 1362
tggaagaaga ggtaagrtat ctccagagcc gct 33

<210> SEQ ID NO 1363
<211> LENGTH: 33
<212> TYPE: DNA
<213> ORGANISM: Homo Sapiens

<400> SEQUENCE: 1363
gtttctccct ttgcccmcac cactaaaata cag 33

<210> SEQ ID NO 1364
<211> LENGTH: 33
<212> TYPE: DNA
<213> ORGANISM: Homo Sapiens

<400> SEQUENCE: 1364
agtccaagca gcacctrgta attaaactga gtc 33

<210> SEQ ID NO 1365
<211> LENGTH: 33
<212> TYPE: DNA
<213> ORGANISM: Homo Sapiens

<400> SEQUENCE: 1365
gcaaatctat acagacrgac acagattcat ggt 33

<210> SEQ ID NO 1366
<211> LENGTH: 33
<212> TYPE: DNA
<213> ORGANISM: Homo Sapiens

<400> SEQUENCE: 1366
tctgaatctg tgtcatragc gagcctgagg gct 33

<210> SEQ ID NO 1367
<211> LENGTH: 33
<212> TYPE: DNA
<213> ORGANISM: Homo Sapiens

<400> SEQUENCE: 1367
ctcagttgta tagcagratc agattctaga gtt 33

<210> SEQ ID NO 1368
<211> LENGTH: 33
<212> TYPE: DNA
<213> ORGANISM: Homo Sapiens

<400> SEQUENCE: 1368
agaaaccagc catttgmatg cgctcaatgg aat 33

<210> SEQ ID NO 1369
<211> LENGTH: 33
<212> TYPE: DNA
<213> ORGANISM: Homo Sapiens

<400> SEQUENCE: 1369
aaaaagctac gcccacmtcc taaccctcgg act 33

<210> SEQ ID NO 1370
<211> LENGTH: 33
<212> TYPE: DNA
<213> ORGANISM: Homo Sapiens

<400> SEQUENCE: 1370
ggggccagcc aatgccrgca acatgaggta cag 33

<210> SEQ ID NO 1371
<211> LENGTH: 33
<212> TYPE: DNA
<213> ORGANISM: Homo Sapiens

<400> SEQUENCE: 1371
tataaccttc caaaaamttc aacatcatct tcc 33

<210> SEQ ID NO 1372
<211> LENGTH: 33
<212> TYPE: DNA
<213> ORGANISM: Homo Sapiens

<400> SEQUENCE: 1372
aaaggaaaag tcattcrggc tgtgataaga aag 33

<210> SEQ ID NO 1373
<211> LENGTH: 33
<212> TYPE: DNA
<213> ORGANISM: Homo Sapiens

<400> SEQUENCE: 1373
taccactaat tccaatrctc aagaagagct gac 33

<210> SEQ ID NO 1374
<211> LENGTH: 33
<212> TYPE: DNA
<213> ORGANISM: Homo Sapiens

<400> SEQUENCE: 1374
ccccacgtga actcgcrgca ggcagagaat cta 33

<210> SEQ ID NO 1375
<211> LENGTH: 33
<212> TYPE: DNA

<213> ORGANISM: Homo Sapiens

<400> SEQUENCE: 1375
gggctcgttt cagaatrcgg ttgggcaagt ttg 33

<210> SEQ ID NO 1376
<211> LENGTH: 33
<212> TYPE: DNA
<213> ORGANISM: Homo Sapiens

<400> SEQUENCE: 1376
tccgtctaca gccaccmagt taaataacag cgg 33

<210> SEQ ID NO 1377
<211> LENGTH: 33
<212> TYPE: DNA
<213> ORGANISM: Homo Sapiens

<400> SEQUENCE: 1377
gttcacctcc tgatgamata aattcttgac cgt 33

<210> SEQ ID NO 1378
<211> LENGTH: 33
<212> TYPE: DNA
<213> ORGANISM: Homo Sapiens

<400> SEQUENCE: 1378
gggctatttg ataggcmcac ggcagcttgg gtt 33

<210> SEQ ID NO 1379
<211> LENGTH: 33
<212> TYPE: DNA
<213> ORGANISM: Homo Sapiens

<400> SEQUENCE: 1379
aatccatgag ttcagcmtgg tgagatcttt ccc 33

<210> SEQ ID NO 1380
<211> LENGTH: 33
<212> TYPE: DNA
<213> ORGANISM: Homo Sapiens

<400> SEQUENCE: 1380
cattgcgtcc tttcccraag agtctgttcc cat 33

<210> SEQ ID NO 1381
<211> LENGTH: 33
<212> TYPE: DNA
<213> ORGANISM: Homo Sapiens

<400> SEQUENCE: 1381
aaagaatttt cccccartgc tctagcaaat tgc 33

<210> SEQ ID NO 1382
<211> LENGTH: 33
<212> TYPE: DNA
<213> ORGANISM: Homo Sapiens

<400> SEQUENCE: 1382
ggctggtgtc tttggaraat atcaagagtc aca 33

<210> SEQ ID NO 1383
<211> LENGTH: 33

<212> TYPE: DNA
<213> ORGANISM: Homo Sapiens

<400> SEQUENCE: 1383
gtcattcagc cctcccrgca accccagaaa tag 33

<210> SEQ ID NO 1384
<211> LENGTH: 33
<212> TYPE: DNA
<213> ORGANISM: Homo Sapiens

<400> SEQUENCE: 1384
gaagtgaccc atctggrccc cagaggcagg ggc 33

<210> SEQ ID NO 1385
<211> LENGTH: 33
<212> TYPE: DNA
<213> ORGANISM: Homo Sapiens

<400> SEQUENCE: 1385
cctgcagcac ccctggmcct catggggcac ttc 33

<210> SEQ ID NO 1386
<211> LENGTH: 33
<212> TYPE: DNA
<213> ORGANISM: Homo Sapiens

<400> SEQUENCE: 1386
ccggcggact cgcaccrtcc gaatggtcac ccg 33

<210> SEQ ID NO 1387
<211> LENGTH: 33
<212> TYPE: DNA
<213> ORGANISM: Homo Sapiens

<400> SEQUENCE: 1387
tgcaaaatgc ttctgaratg ggtcaaccag aag 33

<210> SEQ ID NO 1388
<211> LENGTH: 33
<212> TYPE: DNA
<213> ORGANISM: Homo Sapiens

<400> SEQUENCE: 1388
aaagagaggg ctgactrttg attctgtgca tac 33

<210> SEQ ID NO 1389
<211> LENGTH: 33
<212> TYPE: DNA
<213> ORGANISM: Homo Sapiens

<400> SEQUENCE: 1389
agagggtgcc cccaggrtcc tactgtggat cag 33

<210> SEQ ID NO 1390
<211> LENGTH: 33
<212> TYPE: DNA
<213> ORGANISM: Homo Sapiens

<400> SEQUENCE: 1390
gaagggagca ggtgctrtca atggaaatgg gac 33

<210> SEQ ID NO 1391

-continued

<211> LENGTH: 33
<212> TYPE: DNA
<213> ORGANISM: Homo Sapiens

<400> SEQUENCE: 1391
gaatgtcgta atcaggrcga gagctcgggg cgg 33

<210> SEQ ID NO 1392
<211> LENGTH: 33
<212> TYPE: DNA
<213> ORGANISM: Homo Sapiens

<400> SEQUENCE: 1392
caagtctctc agtgacrggg ccgacacttg gtc 33

<210> SEQ ID NO 1393
<211> LENGTH: 33
<212> TYPE: DNA
<213> ORGANISM: Homo Sapiens

<400> SEQUENCE: 1393
aactttctgt aaagcartgg gagttagggc aac 33

<210> SEQ ID NO 1394
<211> LENGTH: 33
<212> TYPE: DNA
<213> ORGANISM: Homo Sapiens

<400> SEQUENCE: 1394
ctgcctctaa acccgamgtc ttcaagcctg act 33

<210> SEQ ID NO 1395
<211> LENGTH: 33
<212> TYPE: DNA
<213> ORGANISM: Homo Sapiens

<400> SEQUENCE: 1395
gtgtcgtggc agatacmagg tctcacggaa gtc 33

<210> SEQ ID NO 1396
<211> LENGTH: 33
<212> TYPE: DNA
<213> ORGANISM: Homo Sapiens

<400> SEQUENCE: 1396
gtgagctgca catcctrcct agaagggaca tct 33

<210> SEQ ID NO 1397
<211> LENGTH: 33
<212> TYPE: DNA
<213> ORGANISM: Homo Sapiens

<400> SEQUENCE: 1397
tagctattcc aaataarata aaacccaaag aaa 33

<210> SEQ ID NO 1398
<211> LENGTH: 33
<212> TYPE: DNA
<213> ORGANISM: Homo Sapiens

<400> SEQUENCE: 1398
ccaatgtatg tgaagtrgct caaatgaatt ttg 33

METHOD OF TESTING FOR ENDOMETRIOSIS AND TREATMENT THEREFOR

CROSS REFERENCE TO RELATED APPLICATIONS

This nonprovisional utility patent application is a continuation of and claims the benefit under 35 USC §120 to U.S. application Ser. No. 13/788,913 filed Mar. 7, 2013 and scheduled to issue as U.S. Pat. No. 8,932,993 on Jan. 13, 2015, which is a continuation-in-part of and claims the benefit under 35 USC §120 to co-pending U.S. application Ser. No. 12/056,754 filed Mar. 27, 2008, which claims the benefit under 35 USC §119(e) of U.S. provisional application No. 60/943,193, filed Jun. 11, 2007, and which is a continuation-in-part of and claims the benefit under 35 USC §120 to co-pending U.S. application Ser. No. 12/120,322 filed May 14, 2008, and which is a continuation-in-part of and claims the benefit under 35 USC §120 to co-pending U.S. application Ser. No. 12/765,643 filed Apr. 22, 2010, which claims the benefit under 35 USC §119(e) of U.S. provisional application No. 61/171,717, filed Apr. 22, 2009 and of U.S. provisional application No. 61/245,808, filed Sep. 25, 2009, and which is a continuation-in-part of and claims the benefit under 35 USC §120 to co-pending U.S. application Ser. No. 13/159,132 filed Jun. 13, 2011, which is a continuation-in-part of and claims the benefit under 35 USC §120 to co-pending U.S. application Ser. No. 13/071,598 filed Mar. 25, 2011, which claims the benefit under 35 USC §119(e) of U.S. provisional application No. 61/318,145, filed Mar. 26, 2010, and which is a continuation-in-part of and claims the benefit under 35 USC §120 to co-pending U.S. application Ser. No. 13/681,575 filed Nov. 20, 2012, which is a continuation of and claims the benefit under 35 USC §120 to co-pending U.S. application Ser. No. 13/602,409 filed Sep. 4, 2012, which claims the benefit under 35 USC §119(e) of U.S. provisional application Nos. 61/530,944 and 61/530,948, both filed Sep. 3, 2011, and which is a continuation-in-part of and claims the benefit under 35 USC §120 to co-pending U.S. application Ser. No. 13/603,284 filed Sep. 4, 2012, which claims the benefit under 35 USC §119(e) of U.S. provisional application No. 61/530,945, filed Sep. 3, 2011, and which is a continuation-in-part of and claims the benefit under 35 USC §120 to co-pending U.S. application Ser. No. 13/680,414 filed Nov. 19, 2012, which is a continuation of and claims the benefit under 35 USC §120 to co-pending U.S. application Ser. No. 13/603,297 filed Sep. 4, 2012, which claims the benefit under 35 USC §119(e) of U.S. provisional application No. 61/530,947, filed Sep. 3, 2011, and which is a continuation-in-part of and claims the benefit under 35 USC §120 to co-pending U.S. application Ser. No. 13/735,828 filed Jan. 7, 2013, which is a continuation of and claims the benefit under 35 USC §120 to co-pending U.S. application Ser. No. 13/652,018 filed Oct. 15, 2012, which claims the benefit under 35 USC §119(e) of U.S. provisional application No. 61/547,624, filed Oct. 14, 2011, and which claims the benefit under 35 USC §119(e) of U.S. provisional application Nos. 61/717,048 and 61/717,053, both filed Oct. 22, 2012, and which claims the benefit under 35 USC §119(e) of U.S. provisional application No. 61/721,219, filed Nov. 1, 2012, all of which are incorporated, in their entirety, by this reference.

FIELD OF THE INVENTION

The present invention relates to endometriosis prognosis, diagnosis and therapy. In particular, the present invention relates to a novel algorithmic combination of endometriosis associated single nucleotide polymorphisms (SNPs) and Rare Variants (RVs), and endometriosis related clinical analysis to result in an endometriosis predictive and/or diagnostic test and related treatment therefor.

BACKGROUND OF THE INVENTION

Endometriosis may include autoimmune endometriosis, mild endometriosis, moderate endometriosis, severe endometriosis, superficial (peritoneal) endometriosis, deep (invasive) endometriosis, ovarian endometriosis, endometriosis-related cancers, and "endometriosis-associated conditions". For the purpose of this invention the term endometriosis is used to describe any of these conditions.

Endometriosis is most generally defined as the presence of endometrium (glands and stroma) at sites outside of the uterus (ectopic endometrial tissues rather than eutopic or within the uterus). The most common sites are the ovaries, pelvic peritoneum, uterosacral ligaments, pouch of Douglas, and rectovaginal septum although implants have been identified on the peritoneal surfaces of the abdomen (these may grow into the intestines, ureters or bladder), in the thorax, at the umbilicus, and at incision sites of prior surgeries (Child T J, Tan S L (2001) Endometriosis: aetiology, pathogenesis and treatment, Drugs 61:1735-1750; Giudice et al. (1998) Status of current research on endometriosis, The Journal of reproductive medicine 43:252-262).

Endometriosis is a common gynecologic disorder. The prevalence is difficult to know. It has been estimated that it affects approximately 14% of all women (range 1-43%), 40-60% of women with pelvic pain and 30%-50% of infertile women (Di Blasio et al. (2005) Genetics of endometriosis, Minerva ginecologica 57:225-236; Schindler A E (2004) Pathophysiology, diagnosis and treatment of endometriosis, Minerva ginecologica 56:419-435).

A non-surgical method of clinically assessing a predisposition to endometriosis is to determine the answer to three distinct endometriosis related questions, each question having an associated Odds Ratio (OR), as shown in FIG. 1. The results of answers to the FIG. 1 questions are then complied according to the endometriosis clinical factor assessment chart as shown in FIG. 2 resulting in a Raw Clinical Probability Value (RCPV). The RCPV is preferably multiplied by a Relevance Factor (RF) based on a patient's age and race to result in a Final Clinical Probability Value (FCPV). Alternatively, the RCPV may be used with data collected in population surveys.

MultiDimensional Analysis (MDA) is an analysis process that groups data into two or more categories (e.g. cases and controls or patients having a high probability of endometriosis and patients having a low probability of endometriosis).

Logistic regression analysis is a process that is used for prediction of the probability of occurrence of an event by fitting data to a log it function logistic curve.

Bayesian analysis or Bayesian interference is a method of statistical inference in which evidence is used to estimate parameters and predictions in a probability model.

It is known to treat or prevent endometriosis, especially in women who have no outwardly manifest symptoms of endometriosis, by the prophylactic administration of a therapeutic. The administered therapeutic may be any of a hormonal treatment such as an estrogen containing composition, a progesterone containing composition, a progestin containing composition, a gonadotropin releasing-hormone (GnRH) agonist, or other ovulation suppression composition, an advanced reproductive therapy or ART (ART is used to treat endometriosis related infertility and may include any fertility treatments in which the egg or sperm are "handled" in vitro as part of the treatment), or a combination thereof. In particular, the therapeutic may be administered in the form of an oral contraceptive (OC). The GnRH therapeutic may take the form of a GnRH agonist in combination with a patient specific substantially low dose of estrogen, progestin, or tibolone. Such administration of a low dose of estrogen, progestin, or tibolone in combination with a GnRH agonist to compensate potential side effects of the GnRH agonist are commonly referred to as an "add-back" therapy. It is noted that in such add-back therapy, the dosage of estrogen, progestin, or tibolone is relatively small so as to not reduce the effectiveness of the GnRH agonist.

Various genetic markers are known to have a predictive association with endometriosis. Such genetic markers and methods are disclosed for instance in U.S. patent application Ser. Nos. 12/056,754, 12/120,322, 12/566,933, 12/765,643, 13/159,132, 13/602,409, 13/603,284, 13/603,297, 13/652,018, 61/721,219, 61/717,048, and 61/717,053, all of which are incorporated herein in their entirety by this reference.

SUMMARY OF THE INVENTION

The present invention defines a method for endometriosis diagnosis/prognosis that preferably combines known endometriosis clinical factor assessment methods with endometriosis associated biomarkers such as single nucleotide polymorphisms (SNPs), indels, insertions, deletions, genomic rearrangements, Rare Variants (RVs), and more especially the biomarkers identified in table 1 (or diagnostically and predicatively functionally comparable biomarkers), preferably via a statistical assessment method such as MultiDimensional Scaling analysis (MDS), logistic regression, or Bayesian analysis. The markers and related statistical data shown in table 1 were discovered by analyzing a number of endometriosis cases and controls much as has been described in the prior patent applications incorporated herein by reference. It is noted that all of the biomarkers of table 1, being variations or mutations in and of the same structure (i.e. the human genome), share a single structural similarity in that all of the biomarkers of table 1 are endometriosis associated nucleotide substitutions of the same DNA sequence—the human genome DNA sequence, and that the common use of endometriosis diagnosis and prognosis of all of the biomarkers of table 1 flow from such single structural similarity. The present invention further preferably includes the treatment of a subject determined to have or be predisposed to endometriosis by administering to such subject a therapeutic such as an OC that at least partially compensates for endometriosis or that prevents or reduces the severity of endometriosis that the subject would otherwise develop or that prevents endometriosis related complications, cancers, or associated disorders. It shall be noted that preventing or cancelling a procedure, especially an invasive procedure, such as a laparoscopy, that would otherwise have been performed on a subject but for the results of a (negative) diagnosis/prognosis disclosed herein being performed on said subject, shall be consider within the scope of treatment or the "administration of a therapeutic".

It shall be noted that for the purposes of this application, a SNP is understood to be a genetic polymorphism having a Minor Allele Frequency (MAF) of at least 1% in a population (such as for instance the Caucasian population or the CEU population) and an RV is understood to be a genetic polymorphism having a Minor Allele Frequency (MAF) of less than 1% in a population (such as for instance the Caucasian population or the CEU population).

It shall be noted that "Linkage disequilibrium" or "LD" means that a particular combination of alleles (alternative nucleotides) or genetic markers at two or more different SNP (or RV) sites are non-randomly co-inherited (i.e., the combination of alleles at the different SNP (or RV) sites occurs more or less frequently in a population than the separate frequencies of occurrence of each allele or the frequency of a random formation of haplotypes from alleles in a given population). The term "LD" differs from "linkage," which describes the association of two or more loci on a chromosome with limited recombination between them. LD is also used to refer to any non-random genetic association between allele(s) at two or more different SNP (or RV) sites. Therefore, when a SNP (or RV) is in LD with other SNPs (or RVs), the particular allele of the first SNP (or RV) often predicts which alleles will be present in those SNPs (or RVs) in LD. LD is generally, but not exclusively, due to the physical proximity of the two loci along a chromosome. Hence, genotyping one of the SNP (or RV) sites will give almost the same information as genotyping the other SNP (or RV) site that is in LD. Linkage disequilibrium is caused by fitness interactions between genes or by such non-adaptive processes as population structure, inbreeding, and stochastic effects.

It shall also be noted that LD is the non-random association of alleles adjacent loci. When a particular allele at one locus is found together on the same chromosome with a specific allele at a second locus—more often than expected if the loci were segregating independently in a population—the loci are in disequilibrium. This concept of LD is formalized by one of the earliest measures of disequilibrium to be proposed (symbolized by D). D, in common with most other measures of LD, quantifies disequilibrium as the difference between the observed frequency of a two-locus haplotype and the frequency it would be expected to show if the alleles are segregating at random. A wide variety of statistics have been proposed to measure the amount of LD, and these have different strengths, depending on the context. Although the measure D has the intuitive concepts of LD, its numerical value is of little use for measuring the strength of and comparing levels of LD. This is due to the dependence of D on allele frequencies. The two most common measures are the absolute value of D' and $r^2$. The absolute value of D' is determined by dividing D by its maximum possible value, given the allele frequencies at the two loci. The case of D'=1 is known as complete LD (or CLD). The measure $r^2$ is in some ways complementary to D'. An $r^2$ value of 1 indicates complete LD as well while an $r^2$ value of 0 indicates linkage equilibrium. Complete LD demonstrates complete dependency. In other words, in complete LD the number of counts of the minor allele in loci 1 corresponds to the counts of minor allele in loci 2. Although in complete LD the alleles themselves might be different the frequency of Minor allele in loci 1 will be equal to the frequency of Minor allele in loci 2. For example, in comparing two loci such as rs1 having (A/G) and rs2 having (G/C), if it is known that rs1 and rs2 are in complete LD, and if it is known that a person carries a genotype AG on rs1, then it is known that the genotype on rs2 is GC for that person. Similarly in complete LD, if A is the minor allele of rs1 and is associated with the disease (or conversely is not associated with the disease) then the corresponding minor allele of $rs^2$ is also associated with the disease (or conversely or is not associated with the disease).

Furthermore in complete LD, in any analysis of the disease, genotype for rs1 could easily be substituted for rs2 and vice versa.

In yet another embodiment, the invention also provides a kit comprising SNP detection reagents, and methods for detecting the SNPs disclosed herein by employing detection reagents and a questionnaire of non-genetic clinical factors. In one embodiment, the questionnaire would be completed by a medical professional based on medical history physical exam or other clinical findings. In yet another embodiment, the questionnaire would include any other non-genetic clinical factors known to be associated with the risk of developing endometriosis.

In yet another embodiment, the novel SNPs disclosed in '754 as well as other genetic markers are used in the selection of patients to whom a therapeutic will be administered based on the patient's assessed risk of developing endometriosis or based on the patient's assessed risk of endometriosis progression. The administered therapeutic may preferably be a patient specific gene or protein based therapy enabled and informed by SNPs discovered to be associated with endometriosis. Further, the administered therapeutic may be any of a hormonal treatment such as an estrogen containing composition, a progesterone containing composition, a progestin containing composition, a gonadotropin releasing-hormone (GnRH) agonist, or other ovulation suppression composition, or a combination thereof. In particular, the therapeutic may be administered in the form of an OC. Furthermore, the GnRH therapeutic may take the form of a GnRH agonist in combination with a patient specific substantially low dose of estrogen, progestin, or tibolone. Such administration of a low dose of estrogen, progestin, or tibolone in combination with a GnRH agonist to compensate potential side effects of the GnRH agonist are commonly referred to as an "add-back" therapy. It is noted that in such add-back therapy, the dosage of estrogen, progestin, or tibolone is relatively small so as to not reduce the effectiveness of the GnRH agonist.

It shall also be noted that unless indicated otherwise, when a genetic marker (e.g. SNP or RV) is identified as the genetic marker associated with a disease (in this instance endometriosis), it shall be understood that it is the minor allele (MA) of the particular genetic marker that is associated with the disease. Further it shall also be noted that unless indicated otherwise, if the Odds Ratio (OR) of the MA is greater than 1.0, the MA of the genetic marker (in this instance the endometriosis associated genetic marker) is correlated with an increased risk of endometriosis in a case subject as compared to a control subject and shall be considered a causative marker (C), and if the OR of the MA less than 1.0, the MA of the genetic marker is correlated with a decreased risk of endometriosis in a case subject as compared to a control subject and shall be considered a protective marker (P).

It shall also be noted that unless indicated otherwise, the phrase "functional equivalent" as used herein with respect to biomarkers shall mean that a second biomarker is substantially equivalent in its diagnostic and/or prognostic value with respect to a given disease as is a first biomarker's diagnostic and/or prognostic value with respect to the given disease. A second biomarker that is in complete LD with a first biomarker shall be expressly included within the scope of "functional equivalent" with respect to the relationship between the second biomarker to the first biomarker.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1 depicts a "Three Endometriosis Related Clinical Questions" chart, and;

DETAILED DESCRIPTION OF THE INVENTION

Figure 2:
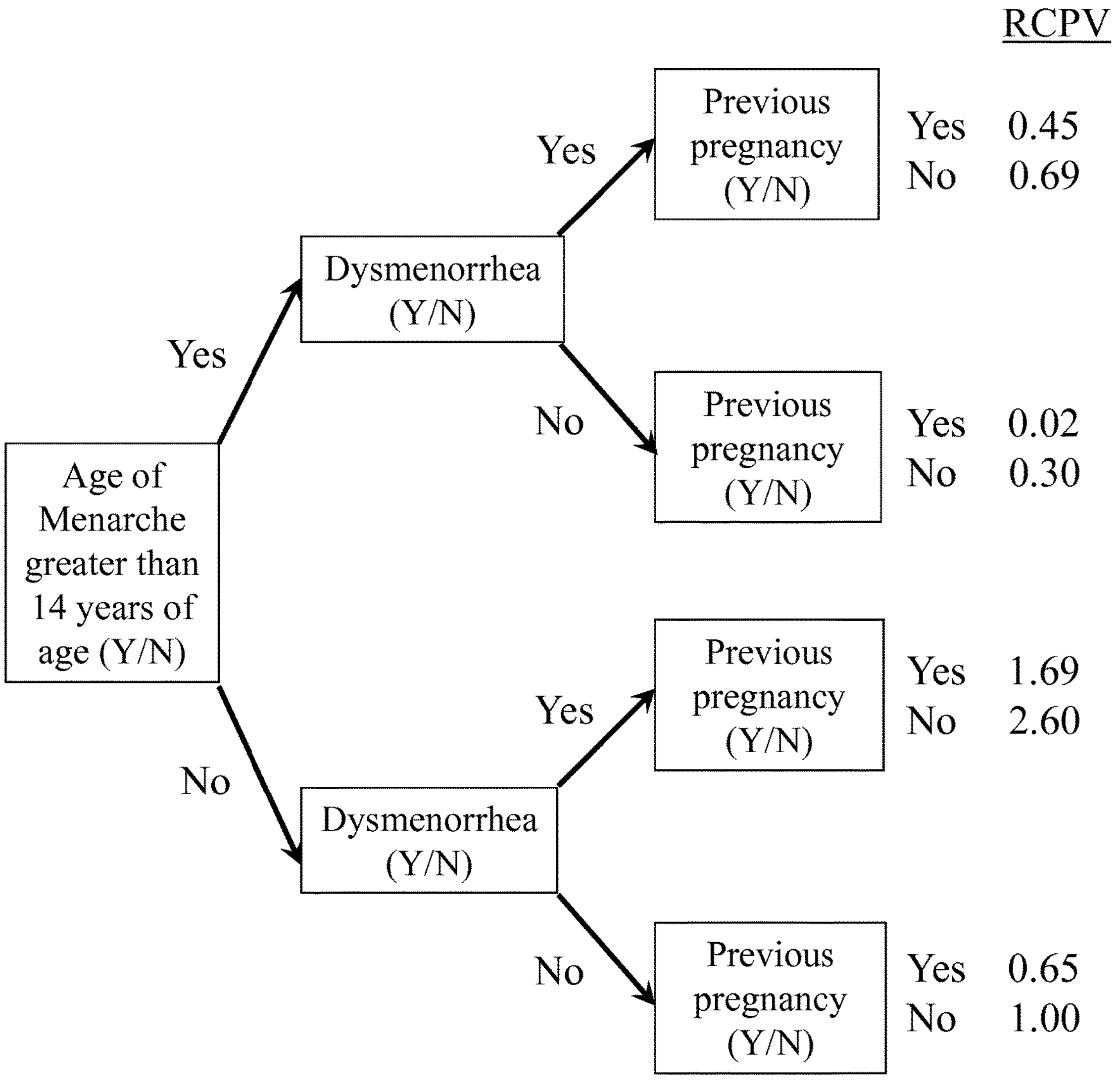
FIG. 2 depicts an "Endometriosis Clinical Factor Assessment" chart.

The method of determining predisposition to endometriosis for a patient is performed according to the following steps. In a first step, answers to the FIG. 1 questions are obtained for the patient. In a second step, an RCPV according to FIG. 2 is determined for the patient based on the answers obtained for the patient in step 1. In an optional third step, the RCPV is optionally multiplied by an RF or otherwise adjusted according to the patient's age and race or according to relevant population survey data to result in a FCPV. In a fourth step, at least one endometriosis associated biomarker preferably drawn from the biomarkers of table 1 is identified in genetic material of the patient. In a fifth step, at least one statistical analysis (preferably MDS) is performed to combine the RCPV (or the FCPV) and the predictive value of the identified genetic biomarker to result in a highly predictive endometriosis prognosis or diagnosis.

"Oral contraceptives" or OCs are contraceptives that are commonly taken orally for the principal purpose of the prevention of conception. Such contraceptives are also commonly referred to as "Oral Contraceptive Pills" or OCPs, or simply as the "Pill". Such OCs typically define a substance in pill form being comprised at least partially of estrogen, progesterone, or a combination thereof. The progesterone component may further be any of Desogestrel, Drospirenone, Ethynodiol, Levonorgestrel, Norethindrone, Norgestimate, and Norgestrel, and the estrogen component may further be any of Mestranol, Estradiol, and Ethinyl. Exemplary OCs that are commercially available are sold under the following names: ALESSE, APRI, ARANELLE, AVIANE, BREVICON, CAMILA, CESIA, CRYSELLE, CYCLESSA, DEMULEN, DESOGEN, ENPRESSE, ERRIN, ESTROSTEP, JOLIVETTE, JUNEL, KARIVA, LEENA, LESSINA, LEVLEN, LEVORA, LOESTRIN, LUTERA, MICROGESTIN, MICRONOR, MIRCETTE, MODICON, MONONESSA, NECON, NORA, NORDETTE, NORINYL, NOR-QD, NORTREL, OGESTREL, ORTHO-CEPT, ORTHO-CYCLEN, ORTHO-NOVUM, ORTHO-TRI-CYCLEN, OVCON, OVRAL, OVRETTE, PORTIA, PREVIFEM, RECLIPSEN, SOLIA, SPRINTEC, TRINESSA, TRI-NORINYL, TRIPHASIL, TRIVORA, VELIVET, YASMIN, AND ZOVIA (the preceding names are the registered trademarks of the respective providers).

"Gonadotropin releasing-hormone (GnRH) agonists" are a group of drugs that are useful in treating patients having endometriosis. Such drugs are modified versions of a naturally occurring hormone known as gonadotropin releasing hormone, which helps to control the menstrual cycle. Administration of such drugs is known to be performed in combination with an "add-back" therapy. In this case, an add-back therapy could be for instance the administration of a low dose of estrogen, progestin, or tibolone in combination with a GnRH agonist to compensate potential side effects of the GnRH agonist. It is noted that in such add-back therapy, the dosage of estrogen, progestin, or tibolone is relatively small so as to not reduce the effectiveness of the GnRH agonist.

The present invention provides SNPs associated with endometriosis, nucleic acid molecules containing SNPs, methods and reagents for the detection of the SNPs disclosed herein, uses of these SNPs for the development of detection reagents, and assays or kits that utilize such reagents. The SNPs disclosed herein are useful for diagnosing, screening for, and evaluating predisposition to endometriosis and progression of endometriosis. Additionally, such SNPs are useful in the determining individual subject treatment plans and design of clinical trials of devices for possible use in the treatment of endometriosis. Furthermore, such SNPs and their encoded products are useful targets for the development of therapeutic agents. Furthermore, such SNPs combined with other non-genetic clinical factors are useful for diagnosing, screening, evaluating predisposition to endometriosis, assessing risk of progression of endometriosis, determining individual subject treatment plans and design of clinical trials of devices for possible use in the treatment of endometriosis. Furthermore, such SNPs and are useful in the selection of recipients for an OC type therapeutic.

Therefore, the invention disclosed herein further teaches a method of selectively administering a therapeutic. Such method of administering a therapeutic preferably includes the following steps: a) Obtaining a genetic material sample of a human female subject, b) Identifying in the genetic material of the subject preferably at least one of the SNPs disclosed in '754 or alternatively identifying any other genetic marker having an association with endometriosis, c) Assessing the subject's risk of endometriosis or risk of endometriosis progression, d) Identifying the subject as having an altered risk of endometriosis or an altered risk of endometriosis progression, and e) administering to the subject a therapeutic. It is noted that the subject may be endometriosis presymptomatic or the subject may exhibit endometriosis symptoms. It is also noted that the assessment of risk may also include non-genetic clinical factors. The therapeutic may be a gene or protein based therapy adapted to the specific needs of a select patient. The therapeutic may alternatively take the form of a testosterone or a modified testosterone such as Danazol. Alternatively, the therapeutic defines a hormonal treatment therapeutic which may be administered alone or in combination with a gene therapy. For instance, the therapeutic may be an estrogen containing composition, a progesterone containing composition, a progestin containing composition, a gonadotropin releasing-hormone (GnRH) agonist, or other ovulation suppression composition, or a combination thereof. Additionally, the GnRH agonist may take the form of a GnRH agonist in combination with a patient specific substantially low dose of estrogen, progestin, or tibolone via an add-back administration. It is further noted that the therapeutic is preferably an OC. The OC preferably defines a substance in pill form that is comprised at least partially of estrogen, progesterone, or a combination thereof. The progesterone component may further be any of Desogestrel, Drospirenone, Ethynodiol, Levonorgestrel, Norethindrone, Norgestimate, and Norgestrel, and the estrogen component may further be any of Mestranol, Estradiol, and Ethinyl. Specifically, the OC may be any commercially available OC including ALESSE, APRI, ARANELLE, AVIANE, BREVICON, CAMILA, CESIA, CRYSELLE, CYCLESSA, DEMULEN, DESOGEN, ENPRESSE, ERRIN, ESTROSTEP, JOLIVETTE, JUNEL, KARIVA, LEENA, LESSINA, LEVLEN, LEVORA, LOESTRIN, LUTERA, MICROGESTIN, MICRONOR, MIRCETTE, MODICON, MONONESSA, NECON, NORA, NORDETTE, NORINYL, NOR-QD, NORTREL, OGESTREL, ORTHO-CEPT, ORTHO-CYCLEN, ORTHO-NOVUM, ORTHO-TRI-CYCLEN, OVCON, OVRAL, OVRETTE, PORTIA, PREVIFEM, RECLIPSEN, SOLIA, SPRINTEC, TRINESSA, TRINORINYL, TRIPHASIL, TRIVORA, VELIVET, YASMIN, AND ZOVIA (the preceding names are the registered trademarks of the respective providers). It is further noted that the therapeutic may comprise any other ovulation suppression substance. It is further noted that the therapeutic is preferably adapted to the specific subject so as to be a proper and effective amount of therapeutic for the subject. It is further noted that the administration of the therapeutic may comprise multiple sequential instances of administration of the therapeutic and that such sequence instances may occur over an extended period of time or may occur on an indefinite on-going basis.

It shall be noted that the markers of table 1 are drawn from build 37 data (or "GRCh37" as defined by the Genome Reference Consortium) and that in the header of table 1: "Set" corresponds to a particular subset (i.e. subset 01, subset 02, or subset 03) of the biomarkers of table 1, "Name" corresponds to a name for a given biomarker and where possible is the reference SNP number (rs) of the particular biomarker, but if not possible then it is the exome variant number (exm) of the particular biomarker (as assigned by Illumina, Incorporated), but if not possible then it is a "JBL" number assigned by applicant, "Chr" corresponds to the chromosome where a given biomarker is located in the human genome, "Arm" corresponds to the arm of the chromosome where a given biomarker is located in the human genome, "Cyto" corresponds to the cytoband of the arm of the chromosome where a given biomarker is located in the human genome, "Gene" corresponds to the gene where a given biomarker is located in the human genome or alternatively if the biomarker is not located within a gene, "Gene" corresponds to the nearest two genes positioned on either side of the given biomarker in the human genome, "position" corresponds to the position of a given biomarker in the human genome, "p-value" corresponds to the p-value of a given biomarker, "OR" corresponds to the Odds Ratio of a given biomarker, "Case MAF" corresponds to the case Minor Allele Frequency of a given biomarker, "Cont MAF" corresponds to the control Minor Allele Frequency of a given biomarker, "MA" corresponds to the Minor Allele of a given biomarker, and "Context Sequence" corresponds to the context sequence in which a given biomarker is located and provides a SEQ ID NO and the identification of the biomarker variation of substitution (e.g. "A/C" or "A/G", etc.). It shall be further noted that values for p-value, OR, Case MAF, and Cont MAF provided in Table 1 were derived by applicant using predetermined statistical methods and a predetermined group of cases and controls, and that while others who might analyze the same set of data may arrive at similar but not necessarily identical results if the identical analytical methods are not used. Moreover, it is believed that substantially similar results would occur based on a similar analysis performed on data drawn from different populations that used herein.

TABLE 1

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7521023 | 1 | p | p13.1 | CASQ2 | 116243380 | 7.63E-05 | 1.11 | 0.435 | 0.409 | G | (SEQ ID NO: 0001) aaggatcatcttggct[A/G]gaggagggatcccaac |
| 03 | rs3811012 | 1 | p | p13.1 | VANGL1 | 116234313 | 8.03E-05 | 1.11 | 0.425 | 0.399 | A | (SEQ ID NO: 0002) cctcgccttacaacta[A/G]ttcctgcctttcgtcc |
| 03 | rs1373291 | 1 | p | p13.2 | KCND3 | 112426851 | 4.79E-04 | 1.14 | 0.214 | 0.192 | A | (SEQ ID NO: 0003) gagaattgagttgaaa[A/C]tttaaagaaggagttg |
| 03 | rs3008527 | 1 | p | p13.2 | KCND3 | 112523095 | 2.53E-03 | 0.90 | 0.253 | 0.274 | G | (SEQ ID NO: 0004) gccaaaacccagaggc[A/G]atagtgttggtttttc |
| 03 | rs3827735 | 1 | p | p13.2 | TRIM33 | 115052708 | 2.52E-04 | 1.19 | 0.130 | 0.112 | A | (SEQ ID NO: 0005) ccatttaatccatagt[A/C]ctcctctctcctatct |
| 03 | rs2640493 | 1 | p | p13.3 | KCNA2 \| KCNA3 | 111187885 | 2.04E-04 | 1.13 | 0.340 | 0.313 | A | (SEQ ID NO: 0006) gcacatgaaagtttaa[A/G]tagcactactaccaga |
| 03 | rs17113362 | 1 | p | p21.3 | LOC729977 | 95782971 | 7.57E-04 | 1.32 | 0.039 | 0.030 | A | (SEQ ID NO: 0007) tcatgaactatgtagg[A/G]aaggaagtgaaatttg |
| 02 | rs4658172 | 1 | p | p22.2 | BARHL2 \| ZNF644 | 91225594 | 1.11E-05 | 1.16 | 0.327 | 0.296 | G | (SEQ ID NO: 0008) gaaacaactgctcagg[A/G]cattttgcaaatttac |
| 02 | rs6656775 | 1 | p | p22.2 | BARHL2 \| ZNF644 | 91219359 | 5.36E-06 | 1.16 | 0.345 | 0.311 | G | (SEQ ID NO: 0009) atcctttctcagcagg[A/G]cccattatttctcatt |
| 02 | rs1526480 | 1 | p | p22.2 | BARHL2 \| ZNF644 | 91209986 | 7.16E-06 | 1.15 | 0.408 | 0.374 | G | (SEQ ID NO: 0010) acagatagttcctatg[A/G]gctagacttggtcaga |
| 01 | rs6699397 | 1 | p | p22.2 | BARHL2 \| ZNF644 | 91212216 | 3.32E-06 | 1.16 | 0.405 | 0.370 | G | (SEQ ID NO: 0011) gaactgcatagtccca[A/G]cttacaaagaatcagc |
| 03 | rs13376108 | 1 | p | p22.2 | GTF2B | 89350741 | 1.15E-02 | 1.30 | 0.024 | 0.018 | G | (SEQ ID NO: 0012) agagcttagtagcttc[A/G]acagaaaccacatgtg |
| 03 | rs3008445 | 1 | p | p22.2 | LMO4 \| PKN2 | 88446605 | 2.37E-03 | 0.91 | 0.432 | 0.456 | A | (SEQ ID NO: 0013) agtaatagacatttac[A/G]tttcctccaggttttt |
| 03 | rs3008453 | 1 | p | p22.2 | LMO4 \| PKN2 | 88427851 | 8.00E-03 | 1.09 | 0.505 | 0.484 | A | (SEQ ID NO: 0014) tctagagttaaatcct[A/G]tctggggactctgggc |
| 03 | rs4537535 | 1 | p | p22.2 | ZNF326 \| BARHL2 | 91080115 | 7.52E-03 | 1.09 | 0.503 | 0.482 | G | (SEQ ID NO: 0015) cactcagaagagagta[A/G]ctagagtaagaagtca |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7527341 | 1 | p | p31.1 | LOC729817 \| LPHN2 | 82009424 | 8.91E-05 | 0.95 | 0.334 | 0.347 | A | (SEQ ID NO: 0016) gaaatgggaaactatc[A/G]tagggttctttgcaga |
| 02 | exm68565 | 1 | p | p31.1 | TNNI3K | 74808620 | 8.37E-13 | Inf | 0.005 | 0.000 | C | (SEQ ID NO: 0017) tgctgcaaagtgattt[C/G]gaagttcaacctcatg |
| 03 | rs17130484 | 1 | p | p31.3 | GPR177 | 68581840 | 2.95E-04 | 0.77 | 0.048 | 0.062 | C | (SEQ ID NO: 0018) gctgctcctggtccct[A/C]ttgtaaggtcctgtga |
| 02 | rs6693065 | 1 | p | p31.3 | IL12RB2 | 67800018 | 3.19E-05 | 1.08 | 0.244 | 0.231 | G | (SEQ ID NO: 0019) gatcatacgatctgtc[A/G]caactgctaaatgtgc |
| 03 | rs4255357 | 1 | p | p31.3 | PDE4B | 66399895 | 8.47E-04 | 1.11 | 0.487 | 0.461 | G | (SEQ ID NO: 0020) gagtaagacataggag[A/G]tcaaggtaggaggatt |
| 03 | rs11208775 | 1 | p | p31.3 | PDE4B | 66410541 | 6.36E-04 | 1.11 | 0.487 | 0.460 | G | (SEQ ID NO: 0021) atttatcatgttctct[A/G]gtaggaatgctcccca |
| 03 | rs7554648 | 1 | p | p32.1 | FGGY \| HOOK1 | 60238762 | 5.87E-03 | 1.17 | 0.087 | 0.075 | A | (SEQ ID NO: 0022) aaaatctcagctccac[A/C]tcagccccaattatct |
| 03 | rs11805025 | 1 | p | p32.2 | DAB1 | 57850717 | 4.08E-03 | 0.89 | 0.195 | 0.214 | C | (SEQ ID NO: 0023) tatacagaaacacaaa[A/C]cccatcttggatcact |
| 03 | rs778406 | 1 | p | p32.2 | USP24 \| LOC100288320 | 56703505 | 7.87E-05 | 1.17 | 0.067 | 0.058 | A | (SEQ ID NO: 0024) tattaatctttttcac[A/C]tcagcacagcagaact |
| 03 | rs12758665 | 1 | p | p32.3 | USP24 \| LOC100288320 | 55839117 | 3.79E-04 | 0.87 | 0.196 | 0.218 | A | (SEQ ID NO: 0025) ttcgtaactacgatga[A/C]tttctcggttaagagt |
| 03 | rs7520205 | 1 | p | p32.3 | USP24 \| LOC100288320 | 55834309 | 1.30E-04 | 0.86 | 0.190 | 0.215 | A | (SEQ ID NO: 0026) agttttgtttcacagg[A/G]ctaaagcctgaacaga |
| 01 | exm49794 | 1 | p | p34.2 | CITED4 | 41327281 | 5.28E-60 | 21.62 | 0.056 | 0.035 | A | (SEQ ID NO: 0027) cgggcggcgcggaccc[A/C]aagtccgagaagcagt |
| 03 | rs219007 | 1 | p | p34.3 | CSF3R \| GRIK3 | 37147203 | 5.68E-05 | 1.10 | 0.395 | 0.372 | A | (SEQ ID NO: 0028) aaaaagaatcagaaat[A/G]tctggtgcatggagcc |
| 02 | rs2484556 | 1 | p | p34.3 | LOC100287202 \| LOC728431 | 37913283 | 4.34E-05 | 0.89 | 0.342 | 0.367 | A | (SEQ ID NO: 0029) gacctccagcaggggc[A/G]tggccagtgggtgcca |
| 03 | rs4970614 | 1 | p | p34.3 | POU3F1 \| LOC400750 | 39135748 | 8.84E-04 | 0.84 | 0.103 | 0.120 | A | (SEQ ID NO: 0030) tagtttccctggaaac[A/G]tatatctttgtacact |
| 01 | rs9438994 | 1 | p | p34.3 | RHBDL2 | 39388838 | 3.11E-06 | 1.23 | 0.158 | 0.132 | G | (SEQ ID NO: 0031) gtgcaatgtatgaggt[A/G]taaattaatgcagcct |

TABLE 1-continued

TABLES
(Based on build 37 or "GRCh37" as defined by the Genome Reference Consortium)

<table>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>02</td><td>rs6422258</td><td>1</td><td>p</td><td>p34.3</td><td>RHBDL2</td><td>39406644</td><td>9.56E-05</td><td>1.21</td><td>0.118</td><td>0.099</td><td>A</td><td>(SEQ ID NO: 0032)<br>ttattttggagtcaca[A/G]agacacttggcttttt</td></tr>
<tr><td>02</td><td>rs4475740</td><td>1</td><td>p</td><td>p34.3</td><td>RHBDL2 |<br>AKIRIN1</td><td>39425489</td><td>9.29E-05</td><td>1.23</td><td>0.101</td><td>0.084</td><td>A</td><td>(SEQ ID NO: 0033)<br>gtgctctagctgcaag[A/G]caggtggaaaaagtgt</td></tr>
<tr><td>02</td><td>rs1138294</td><td>1</td><td>p</td><td>p36.11</td><td>MAP3K6</td><td>27688633</td><td>2.76E-05</td><td>0.89</td><td>0.339</td><td>0.366</td><td>A</td><td>(SEQ ID NO: 0034)<br>agccagcaccacctgg[A/G]tggggtcattggcgag</td></tr>
<tr><td>03</td><td>rs443523</td><td>1</td><td>p</td><td>p36.11</td><td>RUNX3 | SYF2</td><td>25403783</td><td>9.12E-04</td><td>1.12</td><td>0.288</td><td>0.265</td><td>A</td><td>(SEQ ID NO: 0035)<br>gtttgctctcactctt[A/C]atacaatcgccaaaat</td></tr>
<tr><td>03</td><td>rs292005</td><td>1</td><td>p</td><td>p36.12</td><td>C1QB | EPHB2</td><td>22993335</td><td>1.60E-02</td><td>0.93</td><td>0.460</td><td>0.479</td><td>C</td><td>(SEQ ID NO: 0036)<br>taggggatctcattgc[A/C]cagtaaaataggcgac</td></tr>
<tr><td>03</td><td>rs7549747</td><td>1</td><td>p</td><td>p36.12</td><td>C1QB | EPHB2</td><td>22996571</td><td>3.37E-03</td><td>0.91</td><td>0.395</td><td>0.418</td><td>G</td><td>(SEQ ID NO: 0037)<br>gttccattttgtagcc[A/G]aggatataaaagctca</td></tr>
<tr><td>03</td><td>rs294218</td><td>1</td><td>p</td><td>p36.12</td><td>C1QB | EPHB2</td><td>23033257</td><td>1.04E-02</td><td>1.09</td><td>0.393</td><td>0.373</td><td>C</td><td>(SEQ ID NO: 0038)<br>agagacttgggtacac[A/C]gagaggggatgtctat</td></tr>
<tr><td>03</td><td>rs294214</td><td>1</td><td>p</td><td>p36.12</td><td>C1QB | EPHB2</td><td>23026293</td><td>4.51E-03</td><td>1.10</td><td>0.315</td><td>0.294</td><td>A</td><td>(SEQ ID NO: 0039)<br>gggcggaggggaggcg[A/G]gagatttctgagctcc</td></tr>
<tr><td>03</td><td>rs12734877</td><td>1</td><td>p</td><td>p36.12</td><td>C1QC | C1QB</td><td>22977883</td><td>9.54E-02</td><td>0.95</td><td>0.408</td><td>0.421</td><td>C</td><td>(SEQ ID NO: 0040)<br>cactgcttctacccca[A/C]attgacatccatcttt</td></tr>
<tr><td>01</td><td>rs1534949</td><td>1</td><td>p</td><td>p36.12</td><td>CDC42 |<br>LOC100289113</td><td>22426187</td><td>2.18E-06</td><td>1.16</td><td>0.441</td><td>0.405</td><td>C</td><td>(SEQ ID NO: 0041)<br>tgagagaatatgacac[A/C]ttcttcctttagagga</td></tr>
<tr><td>01</td><td>rs2473277</td><td>1</td><td>p</td><td>p36.12</td><td>HSPC157 |<br>CDC42</td><td>22361845</td><td>1.77E-06</td><td>1.16</td><td>0.508</td><td>0.471</td><td>G</td><td>(SEQ ID NO: 0042)<br>gctatacctcccaatc[A/G]tcaacctgtagaacat</td></tr>
<tr><td>01</td><td>rs4654783</td><td>1</td><td>p</td><td>p36.12</td><td>LOC100289113 |<br>WNT4</td><td>22439520</td><td>2.16E-09</td><td>1.22</td><td>0.337</td><td>0.294</td><td>A</td><td>(SEQ ID NO: 0043)<br>tgctggtcaggatgga[A/G]tatgttatcagagccc</td></tr>
<tr><td>01</td><td>rs2235529</td><td>1</td><td>p</td><td>p36.12</td><td>WNT4</td><td>22450487</td><td>4.66E-12</td><td>1.32</td><td>0.189</td><td>0.150</td><td>A</td><td>(SEQ ID NO: 0044)<br>agaaccaggtagagaa[A/G]gctggaggagccgcca</td></tr>
<tr><td>02</td><td>rs7544210</td><td>1</td><td>p</td><td>p36.12</td><td>WNT4</td><td>22455142</td><td>6.02E-06</td><td>1.15</td><td>0.463</td><td>0.428</td><td>G</td><td>(SEQ ID NO: 0045)<br>acagcgtctcctcatc[A/G]aggataagaccacaga</td></tr>
<tr><td>02</td><td>rs1046310</td><td>1</td><td>p</td><td>p36.12</td><td>WNT4 /<br>LOC100289113</td><td>22443887</td><td>7.78E-06</td><td>1.15</td><td>0.492</td><td>0.457</td><td>C</td><td>(SEQ ID NO: 0046)<br>tgctgccccaccccat[A/C]ctccaatttttatact</td></tr>
<tr><td>02</td><td>rs3765351</td><td>1</td><td>p</td><td>p36.12</td><td>WNT4 /</td><td>22445991</td><td>1.14E-05</td><td>1.15</td><td>0.487</td><td>0.452</td><td>G</td><td>(SEQ ID NO: 0047)</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | LOC100289113 | | | | | | | aggtcaagggcaccag[A/G]ttcatttcagccctta |
| 01 | rs12042083 | 1 | p | p36.12 | WNT4 \| ZBTB40 | 22472732 | 4.84E-07 | 1.21 | 0.231 | 0.199 | A | (SEQ ID NO: 0048)<br>aattcttaatgagaaa[A/G]tctcttggaggaaatg |
| 01 | rs4623666 | 1 | p | p36.12 | WNT4 \| ZBTB40 | 22480312 | 3.96E-06 | 1.16 | 0.440 | 0.405 | G | (SEQ ID NO: 0049)<br>atgcacacagaagccc[A/G]gccggtatccccacag |
| 02 | rs221047 | 1 | p | p36.13 | ARHGEF19 | 16530364 | 4.01E-05 | 1.15 | 0.155 | 0.137 | G | (SEQ ID NO: 0050)<br>ccctgatgatatggtt[A/G]tcagaatgtattttca |
| 03 | rs12088541 | 1 | p | p36.22 | MAD2L2 | 11751135 | 5.77E-04 | 0.83 | 0.093 | 0.110 | A | (SEQ ID NO: 0051)<br>ggttctccgagaggtc[A/G]ctcctggatgtagggg |
| 03 | rs641941 | 1 | p | p36.22 | TNFRSF8 \|<br>TNFRSF1B | 12206652 | 4.79E-03 | 1.09 | 0.495 | 0.473 | G | (SEQ ID NO: 0052)<br>actggctcattattcg[A/G]cgtctgtaactctggg |
| 03 | rs17349921 | 1 | p | p36.31 | CAMTA1 | 7170719 | 7.70E-05 | 1.09 | 0.101 | 0.094 | G | (SEQ ID NO: 0053)<br>aatgagtgttcttaga[A/G]gctgggtcggattcct |
| 03 | rs10915329 | 1 | p | p36.32 | AJAP1 \|<br>LOC100287877 | 5114102 | 2.26E-03 | 1.10 | 0.431 | 0.407 | A | (SEQ ID NO: 0054)<br>tcagacctgggagaat[A/G]tcaggtaagctgagat |
| 01 | JBL0002 | 1 | p | p36.33 | RNF223 | 1007306 | 6.27E-05 | 6.765 | 0.020 | 0.005 | A | (SEQ ID NO: 0055)<br>gagcgcgcactgcacc[G/A]gccagagtgccacaca |
| 02 | exm91506 | 1 | q | q21.1 | ANKRD35 | 145560893 | 4.73E-08 | 18.9 | 0.004 | 0.000 | C | (SEQ ID NO: 0056)<br>cttttcttataggtca[C/G]aggctagtccagcacc |
| 02 | exm90634 | 1 | q | q21.1 | PDE4DIP | 144931581 | 6.11E-12 | Inf | 0.004 | 0.000 | G | (SEQ ID NO: 0057)<br>ctcggctttgccatcg[C/G]gggggacatccttgcc |
| 02 | exm90788 | 1 | q | q21.1 | SEC22B | 145115792 | 1.20E-13 | 3.71 | 0.011 | 0.000 | A | (SEQ ID NO: 0058)<br>catgttcaagtacttc[A/G]catcctggcggtattt |
| 03 | rs11204684 | 1 | q | q21.3 | ENSA \|<br>GOLPH3L | 150608894 | 4.02E-04 | 1.12 | 0.481 | 0.454 | A | (SEQ ID NO: 0059)<br>gttggggagtgagcca[A/G]cagttatctggaggga |
| 03 | rs10888510 | 1 | q | q21.3 | LCE4A | 152681835 | 1.53E-04 | 1.56 | 0.019 | 0.012 | A | (SEQ ID NO: 0060)<br>tcagcaacagccccct[A/C]cagagcagcagccaga |
| 03 | rs4970972 | 1 | q | q21.3 | TARS2 | 150468547 | 1.65E-04 | 1.26 | 0.072 | 0.058 | A | (SEQ ID NO: 0061)<br>catatcccattcctgg[A/C]cacatgaaatccaaaa |
| 03 | rs16838078 | 1 | q | q23.1 | ETV3L | 157069261 | 2.43E-03 | 1.31 | 0.032 | 0.025 | C | (SEQ ID NO: 0062)<br>ccaagaggctcacctg[A/C]gatccagttgccgggg |

TABLE 1-continued

TABLES
(Based on build 37 or "GRCh37" as defined by the Genome Reference Consortium)

<table>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>03</td><td>rs4656849</td><td>1</td><td>q</td><td>q23.2</td><td>CRP | DUSP23</td><td>159723521</td><td>2.04E-03</td><td>0.90</td><td>0.361</td><td>0.385</td><td>A</td><td>(SEQ ID NO: 0063) aagggtcagaaaacaa[A/G]taaaaggccaagacag</td></tr>
<tr><td>03</td><td>rs3897374</td><td>1</td><td>q</td><td>q23.3</td><td>NOS1AP</td><td>162168958</td><td>7.13E-05</td><td>1.03</td><td>0.178</td><td>0.174</td><td>G</td><td>(SEQ ID NO: 0064) caaacctccttgagtc[A/G]gctttaagagtttctt</td></tr>
<tr><td>02</td><td>exm129317</td><td>1</td><td>q</td><td>q25.3</td><td>RGS16</td><td>182571142</td><td>7.34E-08</td><td>13.65</td><td>0.004</td><td>0.000</td><td>C</td><td>(SEQ ID NO: 0065) aactcctcaaagatct[C/G]gtgtgccctggaggcc</td></tr>
<tr><td>03</td><td>rs10921412</td><td>1</td><td>q</td><td>q31.2</td><td>CDC73 | KCNT2</td><td>193661626</td><td>1.36E-03</td><td>1.11</td><td>0.361</td><td>0.337</td><td>A</td><td>(SEQ ID NO: 0066) gaagtttttacaacc[A/G]aaatctatgaccgttg</td></tr>
<tr><td>02</td><td>exm133014</td><td>1</td><td>q</td><td>q31.2</td><td>GLRX2</td><td>193074511</td><td>1.85E-17</td><td>4.14</td><td>0.023</td><td>0.006</td><td>G</td><td>(SEQ ID NO: 0067) cgcgcggcgccaaatc[A/G]tggtcagagcccggat</td></tr>
<tr><td>02</td><td>rs6701700</td><td>1</td><td>q</td><td>q31.2</td><td>RGS1 | RGS13</td><td>192556309</td><td>7.80E-05</td><td>1.20</td><td>0.133</td><td>0.113</td><td>A</td><td>(SEQ ID NO: 0068) aaggaattaccaagaa[A/G]agccatgcatctcaca</td></tr>
<tr><td>03</td><td>rs10489873</td><td>1</td><td>q</td><td>q31.2</td><td>RGS1 | RGS13</td><td>192559646</td><td>2.31E-04</td><td>1.25</td><td>0.076</td><td>0.062</td><td>A</td><td>(SEQ ID NO: 0069) ccgggaagtgcacgct[A/G]ccaccgaggagccatc</td></tr>
<tr><td>03</td><td>rs17466945</td><td>1</td><td>q</td><td>q32.1</td><td>CHI3L1 | CHIT1</td><td>203183093</td><td>1.62E-03</td><td>1.16</td><td>0.131</td><td>0.116</td><td>C</td><td>(SEQ ID NO: 0070) gatgagatcccaagtc[A/C]aaggaagatttgccca</td></tr>
<tr><td>03</td><td>rs6662930</td><td>1</td><td>q</td><td>q32.1</td><td>CNTN2</td><td>205041465</td><td>7.66E-03</td><td>0.92</td><td>0.451</td><td>0.472</td><td>G</td><td>(SEQ ID NO: 0071) cgaaacaaagcccatg[A/G]aaatccaaaggttgga</td></tr>
<tr><td>02</td><td>rs880790</td><td>1</td><td>q</td><td>q32.1</td><td>IL10 | 1L19</td><td>206960216</td><td>1.83E-05</td><td>1.17</td><td>0.249</td><td>0.220</td><td>G</td><td>(SEQ ID NO: 0072) gcttgggggctggaga[A/G]cagaatttaacatgtt</td></tr>
<tr><td>03</td><td>rs17434403</td><td>1</td><td>q</td><td>q32.1</td><td>RASSF5</td><td>206737276</td><td>4.07E-03</td><td>0.87</td><td>0.116</td><td>0.131</td><td>C</td><td>(SEQ ID NO: 0073) ttcaaggccctttgag[A/C]tcttgatggcacatga</td></tr>
<tr><td>03</td><td>rs4570460</td><td>1</td><td>q</td><td>q32.1</td><td>SYT2 | KDMSB</td><td>202689028</td><td>1.29E-03</td><td>1.33</td><td>0.034</td><td>0.025</td><td>A</td><td>(SEQ ID NO: 0074) agtatattaggggatt[A/G]atattacaagcaagaa</td></tr>
<tr><td>03</td><td>rs6670957</td><td>1</td><td>q</td><td>q32.2</td><td>PLXNA2 | LOC642587</td><td>209195248</td><td>4.01E-03</td><td>1.21</td><td>0.063</td><td>0.053</td><td>A</td><td>(SEQ ID NO: 0075) gctgtatgttataatt[A/C]tctgatagaacccaca</td></tr>
<tr><td>02</td><td>rs11119874</td><td>1</td><td>q</td><td>q32.3</td><td>DTL | PPP2R5A</td><td>212357017</td><td>4.15E-05</td><td>1.11</td><td>0.189</td><td>0.173</td><td>A</td><td>(SEQ ID NO: 0076) gatgaaataatagact[A/C]cagggatttacttttt</td></tr>
<tr><td>03</td><td>rs2359937</td><td>1</td><td>q</td><td>q32.3</td><td>RPS6KC1 | PROX1</td><td>214033051</td><td>1.14E-02</td><td>0.92</td><td>0.478</td><td>0.497</td><td>G</td><td>(SEQ ID NO: 0077) actctccaaagtcaca[A/G]tattttctggacaagc</td></tr>
<tr><td>02</td><td>rs2789939</td><td>1</td><td>q</td><td>q41</td><td>DISP1]TLR5</td><td>223191495</td><td>2.07E-03</td><td>0.86</td><td>0.281</td><td>0.311</td><td>C</td><td>(SEQ ID NO: 0078) atcaggatcataggag[C/G]actgtctgaggatcag</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs12747035 | 1 | q | q41 | PTPN14 | 214719346 | 5.58E-06 | 1.12 | 0.385 | 0.359 | G | (SEQ ID NO: 0079) acctggctagggatac[A/G]aggccattaaccaagc |
| 02 | rs903695 | 1 | q | q42.13 | CDC42BPA \| ZNF678 | 227733069 | 2.19E-03 | 1.18 | 0.211 | 0.185 | C | (SEQ ID NO: 0080) tggttgttgcatggca[T/C]ttccagataagctgca |
| 03 | rs2493142 | 1 | q | q42.2 | COG2 | 230817384 | 5.27E-03 | 1.11 | 0.262 | 0.243 | G | (SEQ ID NO: 0081) aatgtttgtatttggg[A/G]ttgcccttcttacatg |
| 01 | rs3789649 | 1 | q | q42.2 | COG2 | 230816460 | 8.83E-07 | 1.21 | 0.227 | 0.195 | A | (SEQ ID NO: 0082) caagttctacacttcc[A/G]taactcaaacgtgttt |
| 03 | rs1693210 | 1 | q | q42.2 | KCNK1 | 233800613 | 1.98E-03 | 1.11 | 0.382 | 0.359 | A | (SEQ ID NO: 0083) tcaattataatcacct[A/G]tgtggatttttctcag |
| 02 | rs7545302 | 1 | q | q43 | FMN2 | 240476158 | 9.75E-06 | 0.92 | 0.243 | 0.258 | A | (SEQ ID NO: 0084) cgaactgatcagatcg[A/C]tgccctacacacttta |
| 03 | rs6699695 | 1 | q | q43 | RGS7 \| FH | 241539802 | 6.47E-03 | 1.10 | 0.325 | 0.305 | A | (SEQ ID NO: 0085) caaatattactgcaat[A/G]agtaatatcatacaca |
| 03 | rs987179 | 1 | q | q44 | Clorf101 \| PPPDE1 | 244809936 | 7.12E-05 | 0.87 | 0.256 | 0.283 | A | (SEQ ID NO: 0086) aacagatgccatggta[A/G]actagatgcctgggtg |
| 03 | rs7548336 | 1 | q | q44 | LOC440742 \| Clorf100 | 244401066 | 6.04E-04 | 1.12 | 0.423 | 0.397 | G | (SEQ ID NO: 0087) tctttaaggtgggttc[A/G]gagaaaggagatggaa |
| 03 | rs900895 | 1 | q | q44 | LOC440742 \| Clorf100 | 244510437 | 1.38E-03 | 1.15 | 0.156 | 0.138 | A | (SEQ ID NO: 0088) acagacagggtgtcat[A/G]gaagccgcgtcatatc |
| 03 | rs3755095 | 2 | p | p12 | CTNNA2 | 80097279 | 1.16E-03 | 1.19 | 0.098 | 0.084 | G | (SEQ ID NO: 0089) tccaccagtgaagcaa[A/G]taatctgtggcctgct |
| 03 | rs953222 | 2 | p | p12 | CTNNA2 | 79979967 | 3.88E-03 | 1.14 | 0.135 | 0.120 | A | (SEQ ID NO: 0090) caaaaaagaagtatca[A/G]ggtatatatgaagaga |
| 03 | rs6547260 | 2 | p | p12 | CTNNA2 | 79925969 | 4.27E-04 | 1.18 | 0.137 | 0.119 | A | (SEQ ID NO: 0091) aacagaaaattaagat[A/C]agattggctaacaaga |
| 03 | rs1160581 | 2 | p | p12 | CTNNA2 | 80026432 | 1.33E-04 | 1.14 | 0.284 | 0.257 | G | (SEQ ID NO: 0092) taaaggaatccctgtt[A/G]aaaaaaaagaataagg |
| 03 | rs4284854 | 2 | p | p12 | CTNNA2 | 80025940 | 1.47E-04 | 1.15 | 0.264 | 0.238 | A | (SEQ ID NO: 0093) tttcctttataaaact[A/G]tgttactctagtctga |
| 03 | rs2861911 | 2 | p | p12 | CTNNA2 | 80007717 | 5.79E-03 | 1.11 | 0.208 | 0.191 | G | (SEQ ID NO: 0094) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | ctaaatggtggttcac[A/G]gggaattcatgaaact |
| 03 | rs1397687 | 2 | p | p12 | CTNNA2 | 80015386 | 6.22E-03 | 1.10 | 0.253 | 0.235 | A | (SEQ ID NO: 0095)<br>gggagctcagactcac[A/G]tggtggaaagcctaaa |
| 03 | rs6732862 | 2 | p | p12 | CTNNA2 | 79918572 | 7.64E-05 | 1.16 | 0.239 | 0.213 | A | (SEQ ID NO: 0096)<br>atggcataacaatagt[A/G]actcaaagaggcaaaa |
| 03 | rs4852536 | 2 | p | p12 | CTNNA2 | 80104027 | 1.02E-02 | 1.16 | 0.086 | 0.076 | G | (SEQ ID NO: 0097)<br>tttggaaatttaacac[A/G]tgaatataaccatcaa |
| 03 | rs1265750 | 2 | p | p12 | CTNNA2 \|<br>LOC100289658 | 80951823 | 2.64E-02 | 1.10 | 0.169 | 0.157 | A | (SEQ ID NO: 0098)<br>aacaggactaagtggc[A/G]tataaattagggtaat |
| 02 | rs1443896 | 2 | p | p12 | LRRTM1 \|<br>CTNNA2 | 80572750 | 8.14E-06 | 1.41 | 0.045 | 0.032 | A | (SEQ ID NO: 0099)<br>tatatcatcagtgccc[A/G]gaagagtacctgatgc |
| 03 | rs1239102 | 2 | p | p12 | SNAR-H \|<br>REG3G | 78873621 | 1.21E-04 | 1.13 | 0.367 | 0.338 | G | (SEQ ID NO: 0100)<br>accagtaccatccggt[A/G]tgatttgatggtatga |
| 03 | rs11687801 | 2 | p | p12 | SNAR-H \|<br>REG3G | 78978011 | 2.30E-04 | 1.13 | 0.329 | 0.302 | A | (SEQ ID NO: 0101)<br>tgatgaggccttctcg[A/G]ggaagttttacgatgt |
| 02 | exm204635 | 2 | p | p13.1 | CCDC142 | 74709541 | 8.09E-13 | Inf | 0.005 | 0.000 | A | (SEQ ID NO: 0102)<br>tgcagctgcaggtcgc[A/G]gcaccactggggcaag |
| 03 | rs879511 | 2 | p | p13.2 | SFXN5 | 73179990 | 4.99E-04 | 1.48 | 0.020 | 0.014 | G | (SEQ ID NO: 0103)<br>actcagccccagcccc[A/G]ctcactaagctcacag |
| 03 | rs2312205 | 2 | p | p13.3 | AAK1 | 69704941 | 1.17E-02 | 1.11 | 0.188 | 0.173 | G | (SEQ ID NO: 0104)<br>ccattgcaaaccacag[A/G]ggtgattatttttagt |
| 03 | rs3771452 | 2 | p | p13.3 | ADD2 | 70936861 | 3.88E-04 | 0.89 | 0.334 | 0.360 | A | (SEQ ID NO: 0105)<br>gggggaaagcgggaag[A/G]tctcttgctccaggaa |
| 03 | rs12466648 | 2 | p | p13.3 | GFPT1 | 69560024 | 1.74E-03 | 1.13 | 0.192 | 0.173 | G | (SEQ ID NO: 0106)<br>ggatgagactccctct[A/G]taataaaatcacagtc |
| 03 | rs12473304 | 2 | p | p13.3 | GFPT1 | 69558112 | 1.02E-03 | 1.15 | 0.178 | 0.159 | A | (SEQ ID NO: 0107)<br>ataaaatttatagtac[A/G]ttttgagcctgtgtgt |
| 03 | rs7605572 | 2 | p | p13.3 | NFU1 | 69646504 | 2.19E-03 | 1.14 | 0.177 | 0.159 | A | (SEQ ID NO: 0108)<br>aaacatagcatatttc[A/G]cttgattcttgtgaca |
| 03 | rs1430778 | 2 | p | p14 | ETAA1 \| C1D | 68012459 | 4.27E-03 | 0.91 | 0.312 | 0.333 | G | (SEQ ID NO: 0109)<br>tgcttcaacaatttcc[A/G]tttgtgtatcgttggc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6727061 | 2 | p | p15 | B3GNT2 \| TMEM17 | 62720684 | 3.86E-03 | 1.10 | 0.390 | 0.368 | G | (SEQ ID NO: 0110) tctgtgctgtttttca[A/G]ggaaaaacatctgggt |
| 03 | rs2674061 | 2 | p | p16.1 | LOC730134 \| BCL11A | 59753331 | 1.58E-03 | 1.11 | 0.319 | 0.296 | A | (SEQ ID NO: 0111) cccaagacactgtagc[A/G]tttacatagtaggtag |
| 02 | rs3814360 | 2 | p | p16.3 | LOC100653325 | 47800603 | 8.19E-04 | 1.21 | 0.200 | 0.171 | T | (SEQ ID NO: 0112) atgatcatgtgattga[A/T]gtatctaaaccacagt |
| 02 | rs989373 | 2 | p | p16.3 | LOC646936 \| FSHR | 49158325 | 1.12E-05 | 0.86 | 0.334 | 0.368 | A | (SEQ ID NO: 0113) gaacatatagacaatc[A/G]ggaatgctaaaataaa |
| 03 | rs1067352 | 2 | p | p21 | C2orf34 | 44669724 | 7.70E-04 | 0.89 | 0.290 | 0.314 | A | (SEQ ID NO: 0114) gactccttgcatttca[A/G]tataatgttagctctg |
| 03 | rs1067339 | 2 | p | p21 | C2orf34 | 44624448 | 3.83E-03 | 0.91 | 0.310 | 0.331 | A | (SEQ ID NO: 0115) atgcattgatgacctt[A/C]aatatttattttgtaa |
| 03 | rs1223222 | 2 | p | p21 | C2orf34 | 44756361 | 1.30E-02 | 0.92 | 0.319 | 0.338 | C | (SEQ ID NO: 0116) atatcattatgaactc[A/C]tagatttttttaaccta |
| 03 | rs1067350 | 2 | p | p21 | C2orf34 | 44669946 | 2.56E-03 | 0.89 | 0.227 | 0.247 | A | (SEQ ID NO: 0117) ccagcagctcatcaga[A/G]agagggatgacagaca |
| 03 | rs1067386 | 2 | p | p21 | C2orf34 | 44644257 | 3.92E-03 | 0.91 | 0.311 | 0.332 | C | (SEQ ID NO: 0118) acaacgcaatactact[A/C]ggaataaaaaaggaaa |
| 03 | rs1067343 | 2 | p | p21 | C2orf34 | 44621042 | 4.58E-03 | 0.90 | 0.244 | 0.263 | A | (SEQ ID NO: 0119) agtagtggaacgaaat[A/G]actttggagaaaagga |
| 03 | rs1067364 | 2 | p | p21 | C2orf34 | 44655734 | 3.22E-03 | 0.90 | 0.230 | 0.250 | A | (SEQ ID NO: 0120) tccctgcctcctgtcc[A/G]tatcaatagatgttgg |
| 03 | rs1067405 | 2 | p | p21 | C2orf34 | 44674861 | 3.81E-03 | 0.90 | 0.240 | 0.260 | A | (SEQ ID NO: 0121) actgacaacaggcttc[A/G]ccatgtaaattgctct |
| 03 | rs698793 | 2 | p | p21 | C2orf34 | 44685685 | 3.74E-03 | 0.90 | 0.241 | 0.260 | G | (SEQ ID NO: 0122) taagatgaaaaggtct[A/G]ctttcaggggtttgtg |
| 03 | rs1067370 | 2 | p | p21 | C2orf34 | 44652343 | 4.01E-03 | 0.91 | 0.310 | 0.332 | A | (SEQ ID NO: 0123) aacccagccattaact[A/C]ttgttagatagcttta |
| 03 | rs1067406 | 2 | p | p21 | C2orf34 | 44674450 | 1.84E-03 | 0.90 | 0.302 | 0.325 | G | (SEQ ID NO: 0124) tccttttattctcctc[A/G]ttttatgtaattctgt |
| 03 | rs1065785 | 2 | p | p21 | C2orf34 | 44660699 | 1.98E-03 | 0.90 | 0.298 | 0.321 | A | (SEQ ID NO: 0125) actttttgcttagtct[A/G]aattaaaaaaagtctt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs698813 | 2 | p | p21 | C2orf34 | 44705615 | 1.49E-03 | 0.89 | 0.217 | 0.238 | A | (SEQ ID NO: 0126) ttacaagattttcttt[A/G]gtttatagacctactt |
| 03 | rs698815 | 2 | p | p21 | C2orf34 | 44706974 | 7.55E-04 | 0.88 | 0.235 | 0.259 | C | (SEQ ID NO: 0127) cttgtttggggacaca[A/C]tttcaaatacaaaatg |
| 02 | exm189795 | 2 | p | p21 | PLEKHH2 | 43903164 | 1.13E-27 | 10.09 | 0.020 | 0.002 | C | (SEQ ID NO: 0128) tttttagtatcgtaga[C/G]ctctgctttgtcacag |
| 03 | rs6712059 | 2 | p | p21 | PPM1B \| SLC3A1 | 44475174 | 3.36E-03 | 0.91 | 0.375 | 0.398 | A | (SEQ ID NO: 0129) gactcaggtttgaggc[A/G]ttttgcatctggtggc |
| 03 | rs9309116 | 2 | p | p21 | PREPL | 44557919 | 6.27E-04 | 0.89 | 0.331 | 0.357 | G | (SEQ ID NO: 0130) gggaacaaattaatat[A/G]taaactatagccttga |
| 03 | rs4953089 | 2 | p | p21 | PREPL | 44565024 | 6.86E-04 | 0.89 | 0.293 | 0.318 | G | (SEQ ID NO: 0131) tccctgcatcccctgc[A/G]gataagaaaactggca |
| 03 | rs1056865 | 2 | p | p21 | PREPL / SLC3A1 | 44546741 | 1.62E-03 | 0.90 | 0.294 | 0.318 | A | (SEQ ID NO: 0132) atagtatgtgttcatt[A/G]aagatgatttgggttt |
| 03 | rs698775 | 2 | p | p21 | PREPL \| C2orf34 | 44588941 | 1.09E-03 | 0.89 | 0.300 | 0.324 | G | (SEQ ID NO: 0133) agatggctaccagcaa[A/G]aatggtgcaatggcgt |
| 02 | rs7581914 | 2 | p | p21 | PRKCE | 46078964 | 4.68E-05 | 0.88 | 0.391 | 0.423 | G | (SEQ ID NO: 0134) tcatttattgcttgat[A/G]gacacctctaatgtat |
| 03 | rs2340809 | 2 | p | p21 | SLC3A1 | 44536249 | 2.28E-03 | 0.90 | 0.297 | 0.320 | A | (SEQ ID NO: 0135) aaaagtgtgtaattca[A/G]tgcattaaatacattc |
| 03 | rs698761 | 2 | p | p21 | SLC3A1 | 44547574 | 5.56E-04 | 0.89 | 0.293 | 0.319 | G | (SEQ ID NO: 0136) gccttcccgctaaaat[A/G]agaataaggttaagta |
| 03 | rs2112040 | 2 | p | p21 | SRBD1 | 45752214 | 7.29E-05 | 1.09 | 0.308 | 0.289 | G | (SEQ ID NO: 0137) tgtcggtaggactact[A/G]gatagccacaggcaaa |
| 03 | rs10165323 | 2 | p | p22.2 | LOC100129149 \| LOC344382 | 38010296 | 1.28E-03 | 0.87 | 0.154 | 0.173 | A | (SEQ ID NO: 0138) ttgtggtctgtgttta[A/G]gataatgtggaagcta |
| 03 | rs206811 | 2 | p | p23.1 | XDH | 31636915 | 2.30E-04 | 1.13 | 0.381 | 0.354 | A | (SEQ ID NO: 0139) ggagtggggggaatgc[A/G]ggagatgccctttatg |
| 03 | rs206816 | 2 | p | p23.1 | XDH \| SRD5A2 | 31644983 | 5.04E-04 | 1.12 | 0.408 | 0.381 | A | (SEQ ID NO: 0140) atgatgctgagaatct[A/G]tgaaatgacggaagaa |
| 03 | rs7575607 | 2 | p | p23.1 | XDH \| SRD5A2 | 31640455 | 1.69E-03 | 1.11 | 0.413 | 0.389 | G | (SEQ ID NO: 0141) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2339554 | 2 | p | p23.2 | ALK | 29856155 | 7.90E-04 | 0.89 | 0.272 | 0.296 | A | tttattccttctatct[A/G]actgaaattctgtatt (SEQ ID NO: 0142) |
| 02 | rs2339547 | 2 | p | p23.2 | ALK | 29860061 | 3.38E-05 | 0.88 | 0.239 | 0.263 | A | acctcctgagctcaga[A/C]caagagtgcagccttt (SEQ ID NO: 0143) |
| 03 | rs6734278 | 2 | p | p23.3 | KIF3C | 26202233 | 1.70E-04 | 1.21 | 0.112 | 0.095 | A | gtttaatcatacatcc[A/G]tggaggaacatgttgg (SEQ ID NO: 0144) |
| 02 | rs2384298 | 2 | p | p23.3 | KIF3C | 26156655 | 2.63E-06 | 1.15 | 0.291 | 0.263 | G | ctctcagggttatggg[A/G]aattggatattaactg (SEQ ID NO: 0145) |
| 03 | rs13029647 | 2 | p | p23.3 | OTOF | 26731244 | 7.95E-03 | 1.09 | 0.369 | 0.349 | A | actaatagtgtatgag[A/G]gtttcattttctctac (SEQ ID NO: 0146) |
| 02 | rs13031859 | 2 | p | p23.3 | OTOF | 26741961 | 3.98E-05 | 0.91 | 0.464 | 0.488 | A | ctaactgacattcaac[A/G]cactttcaaagacacc (SEQ ID NO: 0147) |
| 03 | rs4665181 | 2 | p | p24.1 | LOC100129278 \| KLHL29 | 22759343 | 2.42E-03 | 1.11 | 0.350 | 0.327 | A | ttctgcagcaccatgc[A/G]gaaggtcccgatgagc (SEQ ID NO: 0148) |
| 02 | rs851352 | 2 | p | p24.1 | NT5C1B \| OSR1 | 19475331 | 5.32E-06 | 1.14 | 0.253 | 0.229 | A | gcgaaagaacaaacaa[A/G]ccatgtaatacatatg (SEQ ID NO: 0149) |
| 02 | rs851356 | 2 | p | p24.1 | NT5C1B \| OSR1 | 19474112 | 1.05E-05 | 1.13 | 0.252 | 0.230 | G | gccaggtctaggcatt[A/G]ttttggtaagtgactg (SEQ ID NO: 0150) |
| 03 | rs1871959 | 2 | p | p24.3 | TRIB2 \| FAM84A | 13250740 | 2.61E-04 | 1.45 | 0.025 | 0.017 | A | tttaactgctcggccc[A/G]tgtacttgatcatgga (SEQ ID NO: 0151) |
| 03 | rs4669910 | 2 | p | p24.3 | TRIB2 \| FAM84A | 13289018 | 2.44E-04 | 1.45 | 0.025 | 0.018 | A | acatgttgcataggtt[A/C]tccctccattccctgt (SEQ ID NO: 0152) |
| 03 | rs1813530 | 2 | p | p24.3 | TRIB2 \| FAM84A | 13983167 | 1.46E-04 | 1.35 | 0.043 | 0.032 | G | atagctatagcaccgc[A/G]aattgccacatctgta (SEQ ID NO: 0153) |
| 03 | rs16860924 | 2 | p | p24.3 | TRIB2 \| FAM84A | 14031175 | 3.36E-04 | 1.33 | 0.042 | 0.031 | G | ttattgccattcttgt[A/G]gaagtaaggtggtatc (SEQ ID NO: 0154) |
| 03 | rs4669907 | 2 | p | p24.3 | TRIB2 \| FAM84A | 13279945 | 4.64E-04 | 1.43 | 0.025 | 0.018 | A | cataagtggtggaatc[A/G]ttgttcagaaacatta (SEQ ID NO: 0155) |
| 02 | rs1900854 | 2 | p | p24.3 | TRIB2 \| FAM84A | 14422091 | 7.04E-05 | 0.88 | 0.381 | 0.412 | G | tctagaaacttagtac[A/C]tcctgttgcattggta (SEQ ID NO: 0156) |
| | | | | | | | | | | | | tttacatacttttcct[A/G]ttgacttctccatatt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7608117 | 2 | p | p25.1 | KCNF1 \| C2orf50 | 11265972 | 1.99E-04 | 1.12 | 0.503 | 0.473 | A | (SEQ ID NO: 0157) attccttctgggatct[A/C]ttaagggataaaaccg |
| 02 | rs1078589 | 2 | p | p25.2 | SOX11 \| LOC150622 | 5880342 | 1.01E-06 | 1.13 | 0.056 | 0.050 | A | (SEQ ID NO: 0158) caccacattctctctc[A/G]tcagcttctcagacat |
| 02 | rs16864121 | 2 | p | p25.2 | SOX11 \| LOC150622 | 5892514 | 9.24E-07 | 1.15 | 0.051 | 0.045 | G | (SEQ ID NO: 0159) aaaaattcctccatga[A/G]tcttacccagatggag |
| 03 | rs12714428 | 2 | p | p25.3 | LOC100128185 \| LOC391343 | 857713 | 2.00E-03 | 1.11 | 0.341 | 0.318 | A | (SEQ ID NO: 0160) gggaggttcagcagcc[A/G]ccactgcgaggagtgg |
| 01 | rs17025744 | 2 | q | q11.2 | TMEM131 \| VWA3B | 98636132 | 1.13E-06 | 1.34 | 0.075 | 0.057 | G | (SEQ ID NO: 0161) ccagtgcttgaccctc[A/G]ccaacgaccgcactct |
| 03 | rs2302621 | 2 | q | q12.1 | IL1RL2 | 102842124 | 8.49E-04 | 1.11 | 0.411 | 0.385 | C | (SEQ ID NO: 0162) ctcctgggaacttata[A/C]gagtaaaagtctgcag |
| 02 | rs2582974 | 2 | q | q12.1 | LOC644265 \| LOC100287010 | 104578923 | 1.25E-05 | 0.87 | 0.376 | 0.410 | A | (SEQ ID NO: 0163) gcaactaaaattaacc[A/G]tacttctgattgtgtc |
| 03 | rs1159964 | 2 | q | q12.1 | POU3F3 \| LOC100128131 | 105481442 | 3.06E-03 | 1.10 | 0.428 | 0.405 | G | (SEQ ID NO: 0164) tcccatccagcttaag[A/G]catttaaaatacaatt |
| 03 | rs732278 | 2 | q | q12.1 | POU3F3 \| LOC100128131 | 105473698 | 3.91E-03 | 1.10 | 0.446 | 0.424 | A | (SEQ ID NO: 0165) aaatgcctccttggtc[A/C]gtttctcccgcgtttt |
| 03 | rs7602289 | 2 | q | q12.1 | TMEM182 \| LOC644265 | 103445960 | 2.81E-04 | 0.88 | 0.256 | 0.281 | G | (SEQ ID NO: 0166) agcaatttatactggg[A/G]aaatatcagaaggtgt |
| 03 | rs2420589 | 2 | q | q14.1 | DPP10 | 115722009 | 4.55E-03 | 1.10 | 0.369 | 0.347 | G | (SEQ ID NO: 0167) ggacagtaaataagaa[A/G]aaaagaactggagcaa |
| 03 | rs6745631 | 2 | q | q14.1 | DPP10 | 115730919 | 4.01E-03 | 1.10 | 0.295 | 0.275 | C | (SEQ ID NO: 0168) ttcttatggctatttt[A/C]gtgtgtactcctactt |
| 03 | rs13429901 | 2 | q | q14.1 | DPP10 | 116279799 | 2.42E-02 | 1.11 | 0.128 | 0.117 | A | (SEQ ID NO: 0169) taagaatcacagagag[A/G]cggagtaatcagaccg |
| 03 | rs10210316 | 2 | q | q14.1 | DPP10 | 116298589 | 2.20E-02 | 1.11 | 0.128 | 0.117 | C | (SEQ ID NO: 0170) tattttgcatcccttc[A/C]ataaatacaaaaatgc |
| 02 | rs10206874 | 2 | q | q14.2 | INHBB \| LOC84931 | 121160145 | 4.99E-05 | 0.90 | 0.463 | 0.489 | C | (SEQ ID NO: 0171) actctgccacagacac[A/C]ttccctggagccctcc |
| 03 | rs7570552 | 2 | q | q14.2 | MARCO \| C1QL2 | 119883331 | 7.92E-05 | 0.88 | 0.315 | 0.343 | G | (SEQ ID NO: 0172) tgggagaaagggcttc[A/G]actgtggtttcagaca |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs9636365 | 2 | q | q14.2 | MARCO \| C1QL2 | 119886918 | 7.31E-05 | 0.88 | 0.316 | 0.344 | A | (SEQ ID NO: 0173) ctcttcctataaggat[A/G]cactgttggatctagg |
| 03 | rs12469732 | 2 | q | q14.3 | LOC339760 | 127653376 | 2.71E-03 | 1.17 | 0.105 | 0.092 | A | (SEQ ID NO: 0174) gtcatgtaattttgat[A/G]accatcaaaaggattt |
| 03 | rs6728117 | 2 | q | q14.3 | TSN \| LOC100288443 | 123818496 | 7.09E-03 | 0.88 | 0.120 | 0.134 | C | (SEQ ID NO: 0175) ttgatatgaagtgagc[A/C]tgcataaatttcagtt |
| 03 | rs13011089 | 2 | q | q14.3 | TSN \| LOC100288443 | 123828854 | 2.21E-02 | 0.90 | 0.120 | 0.132 | A | (SEQ ID NO: 0176) ttatgaagatctactt[A/C]tattttgtcaatagta |
| 03 | rs309161 | 2 | q | q21.3 | DARS | 136688749 | 7.33E-05 | 1.13 | 0.164 | 0.148 | A | (SEQ ID NO: 0177) atttccaaattcttta[A/G]cccttgactttgctga |
| 03 | rs2322659 | 2 | q | q21.3 | LCT | 136555659 | 1.28E-03 | 1.12 | 0.271 | 0.248 | A | (SEQ ID NO: 0178) aagaatggagattaca[A/G]tgaggtgatgaagacg |
| 02 | rs309152 | 2 | q | q21.3 | MCM6 \| DARS | 136657252 | 1.81E-05 | 1.13 | 0.161 | 0.144 | G | (SEQ ID NO: 0179) gttggatctgtgaccc[A/G]tgctttctacagagaa |
| 02 | rs10187054 | 2 | q | q21.3 | R3HDM1 | 136388473 | 1.04E-05 | 1.31 | 0.176 | 0.140 | C | (SEQ ID NO: 0180) gaggtcctttggggag[T/C]gataccattaataata |
| 03 | rs6739713 | 2 | q | q21.3 | R3HDM1 \| UBXN4 | 136488978 | 3.10E-04 | 1.14 | 0.263 | 0.239 | G | (SEQ ID NO: 0181) tcactcaagaaaaaac[A/G]agaacagacaataata |
| 03 | rs9287442 | 2 | q | q21.3 | UBXN4 | 136522710 | 2.02E-03 | 1.12 | 0.248 | 0.227 | A | (SEQ ID NO: 0182) atgtttcactaaagta[A/G]cagatgtgaaatagga |
| 03 | rs10188066 | 2 | q | q21.3 | UBXN4 | 136539513 | 2.01E-03 | 1.12 | 0.246 | 0.226 | G | (SEQ ID NO: 0183) agctgtgtgtgatagc[A/G]tgtgcctatagtttca |
| 02 | rs1900741 | 2 | q | q21.3 | ZRANB3 | 136002500 | 8.72E-05 | 1.17 | 0.216 | 0.191 | A | (SEQ ID NO: 0184) ttagaacatcacctat[A/G]ctgattactcccatgc |
| 02 | rs10221893 | 2 | q | q22.1 | CXCR4 THSD7B | 137013606 | 2.10E-05 | 1.15 | 0.446 | 0.412 | G | (SEQ ID NO: 0185) gagtgatttgcccatc[A/G]tgtaatggagactggt |
| 02 | rs6430612 | 2 | q | q22.1 | CXCR4 \| THSD7B | 137006198 | 1.84E-05 | 1.15 | 0.444 | 0.411 | G | (SEQ ID NO: 0186) ctcctccttaacatga[A/G]ttgagttcactttacc |
| 03 | rs6755074 | 2 | q | q22.2 | KYNU | 143683066 | 5.38E-04 | 0.89 | 0.360 | 0.386 | C | (SEQ ID NO: 0187) tgaaagagacggttac[A/C]tagtaccctgtttctg |
| 03 | rs11689575 | 2 | q | q22.3 | LOC100131409 | 145527778 | 1.09E-03 | 1.19 | 0.095 | 0.081 | A | (SEQ ID NO: 0188) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | caggatcccgtttagg[A/G]actttcaacacccttg |
| 03 | rs7603516 | 2 | q | q22.3 | LOC100131409 | 145504693 | 1.70E-03 | 1.18 | 0.095 | 0.082 | C | (SEQ ID NO: 0189)<br>ctctgtgttgatgctt[A/C]cttccatttttagcac |
| 03 | rs11691685 | 2 | q | q22.3 | LOC100131409 | 145481827 | 7.74E-04 | 1.21 | 0.087 | 0.074 | G | (SEQ ID NO: 0190)<br>atgagagaacatcact[A/G]tagataatttagactt |
| 03 | rs7560871 | 2 | q | q22.3 | LOC100131409 \| PABPCP2 | 145616899 | 4.59E-03 | 1.18 | 0.079 | 0.067 | A | (SEQ ID NO: 0191)<br>aaacattttaaaatgt[A/G]agtgggataaaacatg |
| 03 | rs4422110 | 2 | q | q22.3 | LOC100131409 \| PABPCP2 | 146114898 | 9.30E-05 | 0.89 | 0.448 | 0.478 | G | (SEQ ID NO: 0192)<br>tcctgcctttgtataa[A/G]catgctatttattcca |
| 03 | rs11690035 | 2 | q | q22.3 | LOC100131409 \| PABPCP2 | 145603306 | 5.95E-03 | 1.18 | 0.080 | 0.068 | A | (SEQ ID NO: 0193)<br>atgatgtcttgtgaca[A/G]ataataaagctatggg |
| 02 | rs12621827 | 2 | q | q23.2 | LYPD6B | 149981717 | 3.03E-05 | 0.93 | 0.230 | 0.244 | A | (SEQ ID NO: 0194)<br>cagtcagtgctgtaac[A/G]tcacaaatcactaatc |
| 01 | rs1519761 | 2 | q | q23.3 | RND3 \| RBM43 | 151633204 | 4.13E-10 | 1.22 | 0.446 | 0.398 | G | (SEQ ID NO: 0195)<br>ttgtatatgagaaaaa[A/G]agaggcaattttttaa |
| 03 | rs12328269 | 2 | q | q23.3 | RND3 \| RBM43 | 151774643 | 2.59E-04 | 1.12 | 0.445 | 0.417 | A | (SEQ ID NO: 0196)<br>atgtctattgaagccc[A/G]cctttgacatttatga |
| 01 | rs7580162 | 2 | q | q23.3 | RND3 \| RBM43 | 151655513 | 1.53E-06 | 1.18 | 0.279 | 0.246 | G | (SEQ ID NO: 0197)<br>cttttttcttttccca[A/G]ttgcttcagtgatagc |
| 01 | rs6734792 | 2 | q | q23.3 | RND3 \| RBM43 | 151624882 | 6.83E-10 | 1.22 | 0.449 | 0.401 | G | (SEQ ID NO: 0198)<br>aaagcaaaaggtgaag[A/G]agttatttattatcca |
| 01 | rs9789673 | 2 | q | q23.3 | RND3 \| RBM43 | 151627106 | 1.72E-07 | 1.19 | 0.325 | 0.288 | A | (SEQ ID NO: 0199)<br>aataattttcagattt[A/C]tttgaacttactttct |
| 01 | rs1519768 | 2 | q | q23.3 | RND3 \| RBM43 | 151648276 | 9.30E-10 | 1.22 | 0.413 | 0.366 | A | (SEQ ID NO: 0200)<br>tcattgactttgaaaa[A/G]aattccagtcattatc |
| 01 | rs1519754 | 2 | q | q23.3 | RND3 \| RBM43 | 151619693 | 1.29E-09 | 1.21 | 0.446 | 0.400 | C | (SEQ ID NO: 0201)<br>tgaagagttagacaat[A/C]atttatttgagcatga |
| 01 | rs6728560 | 2 | q | q23.3 | RND3 \| RBM43 | 151653870 | 3.30E-06 | 1.18 | 0.278 | 0.246 | A | (SEQ ID NO: 0202)<br>acagaaagaaaatgcc[A/G]tcttgtagtaatccac |
| 01 | rs10515926 | 2 | q | q23.3 | RND3 \| RBM43 | 151645865 | 6.00E-09 | 1.20 | 0.415 | 0.370 | A | (SEQ ID NO: 0203)<br>cttgggaaggaacaca[A/G]tggattttccctggaa |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs12465911 | 2 | q | q23.3 | RND3 \| RBM43 | 151785742 | 1.40E-05 | 1.16 | 0.300 | 0.270 | A | (SEQ ID NO: 0204) gcctccttgcctacaa[A/G]tcaaatagtaggattt |
| 01 | rs6757804 | 2 | q | q23.3 | RND3 \| RBM43 | 151635832 | 3.85E-10 | 1.22 | 0.446 | 0.398 | G | (SEQ ID NO: 0205) cagtggggtgataggt[A/G]tgtcatggaaataata |
| 03 | rs12987780 | 2 | q | q24.3 | CSRNP3 | 166470623 | 5.14E-03 | 1.09 | 0.416 | 0.395 | A | (SEQ ID NO: 0206) acaaaccttagcgagg[A/C]atagtggtgtgatgaa |
| 03 | rs1551825 | 2 | q | q24.3 | KCNH7 \| FIGN | 164340544 | 2.62E-03 | 1.10 | 0.365 | 0.343 | G | (SEQ ID NO: 0207) gaatatgaaatccacc[A/G]cactggctgtcaataa |
| 03 | rs11896706 | 2 | q | q24.3 | SCN1A \| SCN9A | 166993034 | 5.32E-04 | 0.88 | 0.238 | 0.262 | G | (SEQ ID NO: 0208) agatagagatacatat[A/G]aagctactgctgtcct |
| 03 | rs7587026 | 2 | q | q24.3 | SCN1A \| SCN9A | 166978750 | 2.80E-03 | 0.90 | 0.256 | 0.277 | A | (SEQ ID NO: 0209) aaaagcatactagcaa[A/C]atatattacaaagaac |
| 03 | rs7562413 | 2 | q | q24.3 | STK39 | 168979569 | 3.66E-03 | 1.10 | 0.344 | 0.323 | A | (SEQ ID NO: 0210) cttaatatgatacaga[A/G]aagaacccaacatcac |
| 03 | rs2287618 | 2 | q | q31.1 | ABCB11 | 169842809 | 5.79E-03 | 1.10 | 0.326 | 0.306 | A | (SEQ ID NO: 0211) cgaaattgactcaagc[A/G]ttttgtcttcacaggt |
| 03 | rs16864421 | 2 | q | q31.1 | LOC375295 \| HNRNPA3 | 177628237 | 3.38E-04 | 1.27 | 0.060 | 0.048 | A | (SEQ ID NO: 0212) tgagagtcaaagaaga[A/G]gggaaaactccaggaa |
| 02 | exm244817 | 2 | q | q31.2 | MIR548N | 179315031 | 4.38E-62 | Inf | 0.056 | 0.010 | G | (SEQ ID NO: 0213) gaatgtgaaagatctg[A/G]tgtgcaaatacacgtg |
| 02 | rs4563185 | 2 | q | q31.3 | CWC22 \| LOC729009 | 181684892 | 6.96E-04 | 1.23 | 0.168 | 0.141 | A | (SEQ ID NO: 0214) ccaatcctttgggtta[A/G]ctgatttagtaggtaa |
| 03 | rs13034731 | 2 | q | q32.2 | GULP1 | 189414364 | 5.29E-04 | 0.89 | 0.356 | 0.382 | A | (SEQ ID NO: 0215) gttttgatttctctgg[A/G]ataaatgtccaagtat |
| 02 | rs2709387 | 2 | q | q33.3 | CREB1 | 208442095 | 9.76E-03 | 0.87 | 0.170 | 0.191 | A | (SEQ ID NO: 0216) tgctgattctttcaac[A/G]ctttagccagaatcat |
| 02 | rs1263628 | 2 | q | q33.3 | KLF7 | 207977132 | 8.58E-03 | 0.85 | 0.146 | 0.167 | C | (SEQ ID NO: 0217) gaaatgattccataaa[C/G]cctgaatttatcttat |
| 02 | rs7582864 | 2 | q | q33.3 | ZDBF2 | 207172627 | 3.60E-05 | 1.13 | 0.425 | 0.396 | A | (SEQ ID NO: 0218) ctgatgtttctgtcca[A/G]tctgtggctgatcaac |
| 02 | rs3732084 | 2 | q | q33.3 | ZDBF2 | 207174316 | 4.57E-05 | 1.13 | 0.417 | 0.388 | A | (SEQ ID NO: 0219) ttggatccttccgaag[A/G]ctggcttctttgtgag |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs4673350 | 2 | q | q33.3 | ZDBF2 | 207178872 | 4.33E-05 | 1.12 | 0.426 | 0.398 | G | (SEQ ID NO: 0220) tacaataaaaatctac[A/G]caaaatactgaacaag |
| 02 | rs1448902 | 2 | q | q33.3 | ZDBF2 | 207178422 | 3.15E-05 | 1.13 | 0.358 | 0.330 | G | (SEQ ID NO: 0221) agagagaacagttcct[A/G]taattcaagtaattaa |
| 03 | rs2033645 | 2 | q | q34 | ERBB4 | 212325378 | 2.59E-03 | 1.23 | 0.058 | 0.048 | G | (SEQ ID NO: 0222) tacagacagtttttgt[A/G]tatttcaacttgccat |
| 03 | rs1250258 | 2 | q | q35 | FN1 | 216300185 | 3.96E-04 | 1.13 | 0.285 | 0.261 | G | (SEQ ID NO: 0223) ctgggatgataagacc[A/G]tgcattggaggacgag |
| 03 | rs12053317 | 2 | q | q35 | WNT6 | 219733973 | 2.71E-04 | 0.85 | 0.148 | 0.170 | G | (SEQ ID NO: 0224 aaacacgtgtgtgtgc[A/G]cgtgcattctcatgct |
| 01 | rs10184043 | 2 | q | q36.1 | KCNE4 \| SCG2 | 224204870 | 2.30E-07 | 1.20 | 0.283 | 0.248 | A | (SEQ ID NO: 0225) tactgggtctgaagga[A/G]catgtggaggaggcag |
| 01 | rs10445738 | 2 | q | q36.1 | KCNE4 \| SCG2 | 224186245 | 8.46E-07 | 1.19 | 0.266 | 0.233 | A | (SEQ ID NO: 0226) ccattcagcatttaca[A/G]tggtaccccaatagga |
| 03 | rs17190891 | 2 | q | q36.1 | KCNE4 \| SCG2 | 224046645 | 4.07E-04 | 1.18 | 0.138 | 0.120 | A | (SEQ ID NO: 0227) ttgtccccaagttttc[A/G]tgtttagcacaatata |
| 01 | rs1400797 | 2 | q | q36.1 | KCNE4 \| SCG2 | 224226772 | 4.31E-09 | 1.23 | 0.293 | 0.252 | A | (SEQ ID NO: 0228) attcaaactccaatat[A/G]gtcccaagtttaaaac |
| 03 | rs7580493 | 2 | q | q36.3 | SPHKAP \| PID1 | 229427172 | 1.51E-03 | 1.48 | 0.017 | 0.012 | A | (SEQ ID NO: 0229) tctacattgcttttct[A/G]tctgctatcaccccctc |
| 03 | rs6431586 | 2 | q | q37.1 | INPP5D \| ATG16L1 | 234119635 | 4.44E-04 | 1.19 | 0.115 | 0.099 | A | (SEQ ID NO: 0230) tttgtgccccacggcg[A/G]ttctggacgcacctgt |
| 03 | rs10084197 | 2 | q | q37.1 | NPPC \| DIS3L2 | 232810183 | 2.86E-03 | 1.11 | 0.308 | 0.286 | G | (SEQ ID NO: 0231) cattaccaatagtaat[A/G]tcagaaatgaaacacc |
| 03 | rs838425 | 2 | q | q37.1 | PTMA \| PDE6D | 232597042 | 8.82E-04 | 0.81 | 0.062 | 0.076 | G | (SEQ ID NO: 0232) gtatttcactccagga[A/G]tggaactgatagatct |
| 02 | exm284033 | 2 | q | q37.3 | ANO7 | 242154318 | 6.11E-12 | Inf | 0.004 | 0.000 | A | (SEQ ID NO: 0233) aggaggtcctcatccc[A/G]tgagtccccccactcct |
| 03 | rs7605254 | 2 | q | q37.3 | ASB1 \| LOC100287050 | 239362938 | 9.60E-03 | 0.91 | 0.274 | 0.293 | A | (SEQ ID NO: 0234) ctacccattttccttg[A/G]agttacgtcccttggt |
| 02 | exm284661 | 2 | q | q37.3 | BOK | 242498984 | 8.95E-16 | 3.49 | 0.021 | 0.008 | G | (SEQ ID NO: 0235) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | gacaaggagctggtgg[C/G]ccaggccaaggcgctg |
| 03 | rs4073396 | 2 | q | q37.3 | COPS8 \| COL6A3 | 238111471 | 6.38E-04 | 0.88 | 0.209 | 0.232 | C | (SEQ ID NO: 0236) cccacatctaagatac[A/C]caaaggtcagtgacgc |
| 03 | rs7585432 | 2 | q | q37.3 | CXCR7 \| LOC93463 | 237626734 | 1.22E-03 | 1.16 | 0.132 | 0.115 | C | (SEQ ID NO: 0237) tgagcgtttaactcct[A/C]cctccccttactcaca |
| 03 | rs2067620 | 2 | q | q37.3 | CXCR7 \| LOC93463 | 237642373 | 8.83E-04 | 1.17 | 0.124 | 0.108 | G | (SEQ ID NO: 0238) aggccttaaggacact[A/G]gtagactgaaggaggt |
| 03 | rs11679123 | 2 | q | q37.3 | CXCR7 \| LOC93463 | 237647424 | 7.96E-04 | 1.17 | 0.124 | 0.108 | A | (SEQ ID NO: 0239) atccacatatccatcc[A/G]tccctctattctgaca |
| 01 | exm281099 | 2 | q | q37.3 | HDAC4 | 240056067 | 7.45E-63 | 125.80 | 0.013 | 0.001 | A | (SEQ ID NO: 0240) gctctcccttttcccc[A/G]gcacccacctcactcc |
| 03 | rs1796449 | 2 | q | q37.3 | HDAC4 \| FLJ45964 | 240420675 | 2.21E-04 | 0.89 | 0.423 | 0.452 | A | (SEQ ID NO: 0241) ctgaactacacggagg[A/G]ggatgacacgggggct |
| 03 | rs1564974 | 2 | q | q37.3 | HDAC4 \| FLJ45964 | 240436304 | 1.12E-03 | 0.90 | 0.441 | 0.467 | C | (SEQ ID NO: 0242) ggcaagccatcccgga[A/C]ggacgtcagatcctgg |
| 03 | rs1486323 | 2 | q | q37.3 | HDAC4 \| FLJ45964 | 240417788 | 1.64E-04 | 0.88 | 0.325 | 0.353 | G | (SEQ ID NO: 0243) ctgggcacgtgcttca[A/G]taagaacagctgctca |
| 03 | rs4414678 | 2 | q | q37.3 | KIF1A | 241680633 | 4.58E-04 | 1.12 | 0.372 | 0.346 | A | (SEQ ID NO: 0244) tgtgtcggggggtgcg[A/C]ggagagggacgaggac |
| 03 | rs1845754 | 3 | p | p11.1 | C3orf38 \| EPHA3 | 88765697 | 4.79E-03 | 1.10 | 0.358 | 0.337 | A | (SEQ ID NO: 0245) ataaatcccacttggt[A/C]atgatgaatgctcttt |
| 03 | rs1473624 | 3 | p | p12.2 | GBE1 \| LOC100289598 | 83169976 | 1.76E-04 | 1.16 | 0.193 | 0.171 | G | (SEQ ID NO: 0246) cttgaatttgtggatg[A/G]tttgtgaaatgtaata |
| 02 | rs7618878 | 3 | p | p12.2 | GBE1 \| LOC100289598 | 83089596 | 9.01E-07 | 1.13 | 0.474 | 0.444 | A | (SEQ ID NO: 0247) ttattttatggacata[A/G]tgtgtgggagcttgaa |
| 03 | rs1080728 | 3 | p | p12.2 | GBE1 \| LOC100289598 | 83107505 | 7.42E-05 | 0.89 | 0.239 | 0.260 | A | (SEQ ID NO: 0248) gaagcgcgcatgcaat[A/G]gatccagggtgtatgc |
| 03 | rs1995065 | 3 | p | p12.2 | GBE1 \| LOC100289598 | 82913445 | 6.05E-05 | 1.11 | 0.407 | 0.383 | A | (SEQ ID NO: 0249) taacaaataggcagaa[A/G]ttttgagcaacattaa |
| 02 | rs11127807 | 3 | p | p12.2 | GBE1 \| LOC100289598 | 83130081 | 3.10E-07 | 1.14 | 0.474 | 0.443 | G | (SEQ ID NO: 0250) atattgtactttgtat[A/G]cagaatttcaacttgg |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6806032 | 3 | p | p12.2 | GBE1 \| LOC100289598 | 83132865 | 7.90E-05 | 0.89 | 0.236 | 0.258 | G | (SEQ ID NO: 0251) tttctttatctagtgg[A/G]cacttttaggtcgatt |
| 03 | rs2121783 | 3 | p | p13 | FOXP1 | 71174475 | 6.22E-04 | 0.90 | 0.404 | 0.431 | G | (SEQ ID NO: 0252) tttttgtgtgtatgtc[A/G]ttcttgaatacagtga |
| 03 | rs9862251 | 3 | p | p14.2 | PTPRG | 61587570 | 2.48E-02 | 1.12 | 0.120 | 0.109 | G | (SEQ ID NO: 0253) aaggaggtaaagttaa[A/G]agttaggagcagaggg |
| 01 | exm321427 | 3 | p | p21.1 | SEMA3G | 52475886 | 1.55E-20 | Inf | 0.004 | 0.000 | A | (SEQ ID NO: 0254) tgagggcaccgccccc[A/G]gccactttccacactg |
| 03 | rs375544 | 3 | p | p21.2 | MAPKAPK3 | 50657826 | 1.28E-04 | 1.19 | 0.151 | 0.130 | G | (SEQ ID NO: 0255) ctgcctccctggtgat[A/G]tactccaggttaacca |
| 01 | rs4688718 | 3 | p | p21.31 | CACNA2D2 | 50522063 | 4.92E-06 | 1.16 | 0.423 | 0.387 | A | (SEQ ID NO: 0256) tcacctgctccgtgaa[A/G]acctccttgcccctcc |
| 02 | rs2236951 | 3 | p | p21.31 | CACNA2D2 | 50421081 | 2.54E-05 | 1.17 | 0.223 | 0.197 | G | (SEQ ID NO: 0257) gccaggagctggggat[A/G]taaggaagggggatgt |
| 02 | exm311992 | 3 | p | p21.31 | COL7A1 | 48623625 | 4.98E-08 | 4.22 | 0.009 | 0.002 | A | (SEQ ID NO: 0258) ccagagcagctgcgtc[A/G]cttggcgccgggtatg |
| 02 | rs2233474 | 3 | p | p21.31 | TUSC4 \| CYB561D2 | 50388607 | 1.37E-05 | 1.21 | 0.160 | 0.136 | A | (SEQ ID NO: 0259) ttacatggctttgcgc[A/C]tcctacctggaaggcg |
| 02 | exm304730 | 3 | p | p22.1 | CYP8B1 | 42916596 | 2.38E-09 | Inf | 0.003 | 0.000 | G | (SEQ ID NO: 0260) cagcgtctctttcaca[A/G]gatgctctccgtgagc |
| 03 | rs5029848 | 3 | p | p22.1 | LOC100287063 | 42110843 | 1.99E-03 | 0.91 | 0.400 | 0.424 | C | (SEQ ID NO: 0261) tgcaccatccgaccca[A/C]ccataacttttctttt |
| 03 | rs7644110 | 3 | p | p22.1 | LOC100287063 | 42115488 | 1.85E-03 | 0.91 | 0.401 | 0.425 | G | (SEQ ID NO: 0262) gagttcctttgcccct[A/G]ttacgacaagagggtt |
| 03 | rs1995137 | 3 | p | p22.1 | LOC100287063 \| TRAK1 | 42131415 | 1.60E-03 | 0.90 | 0.405 | 0.429 | A | (SEQ ID NO: 0263) gtgtatcaattgtgtc[A/G]atttgtgcagtgagta |
| 03 | rs10514703 | 3 | p | p22.1 | LOC729505 \| CTNNB1 | 40901256 | 7.31E-03 | 0.80 | 0.037 | 0.046 | A | (SEQ ID NO: 0264) aaacaatgaagccaag[A/G]acagaagtgactggac |
| 03 | rs6798614 | 3 | p | p22.1 | LOC729505 \| CTNNB1 | 40930857 | 7.30E-03 | 0.80 | 0.037 | 0.045 | A | (SEQ ID NO: 0265) gtttttatgtcagctc[A/G]acctttgcttttaagt |
| 02 | exm302831 | 3 | p | p22.1 | MYRIP | 40085729 | 1.94E-08 | 34.64 | 0.004 | 0.000 | G | (SEQ ID NO: 0266) taccagaagcacgaaa[A/G]ggcctgggtctgctgc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4293737 | 3 | p | p22.3 | CMTM8 | 32373530 | 1.28E-02 | 1.10 | 0.209 | 0.193 | A | (SEQ ID NO: 0267) tcttttgaccacacgc[A/G]cacacacacacacaca |
| 03 | rs11713777 | 3 | p | p22.3 | GPD1L \| LOC100129194 | 32245557 | 3.18E-04 | 1.21 | 0.101 | 0.085 | G | (SEQ ID NO: 0268) atggatatgcagttag[A/G]aaaatgagtcatcact |
| 03 | rs12493245 | 3 | p | p24.1 | EOMES \| CMC1 | 27797810 | 2.08E-03 | 1.11 | 0.370 | 0.347 | A | (SEQ ID NO: 0269) gtcgtaacttaaaatc[A/G]tattcaaagctgtgat |
| 03 | rs4343572 | 3 | p | p24.2 | LOC644990 \| LOC100130354 | 24732019 | 1.36E-02 | 0.92 | 0.361 | 0.379 | A | (SEQ ID NO: 0270) ttcataattctacttt[A/G]ctggaatcagctgaga |
| 03 | rs4600774 | 3 | p | p24.2 | LOC644990 \| LOC100130354 | 24731037 | 2.65E-03 | 0.90 | 0.297 | 0.319 | A | (SEQ ID NO: 0271) aagcaaagcaagcaaa[A/G]catcatctgtatttat |
| 03 | rs7610222 | 3 | p | p24.2 | THRB | 24357286 | 6.07E-03 | 0.91 | 0.253 | 0.272 | A | (SEQ ID NO: 0272) attagtggagtgaact[A/G]cttctccctgcaatta |
| 01 | exm2265568 | 3 | p | p24.3 | VENTXP7 \| UBE2E2 | 23242050 | 1.34E-08 | 2.49 | 0.004 | 0.000 | G | (SEQ ID NO: 0273) aactaactgtggetct[A/G]cttactcacgaagttg |
| 03 | rs6442476 | 3 | p | p25.1 | C3orf20 | 14812460 | 2.43E-03 | 1.10 | 0.486 | 0.462 | G | (SEQ ID NO: 0274) tgtgaggtgtggcaca[A/G]aggtaaggaatagcca |
| 02 | rs7651825 | 3 | p | p25.1 | C3orf20 | 14812118 | 4.03E-05 | 0.90 | 0.418 | 0.444 | A | (SEQ ID NO: 0275) cccagagetacctcaa[A/G]ccecctecccaagcca |
| 03 | rs2697149 | 3 | p | p25.3 | SLC6A1 | 11036480 | 6.59E-03 | 1.11 | 0.240 | 0.222 | C | (SEQ ID NO: 0276) gggtaaagatgaggca[A/C]aatcaagtccatcgaa |
| 03 | rs6792001 | 3 | p | p26.1 | EDEM1 \| GRM7 | 6106251 | 2.02E-04 | 1.16 | 0.183 | 0.161 | A | (SEQ ID NO: 0277) gatgcaattagagata[A/G]gctttaggaagatctt |
| 02 | exm285495 | 3 | p | p26.3 | CHL1 | 391100 | 7.65E-11 | 44.12 | 0.005 | 0.000 | A | (SEQ ID NO: 0278) accaaaggggagagaa[A/G]caaaagaaaattatgg |
| 03 | rs2044602 | 3 | p | p26.3 | CNTN4 | 2315400 | 3.66E-03 | 0.91 | 0.416 | 0.438 | A | (SEQ ID NO: 0279) attttcctcttaatgc[A/G]gtactaatatatgttg |
| 03 | rs16840752 | 3 | q | q12.1 | DCBLD2 \| COL8A1 | 98924050 | 6.69E-02 | 1.15 | 0.046 | 0.040 | A | (SEQ ID NO: 0280) gacttcacatagtgcc[A/G]ectagttettccaatg |
| 03 | rs1848252 | 3 | q | q12.2 | ABI3BP \| IMPG2 | 100818827 | 5.34E-05 | 1.15 | 0.210 | 0.187 | G | (SEQ ID NO: 0281) cctctacccccaggct[A/G]aaaaggcctgacacaa |
| 02 | rs16843225 | 3 | q | q12.2 | ABI3BP \| IMPG2 | 100801257 | 1.13E-05 | 0.81 | 0.122 | 0.146 | C | (SEQ ID NO: 0282) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | ctgtgtagetatttga[A/C]gatatgctggcctgta |
| 02 | rs2036650 | 3 | q | q12.2 | ABI3BP \| IMPG2 | 100834729 | 2.07E-05 | 1.17 | 0.201 | 0.177 | C | (SEQ ID NO: 0283)<br>aaaaaaaaaaaataagt[A/C]ctcttaaagetagcac |
| 02 | rs650567 | 3 | q | q12.3 | NFKBIZ \|<br>LOC152225 | 101594402 | 4.53E-05 | 0.88 | 0.397 | 0.428 | A | (SEQ ID NO: 0284)<br>ttctaaaaaagcaact[A/C]ctcatgagaagctgta |
| 02 | rs641432 | 3 | q | q12.3 | NFKBIZ \|<br>LOC152225 | 101587566 | 2.88E-05 | 0.88 | 0.425 | 0.458 | A | (SEQ ID NO: 0285)<br>gttgagtccttctcag[A/G]cttggaatctctaaga |
| 03 | rs16844076 | 3 | q | q12.3 | PCNP | 101296067 | 1.06E-04 | 1.32 | 0.052 | 0.040 | G | (SEQ ID NO: 0286)<br>tctcctccctttggtt[A/G]aatctttgtagctgtt |
| 02 | rs2303476 | 3 | q | q12.3 | RG9MTD1 | 101280993 | 9.87E-05 | 1.32 | 0.052 | 0.040 | G | (SEQ ID NO: 0287)<br>ttgtttcaggtactgt[A/G]ctagttatagtttatt |
| 03 | rs6793744 | 3 | q | 813.11 | CBLB \|<br>LOC344593 | 105897816 | 5.72E-05 | 1.11 | 0.057 | 0.052 | G | (SEQ ID NO: 0288)<br>ccagccaggatattca[A/G]aggaccgaaccctctt |
| 03 | rs6774644 | 3 | q | 813.12 | CBLB \|<br>LOC344593 | 106379000 | 5.37E-04 | 0.86 | 0.144 | 0.164 | G | (SEQ ID NO: 0289)<br>ttgagtgtgaaagaat[A/G]taacagtaaaaataaa |
| 03 | rs12633892 | 3 | q | 813.12 | CBLB \|<br>LOC344593 | 106380005 | 9.96E-04 | 0.86 | 0.145 | 0.164 | G | (SEQ ID NO: 0290)<br>ctacatgagaaacctg[A/G]gagctatcttcaaatc |
| 03 | rs7613153 | 3 | q | 813.12 | CBLB \|<br>LOC344593 | 106380604 | 1.03E-03 | 0.86 | 0.144 | 0.163 | A | (SEQ ID NO: 0291)<br>taatgctagccttcct[A/G]gagtctagtatttcag |
| 03 | rs7617430 | 3 | q | q13.12 | CBLB \|<br>LOC344593 | 106392429 | 4.80E-04 | 0.85 | 0.122 | 0.141 | A | (SEQ ID NO: 0292)<br>ctagcacgttttattg[A/G]ccatcattcttttcat |
| 02 | exm337642 | 3 | q | q13.2 | CCDC80 | 112357336 | 2.19E-15 | 5.62 | 0.015 | 0.003 | A | (SEQ ID NO: 0293)<br>gggtcteggtggccat[A/G]tteccgcctgtccatg |
| 03 | rs16824243 | 3 | q | q13.31 | LSAMP | 115603783 | 5.66E-04 | 0.83 | 0.091 | 0.108 | G | (SEQ ID NO: 0294)<br>ttcaaaggtcaggcaa[A/G]ttgattttgaaaagaa |
| 03 | rs1731596 | 3 | q | q13.31 | LSAMP | 116131208 | 2.13E-04 | 1.15 | 0.218 | 0.195 | C | (SEQ ID NO: 0295)<br>ctgcatagtgagactg[A/C]atgtttttcaggagtt |
| 03 | rs9838534 | 3 | q | q13.31 | LSAMP | 116113609 | 2.48E-04 | 1.15 | 0.218 | 0.195 | A | (SEQ ID NO: 0296)<br>tgtggaagaaaaacac[A/G]tattagttcaataaat |
| 03 | rs6782605 | 3 | q | q13.31 | LSAMP | 116047619 | 1.55E-03 | 1.19 | 0.094 | 0.081 | A | (SEQ ID NO: 0297)<br>tgatgaatgataatta[A/G]cttttcctctagagca |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs1265646 | 3 | q | q21.2 | ITGB5 | 124592700 | 6.86E-06 | 0.90 | 0.368 | 0.394 | A | (SEQ ID NO: 0298) tacacttagtetatcc[A/G]aaatgacaaaaatagt |
| 02 | exm347865 | 3 | q | q21.3 | KBTBD12 | 127642561 | 1.95E-54 | 5.97 | 0.025 | 0.007 | C | (SEQ ID NO: 0299) ttgagcttttgaagca[A/C]gtcagattggaacttg |
| 03 | rs4683547 | 3 | q | q23 | SPSB4 | 140801587 | 7.54E-03 | 0.87 | 0.102 | 0.116 | A | (SEQ ID NO: 0300) aaactgaggctgtgaa[A/C]ggctgaaaggtttcag |
| 03 | rs12489920 | 3 | q | q26.1 | OTOL1 \| LOC730129 | 162391801 | 1.21E-03 | 1.12 | 0.284 | 0.262 | A | (SEQ ID NO: 0301) gaaccagagcataagc[A/G]gcattgttcatatggt |
| 02 | rs7643215 | 3 | q | q26.1 | ZBBX | 167023279 | 2.99E-05 | 0.85 | 0.221 | 0.249 | G | (SEQ ID NO: 0302) attaatgttctctccc[A/G]tatgagtcactcttca |
| 02 | rs9881097 | 3 | q | q26.31 | GHSR \| TNFSF10 | 172185376 | 5.44E-03 | 1.13 | 0.496 | 0.465 | A | (SEQ ID NO: 0303) aggatgaagcttaact[A/G]aggaaggtagaaccaa |
| 03 | rs7632772 | 3 | q | q26.32 | NAALADL2 \| TBL1XR1 | 176103902 | 7.34E-03 | 1.15 | 0.101 | 0.089 | G | (SEQ ID NO: 0304) caaaagcctgaggaag[A/G]gtgaaaagaacaaagc |
| 03 | rs1106387 | 3 | q | q26.32 | TBL1XR1 \| KCNMB2 | 177490268 | 7.34E-05 | 1.12 | 0.293 | 0.271 | A | (SEQ ID NO: 0305) ttggaagagaaaggaa[A/G]aaaattttatgtggct |
| 03 | rs1106388 | 3 | q | q26.32 | TBL1XR1 \| KCNMB2 | 177490311 | 8.87E-05 | 1.12 | 0.293 | 0.271 | G | (SEQ ID NO: 0306) cagcccagaaaatatt[A/G]aaaagataatgagcaa |
| 02 | rs6443448 | 3 | q | q26.32 | TBL1XR1 \| KCNMB2 | 177074926 | 2.16E-05 | 0.91 | 0.393 | 0.416 | G | (SEQ ID NO: 0307) aaagtaacatcaggga[A/G]gtctggaaataaaatg |
| 02 | exm372681 | 3 | q | q28 | CCDC50 | 191098660 | 1.05E-21 | 19.01 | 0.012 | 0.001 | G | (SEQ ID NO: 0308) gaaaagaaagcttaca[A/G]aaaagccaaggagcgg |
| 03 | rs890348 | 3 | q | q28 | LPP | 188241949 | 5.79E-05 | 1.08 | 0.168 | 0.158 | G | (SEQ ID NO: 0309) ggtcttgccatctctc[A/G]cacacatgcataccta |
| 02 | exm376611 | 3 | q | q29 | C3orf43 | 196236401 | 6.01E-31 | Inf | 0.012 | 0.000 | A | (SEQ ID NO: 0310) actcactggagtgccc[A/G]aactgctgtccacatc |
| 02 | rs6444670 | 3 | q | q29 | C3orf59 | 192599336 | 8.91E-06 | 0.86 | 0.360 | 0.394 | C | (SEQ ID NO: 0311) agaaaactgtactgac[A/C]gctacgaagtttgagc |
| 02 | rs6799698 | 3 | q | q29 | LRRC15 \| GP5 | 194105437 | 5.36E-03 | 1.21 | 0.126 | 0.106 | A | (SEQ ID NO: 0312) cccaagccaactcaac[A/G]cctgcagatggctctt |
| 03 | rs10021613 | 4 | p | p13 | APBB2 | 41201819 | 8.45E-04 | 1.17 | 0.135 | 0.118 | A | (SEQ ID NO: 0313) gcttcactgttcttcc[A/G]gtgtctagtggcaaac |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7683746 | 4 | p | p13 | APBB2 | 41203125 | 9.13E-04 | 1.17 | 0.136 | 0.119 | A | (SEQ ID NO: 0314) gacagttgccttatac[A/G]gagggctcattaaaca |
| 02 | rs1373475 | 4 | p | p14 | FLJ16686 \| KIAA1239 | 36931424 | 7.58E-05 | 1.18 | 0.171 | 0.148 | A | (SEQ ID NO: 0315) ggaagagtgaagaaga[A/G]gagaagatgcccaagc |
| 02 | rs1020808 | 4 | p | p14 | FLJ16686 \| KIAA1239 | 36949073 | 1.88E-05 | 1.20 | 0.177 | 0.153 | A | (SEQ ID NO: 0316) tagtgaccttataaga[A/G]gagatgtcagaaaatt |
| 03 | rs4832890 | 4 | p | p14 | KIAA1239 | 37264627 | 1.41E-02 | 0.92 | 0.360 | 0.379 | A | (SEQ ID NO: 0317) catcatgaagttcatg[A/G]agccgagaccaccagt |
| 03 | rs10001618 | 4 | p | p14 | KIAA1239 | 37340671 | 1.20E-02 | 1.28 | 0.027 | 0.021 | G | (SEQ ID NO: 0318) gaaatgatgtgtgact[A/G]aacaaagagacatgca |
| 02 | rs3796533 | 4 | p | p14 | KLF3 | 38692806 | 9.85E-06 | 1.20 | 0.181 | 0.155 | A | (SEQ ID NO: 0319) ggcaaagtgattacct[A/G]agacattagataactc |
| 01 | rs17582575 | 4 | p | p14 | KLF3 \| TLR10 | 38703734 | 2.66E-06 | 1.21 | 0.193 | 0.165 | A | (SEQ ID NO: 0320) cttcccacatgactta[A/C]tttcacaggttggaga |
| 02 | rs6838865 | 4 | p | p14 | KLF3 \| TLR10 | 38745883 | 2.27E-05 | 1.22 | 0.115 | 0.096 | A | (SEQ ID NO: 0321) agactccttacctcta[A/C]tgaaatcatcccaaac |
| 02 | rs12233656 | 4 | p | p14 | KLF3 \| TLR10 | 38737018 | 4.07E-05 | 1.22 | 0.096 | 0.080 | G | (SEQ ID NO: 0322) attgctccaataatag[A/G]cgtgtatttctcatgt |
| 03 | rs6849452 | 4 | p | p15.1 | PCDH7 \| ARAP2 | 31216675 | 1.12E-04 | 1.14 | 0.311 | 0.283 | A | (SEQ ID NO: 0323) tgcaatatttcctctc[A/G]ctccttatgtctactc |
| 03 | rs7659139 | 4 | p | p15.2 | KCNIP4 \| GPR125 | 22297899 | 2.66E-04 | 0.84 | 0.122 | 0.142 | G | (SEQ ID NO: 0324) taggcctcagcccccc[A/G]tttaaacagagggtaa |
| 03 | rs6448143 | 4 | p | p15.2 | KCNIP4 \| GPR125 | 22303196 | 8.02E-04 | 0.86 | 0.130 | 0.148 | G | (SEQ ID NO: 0325) cacactgttagagtgt[A/G]tttgagcatgtgggag |
| 02 | rs7697101 | 4 | p | p15.2 | KCNIP4 \| LOC100505912 | 22174771 | 5.99E-04 | 0.86 | 0.478 | 0.516 | C | (SEQ ID NO: 0326) tcctgcataggtgtcc[T/C]tcttaaaaaataattg |
| 02 | exm393187 | 4 | p | p15.2 | SEL1L3 | 25834624 | 9.17E-08 | 8.41 | 0.005 | 0.001 | A | (SEQ ID NO: 0327) gatatctcttttaacg[A/G]aggccaggtatctgta |
| 02 | rs11721812 | 4 | p | p15.2 | SLC34A2 \| KIAA0746 | 25730546 | 1.49E-05 | 1.23 | 0.121 | 0.101 | A | (SEQ ID NO: 0328) aaggtctccttggcca[A/G]taagagtctgttcagt |
| 03 | rs210777 | 4 | p | p15.2 | STIM2 \| PCDH7 | 27432523 | 1.44E-03 | 1.14 | 0.188 | 0.170 | A | (SEQ ID NO: 0329) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | agatttttatgtgcct[A/G]atgatagtctcaaaat |
| 03 | rs7693245 | 4 | p | p15.31 | LCORL \| SLIT2 | 18321896 | 2.13E-03 | 1.10 | 0.471 | 0.447 | G | (SEQ ID NO: 0330) ccccactacactcata[A/G]gcagctgatttgcaca |
| 03 | rs4140904 | 4 | p | p15.31 | LCORL \| SLIT2 | 18315992 | 2.96E-02 | 1.08 | 0.253 | 0.238 | G | (SEQ ID NO: 0331) tgaagatagaatggca[A/G]ataccctatcctatcc |
| 03 | rs3846386 | 4 | p | p15.33 | LOC391636 \| LOC441009 | 14102069 | 3.29E-03 | 1.11 | 0.269 | 0.248 | G | (SEQ ID NO: 0332) gattctatccgtctgc[A/G]accccccacccttgca |
| 03 | rs4689003 | 4 | p | p16.1 | PPP2R2C | 6428296 | 9.71E-05 | 1.14 | 0.182 | 0.163 | G | (SEQ ID NO: 0333) ggcaattgtggtcctt[A/G]tatttcagacacaagc |
| 02 | exm379901 | 4 | p | p16.3 | DGKQ | 961122 | 4.35E-11 | Inf | 0.004 | 0.000 | A | (SEQ ID NO: 0334) gcgggcccaccacatc[A/C]ccgaggaccctggcca |
| 02 | rs4865455 | 4 | p | p16.3 | FAM53A | 1653352 | 3.18E-03 | 1.15 | 0.355 | 0.324 | C | (SEQ ID NO: 0335) aaggcctgaggcagaa[C/T]aaccggggtcaagagg |
| 03 | rs12331507 | 4 | q | q12 | KDR \| SRD5A3 | 56011889 | 1.83E-04 | 0.88 | 0.304 | 0.332 | A | (SEQ ID NO: 0336) accatcagcctctcac[A/G]atttttgagtagttcc |
| 02 | rs12505096 | 4 | q | q12 | KDR \| SRD5A3 | 56006102 | 4.20E-05 | 0.87 | 0.269 | 0.298 | A | (SEQ ID NO: 0337) tggggctgaagaatac[A/C]tttctggtgtgactca |
| 02 | exm400714 | 4 | q | q12 | KIAA1211 | 57180701 | 5.39E-15 | 7.33 | 0.012 | 0.002 | G | (SEQ ID NO: 0338) caggctggaggagcgg[A/G]ggcggcaggaggagga |
| 02 | rs6554072 | 4 | q | q12 | SCFD2 | 54079547 | 2.04E-04 | 0.84 | 0.345 | 0.384 | G | (SEQ ID NO: 0339) aatgaatcaagtcaga[C/G]gcatttttttctactc |
| 02 | rs11724057 | 4 | q | q13.1 | LPHN3 | 62686490 | 7.24E-06 | 1.23 | 0.135 | 0.113 | A | (SEQ ID NO: 0340) ttgtaaataagtacat[A/G]agagttcttagcagga |
| 03 | rs7683391 | 4 | q | q13.1 | LPHN3 | 62676117 | 2.73E-04 | 1.17 | 0.154 | 0.134 | G | (SEQ ID NO: 0341) tctcatcctaaaatgt[A/G]gattctggaatataag |
| 03 | rs1901223 | 4 | q | q13.1 | LPHN3 | 62660731 | 3.78E-04 | 1.12 | 0.434 | 0.406 | A | (SEQ ID NO: 0342) taaaagcactttacat[A/G]aataattttatgtcag |
| 03 | rs65344473 | 4 | q | q13.3 | DKFZP564O0823 \| RCHY1 | 76005892 | 1.62E-04 | 0.78 | 0.062 | 0.078 | A | (SEQ ID NO: 0343) tgtcacttgttaatga[A/C]cttccaatcttctaag |
| 02 | exm407053 | 4 | q | q21.1 | ART3 | 76956246 | 6.81E-08 | 13.75 | 0.004 | 0.000 | G | (SEQ ID NO: 0344) aaagaaaataaaggac[A/G]acgatgcctaaatccc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs953534 | 4 | q | q21.22 | SCD5 | 83617849 | 1.47E-03 | 1.11 | 0.332 | 0.309 | A | (SEQ ID NO: 0345) cagctgggggagaaat[A/C]atccaaaatgcaatat |
| 03 | rs2869362 | 4 | q | q21.23 | ARHGAP24 | 86591202 | 8.95E-03 | 1.16 | 0.083 | 0.072 | A | (SEQ ID NO: 0346) atttttattcagttgg[A/G]atggggtggctgcaaa |
| 03 | rs1482090 | 4 | q | q21.23 | ARHGAP24 | 86523580 | 3.91E-03 | 1.18 | 0.086 | 0.074 | G | (SEQ ID NO: 0347) ttgtgctcaggcaagt[A/G]tgttgattggataaat |
| 03 | rs1161262 | 4 | q | q21.23 | ARHGAP24 | 86508815 | 6.41E-05 | 1.19 | 0.083 | 0.070 | G | (SEQ ID NO: 0348) tcatttattaaaacac[A/G]gcatgattagaccact |
| 03 | rs7697141 | 4 | q | q22.1 | KIAA1680 | 92457618 | 2.43E-04 | 1.26 | 0.067 | 0.054 | G | (SEQ ID NO: 0349) gtctctaccttttct[A/G]ccctgctttgctccct |
| 03 | rs6847228 | 4 | q | q22.1 | TIGD2 \|GPRIN3 | 90155694 | 2.76E-04 | 1.32 | 0.045 | 0.034 | A | (SEQ ID NO: 0350) agggagtggaaagaaa[A/G]agtgctgcaatttttt |
| 03 | rs17020045 | 4 | q | q22.2 | GRID2 | 93892487 | 2.03E-02 | 0.93 | 0.463 | 0.482 | G | (SEQ ID NO: 0351) tagtacagatttttat[A/G]ttgcaatcaaatccta |
| 03 | rs1354296 | 4 | q | q22.2 | GRID2 | 94075263 | 7.45E-03 | 1.09 | 0.457 | 0.436 | A | (SEQ ID NO: 0352) tgttaccaactgatta[A/G]ggtacaagttttagga |
| 03 | rs11727464 | 4 | q | q22.2 | GRID2 | 94324475 | 2.55E-04 | 0.89 | 0.399 | 0.427 | A | (SEQ ID NO: 0353) ccagaagtgaaactgt[A/G]ggaactgtgttcttaa |
| 02 | rs11097364 | 4 | q | q22.2 | GRID2 | 94367364 | 4.23E-05 | 0.89 | 0.453 | 0.482 | A | (SEQ ID NO: 0354) taggactcattcacat[A/G]gtgatccagggttcct |
| 03 | rs2174558 | 4 | q | q25 | ANK2 | 113927365 | 6.72E-03 | 1.15 | 0.106 | 0.094 | A | (SEQ ID NO: 0355) gttgtttgggctatcc[A/G]tcttctcaactgttta |
| 03 | rs378405 | 4 | q | q25 | DKK2 \| LOC100288317 | 108000247 | 1.62E-03 | 1.13 | 0.192 | 0.173 | A | (SEQ ID NO: 0356) atttagtatataataa[A/C]agtaacactacagcac |
| 03 | rs425273 | 4 | q | q25 | DKK2 \| LOC100288317 | 108016162 | 2.58E-03 | 1.13 | 0.199 | 0.180 | G | (SEQ ID NO: 0357) gggccccttccttgct[A/G]acctgcagtagcatgt |
| 03 | rs852269 | 4 | q | q25 | LEF1 \| LOC285456 | 109236454 | 1.95E-02 | 0.90 | 0.126 | 0.139 | G | (SEQ ID NO: 0358) caaagggaagtatacc[A/G]ctaaataaggaaggca |
| 03 | rs220634 | 4 | q | q25 | LEF1 \| LOC285456 | 109235238 | 1.88E-02 | 0.89 | 0.124 | 0.137 | A | (SEQ ID NO: 0359) cgtggctccaggactg[A/G]tctcagcctttgcata |
| 03 | rs1476569 | 4 | q | q26 | CAMK2D \| ARSJ | 114698696 | 3.28E-03 | 1.11 | 0.305 | 0.284 | G | (SEQ ID NO: 0360) tatctcagattcatga[A/G]atggtaacttctatgt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4629529 | 4 | q | q26 | NDST4 \| TRAM1L1 | 117572163 | 1.10E-03 | 0.88 | 0.221 | 0.243 | C | (SEQ ID NO: 0361) tctcaccaaggtcacc[A/C]gtgacttctagctgag |
| 02 | rs1503535 | 4 | q | q27 | LOC730456 \| MAD2L1 | 120898509 | 9.10E-05 | 1.13 | 0.396 | 0.367 | G | (SEQ ID NO: 0362) ctaaagagtactgtaa[A/G]gttaaagggatcatgt |
| 03 | rs7684836 | 4 | q | q27 | QRFPR \| ANXA5 | 122526728 | 3.27E-03 | 1.17 | 0.096 | 0.083 | A | (SEQ ID NO: 0363) acaatgacttaacaat[A/C]cctttcctttctgatt |
| 03 | rs10857108 | 4 | q | q28.1 | FAT4 \| LOC729424 | 126780071 | 2.20E-03 | 1.14 | 0.174 | 0.157 | A | (SEQ ID NO: 0364) taaccttgatcactgg[A/G]ctgaagtagtgtttgt |
| 03 | rs1911014 | 4 | q | q28.1 | FAT4 \| LOC729424 | 126774098 | 7.02E-03 | 1.12 | 0.172 | 0.157 | A | (SEQ ID NO: 0365) cttaagaaggatacac[A/G]aaatatgtatgtatat |
| 03 | rs958632 | 4 | q | q28.3 | PABPC4L \| LOC100289626 | 136572585 | 1.39E-03 | 1.18 | 0.109 | 0.094 | A | (SEQ ID NO: 0366) ccctggcaaccaaaga[A/G]ggagcttttacaccag |
| 02 | rs2035469 | 4 | q | q28.3 | PABPC4L \| LOC100289626 | 136288768 | 1.19E-03 | 1.16 | 0.433 | 0.398 | G | (SEQ ID NO: 0367) ctgccttctcagagtt[A/G]aacctgacataattta |
| 03 | rs13435856 | 4 | q | q31.1 | SLC7A11 \| CCRN4L | 139535299 | 3.61E-04 | 1.36 | 0.035 | 0.026 | A | (SEQ ID NO: 0368) gcaaatgagaataatc[A/G]ttttttgtcttttcca |
| 01 | rs4835378 | 4 | q | q31.22 | LOC100287219 \| EDNRA | 148040980 | 3.46E-06 | 1.20 | 0.216 | 0.188 | C | (SEQ ID NO: 0369) ggaatgaacttctaaa[A/C]tgctgtaatctcttga |
| 02 | rs3749574 | 4 | q | q31.3 | LRBA | 151207127 | 1.98E-05 | 0.86 | 0.277 | 0.307 | A | (SEQ ID NO: 0370) tgaggtcacatgtgct[A/G]cggtgtgtgcggagct |
| 03 | rs9995821 | 4 | q | q31.3 | SFRP2 \| DCHS2 | 154828366 | 4.02E-04 | 1.15 | 0.211 | 0.189 | G | (SEQ ID NO: 0371) tagtcaaattcattca[A/G]tgtggctcagatatga |
| 02 | rs11941518 | 4 | q | q32.1 | CTSO \| PDGFC | 156950378 | 6.42E-06 | 1.22 | 0.146 | 0.123 | G | (SEQ ID NO: 0372) atgtgaacattttttt[A/G]gacaagtttattgcta |
| 03 | rs6536518 | 4 | q | q32.1 | RAPGEF2 \| FSTL5 | 161308423 | 3.53E-04 | 1.12 | 0.463 | 0.435 | A | (SEQ ID NO: 0373) aacacagccaacatca[A/G]ttaagcctaatttaca |
| 02 | rs1898871 | 4 | q | q32.1 | RAPGEF2 \| FSTL5 | 161402299 | 2.83E-06 | 1.11 | 0.381 | 0.358 | A | (SEQ ID NO: 0374) ggaaaagtggaatgcc[A/G]agaacagaaactaaga |
| 02 | rs1371251 | 4 | q | q32.1 | RAPGEF2 \| FSTL5 | 161381482 | 1.70E-05 | 1.13 | 0.458 | 0.428 | A | (SEQ ID NO: 0375) ctctctagagtttact[A/G]tcatctggcattcatg |
| 02 | rs6827968 | 4 | q | q32.1 | RAPGEF2 \| | 161399652 | 1.96E-06 | 1.12 | 0.393 | 0.366 | A | (SEQ ID NO: 0376) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | FSTL5 | | | | | | | ctacatggaaaattga[A/C]gtagcaaggtaggtca |
| 02 | rs13151634 | 4 | q | q32.1 | RAPGEF2 \| FSTL5 | 161411394 | 2.21E-07 | 1.14 | 0.480 | 0.448 | A | (SEQ ID NO: 0377) agcctgtctcctctgg[A/G]agtcttatctctcagt |
| 02 | rs4690982 | 4 | q | q32.1 | RAPGEF2 \| FSTL5 | 161428827 | 2.06E-05 | 1.10 | 0.394 | 0.371 | A | (SEQ ID NO: 0378) ttccatatcctcgtcc[A/G]caattagtacgcacag |
| 02 | rs4690983 | 4 | q | q32.1 | RAPGEF2 \| FSTL5 | 161429238 | 1.58E-05 | 1.10 | 0.393 | 0.370 | A | (SEQ ID NO: 0379) catgtttactatctct[A/G]taggtttgcctttttg |
| 03 | rs1946867 | 4 | q | q32.1 | RAPGEF2 \| FSTL5 | 161307463 | 1.06E-04 | 0.88 | 0.446 | 0.476 | A | (SEQ ID NO: 0380) taccaaattgtatggt[A/G]tcagtgatggcagcag |
| 01 | rs4525928 | 4 | q | q32.1 | RAPGEF2 \| FSTL5 | 161421752 | 8.63E-08 | 1.15 | 0.489 | 0.454 | C | (SEQ ID NO: 0381) cagaactgaaataatt[A/C]tccataggatccttag |
| 03 | rs17039615 | 4 | q | q32.1 | RAPGEF2 \| FSTL5 | 161406478 | 8.21E-04 | 1.14 | 0.204 | 0.183 | A | (SEQ ID NO: 0382) ttttaatgaagcccct[A/G]taggctagttgtcaag |
| 03 | rs9996901 | 4 | q | q32.2 | FSTL5 | 162482595 | 7.20E-04 | 1.19 | 0.112 | 0.096 | A | (SEQ ID NO: 0383) catctcaaaccatgca[A/G]ttcctggaaatcacta |
| 03 | rs6536728 | 4 | q | q32.2 | NPY5R \| TKTL2 | 164333380 | 3.09E-03 | 1.14 | 0.155 | 0.139 | G | (SEQ ID NO: 0384) tgcaaggaaaccattt[A/G]ccagcctcctgcaatt |
| 03 | rs10024430 | 4 | q | q32.2 | NPY5R \| TKTL2 | 164295108 | 1.44E-03 | 1.33 | 0.033 | 0.025 | G | (SEQ ID NO: 0385) ctgaaaataagttccc[A/G]catatatattgtagaa |
| 02 | rs1534578 | 4 | q | q32.3 | ANP32C \| LOC100131276 | 165514302 | 2.48E-05 | 1.16 | 0.252 | 0.226 | G | (SEQ ID NO: 0386) tgatgctataattcct[A/G]gattttgtttgatttc |
| 03 | rs1459509 | 4 | q | q32.3 | CPE \| TLL1 | 166602111 | 1.15E-02 | 1.16 | 0.076 | 0.066 | A | (SEQ ID NO: 0387) ctagagaagatgaagg[A/G]atgtgcattccaggca |
| 03 | rs7695819 | 4 | q | q33 | AADAT \| LOC441052 | 171808256 | 5.63E-05 | 1.09 | 0.232 | 0.217 | A | (SEQ ID NO: 0388) tgctcaagagcagacc[A/G]gatgagccacacatgg |
| 02 | rs1432083 | 4 | q | q33 | AADAT \| LOC441052 | 171813412 | 1.91E-05 | 1.14 | 0.345 | 0.317 | G | (SEQ ID NO: 0389) agggatcaattcttac[A/G]ataaaattttaaaacc |
| 03 | rs2584393 | 4 | q | q34.3 | LOC100288304 \| LOC100288373 | 180591910 | 1.07E-03 | 1.15 | 0.176 | 0.157 | A | (SEQ ID NO: 0390) tgaaactgagtaaacc[A/G]ttaagaatgaattatt |
| 03 | rs6852438 | 4 | q | q34.3 | LOC100288304 \| LOC100288373 | 182061996 | 3.50E-04 | 1.14 | 0.242 | 0.219 | G | (SEQ ID NO: 0391) ctgcataagccctggc[A/G]tgctaccacagcccaa |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs6837023 | 4 | q | q34.3 | LOC100288304 \| LOC100288373 | 180330521 | 2.38E-04 | 1.23 | 0.088 | 0.073 | A | (SEQ ID NO: 0392) gtgtgtcccatgtggc[A/G]agagctcaaacaaggc |
| 03 | rs4861466 | 4 | q | q34.3 | LOC100288304 \| LOC100288373 | 182064722 | 2.53E-03 | 1.10 | 0.470 | 0.446 | G | (SEQ ID NO: 0393) atctaagttaaggtag[A/G]aatgatgaggtcaaaa |
| 03 | rs4400034 | 4 | q | q35.1 | C4orf41 | 184586738 | 6.03E-03 | 1.14 | 0.135 | 0.121 | A | (SEQ ID NO: 0394) acttcatggtgatcca[A/C]tgtctacctccagcaa |
| 03 | rs12108497 | 4 | q | q35.1 | CCDC111 | 185571557 | 6.43E-05 | 1.12 | 0.316 | 0.291 | A | (SEQ ID NO: 0395) gtgactataaaagatg[A/G]ggccttcggcagctcc |
| 03 | rs6850330 | 4 | q | q35.1 | CDKN2AIP \| ING2 | 184415303 | 2.55E-04 | 1.26 | 0.068 | 0.055 | C | (SEQ ID NO: 0396) atattaatacgtggct[A/C]agattaatgacagcaa |
| 02 | rs4861551 | 4 | q | q35.1 | CLDN24 \| LOC100131811 | 184362068 | 6.81E-05 | 1.15 | 0.280 | 0.253 | G | (SEQ ID NO: 0397) ggcaactcacagaaaa[A/G]gagagtttgaggatct |
| 03 | rs766908 | 4 | q | q35.1 | IRF2 \| CASP3 | 185468885 | 4.92E-03 | 1.15 | 0.120 | 0.107 | G | (SEQ ID NO: 0398) aaacaatgctgaggag[A/G]ctttatctttacagtt |
| 02 | rs11939575 | 4 | q | q35.2 | FAT1 | 187627792 | 3.04E-05 | 0.85 | 0.187 | 0.214 | A | (SEQ ID NO: 0399) tcatgatgaggacgcc[A/G]gaagagatggggagat |
| 02 | rs13123522 | 4 | q | q35.2 | FAT1 | 187627160 | 2.65E-05 | 0.85 | 0.188 | 0.215 | G | (SEQ ID NO: 0400) tggcatgctgaactga[A/G]aagacctggcttggaa |
| 03 | rs327080 | 4 | q | q35.2 | FAT1 | 187593959 | 4.71E-04 | 0.89 | 0.305 | 0.331 | G | (SEQ ID NO: 0401) tccctccaattgaagg[A/G]caggcagggactccaa |
| 03 | rs2279551 | 4 | q | q35.2 | TRIML2 | 189012809 | 4.98E-03 | 1.20 | 0.062 | 0.052 | A | (SEQ ID NO: 0402) tcttgctcacggggtc[A/G]gtgatggggaccgagt |
| 03 | rs6849766 | 4 | q | q35.2 | ZFP42 \| TRIML2 | 189010521 | 2.37E-02 | 1.10 | 0.174 | 0.161 | A | (SEQ ID NO: 0403) agtgtttcaaataatt[A/G]tctcacttccagctca |
| 01 | rs4611976 | 4 | q | q35.2 | ZFP42 \| TRIML2 | 188990955 | 1.78E-06 | 1.39 | 0.055 | 0.040 | C | (SEQ ID NO: 0404) acctggagagaggggc[A/C]cagctcagagctttcc |
| 03 | rs1895435 | 5 | p | p13.2 | GDNF \| EGFLAM | 37892952 | 8.57E-04 | 1.19 | 0.104 | 0.089 | C | (SEQ ID NO: 0405) catctgtggatatggc[A/C]gttttaccctcctggc |
| 03 | rs13362367 | 5 | p | p13.3 | LOC729862 \| LOC100130803 | 29329716 | 2.03E-03 | 0.89 | 0.207 | 0.227 | A | (SEQ ID NO: 0406) gttttgaccccttgga[A/G]acactcatgaacaacc |
| 03 | rs12109819 | 5 | p | p13.3 | PDZD2 | 32068026 | 4.13E-02 | 0.93 | 0.302 | 0.317 | A | (SEQ ID NO: 0407) tgtaccccatggtttt[A/G]gcatcattgactatta |

TABLE 1-continued

<table>
<tr><th colspan="13">TABLES<br>(Based on build 37 or "GRCh37" as defined by the Genome Reference Consortium)</th></tr>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>03</td><td>rs2303748</td><td>5</td><td>p</td><td>p14.3</td><td>CDH12</td><td>21760602</td><td>8.97E-04</td><td>1.13</td><td>0.279</td><td>0.256</td><td>C</td><td>(SEQ ID NO: 0408) aagaaaagtattgatt[A/C]ctccctttgtgccttt</td></tr>
<tr><td>03</td><td>rs6555477</td><td>5</td><td>p</td><td>p15.31</td><td>ADCY2</td><td>7587939</td><td>2.36E-04</td><td>1.13</td><td>0.316</td><td>0.290</td><td>A</td><td>(SEQ ID NO: 0409) aagaggatagggaaac[A/G]ttgagagaatcggttg</td></tr>
<tr><td>02</td><td>exm443730</td><td>5</td><td>p</td><td>p15.31</td><td>C5orf49</td><td>7831992</td><td>2.13E-08</td><td>8.93</td><td>0.006</td><td>0.001</td><td>A</td><td>(SEQ ID NO: 0410) atgtgcccaaagccgg[A/G]ttccttgaggctgggg</td></tr>
<tr><td>03</td><td>rs275447</td><td>5</td><td>p</td><td>p15.31</td><td>POLS | LOC442132</td><td>6825016</td><td>3.29E-03</td><td>1.13</td><td>0.182</td><td>0.164</td><td>A</td><td>(SEQ ID NO: 0411) ttttctgtgccttcac[A/G]tgtacttacacgcaca</td></tr>
<tr><td>03</td><td>rs13177725</td><td>5</td><td>p</td><td>p15.31</td><td>POLS | LOC442132</td><td>6795764</td><td>1.21E-02</td><td>0.90</td><td>0.194</td><td>0.210</td><td>G</td><td>(SEQ ID NO: 0412) gattagtgcacttaca[A/G]ggggatgaagagacca</td></tr>
<tr><td>03</td><td>rs275442</td><td>5</td><td>p</td><td>p15.31</td><td>POLS | LOC442132</td><td>6827513</td><td>7.70E-04</td><td>1.11</td><td>0.438</td><td>0.412</td><td>A</td><td>(SEQ ID NO: 0413) atgaataagctaactt[A/G]agccgaaatgttaaca</td></tr>
<tr><td>03</td><td>rs37006</td><td>5</td><td>p</td><td>p15.33</td><td>CLPTM1L | SLC6A3</td><td>1355058</td><td>2.05E-02</td><td>0.93</td><td>0.417</td><td>0.435</td><td>A</td><td>(SEQ ID NO: 0414) cactgcaacattttca[A/G]acttgaatctcacaga</td></tr>
<tr><td>03</td><td>rs6861105</td><td>5</td><td>p</td><td>p15.33</td><td>IRX4 | IRX2</td><td>1897640</td><td>4.38E-04</td><td>0.80</td><td>0.064</td><td>0.079</td><td>G</td><td>(SEQ ID NO: 0415) tgccagctgaggctcc[A/G]gcagacacaggtttgc</td></tr>
<tr><td>03</td><td>rs12188301</td><td>5</td><td>p</td><td>p15.33</td><td>NDUFS6 | IRX4</td><td>1847639</td><td>9.14E-05</td><td>0.83</td><td>0.108</td><td>0.127</td><td>A</td><td>(SEQ ID NO: 0416) agaaatgggatgtagc[A/G]tgagttgtgagttgtt</td></tr>
<tr><td>02</td><td>exm442113</td><td>5</td><td>p</td><td>p15.33</td><td>TERT</td><td>1293767</td><td>9.52E-14</td><td>7.19</td><td>0.011</td><td>0.002</td><td>A</td><td>(SEQ ID NO: 0417) gctcgcagcgggcagt[A/G]cgtcttgaggagcacc</td></tr>
<tr><td>03</td><td>rs7722066</td><td>5</td><td>q</td><td>q11.2</td><td>LOC257396 | FST</td><td>52417217</td><td>2.80E-04</td><td>0.89</td><td>0.386</td><td>0.415</td><td>A</td><td>(SEQ ID NO: 0418) catatgtttgtgtgag[A/C]agatattgtaagttt</td></tr>
<tr><td>03</td><td>rs10060367</td><td>5</td><td>q</td><td>q12.3</td><td>FLJ46010 | MAST4</td><td>65859130</td><td>3.38E-03</td><td>1.12</td><td>0.212</td><td>0.193</td><td>A</td><td>(SEQ ID NO: 0419) agagtcgagtagatga[A/G]gtgtgcttcaggtttt</td></tr>
<tr><td>03</td><td>rs10056426</td><td>5</td><td>q</td><td>q12.3</td><td>MAST4</td><td>66203615</td><td>8.76E-03</td><td>1.15</td><td>0.097</td><td>0.085</td><td>G</td><td>(SEQ ID NO: 0420) aaaatctcacaaatgc[A/G]attcaagtaagttgaa</td></tr>
<tr><td>03</td><td>rs26923</td><td>5</td><td>q</td><td>q12.3</td><td>MAST4</td><td>66170504</td><td>5.15E-03</td><td>1.16</td><td>0.098</td><td>0.086</td><td>C</td><td>(SEQ ID NO: 0421) tacagcagaccgaaac[A/C]atgtattttagaatta</td></tr>
<tr><td>03</td><td>rs734828</td><td>5</td><td>q</td><td>q12.3</td><td>MAST4</td><td>66221262</td><td>6.08E-03</td><td>1.16</td><td>0.101</td><td>0.088</td><td>G</td><td>(SEQ ID NO: 0422) aatcactctaaacaac[A/G]catttaataggttcca</td></tr>
<tr><td>02</td><td>rs12521058</td><td>5</td><td>q</td><td>q13.3</td><td>LOC728723</td><td>76426987</td><td>3.31E-05</td><td>1.14</td><td>0.416</td><td>0.384</td><td>A</td><td>(SEQ ID NO: 0423)</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7732628 | 5 | q | q13.3 | LOC728723 | 76435346 | 4.66E-04 | 0.89 | 0.413 | 0.440 | G | aataaacgagagacat[A/C]tggagaaaggagacct (SEQ ID NO: 0424) |
| 02 | rs2972341 | 5 | q | q13.3 | LOC728723 \| PDE8B | 76468843 | 1.15E-05 | 0.90 | 0.443 | 0.468 | A | atctgagaaaattctc[A/G]gtcactgtcacttcaa (SEQ ID NO: 0425) |
| 03 | rs6862414 | 5 | q | q13.3 | LOC728723 \| PDE8B | 76454559 | 9.74E-05 | 0.90 | 0.248 | 0.269 | G | cactgattagctgatg[A/G]gactctaccctatata (SEQ ID NO: 0426) |
| 03 | rs16875951 | 5 | q | q14.1 | ARSB | 78101191 | 2.19E-02 | 1.11 | 0.137 | 0.125 | A | ggacaggccacaccca[A/G]aggaaaacctggagtc (SEQ ID NO: 0427) |
| 02 | rs1129770 | 5 | q | q14.1 | CMYA5 | 79086883 | 2.40E-06 | 1.10 | 0.195 | 0.181 | A | gaacctaaactgttgt[A/G]attttataccaagtat (SEQ ID NO: 0428) |
| 03 | rs293045 | 5 | q | q15 | MCTP1 | 94289131 | 7.79E-04 | 1.33 | 0.037 | 0.028 | G | tttggtgagaggagac[A/G]gctgacggagtaagta (SEQ ID NO: 0429) |
| 03 | rs1990745 | 5 | q | q21.2 | NUDT12 \| RAB9P1 | 103381922 | 1.59E-03 | 1.15 | 0.150 | 0.133 | A | actttttgttgtttca[A/G]aagagtggttctcttg (SEQ ID NO: 0430) |
| 03 | rs10464035 | 5 | q | q21.3 | LOC100287833 \| EFNA5 | 106562841 | 2.35E-03 | 1.14 | 0.167 | 0.150 | A | cactttggtattaatc[A/G]ttgatcttgcagttag (SEQ ID NO: 0431) |
| 03 | rs10455070 | 5 | q | q21.3 | LOC100287833 \| EFNA5 | 106569691 | 8.74E-03 | 1.11 | 0.186 | 0.170 | A | gacactccttgagact[A/G]caaaccacatacctgg (SEQ ID NO: 0432) |
| 03 | rs4957696 | 5 | q | q21.3 | LOC100287833 \| EFNA5 | 106558682 | 2.53E-03 | 1.14 | 0.168 | 0.151 | C | aaacctaaaagatcaa[A/G]ttggctaaacacgtac (SEQ ID NO: 0433) |
| 03 | rs11749864 | 5 | q | q22.2 | MCC | 112612123 | 1.06E-02 | 1.19 | 0.058 | 0.049 | G | tccgggcatttcttgg[A/C]tatttctttaataatg (SEQ ID NO: 0434) |
| 03 | rs11740353 | 5 | q | q22.2 | MCC | 112577696 | 1.12E-02 | 1.19 | 0.057 | 0.049 | A | agaaactgagcagtgt[A/G]ttgtgcagaattggtg (SEQ ID NO: 0435) |
| 03 | rs1965429 | 5 | q | q22.2 | MCC | 112679373 | 1.09E-02 | 0.92 | 0.349 | 0.368 | C | cagcagaatagagaac[A/G]accaaatcaaacaaca (SEQ ID NO: 0436) |
| 03 | rs10519343 | 5 | q | q22.2 | MCC | 112592606 | 5.94E-03 | 1.20 | 0.058 | 0.049 | A | atggcctgtgacatag[A/C]tagcatttaataaaca (SEQ ID NO: 0437) |
| 03 | rs17333442 | 5 | q | q22.2 | YTHDC2 \| KCNN2 | 112947050 | 1.27E-02 | 0.88 | 0.101 | 0.113 | C | acccataaaccattct[A/G]agggccagattaaaac (SEQ ID NO: 0438) |
| | | | | | | | | | | | | aaatatgttatattta[A/C]tggcagttatctttct |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2112614 | 5 | q | q22.3 | CCDC112 \| FEM1C | 114812584 | 1.10E-03 | 1.16 | 0.135 | 0.118 | G | (SEQ ID NO: 0439) taaagtaaacgtactc[A/G]tcttagcttagacaca |
| 03 | rs9637896 | 5 | q | q22.3 | YTHDC2 \| KCNN2 | 113561408 | 9.39E-05 | 1.17 | 0.132 | 0.115 | G | (SEQ ID NO: 0440) agaaaatcaaattttt[A/G]taagacttaccaaaaa |
| 03 | rs2896965 | 5 | q | q23.1 | HSD17B4 \| FAM170A | 118921139 | 2.37E-03 | 0.87 | 0.136 | 0.153 | G | (SEQ ID NO: 0441) tagatggtaaccaggc[A/G]tgaagagacagctgac |
| 03 | rs37391 | 5 | q | q23.2 | CSNK1G3 \| ZNF608 | 123525965 | 2.95E-04 | 0.88 | 0.308 | 0.334 | G | (SEQ ID NO: 0442) agacaagcagcgcctc[A/G]tttatgtgatgtattt |
| 02 | rs7721313 | 5 | q | q31.1 | H2AFY | 134673961 | 3.90E-02 | 1.20 | 0.076 | 0.065 | C | (SEQ ID NO: 0443) ggttaagagctcagga[T/C]ttcccggagtcacaca |
| 03 | rs40273 | 5 | q | q31.1 | TCF7 | 133482348 | 3.98E-03 | 0.80 | 0.044 | 0.054 | G | (SEQ ID NO: 0444) atttcagaggctgcag[A/G]acttctgcctgaacct |
| 02 | rs165179 | 5 | q | q31.2 | UBE2D2 / UBE2D2 | 138985694 | 1.26E-05 | 1.29 | 0.074 | 0.058 | G | (SEQ ID NO: 0445) atgagactgaatcccc[A/G]gagacctacacttgaa |
| 02 | rs10476878 | 5 | q | q32 | POU4F3 \| TCERG1 | 145797485 | 4.95E-05 | 0.85 | 0.194 | 0.221 | G | (SEQ ID NO: 0446) caaacttatcacagta[A/G]tcacatttttaaggag |
| 03 | rs979893 | 5 | q | q32 | POU4F3 \| TCERG1 | 145797020 | 8.30E-04 | 0.87 | 0.179 | 0.200 | A | (SEQ ID NO: 0447) agtgtgttaagctttc[A/C]tgctcagaaatgacag |
| 03 | rs10056189 | 5 | q | q32 | POU4F3 \| TCERG1 | 145804118 | 4.51E-03 | 0.87 | 0.121 | 0.136 | A | (SEQ ID NO: 0448) ccagtaccaccattg[A/G]agctttacttgttttg |
| 02 | rs7718446 | 5 | q | q32 | POU4F3 \| TCERG1 | 145749535 | 4.40E-06 | 0.87 | 0.264 | 0.292 | G | (SEQ ID NO: 0449) tccaacacttagggta[A/G]gtaagtagctagttac |
| 02 | rs11747475 | 5 | q | q32 | POU4F3 \| TCERG1 | 145784922 | 5.98E-05 | 0.85 | 0.194 | 0.220 | G | (SEQ ID NO: 0450) cacgatgtcatgtgtt[A/G]attgagttgtatactt |
| 02 | rs6886412 | 5 | q | q32 | POU4F3 \| TCERG1 | 145777478 | 5.42E-06 | 0.86 | 0.262 | 0.291 | G | (SEQ ID NO: 0451) atgcttcaccgtctac[A/G]tcccctaattctaacc |
| 02 | exm494153 | 5 | q | q32 | PPARGC1B | 149213060 | 2.10E-16 | 20.56 | 0.008 | 0.000 | A | (SEQ ID NO: 0452) gagagctctgtgtgcc[A/C]cgtgcggcgttctcgg |
| 02 | exm497501 | 5 | q | q33.1 | FAT2 | 150946613 | 4.47E-11 | Inf | 0.004 | 0.000 | G | (SEQ ID NO: 0453) aaacgcccttttatca[A/G]tcttactgctggtcaa |
| 03 | rs1438937 | 5 | q | q33.1 | NMUR2 \| GRIA1 | 152370448 | 2.03E-04 | 0.89 | 0.412 | 0.441 | A | (SEQ ID NO: 0454) cccaagcaaatgatag[A/C]tattgccaattaaact |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs918509 | 5 | q | q33.2 | GALNT10 | 153762653 | 4.81E-04 | 0.88 | 0.225 | 0.249 | A | (SEQ ID NO: 0455) ccagtgactgccaacc[A/G]tggccacacataagca |
| 02 | rs954929 | 5 | q | q34 | LOC285629 \| GABRB2 | 160380401 | 2.37E-05 | 1.07 | 0.359 | 0.343 | A | (SEQ ID NO: 0456) ctctctatactacccc[A/G]tcagtgactcgcttta |
| 02 | rs7725726 | 5 | q | q35.1 | GABRP | 170215670 | 1.65E-05 | 1.24 | 0.090 | 0.074 | A | (SEQ ID NO: 0457) tgagtctcttcactga[A/G]aggtgagctttgctac |
| 03 | rs11134653 | 5 | q | q35.1 | GABRP | 170213757 | 6.23E-05 | 1.22 | 0.087 | 0.072 | A | (SEQ ID NO: 0458) cttacaactgtgccac[A/G]catatctagaatcctc |
| 02 | rs258878 | 5 | q | q35.2 | BOD1 | 173051169 | 1.51E-02 | 0.89 | 0.357 | 0.383 | A | (SEQ ID NO: 0459) accaccaggagaggtt[C/A]tctctcttcttggagc |
| 02 | exm505619 | 5 | q | q35.2 | EIF4E1B | 176072243 | 1.70E-12 | 50.73 | 0.005 | 0.000 | A | (SEQ ID NO: 0460) cctcctccaactcacc[A/G]tctccagccacagccg |
| 03 | rs11134853 | 5 | q | q35.2 | HMP19 \| LOC100127922 | 173970989 | 1.81E-04 | 1.18 | 0.163 | 0.142 | C | (SEQ ID NO: 0461) gtagtatgaacaaaag[A/C]gccctgggcttggagt |
| 01 | rs2770967 | 5 | q | q35.3 | LOC100289627 \| TRIM52 | 180678717 | 4.44E-06 | 1.28 | 0.094 | 0.075 | G | (SEQ ID NO: 0462) tgtgataaatttaatc[A/G]tagtctgtccaaacca |
| 03 | rs7727897 | 5 | q | q35.3 | LOC202181 | 177047009 | 8.02E-03 | 1.15 | 0.097 | 0.085 | G | (SEQ ID NO: 0463) cagagtcttcccccca[A/G]tctgactcttctccat |
| 03 | rs3940643 | 5 | q | q35.3 | RASGEF1C | 179585309 | 6.16E-04 | 1.13 | 0.302 | 0.277 | A | (SEQ ID NO: 0464) tttaaatacaggagac[A/Giggagcccaacacataa |
| 03 | rs4440459 | 6 | p | p12.1 | ELOVL5 \| GCLC | 53293410 | 8.62E-04 | 1.17 | 0.136 | 0.119 | A | (SEQ ID NO: 0465) tgagcctgacctccaa[A/C]acctcagcagcagcat |
| 02 | rs9370209 | 6 | p | p12.1 | ELOVL5 \| GCLC | 53296156 | 4.28E-05 | 1.21 | 0.142 | 0.121 | A | (SEQ ID NO: 0466) atgagggttttagaat[A/G]tatttgaatgctgaca |
| 03 | rs6458934 | 6 | p | p12.1 | ELOVL5 \| GCLC | 53291466 | 2.82E-04 | 1.18 | 0.136 | 0.117 | G | (SEQ ID NO: 0467) taactccaagttaaag[A/G]ctatactaccacatc |
| 03 | rs12192659 | 6 | p | p12.1 | FAM83B | 54726327 | 2.63E-04 | 1.12 | 0.485 | 0.456 | A | (SEQ ID NO: 0468) tgacactgctgacaga[A/G]gaagaccccacctcca |
| 03 | rs13200042 | 6 | p | p12.1 | FAM83B \| HCRTR2 | 55033223 | 2.49E-03 | 0.89 | 0.212 | 0.232 | G | (SEQ ID NO: 0469) tctactgtggaaacag[A/G]atagagtaacagcaaa |
| 03 | rs3134704 | 6 | p | p12.1 | HCRTR2 | 55072273 | 1.42E-02 | 0.91 | 0.219 | 0.236 | G | (SEQ ID NO: 0470) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | atgtgatttattttaa[A/G]cctcaccatttgaagt |
| 02 | exm555738 | 6 | p | p12.2 | GSTA5 | 52696737 | 1.81E-08 | Inf | 0.003 | 0.000 | A | (SEQ ID NO: 0471)<br>cagaaacttcttcacc[A/G]tgggcaggttgctgat |
| 03 | rs4712023 | 6 | p | p12.2 | LOC100287869 \| GSTA3 | 52758653 | 6.91E-05 | 1.15 | 0.072 | 0.064 | A | (SEQ ID NO: 0472)<br>taagttgttgaaccac[A/G]agcatgacagtcttta |
| 02 | rs9296695 | 6 | p | p12.2 | LOC100287869 \| GSTA3 | 52758076 | 4.34E-05 | 1.13 | 0.069 | 0.061 | A | (SEQ ID NO: 0473)<br>gaaaaccttgacaaac[A/G]gagctggaaaaccatg |
| 03 | rs2505276 | 6 | p | p12.3 | TFAP2B \| LOC646517 | 51087831 | 2.04E-04 | 0.89 | 0.430 | 0.459 | A | (SEQ ID NO: 0474)<br>cagaggatgccagttt[A/G]cttgaatgccaaaatt |
| 03 | rs9381940 | 6 | p | p12.3 | TFAP2B \| LOC646517 | 51073648 | 2.14E-03 | 0.91 | 0.383 | 0.406 | A | (SEQ ID NO: 0475)<br>tcattttgatcactct[A/G]tggcatttgacacttt |
| 02 | exm551051 | 6 | p | p21.1 | CAPN11 | 44143862 | 1.57E-14 | Inf | 0.005 | 0.000 | A | (SEQ ID NO: 0476)<br>gctggtgagagggcac[A/G]cttactctgtgactgg |
| 02 | rs9381299 | 6 | p | p21.1 | SLC29A1 \| HSP90AB1 | 44211867 | 4.19E-05 | 1.14 | 0.141 | 0.126 | G | (SEQ ID NO: 0477)<br>aaaggaacagagcccc[A/G]ttagaggaaccatagc |
| 03 | rs3187 | 6 | p | p21.1 | SLC35B2 | 44222047 | 6.79E-05 | 1.20 | 0.106 | 0.091 | A | (SEQ ID NO: 0478)<br>cattggagcctacacc[A/G]cttgtgcttttctcac |
| 02 | exm542389 | 6 | p | p21.31 | ETV7 | 36339143 | 2.60E-19 | 8.74 | 0.014 | 0.002 | A | (SEQ ID NO: 0479)<br>ggtctgttccttcccc[A/G]cgatgccgcaggcccc |
| 02 | rs2499724 | 6 | p | p21.31 | GRM4 | 34086671 | 1.08E-02 | 0.89 | 0.441 | 0.468 | C | (SEQ ID NO: 0480)<br>aatgaatacaactgta[A/C]aaactggaaccaaacc |
| 02 | rs2451330 | 6 | p | p21.31 | GRM4 \| HMGA1 | 34118586 | 8.40E-05 | 0.88 | 0.380 | 0.411 | G | (SEQ ID NO: 0481)<br>agttgagagaagccag[A/G]gtgaaattcctcctgc |
| 02 | rs914813 | 6 | p | p21.31 | GRM4 \| HMGA1 | 34103954 | 1.44E-05 | 0.87 | 0.358 | 0.392 | G | (SEQ ID NO: 0482)<br>tagggataaaaatacc[A/G]tgaagctcatagggat |
| 03 | rs2070600 | 6 | p | p21.32 | AGER | 32151443 | 1.63E-04 | 0.73 | 0.038 | 0.051 | A | (SEQ ID NO: 0483)<br>tcgtgtccttcccaac[A/G]gctccctcttccttcc |
| 02 | rs176248 | 6 | p | p21.32 | BRD2 \| HLA-DOA | 32965942 | 2.07E-05 | 0.85 | 0.244 | 0.275 | A | (SEQ ID NO: 0484)<br>agaagagagagagtaa[A/G]tgtattccaccaagaa |
| 03 | rs2076524 | 6 | p | p21.32 | BTNL2 | 32370684 | 6.48E-03 | 0.91 | 0.268 | 0.287 | G | (SEQ ID NO: 0485)<br>tcctgctgatctgagc[A/G]tgtgggtcctagaggc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2076525 | 6 | p | p21.32 | BTNL2 | 32370616 | 4.01E-03 | 0.90 | 0.267 | 0.287 | G | (SEQ ID NO: 0486) tttatcaagagacatt[A/G]tctatcatatagcaat |
| 03 | rs2395175 | 6 | p | p21.32 | BTNL2 ¦ HLA-DRA | 32405026 | 1.78E-03 | 0.87 | 0.150 | 0.168 | A | (SEQ ID NO: 0487) ctgcaacatcagcaga[A/G]gcttcctgtgggttcc |
| 03 | rs3763316 | 6 | p | p21.32 | BTNL2 ¦ HLA-DRA | 32376746 | 5.49E-03 | 0.91 | 0.267 | 0.287 | A | (SEQ ID NO: 0488) ctaaggggaggtgact[A/G]gtaagtttcaggtggc |
| 03 | rs2073045 | 6 | p | p21.32 | C6orf10 | 32339548 | 2.82E-03 | 0.91 | 0.350 | 0.373 | A | (SEQ ID NO: 0489) tcagagagagatcaag[A/G]taaaacgaaaaactca |
| 03 | rs2050188 | 6 | p | p21.32 | C6orf10 ¦ BTNL2 | 32339897 | 1.47E-03 | 1.11 | 0.365 | 0.341 | G | (SEQ ID NO: 0490) tacaaagattaatgat[A/G]tacaatctctggcctt |
| 03 | rs9268474 | 6 | p | p21.32 | C6orf10 ¦ BTNL2 | 32357165 | 4.56E-03 | 0.90 | 0.267 | 0.287 | G | (SEQ ID NO: 0491) tatttcttgatgaaat[A/G]tgtaagcctcccttta |
| 03 | rs9268461 | 6 | p | p21.32 | C6orf10 ¦ BTNL2 | 32351901 | 1.33E-02 | 0.92 | 0.268 | 0.286 | A | (SEQ ID NO: 0492) tttggtgccttcctac[A/C]gttatggaaggaagct |
| 03 | rs9268456 | 6 | p | p21.32 | C6orf10 ¦ BTNL2 | 32349946 | 6.07E-03 | 0.91 | 0.268 | 0.287 | A | (SEQ ID NO: 0493) cctatagtcaagtaag[A/C]ctgtaataataaatat |
| 03 | rs9268403 | 6 | p | p21.32 | C6orf10 ¦ BTNL2 | 32341473 | 6.93E-03 | 0.91 | 0.268 | 0.287 | G | (SEQ ID NO: 0494) gggagatctcttacac[A/G]tgatgtttctttcaga |
| 03 | rs9268425 | 6 | p | p21.32 | C6orf10 ¦ BTNL2 | 32344376 | 8.36E-03 | 0.91 | 0.268 | 0.287 | A | (SEQ ID NO: 0495) agaaatccacttagat[A/G]tctaccctacttcccc |
| 03 | rs9268428 | 6 | p | p21.32 | C6orf10 ¦ BTNL2 | 32344973 | 5.96E-03 | 0.91 | 0.268 | 0.287 | A | (SEQ ID NO: 0496) tttcttaacacagcag[A/C]aaaattgttttatgtc |
| 03 | rs2894252 | 6 | p | p21.32 | C6orf10 ¦ BTNL2 | 32345443 | 6.38E-03 | 0.91 | 0.268 | 0.287 | A | (SEQ ID NO: 0497) gtagattctaatctta[A/G]gccctttgccatagac |
| 03 | rs2395157 | 6 | p | p21.32 | C6orf10 ¦ BTNL2 | 32348145 | 6.94E-03 | 0.91 | 0.268 | 0.287 | G | (SEQ ID NO: 0498) agaaaataaaaactat[A/G]taatcttagatggcac |
| 03 | rs9268454 | 6 | p | p21.32 | C6orf10 ¦ BTNL2 | 32349711 | 6.03E-03 | 0.91 | 0.268 | 0.287 | G | (SEQ ID NO: 0499) ataacactgatgatat[A/G]gatttgaggtgagaga |
| 02 | rs1061807 | 6 | p | p21.32 | EGFL8 / AGPAT1 | 32136838 | 1.27E-05 | 1.18 | 0.264 | 0.234 | A | (SEQ ID NO: 0500) gggggtcaagagtgga[A/G]actgcaccgaggcaag |
| 02 | exm536563 | 6 | p | p21.32 | HLA-DQA2 | 32714067 | 3.35E-29 | Inf | 0.026 | 0.000 | A | (SEQ ID NO: 0501) agagactttggtctgc[A/G]ccctggggttgtctgt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm536439 | 6 | p | p21.32 | HLA-DQB1 | 32634282 | 2.16E-08 | 5.59 | 0.007 | 0.001 | G | (SEQ ID NO: 0502) ctgcacttaccgggag[A/G]gtctctgccctcagcc |
| 03 | rs1964995 | 6 | p | p21.32 | HLA-DRA \| HLA-DRB5 | 32449411 | 2.88E-03 | 0.91 | 0.417 | 0.440 | G | (SEQ ID NO: 0503) agaatcaaggaataag[A/G]aaaataatgtgagctg |
| 03 | rs9267833 | 6 | p | p21.32 | NOTCH4 | 32177900 | 8.69E-04 | 1.13 | 0.272 | 0.249 | G | (SEQ ID NO: 0504) catcttcttcaggaag[A/G]tgtccctaacttctcc |
| 02 | rs206015 | 6 | p | p21.32 | NOTCH4 | 32182759 | 6.17E-05 | 0.81 | 0.098 | 0.118 | A | (SEQ ID NO: 0505) ttcgccctgggattta[A/G]tgctcttctttctgct |
| 03 | rs2071277 | 6 | p | p21.32 | NOTCH4 | 32171683 | 3.77E-04 | 1.12 | 0.510 | 0.482 | G | (SEQ ID NO: 0506) tgatgcagtgtgtgac[A/G]tctaatctcccccata |
| 02 | rs206016 | 6 | p | p21.32 | NOTCH4 | 32181182 | 4.04E-05 | 0.81 | 0.096 | 0.116 | A | (SEQ ID NO: 0507) tatatgatattttatt[A/G]tttnagatagggtct |
| 03 | rs394657 | 6 | p | p21.32 | NOTCH4 | 32187023 | 7.27E-04 | 1.11 | 0.469 | 0.442 | G | (SEQ ID NO: 0508) ggagcattctgggttg[A/G]cctgagcaaaggctgc |
| 03 | rs3134799 | 6 | p | p21.32 | NOTCH4 | 32184221 | 6.64E-04 | 1.11 | 0.464 | 0.438 | A | (SEQ ID NO: 0509) tctgcttatctttcaa[A/G]actcatctcagccatc |
| 02 | rs2071286 | 6 | p | p21.32 | NOTCH4 | 32179896 | 6.41E-05 | 1.16 | 0.225 | 0.200 | A | (SEQ ID NO: 0510) tccagctacactcaac[A/G]catttcaccccacccc |
| 03 | rs9357138 | 6 | p | p21.32 | NOTCH4 \| C6orf10 | 32219838 | 2.54E-03 | 1.14 | 0.154 | 0.138 | A | (SEQ ID NO: 0511) tattaattgccccaga[A/G]atctatcctcacatcc |
| 02 | rs9267810 | 6 | p | p21.32 | PPT2 | 32121594 | 3.97E-06 | 1.18 | 0.269 | 0.237 | G | (SEQ ID NO: 0512) tctggctccgcagcag[A/G]acacgaagtttgcatt |
| 02 | rs2269424 | 6 | p | p21.32 | PPT2 \| EGFL8 | 32132233 | 9.13E-06 | 1.18 | 0.265 | 0.234 | A | (SEQ ID NO: 0513) ggagccctttgctggg[A/G]tggggatgagggtagt |
| 03 | rs35502919 | 6 | p | p21.33 | BAT2 | 31604355 | 1.15E-04 | 0.72 | 0.034 | 0.047 | A | (SEQ ID NO: 0514) ctggtggccaaagtgg[A/C]tttctcccttcagggg |
| 03 | rs3130977 | 6 | p | p21.33 | C6orf15 \| PSORS1C1 | 31081989 | 6.61E-04 | 0.89 | 0.310 | 0.335 | G | (SEQ ID NO: 0515) aagtctggaatcagca[A/G]aaatgtattacattga |
| 02 | exm-rs407283 | 6 | p | p21.33 | C6orf25 | 31692970 | 1.15E-13 | Inf | 0.017 | 0.003 | A | (SEQ ID NO: 0516) atagaaataagtgcta[A/G]actgggagttgggaga |
| 03 | rs3132550 | 6 | p | p21.33 | CDSN | 31086048 | 3.46E-04 | 0.87 | 0.212 | 0.236 | A | (SEQ ID NO: 0517) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2844456 | 6 | p | p21.33 | EHMT2 | 31864674 | 1.55E-04 | 0.73 | 0.035 | 0.048 | G | gtgagagcccaggctg[A/G]ggtcaggaatggaaac (SEQ ID NO: 0518) |
| 02 | rs9263582 | 6 | p | p21.33 | HCG22 \| C6orf15 | 31070664 | 4.06E-05 | 0.77 | 0.063 | 0.080 | A | gctaaaacgggcccca[A/G]ttggaccgtcaccttc (SEQ ID NO: 0519) |
| 01 | rs35718543 | 6 | p | p21.33 | HCG27 \| HLA-C | 31177845 | 1.38E-06 | 1.28 | 0.106 | 0.085 | A | cacttaaagcccaaag[A/G]tggccggctgtggtgg (SEQ ID NO: 0520) |
| 03 | rs2523457 | 6 | p | p21.33 | HLA-B \| MICA | 31365707 | 3.63E-03 | 0.90 | 0.292 | 0.313 | A | tgtggatcttcagcac[A/G]tctacaactccctcca (SEQ ID NO: 0521) |
| 02 | rs2853925 | 6 | p | p21.33 | HLA-C \| HLA-B | 31264922 | 1.63E-05 | 0.81 | 0.112 | 0.135 | G | acaaaccttcttggaa[A/G]gtggaaagttttgcaa (SEQ ID NO: 0522) |
| 02 | rs9264869 | 6 | p | p21.33 | HLA-C \| HLA-B | 31271630 | 1.33E-05 | 0.81 | 0.112 | 0.135 | G | acaaaagctaccagat[A/G]aaaacactcactatgg (SEQ ID NO: 0523) |
| 02 | rs7759127 | 6 | p | p21.33 | HLA-C \| HLA-B | 31240988 | 5.21E-06 | 0.80 | 0.110 | 0.133 | C | cctgagagatctgagt[A/G]atcaagacccagtgtt (SEQ ID NO: 0524) |
| 02 | rs2524043 | 6 | p | p21.33 | HLA-C \| HLA-B | 31257012 | 1.42E-05 | 0.81 | 0.112 | 0.135 | G | attcggtatttaatac[A/C]ttttgtgtgactgcct (SEQ ID NO: 0525) |
| 02 | rs2524132 | 6 | p | p21.33 | HLA-C \| HLA-B | 31264912 | 1.67E-05 | 0.81 | 0.112 | 0.135 | A | ctttcatttattgaac[A/G]ccttagatatgagcta (SEQ ID NO: 0526) |
| 02 | rs364415 | 6 | p | p21.33 | HLA-C \| HLA-B | 31273224 | 1.33E-05 | 0.81 | 0.112 | 0.135 | A | ttacagctcaacaaaa[A/G]ctaccagataaaaaca (SEQ ID NO: 0527) |
| 02 | rs3873385 | 6 | p | p21.33 | HLA-C \| HLA-B | 31269308 | 1.91E-05 | 0.84 | 0.137 | 0.159 | A | ggaggaagtgtggggt[A/G]tgggtagactcctcct (SEQ ID NO: 0528) |
| 02 | rs9264870 | 6 | p | p21.33 | HLA-C \| HLA-B | 31271662 | 1.51E-05 | 0.81 | 0.113 | 0.135 | A | gtgtgtgatgcagtat[A/G]gggtagaaccaggaga (SEQ ID NO: 0529) |
| 02 | rs2524160 | 6 | p | p21.33 | HLA-C \| HLA-B | 31259854 | 1.77E-05 | 0.81 | 0.113 | 0.135 | A | ttcacacatggaaaat[A/G]aggtggaaaaggagaa (SEQ ID NO: 0530) |
| 02 | rs2524048 | 6 | p | p21.33 | HLA-C \| HLA-B | 31256561 | 1.56E-05 | 0.81 | 0.112 | 0.135 | G | gtttgtgataaggagc[A/G]ttggggaggagatttg (SEQ ID NO: 0531) |
| 03 | rs2524050 | 6 | p | p21.33 | HLA-C \| HLA-B | 31255541 | 5.39E-05 | 0.82 | 0.109 | 0.130 | G | tttaaggaggctaact[A/G]cttccacattagatca (SEQ ID NO: 0532) |
| | | | | | | | | | | | | cttttttgtcttcccc[A/G]tgcattcgcccccaca |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs2524162 | 6 | p | p21.33 | HLA-C \| HLA-B | 31259750 | 4.11E-05 | 0.82 | 0.123 | 0.146 | A | (SEQ ID NO: 0533) gacccaacagtaagac[A/G]tttctccttttggtaa |
| 02 | rs2524115 | 6 | p | p21.33 | HLA-C \| HLA-B | 31265554 | 1.44E-05 | 0.81 | 0.112 | 0.135 | A | (SEQ ID NO: 0534) cgttgaagaatcagta[A/C]aatttggagactttga |
| 01 | rs2853930 | 6 | p | p21.33 | HLA-C \| HLA-B | 31255424 | 3.02E-06 | 0.79 | 0.106 | 0.131 | C | (SEQ ID NO: 0535) atcctgcaccttttcc[A/C]gtcaaatccccattcc |
| 03 | rs13220225 | 6 | p | p21.33 | IER3 \| DDR1 | 30747802 | 1.36E-04 | 1.17 | 0.187 | 0.165 | A | (SEQ ID NO: 0536) taagagaagactcacc[A/G]ttctgaggctgtctga |
| 02 | rs28780111 | 6 | p | p21.33 | IER3 \| DDR1 | 30720311 | 4.13E-05 | 1.18 | 0.188 | 0.164 | A | (SEQ ID NO: 0537) tccttcccagaaaacc[A/G]cctcagggctcacccc |
| 02 | rs2535323 | 6 | p | p21.33 | IER3 \| DDR1 | 30718180 | 3.71E-05 | 1.18 | 0.196 | 0.171 | G | (SEQ ID NO: 0538) gaactggaatgagaaa[A/G]taacctctaactgcta |
| 03 | rs10947091 | 6 | p | p21.33 | IER3 \| DDR1 | 30747216 | 1.51E-03 | 1.11 | 0.322 | 0.299 | A | (SEQ ID NO: 0539) agctcctactcagata[A/G]cagaactcacaaactt |
| 03 | rs986475 | 6 | p | p21.33 | LST1 / NCR3 | 31556709 | 8.74E-04 | 1.19 | 0.100 | 0.086 | G | (SEQ ID NO: 0540) ggtcaaatagtaattt[A/G]ttgggtgaatgacagt |
| 03 | rs6916921 | 6 | p | p21.33 | NFKBIL1 | 31520426 | 8.60E-04 | 1.19 | 0.104 | 0.088 | A | (SEQ ID NO: 0541) atttaccagatcaacc[A/G]ttctcaatgctcttta |
| 03 | rs9263699 | 6 | p | p21.33 | PSORS1C1 | 31093699 | 1.16E-03 | 1.14 | 0.211 | 0.191 | A | (SEQ ID NO: 0542) tggaagaatgtgtcca[A/G]gctgtgcttccccttt |
| 03 | rs3815087 | 6 | p | p21.33 | PSORS1C1 | 31093587 | 6.83E-04 | 1.14 | 0.213 | 0.192 | A | (SEQ ID NO: 0543) ccatcacccccggacc[A/G]tgggctccatgccagt |
| 03 | rs9263715 | 6 | p | p21.33 | PSORS1C1 | 31095801 | 6.12E-04 | 1.14 | 0.211 | 0.190 | A | (SEQ ID NO: 0544) tcctctcctgtagacc[A/G]ctggctcatgaaataa |
| 03 | rs9468877 | 6 | p | p21.33 | PSORS1C3 | 31142903 | 3.81E-04 | 1.16 | 0.160 | 0.141 | A | (SEQ ID NO: 0545) cagactgctggctctg[A/G]gcatctgagcagcgcc |
| 03 | rs9393228 | 6 | p | p22.3 | FLJ22536 | 22112043 | 1.16E-03 | 1.11 | 0.437 | 0.412 | A | (SEQ ID NO: 0546) agggttttcttgaatg[A/G]catttctcattgctaa |
| 03 | rs952578 | 6 | p | p22.3 | FLJ22536 | 21884519 | 1.16E-03 | 1.11 | 0.357 | 0.333 | A | (SEQ ID NO: 0547) agaatagacgtgttag[A/G]aaccaggttagcctgg |
| 03 | rs199091 | 6 | p | p22.3 | LOC389370 \| LOC100129616 | 23533562 | 1.76E-04 | 1.13 | 0.359 | 0.331 | G | (SEQ ID NO: 0548) tcttgggggtcttttg[A/G]gggaacagagaacaat |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 01 | rs6907340 | 6 | p | p22.3 | RNF144B \| ID4 | 19803768 | 3.67E-10 | 1.20 | 0.416 | 0.373 | A | (SEQ ID NO: 0549) ttgatgatggtgatat[A/G]gaatgattaataacca |
| 02 | rs7759616 | 6 | p | p22.3 | RNF144B \| ID4 | 19794585 | 1.70E-05 | 1.14 | 0.521 | 0.487 | A | (SEQ ID NO: 0550) tgatgggagagaaata[A/G]gaattcaacttgtagc |
| 02 | rs760794 | 6 | p | p22.3 | RNF144B \| ID4 | 19790560 | 1.84E-07 | 1.17 | 0.469 | 0.431 | A | (SEQ ID NO: 0551) tttttccctgaaactc[A/G]gccaaaagtttttcct |
| 01 | rs6904518 | 6 | p | p22.3 | RNF144B \| 1D4 | 19798704 | 7.31E-10 | 1.19 | 0.426 | 0.385 | G | (SEQ ID NO: 0552) gctatattaaaagaaa[A/G]tagacttcaaagcaaa |
| 02 | rs7766034 | 6 | p | p22.3 | RNF144B \| 1D4 | 19753061 | 5.48E-06 | 1.15 | 0.464 | 0.429 | A | (SEQ ID NO: 0553) aggggcctaagcccag[A/G]tgtcagaggcacagta |
| 02 | rs6916251 | 6 | p | p22.3 | RNF144B \| ID4 | 19761215 | 3.39E-07 | 1.16 | 0.465 | 0.428 | G | (SEQ ID NO: 0554) gtttccagccacctct[A/G]tttccattcccttaaa |
| 02 | rs6920825 | 6 | p | p22.3 | RNF144B \| ID4 | 19732492 | 6.00E-05 | 1.16 | 0.223 | 0.198 | G | (SEQ ID NO: 0555) gacgcagtctgtaggc[A/G]cttggcaagtgtttgc |
| 02 | rs6456259 | 6 | p | p22.3 | RNF144B \| ID4 | 19761718 | 5.65E-05 | 1.18 | 0.180 | 0.157 | G | (SEQ ID NO: 0556) tcccctgccactccct[A/G]tttaatgcctttgtaa |
| 01 | rs2206034 | 6 | p | p22.3 | RNF144B \| 1D4 | 19796863 | 2.22E-08 | 1.16 | 0.479 | 0.441 | A | (SEQ ID NO: 0557) gtgtgagggactcctc[A/G]taactcctgggcaagg |
| 02 | rs2223361 | 6 | p | p22.3 | RNF144B \| 1D4 | 19790809 | 1.76E-07 | 1.17 | 0.469 | 0.431 | A | (SEQ ID NO: 0558) gttgtcatgagttacc[A/G]tgattaaagtggtgga |
| 01 | rs6903595 | 6 | p | p22.3 | RNF144B \| ID4 | 19798141 | 9.39E-09 | 1.18 | 0.423 | 0.383 | A | (SEQ ID NO: 0559) tataatctttgtctca[A/G]tagtcaaatacttaga |
| 02 | rs7739264 | 6 | p | p22.3 | RNF144B \| 1D4 | 19785588 | 3.29E-05 | 0.90 | 0.451 | 0.477 | G | (SEQ ID NO: 0560) tccccatagctatcca[A/G]ttgagccagaaccatt |
| 03 | rs2842934 | 6 | p | p22.3 | TPMT | 18139214 | 2.14E-03 | 1.12 | 0.236 | 0.216 | G | (SEQ ID NO: 0561) tgcgatcacctggatt[A/G]atggcaactaatgctc |
| 03 | rs2842947 | 6 | p | p22.3 | TPMT | 18132822 | 1.62E-03 | 1.12 | 0.237 | 0.216 | G | (SEQ ID NO: 0562) tctggaggtggagtct[A/G]aggatactgctcttag |
| 03 | rs2842950 | 6 | p | p22.3 | TPMT | 18135178 | 3.62E-03 | 1.11 | 0.233 | 0.215 | A | (SEQ ID NO: 0563) agtctagccaggctcc[A/G]tagaaactggagtgcc |
| 02 | rs9462160 | 6 | p | p24.1 | LOC389369 \| | 11834883 | 1.60E-06 | 1.12 | 0.277 | 0.254 | G | (SEQ ID NO: 0564) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | HIVEP1 | | | | | | | gaattttggaattcag[A/G]tatcagaaaaaagctg |
| 03 | rs12193156 | 6 | p | p24.1 | PHACTR1 | 13203570 | 4.07E-03 | 0.90 | 0.264 | 0.285 | G | (SEQ ID NO: 0565) agttatgtaaacagga[A/G]gtgcagcatagtgtct |
| 03 | rs201051 | 6 | p | p25.1 | LY86 \| RREB1 | 6721713 | 1.50E-04 | 1.15 | 0.261 | 0.236 | A | (SEQ ID NO: 0566) ttctttcatccttatg[A/G]cctttcttgtataggt |
| 02 | rs11242762 | 6 | p | p25.2 | LOC100128372 \| C6orf195 | 2379182 | 2.87E-05 | 0.88 | 0.446 | 0.477 | G | (SEQ ID NO: 0567) atatatcattttattt[A/G]atttcccagtcacctt |
| 03 | rs9503159 | 6 | p | p25.2 | LOC100128372 \| C6orf195 | 2371304 | 7.88E-05 | 0.88 | 0.445 | 0.476 | G | (SEQ ID NO: 0568) cgtacccatgtgtcac[A/G]agtacacatgcttttc |
| 03 | rs4959652 | 6 | p | p25.2 | LOC100128372 \| C6orf195 | 2386913 | 8.38E-05 | 1.10 | 0.420 | 0.397 | A | (SEQ ID NO: 0569) aatcatttttcaaaa[A/G]tgtagtcttttgtgag |
| 03 | rs1715026 | 6 | q | q11.1 | KHDRBS2 | 62515691 | 2.76E-02 | 1.08 | 0.287 | 0.271 | G | (SEQ ID NO: 0570) aggaggtgattagatc[A/G]tagaggttgttcccac |
| 03 | rs6929584 | 6 | q | q13 | BAI3 \| LMBRD1 | 70382870 | 8.84E-04 | 0.83 | 0.084 | 0.099 | G | (SEQ ID NO: 0571) ctttgaagtccttctg[A/G]aaaatacctaaattag |
| 03 | rs1114785 | 6 | q | q13 | BAI3 \| LMBRD1 | 70367148 | 4.75E-03 | 0.89 | 0.180 | 0.198 | A | (SEQ ID NO: 0572) aacccactccactaag[A/G]ccttcagtctgtgctc |
| 02 | exm563585 | 6 | q | q14.2 | SNAP91 | 84303230 | 3.86E-09 | 4.18 | 0.011 | 0.003 | G | (SEQ ID NO: 0573) ctccgctgccaccgcc[A/G]ccactgctcctcctgc |
| 02 | rs9359587 | 6 | q | q14.3 | KIAA1009 \| TBX18 | 85105960 | 4.29E-05 | 1.15 | 0.232 | 0.208 | G | (SEQ ID NO: 0574) tttgccatactaattt[A/G]gtaactttagctaggt |
| 03 | rs9294298 | 6 | q | q14.3 | KIAA1009 \| TBX18 | 85147411 | 8.77E-03 | 0.92 | 0.385 | 0.405 | A | (SEQ ID NO: 0575) gcctctagtcactaag[A/G]aaagtctaagtatctt |
| 03 | rs4053608 | 6 | q | q15 | BACH2 | 90787599 | 2.00E-03 | 1.11 | 0.290 | 0.268 | A | (SEQ ID NO: 0576) ttcaggattagatgct[A/G]agacttcaaatcagtc |
| 03 | rs9342219 | 6 | q | q15 | BACH2 | 90756453 | 6.39E-03 | 1.10 | 0.305 | 0.285 | A | (SEQ ID NO: 0577) acttgtttacaaaagc[A/G]tctctataggtctgtg |
| 03 | rs453561 | 6 | q | q15 | GABRR1 | 89904872 | 1.78E-03 | 1.11 | 0.404 | 0.380 | A | (SEQ ID NO: 0578) aagataaataagacaa[A/G]taacacattaaaaagc |
| 03 | rs6908196 | 6 | q | q16.2 | PRDM13 \| MCHR2 | 100185261 | 6.25E-04 | 0.90 | 0.400 | 0.427 | C | (SEQ ID NO: 0579) atgggcaaacttctct[A/C]atgctaacagtgatga |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2198337 | 6 | q | q16.3 | FLJ10088 \| HACE1 | 104756256 | 1.56E-03 | 1.16 | 0.139 | 0.123 | A | (SEQ ID NO: 0580) ctgtcttcattcctcc[A/G]gctactatccctaccc |
| 03 | rs9386412 | 6 | q | q16.3 | FLJ10088 \| HACE1 | 104760556 | 7.99E-04 | 1.17 | 0.139 | 0.122 | A | (SEQ ID NO: 0581) tactgccaaacctcca[A/C]tcaaaatagctagggc |
| 03 | rs6918769 | 6 | q | q16.3 | FLJ10088 \| HACE1 | 104952471 | 2.49E-03 | 1.17 | 0.100 | 0.087 | A | (SEQ ID NO: 0582) ctgtctgctaggagta[A/G]catcaggaagtgtctg |
| 03 | rs404900 | 6 | q | q16.3 | FLJ10088 \| HACE1 | 104765922 | 7.45E-04 | 1.16 | 0.145 | 0.127 | C | (SEQ ID NO: 0583) accctagatctttctc[A/C]ttctcttcatacacat |
| 02 | rs2852525 | 6 | q | q16.3 | GRIK2 | 101875714 | 1.52E-05 | 0.88 | 0.433 | 0.466 | C | (SEQ ID NO: 0584) attgctagcatttatt[A/C]agtgaatgaataaatg |
| 03 | rs7759938 | 6 | q | q16.3 | HACE1 \| LOC100129852 | 105378954 | 8.66E-05 | 0.91 | 0.302 | 0.323 | G | (SEQ ID NO: 0585) agcctcaaaggtagca[A/G]cctttagaaagaaaaa |
| 03 | rs314286 | 6 | q | q16.3 | LIN28B | 105436053 | 3.63E-04 | 0.89 | 0.309 | 0.335 | G | (SEQ ID NO: 0586) aaaaactctgtagcta[A/G]tatcatgcttaatgat |
| 03 | rs369065 | 6 | q | q16.3 | LIN28B | 105444058 | 6.34E-04 | 0.89 | 0.314 | 0.339 | G | (SEQ ID NO: 0587) tttctgatggcatcca[A/G]tccagagcaaatccct |
| 03 | rs314272 | 6 | q | q16.3 | LIN28B | 105462004 | 7.45E-04 | 0.90 | 0.417 | 0.443 | G | (SEQ ID NO: 0588) tagtttgaaaccctat[A/G]atgttctttgaaacct |
| 03 | rs453530 | 6 | q | q16.3 | LOC100287035 \| SIM1 | 100829135 | 1.39E-03 | 1.34 | 0.031 | 0.024 | A | (SEQ ID NO: 0589) agagcatcctaaatcc[A/G]actcttaggggaagac |
| 03 | rs7769704 | 6 | q | q22.31 | PKIB | 122998592 | 8.72E-03 | 0.92 | 0.321 | 0.340 | G | (SEQ ID NO: 0590) ctgtgctgcttaccat[A/G]tatggatgaggggttg |
| 02 | rs7774820 | 6 | q | q22.31 | TRDN | 123955723 | 2.22E-05 | 1.16 | 0.051 | 0.045 | G | (SEQ ID NO: 0591) aaaagactggaggaag[A/G]caattgtagctagggc |
| 03 | rs3757169 | 6 | q | q23.3 | MAP3K5 \| PEX7 | 137142946 | 1.24E-03 | 1.11 | 0.434 | 0.409 | G | (SEQ ID NO: 0592) ggtatatggttaagat[A/G]atcatacgacttggtt |
| 03 | rs899894 | 6 | q | q23.3 | PDE7B | 136392020 | 1.13E-03 | 1.11 | 0.409 | 0.385 | G | (SEQ ID NO: 0593) tcaattgttcatttgg[A/G]caagagtttgggtttg |
| 03 | rs1013020 | 6 | q | q23.3 | PDE7B | 136394895 | 1.00E-03 | 1.11 | 0.412 | 0.387 | A | (SEQ ID NO: 0594) tccagatttttactat[A/G]tgtggctgtaaaaatg |
| 03 | rs844562 | 6 | q | q24.3 | SAMD5 \| SASH1 | 147908995 | 9.13E-05 | 1.11 | 0.438 | 0.413 | A | (SEQ ID NO: 0595) taaacttagacatgaa[A/G]tagagaaaggaggtta |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2294806 | 6 | q | q24.3 | SAMD5 \| SASH1 | 148183190 | 1.94E-04 | 1.13 | 0.381 | 0.353 | G | (SEQ ID NO: 0596) ataaaggaaggtaaaa[A/G]ctcagaaggccaaagg |
| 03 | rs6924763 | 6 | q | q24.3 | STXBP5 | 147685480 | 3.09E-03 | 1.13 | 0.173 | 0.156 | A | (SEQ ID NO: 0597) catgattaaaagtatc[A/G]tcttcagacatctgct |
| 03 | rs12201953 | 6 | q | q25.1 | UST \| MAP3K7IP2 | 149546620 | 4.05E-03 | 1.30 | 0.032 | 0.025 | A | (SEQ ID NO: 0598) gcctggtattccatgg[A/G]tcatgtcaaaaaacct |
| 03 | rs1544041 | 6 | q | q25.3 | ARID1B | 157408118 | 1.80E-04 | 0.86 | 0.169 | 0.193 | G | (SEQ ID NO: 0599) acactttaaataacgt[A/G]tccaagaaagtggaaa |
| 02 | rs240863 | 6 | q | q25.3 | FNDC1 \| SOD2 | 159915825 | 1.87E-05 | 1.21 | 0.149 | 0.127 | A | (SEQ ID NO: 0600) tggtcattcgaccttc[A/G]ccccataaatagtggt |
| 03 | rs2201886 | 6 | q | q25.3 | NOX3 \| ARID1B | 155999177 | 1.87E-04 | 0.89 | 0.378 | 0.407 | A | (SEQ ID NO: 0601) ggccaatctaacacaa[A/G]catgactagtgggttc |
| 03 | rs7739122 | 6 | q | q25.3 | NOX3 \| ARID1B | 155998741 | 7.46E-05 | 1.10 | 0.319 | 0.298 | G | (SEQ ID NO: 0602) tatggtctgctgagtc[A/G]ataatctatgttttta |
| 03 | rs6913088 | 6 | q | q25.3 | NOX3 \| ARID1B | 155970936 | 3.43E-03 | 1.10 | 0.512 | 0.488 | G | (SEQ ID NO: 0603) ctgtgtataattcaaa[A/G]catctcctttttttgtt |
| 02 | rs9397831 | 6 | q | q25.3 | NOX3 \| ARID1B | 155994436 | 3.48E-06 | 1.12 | 0.419 | 0.393 | G | (SEQ ID NO: 0604) aacaatcacaattttc[A/G]ttgatttatctcccca |
| 03 | rs16892910 | 6 | q | q26 | PARK2 | 162096342 | 1.20E-02 | 1.11 | 0.169 | 0.155 | A | (SEQ ID NO: 0605) gataccttatgtgacc[A/G]tagttagtcggtgatc |
| 02 | rs4710698 | 6 | q | q27 | C6orf208 \| LOC154449 | 170439874 | 2.24E-05 | 1.12 | 0.414 | 0.386 | A | (SEQ ID NO: 0606) ttaaatatctaaatgt[A/G]taaaacagacctgatc |
| 02 | rs4710879 | 6 | q | q27 | C6orf208 \| LOC154449 | 170426027 | 4.60E-05 | 1.12 | 0.415 | 0.389 | G | (SEQ ID NO: 0607) cgacaaggctgggatc[A/G]gtgctctccttccagc |
| 03 | rs4710811 | 6 | q | q27 | C6orf208 \| LOC154449 | 170369459 | 1.02E-04 | 1.17 | 0.182 | 0.160 | A | (SEQ ID NO: 0608) caattcattctgtgcc[A/G]actcacccctggggtc |
| 03 | rs698626 | 7 | p | p11.2 | LOC389493 \| LOC441228 | 56282855 | 1.27E-02 | 0.92 | 0.454 | 0.474 | A | (SEQ ID NO: 0609) gtctagcaatccttgt[A/G]tatgctttaatcacag |
| 03 | rs9690458 | 7 | p | p12.1 | DKFZp564N2472 \| FLJ45974 | 53360479 | 1.32E-03 | 1.20 | 0.082 | 0.070 | G | (SEQ ID NO: 0610) caggtttagtttgaga[A/G]ccagcaaactgaaaag |
| 02 | rs4326334 | 7 | p | p12.1 | LOC100131871 \| | 52996013 | 1.19E-05 | 0.87 | 0.411 | 0.445 | G | (SEQ ID NO: 0611) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | DKFZp564N2472 | | | | | | | ggaagtcaattaaaaa[A/G]tctaaatataaatttg |
| 02 | rs1358603 | 7 | p | p12.1 | LOC100131871 \| DKFZp564N2472 | 52757480 | 5.71E-05 | 1.14 | 0.501 | 0.469 | A | (SEQ ID NO: 0612) gaatttaaaaatatca[A/G]tacaagaaagtcatta |
| 03 | rs6967460 | 7 | p | p12.1 | LOC100131871 \| DKFZp564N2472 | 52950472 | 3.33E-04 | 1.25 | 0.068 | 0.055 | G | (SEQ ID NO: 0613) ttagcatgagccacag[A/G]aaaggtttttgagcca |
| 01 | exm2264261 | 7 | p | p12.3 | TNS3 \| C7orf65 | 47641920 | 4.47E-11 | Inf | 0.011 | 0.001 | C | (SEQ ID NO: 0614) agtttctgtgttttaa[A/C]ggaatagcctgctgtg |
| 03 | rs1434960 | 7 | p | p13 | DDX56 | 44612992 | 3.58E-04 | 1.38 | 0.032 | 0.023 | G | (SEQ ID NO: 0615) gtccggccctgctacc[A/G]ccaacctttgcgtaat |
| 03 | rs11535191 | 7 | p | p14.1 | ELMO1 \| GPR141 | 37747276 | 1.18E-03 | 0.87 | 0.171 | 0.191 | G | (SEQ ID NO: 0616) aagtaaattgcccaag[A/G]tggcccagctagtaaa |
| 03 | rs1364729 | 7 | p | p14.1 | ELMO1 \| GPR141 | 37618173 | 1.26E-03 | 0.87 | 0.163 | 0.182 | G | (SEQ ID NO: 0617) tgtctgtctctaaatc[A/G]tgtgctgttaaaaaat |
| 03 | rs3801216 | 7 | p | p14.1 | GLI3 | 42233283 | 1.54E-04 | 1.13 | 0.403 | 0.374 | A | (SEQ ID NO: 0618) gctccttttttaactca[A/G]tattacctgtggtttt |
| 03 | rs2392465 | 7 | p | p14.2 | AOAH \| ELMO1 | 36800555 | 4.78E-03 | 0.92 | 0.446 | 0.468 | A | (SEQ ID NO: 0619) tggggggtccatgtgg[A/G]aaagactgtgagtggc |
| 03 | rs10488088 | 7 | p | p14.3 | C7orf41 | 30182813 | 5.48E-04 | 0.85 | 0.117 | 0.135 | G | (SEQ ID NO: 0620) tgttttatctgtggac[A/G]ctacctcgtgagattg |
| 02 | rs2270221 | 7 | p | p14.3 | PDE1C | 31904027 | 5.19E-07 | 1.20 | 0.302 | 0.266 | A | (SEQ ID NO: 0621) ttccttgcttcttttg[A/G]cccaacattttagcgc |
| 03 | rs38523 | 7 | p | p15.1 | JAZF1 \| LOC100128081 | 28039797 | 1.38E-02 | 0.92 | 0.350 | 0.368 | G | (SEQ ID NO: 0622) ttctgaagtatctcta[A/G]aaagtgtctctataaa |
| 03 | rs6949451 | 7 | p | p15.2 | HOXA10 | 27215041 | 1.84E-04 | 1.12 | 0.493 | 0.464 | A | (SEQ ID NO: 0623) gactgccctagctgag[A/G]gtatgggagggagggg |
| 02 | rs11773804 | 7 | p | p15.2 | LOC100289444 | 27206688 | 1.84E-05 | 1.15 | 0.444 | 0.411 | C | (SEQ ID NO: 0624) tgattacccctgttct[A/C]ggagtcgctgctttct |
| 03 | rs7795246 | 7 | p | p15.3 | CDCA7L \| RAPGEFS | 22047162 | 7.08E-03 | 1.09 | 0.489 | 0.468 | A | (SEQ ID NO: 0625) gaattgactactgcaa[A/C]tgtgcatgattttatc |
| 03 | rs2285942 | 7 | p | p15.3 | DNAH11 | 21582917 | 6.99E-02 | 0.92 | 0.134 | 0.144 | A | (SEQ ID NO: 0626) ccgaggttaggcgaag[A/G]gtcggggcttctctga |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs12534005 | 7 | p | p15.3 | IGF2BP3 | 23502518 | 6.44E-04 | 0.85 | 0.122 | 0.141 | G | (SEQ ID NO: 0627) gatggcaagcatacat[A/G]gttttgagtgttccat |
| 02 | rs11772760 | 7 | p | p15.3 | RAPGEF5 | 22246644 | 1.88E-05 | 1.15 | 0.357 | 0.326 | G | (SEQ ID NO: 0628) gtagttgaatatttgc[A/G]acttatatcaacctat |
| 02 | rs6461639 | 7 | p | p15.3 | RAPGEFS | 22186955 | 2.47E-05 | 1.12 | 0.382 | 0.356 | A | (SEQ ID NO: 0629) tgatttcggggctttc[A/G]ctttcattatgctgtc |
| 03 | rs2723512 | 7 | p | p21.1 | AHR \| SNX13 | 17815402 | 7.51E-05 | 1.19 | 0.133 | 0.114 | A | (SEQ ID NO: 0630) tgagtcaacatgaagt[A/G]agggaaatgaaaaggg |
| 03 | rs697521 | 7 | p | p21.1 | BZW2 \| TSPAN13 | 16764156 | 7.81E-04 | 1.18 | 0.116 | 0.100 | A | (SEQ ID NO: 0631) ctactgcttacttctg[A/C]ctccatgtagaataaa |
| 03 | rs17437739 | 7 | p | p21.1 | FERD3L \| TWISTNB | 19437424 | 1.41E-03 | 1.11 | 0.457 | 0.432 | A | (SEQ ID NO: 0632) aaaggagcattcacac[A/C]gcttctcttgtcatga |
| 03 | rs4286843 | 7 | p | p21.1 | FERD3L \| TWISTNB | 19463247 | 9.35E-03 | 1.09 | 0.484 | 0.464 | A | (SEQ ID NO: 0633) ggcagaacttttattg[A/G]ctaggagtttcttttt |
| 03 | rs9648255 | 7 | p | p21.1 | FERD3L \| TWISTNB | 19450683 | 1.38E-02 | 0.93 | 0.465 | 0.484 | G | (SEQ ID NO: 0634) gtgagcacatgcctct[A/G]taagtgattttaaaat |
| 03 | rs6461452 | 7 | p | p21.1 | FERD3L \| TWISTNB | 19691229 | 7.69E-05 | 1.11 | 0.316 | 0.294 | A | (SEQ ID NO: 0635) aagagccagggttgac[A/G]gctctcagagagaaga |
| 03 | rs17140423 | 7 | p | p21.1 | HDAC9 | 19007884 | 2.44E-04 | 1.13 | 0.314 | 0.288 | G | (SEQ ID NO: 0636) gaatgtttgaacatct[A/G]tagtaatattgaacca |
| 03 | rs6955426 | 7 | p | p21.2 | DGKB | 14310702 | 1.05E-02 | 1.12 | 0.138 | 0.124 | A | (SEQ ID NO: 0637) ttctacagaaatacaa[A/G]ctgtcttatgagtaaa |
| 03 | rs17614094 | 7 | p | p21.3 | PHF14 \| THSD7A | 11328154 | 2.72E-04 | 1.19 | 0.133 | 0.115 | A | (SEQ ID NO: 0638) agaagtaaaacagttc[A/G]tataaaagtgaatttt |
| 03 | rs10261632 | 7 | p | p21.3 | PHF14 \| THSD7A | 11383722 | 1.79E-04 | 1.13 | 0.402 | 0.373 | A | (SEQ ID NO: 0639) gaaaggaggaatttct[A/G]tttcaagcgacaccgt |
| 02 | rs2895215 | 7 | p | p22.3 | ELFN1 \| MAD1L1 | 1837636 | 2.11E-05 | 1.16 | 0.251 | 0.224 | A | (SEQ ID NO: 0640) ttagtatattgtatcc[A/G]gtgaatttcgctaaat |
| 03 | rs160646 | 7 | q | q11.21 | ASL | 65556280 | 1.98E-04 | 1.19 | 0.126 | 0.107 | A | (SEQ ID NO: 0641) ctgggattacaagcat[A/G]agccaccaggcctagc |
| 03 | rs419603 | 7 | q | q11.21 | CRCP | 65597341 | 2.04E-04 | 1.19 | 0.126 | 0.108 | A | (SEQ ID NO: 0642) actttggaagtgtcaa[A/G]gtcatggaagacaaag |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2243480 | 7 | q | q11.21 | CRCP | 65599196 | 2.24E-04 | 1.19 | 0.126 | 0.108 | A | (SEQ ID NO: 0643) tttaattacagtcatt[A/G]cctttgttttttctca |
| 02 | rs1039664 | 7 | q | q11.21 | GUSB \| ASL | 65449716 | 7.60E-05 | 1.21 | 0.124 | 0.104 | C | (SEQ ID NO: 0644) atgaaaataaaaaaac[A/C]atgtaaacatttggga |
| 03 | rs1267818 | 7 | q | q11.21 | KCTD7 | 66107024 | 3.02E-04 | 1.19 | 0.125 | 0.108 | A | (SEQ ID NO: 0645) tgataactactggccc[A/G]tctcaaggcaagatga |
| 03 | rs1267817 | 7 | q | q11.21 | KCTD7 \| LOC100289135 | 66110040 | 3.00E-04 | 1.19 | 0.125 | 0.108 | A | (SEQ ID NO: 0646) tgagtcccaagccagg[A/C]acatggcatcccctga |
| 02 | rs6460260 | 7 | q | q11.21 | LOC100131973 | 65215455 | 4.87E-05 | 1.22 | 0.124 | 0.104 | A | (SEQ ID NO: 0647) atgctgctgaggccct[A/G]ggcttctatggtagat |
| 03 | rs2178742 | 7 | q | q11.21 | LOC100289135 \| RABGEF1 | 66197799 | 1.84E-04 | 1.20 | 0.126 | 0.107 | A | (SEQ ID NO: 0648) tctcgcttttgctctc[A/G]ctctcactctgtagcc |
| 03 | rs35315599 | 7 | q | q11.21 | RABGEF1 | 66254767 | 1.56E-04 | 1.20 | 0.126 | 0.108 | A | (SEQ ID NO: 0649) atttaagtttcccctc[A/G]cctatcactatgtgct |
| 02 | rs35391607 | 7 | q | q11.21 | VKORC1L1 | 65360829 | 7.76E-05 | 1.21 | 0.124 | 0.105 | A | (SEQ ID NO: 0650) tagtaaatggtattgg[A/G]tgaactgagtagccat |
| 02 | rs6949812 | 7 | q | q11.21 | VKORC1L1 | 65387101 | 8.77E-05 | 1.21 | 0.124 | 0.105 | A | (SEQ ID NO: 0651) ttcatttaccaatcac[A/G]taccttttttgtcatt |
| 03 | rs11983901 | 7 | q | q11.22 | STAG3L4 \| AUTS2 | 68571255 | 6.12E-03 | 0.82 | 0.050 | 0.060 | C | (SEQ ID NO: 0652) tattggttcagccctg[A/C]aacacaggccatcttg |
| 03 | rs5745774 | 7 | q | q21.11 | LOC100128317 \| HGF | 81330627 | 2.04E-02 | 1.17 | 0.057 | 0.049 | A | (SEQ ID NO: 0653) ggaaagaaactagttt[A/G]tctcaactctgtattc |
| 03 | rs17166931 | 7 | q | q21.13 | C7orf62 \| ZNF804B | 88760129 | 1.81E-04 | 1.41 | 0.032 | 0.023 | A | (SEQ ID NO: 0654) gatcttctctaccttg[A/G]tataaaaatcacctca |
| 03 | rs10255948 | 7 | q | q21.13 | ZNF804B \| DPY19L2P4 | 89536358 | 2.57E-03 | 1.10 | 0.449 | 0.425 | A | (SEQ ID NO: 0655) ttggttaatttgaact[A/C]ttccctctgatatatt |
| 03 | rs4466326 | 7 | q | q21.13 | ZNF804B \| DPY19L2P4 | 89645073 | 3.30E-04 | 0.89 | 0.373 | 0.401 | A | (SEQ ID NO: 0656) ataccaggccatactt[A/G]gccatcaaaagtttga |
| 03 | rs2214213 | 7 | q | q21.3 | CALCR | 93078060 | 3.44E-03 | 1.10 | 0.445 | 0.423 | A | (SEQ ID NO: 0657) tgctaatctgttcctt[A/G]taaattttcacacaaa |
| 03 | rs2240293 | 7 | q | q21.3 | LOC402679 | 96622720 | 1.19E-03 | 0.90 | 0.460 | 0.485 | G | (SEQ ID NO: 0658) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | gcggccggccgccaat[A/G]gaatcttgctcctact |
| 03 | rs10282336 | 7 | q | q21.3 | OCM2 \| LMTK2 | 97731700 | 2.78E-04 | 1.26 | 0.065 | 0.052 | A | (SEQ ID NO: 0659) tattttcaacaaacag[A/G]ataggactattttcac |
| 03 | rs12532957 | 7 | q | q21.3 | SLC25A13 | 95805504 | 1.14E-03 | 1.26 | 0.051 | 0.041 | A | (SEQ ID NO: 0660) agagagtctaggtgag[A/G]cacttcatcacaacca |
| 03 | rs4727590 | 7 | q | q22.2 | ORC5L \| LHFPL3 | 103879276 | 1.50E-03 | 1.15 | 0.144 | 0.128 | G | (SEQ ID NO: 0661) tctctctcaaaatcat[A/G]cacttctttccactac |
| 03 | rs212438 | 7 | q | q22.3 | ATXN7L1 \| FLJ23834 | 105528339 | 2.50E-03 | 1.13 | 0.204 | 0.185 | G | (SEQ ID NO: 0662) atctgatgtgcaggta[A/G]gaaatgtcacaggagg |
| 02 | rs2111201 | 7 | q | q31.1 | NRCAM | 107965942 | 2.99E-05 | 1.13 | 0.316 | 0.291 | A | (SEQ ID NO: 0663) tgagggggaaagcaac[A/G]tagatactgggaacaa |
| 03 | rs4142284 | 7 | q | q31.1 | NRCAM | 107940173 | 5.92E-05 | 1.12 | 0.315 | 0.290 | A | (SEQ ID NO: 0664) ttctggtcaatgtgct[A/G]tatgtacatgacaaat |
| 03 | rs2267887 | 7 | q | q31.1 | NRCAM | 107968803 | 3.06E-04 | 1.12 | 0.423 | 0.395 | G | (SEQ ID NO: 0665) ggaggaacaaaaacca[A/G]ccagtctctggactgt |
| 02 | rs10215206 | 7 | q | q31.1 | PNPLA8 | 108117088 | 2.07E-05 | 1.18 | 0.205 | 0.179 | A | (SEQ ID NO: 0666) caatttcatttccttc[A/G]gacatatacccggagt |
| 03 | rs10249427 | 7 | q | q31.1 | PNPLA8 | 108116481 | 3.62E-04 | 1.15 | 0.200 | 0.178 | G | (SEQ ID NO: 0667) taagaaaaggaatgag[A/G]aaacttgattggtgta |
| 03 | rs40851 | 7 | q | q31.1 | PNPLA8 | 108145121 | 1.08E-03 | 0.90 | 0.385 | 0.410 | A | (SEQ ID NO: 0668) ccatgccaacaacatt[A/G]agaagaacaaggttgg |
| 03 | rs3823855 | 7 | q | q31.32 | CADPS2 | 122057923 | 7.65E-04 | 1.12 | 0.318 | 0.294 | A | (SEQ ID NO: 0669) ttagagaagaaatact[A/G]tatgacacagatgagg |
| 03 | rs1582258 | 7 | q | q31.33 | GRM8 | 126122354 | 1.22E-02 | 0.92 | 0.352 | 0.371 | G | (SEQ ID NO: 0670) gcaattccacttctgg[A/G]tatatgccacaaagta |
| 02 | exm657854 | 7 | q | q32.2 | CPA1 | 130023245 | 1.18E-11 | 47.29 | 0.005 | 0.000 | A | (SEQ ID NO: 0671) cagttcagcacgggggg[A/G]cagtaagcgtccagcc |
| 02 | rs13234407 | 7 | q | q32.3 | KLF14 \| FLJ43663 | 130438214 | 4.72E-05 | 0.89 | 0.461 | 0.491 | A | (SEQ ID NO: 0672) gaatctgttactctgg[A/G]acacagatgcagggtt |
| 03 | rs7795357 | 7 | q | q32.3 | KLF14 \| FLJ43663 | 130458874 | 2.68E-03 | 1.22 | 0.058 | 0.048 | G | (SEQ ID NO: 0673) cccagcagcttacacc[A/G]cacctccctgttacat |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs157950 | 7 | q | q32.3 | LOC100506860 | 130601205 | 9.29E-03 | 1.26 | 0.075 | 0.060 | G | (SEQ ID NO: 0674) aatgaagattcaggac[A/G]acgaagcagtggtaac |
| 03 | rs13228664 | 7 | q | q32.3 | MKLN1 | 131132340 | 4.56E-03 | 0.91 | 0.442 | 0.464 | G | (SEQ ID NO: 0675) gtaatactccttctac[A/G]atcctaagatgggtct |
| 03 | rs4725613 | 7 | q | q34 | CLCN1 | 143025985 | 1.63E-03 | 1.10 | 0.474 | 0.450 | G | (SEQ ID NO: 0676) gaatgtctattctctg[A/G]atgagcaggggaggag |
| 03 | rs6973542 | 7 | q | q35 | CNTNAP2 | 147029028 | 3.45E-03 | 0.91 | 0.399 | 0.422 | G | (SEQ ID NO: 0677) atggtcagctggcttt[A/G]ctgttcacaacatgtt |
| 02 | exm2262270 | 7 | q | q36.1 | FABP5P3 \| XRCC2 | 152211627 | 4.47E-11 | Inf | 0.010 | 0.002 | A | (SEQ ID NO: 0678) tttccagtcttatttc[A/C]ggggctggcggtggta |
| 02 | exm674318 | 7 | q | q36.1 | MLL3 | 151882672 | 4.52E-15 | 3.24 | 0.026 | 0.008 | A | (SEQ ID NO: 0679) ctttcttgtgagcttg[A/C]ttttctccacaatttg |
| 03 | rs4609156 | 8 | p | p12 | LOC642513 \| NRG1 | 31133658 | 2.74E-03 | 1.10 | 0.478 | 0.454 | G | (SEQ ID NO: 0680) tcctgaaaaggtctca[A/G]ttctcatcagccagcg |
| 03 | rs16879927 | 8 | p | p12 | NRG1 | 32612705 | 4.22E-04 | 0.82 | 0.088 | 0.105 | G | (SEQ ID NO: 0681) accaaacttcaagacc[A/G]aacatagggaacccaa |
| 03 | rs17671468 | 8 | p | p12 | NRG1 \| FUT10 | 32633362 | 7.92E-04 | 0.83 | 0.089 | 0.105 | A | (SEQ ID NO: 0682) ctatttgcaagggaga[A/G]gaagggcacctaatat |
| 03 | rs4732639 | 8 | p | p21.2 | DPYSL2 \| ADRA1A | 26605110 | 8.05E-04 | 1.12 | 0.305 | 0.282 | G | (SEQ ID NO: 0683) gaagagcaccacttag[A/G]cacttcagagacccat |
| 03 | rs7826422 | 8 | p | p21.2 | DPYSL2 \| ADRA1A | 26602648 | 2.88E-04 | 1.25 | 0.073 | 0.059 | A | (SEQ ID NO: 0684) tgaaccaggaaactga[A/G]ggctcttgtggtccag |
| 03 | rs10503799 | 8 | p | p21.2 | DPYSL2 \| ADRA1A | 26605624 | 2.69E-04 | 1.25 | 0.073 | 0.059 | A | (SEQ ID NO: 0685) ctacccccttcaacagc[A/G]atttactacttgatcc |
| 03 | rs7013854 | 8 | p | p21.2 | EBF2 | 25733066 | 1.20E-04 | 1.17 | 0.185 | 0.163 | G | (SEQ ID NO: 0686) cttgaattctttagaa[A/G]tcatagaaattatcct |
| 03 | rs9203006 | 8 | p | p21.2 | NKX3-1 \| NKX2-6 | 23554565 | 2.33E-03 | 1.11 | 0.266 | 0.246 | G | (SEQ ID NO: 0687) ggctccctgtcctttc[A/G]cccctcggttccttcc |
| 03 | rs12543268 | 8 | p | p21.2 | NKX3-1 \| NKX2-6 | 23556615 | 6.68E-05 | 0.90 | 0.358 | 0.383 | A | (SEQ ID NO: 0688) gagagattacggagac[A/G]gaagacaggcagctgg |
| 03 | rs977262 | 8 | p | p21.3 | LOC100128993 \| SH2D4A | 19081781 | 7.08E-04 | 1.12 | 0.301 | 0.277 | G | (SEQ ID NO: 0689) atgaaagatgagggga[A/G]agagagatgtgcaaaa |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7012411 | 8 | p | p22 | TUSC3 \| MSR1 | 15788332 | 1.41E-03 | 0.90 | 0.470 | 0.496 | A | (SEQ ID NO: 0690) tgcaattcatccacac[A/C]ctgaaagatcctgtta |
| 03 | rs2980418 | 8 | p | p23.1 | FLJ10661 \| PRAGMIN | 8114228 | 3.75E-02 | 1.09 | 0.194 | 0.181 | G | (SEQ ID NO: 0691) tgcacctttgttaaaa[A/G]acaaatgactgtatgt |
| 03 | rs7014329 | 8 | p | p23.1 | LOC340357 | 12626394 | 5.44E-02 | 0.94 | 0.478 | 0.493 | A | (SEQ ID NO: 0692) catgctgcccttttct[A/G]ctgtctcaaacttgat |
| 03 | rs7011215 | 8 | p | p23.1 | MSRA \| LOC346702 | 10312694 | 5.53E-05 | 1.13 | 0.359 | 0.332 | G | (SEQ ID NO: 0693) cctgaacattataaac[A/G]agacaagtataaacag |
| 03 | rs7816211 | 8 | p | p23.2 | CSMD1 | 3980317 | 7.75E-03 | 1.10 | 0.235 | 0.218 | G | (SEQ ID NO: 0694) tcactgtcttccatca[A/G]aaaaacaaatgattta |
| 03 | rs2617009 | 8 | p | p23.2 | CSMD1 | 4496463 | 2.32E-02 | 0.92 | 0.202 | 0.217 | A | (SEQ ID NO: 0695) agggttctattctttc[A/G]aactactccagcagtc |
| 03 | rs4523281 | 8 | p | p23.2 | CSMD1 | 3496633 | 1.28E-04 | 1.33 | 0.049 | 0.038 | A | (SEQ ID NO: 0696) aatcttttgctagaat[A/G]aagtcctttgcatttt |
| 02 | exm678864 | 8 | p | p23.2 | CSMD1 | 3216809 | 1.26E-07 | Inf | 0.003 | 0.000 | G | (SEQ ID NO: 0697) tgccttcagccgaaga[A/G]ttggttttcactttgg |
| 03 | rs2724974 | 8 | p | p23.2 | CSMD1 | 4494520 | 4.03E-03 | 0.90 | 0.224 | 0.244 | G | (SEQ ID NO: 0698) gaatgcccttttttca[A/G]tcctccgtgtgattgg |
| 03 | rs17071029 | 8 | p | p23.2 | CSMD1 | 4536253 | 2.02E-03 | 1.14 | 0.166 | 0.148 | A | (SEQ ID NO: 0699) ctgttgttaaacacat[A/G]tgctaatttcaaaata |
| 03 | rs17073854 | 8 | p | p23.2 | CSMD1 \| LOC100287015 | 5377735 | 7.16E-03 | 1.16 | 0.095 | 0.083 | A | (SEQ ID NO: 0700) aggaggtttgtctttg[A/G]ttcgcctgcaccttcc |
| 03 | rs6990815 | 8 | p | p23.2 | CSMD1 \| LOC100287015 | 5713881 | 5.53E-03 | 1.27 | 0.036 | 0.029 | A | (SEQ ID NO: 0701) gtggactagtgcctct[A/G]ttttctctaatgcttt |
| 03 | rs17073881 | 8 | p | p23.2 | CSMD1 \| LOC100287015 | 5380363 | 6.09E-03 | 1.16 | 0.094 | 0.082 | G | (SEQ ID NO: 0702) tttctcagaaacctct[A/G]aaagccatcttctgct |
| 02 | exm2173787 | 8 | q | 811.22 | PXDNL | 52233381 | 2.20E-09 | Inf | 0.003 | 0.000 | G | (SEQ ID NO: 0703) gtcttctttcatccag[C/G]gctcctcggccttcct |
| 03 | rs1812576 | 8 | q | q12.2 | LOC100130298 \| RLBP1L1 | 62173034 | 3.45E-03 | 1.14 | 0.149 | 0.134 | G | (SEQ ID NO: 0704) tccctcttcttcatac[A/G]cagccactgaatagga |
| 03 | rs1866694 | 8 | q | q12.2 | LOC100130298 \| | 62172668 | 1.61E-03 | 1.13 | 0.209 | 0.189 | A | (SEQ ID NO: 0705) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | RLBP1L1 | | | | | | | tccctccgtcatgtaa[A/C]gtaggatggcagttac |
| 03 | rs17802118 | 8 | q | q12.3 | LOC100287835 \| NKAIN3 | 62694154 | 9.69E-03 | 1.10 | 0.265 | 0.247 | A | (SEQ ID NO: 0706) catgagtccactggag[A/G]tgttttgtagacttac |
| 02 | rs896486 | 8 | q | q12.3 | NKAIN3 | 63415467 | 3.74E-05 | 1.14 | 0.283 | 0.258 | A | (SEQ ID NO: 0707) tacaggaccttggaaa[A/C]catgcttgaacttctt |
| 03 | rs10217013 | 8 | q | q12.3 | YTHDF3 \| LOC100130155 | 64878574 | 2.00E-03 | 1.11 | 0.377 | 0.354 | A | (SEQ ID NO: 0708) aaatgagtgaggacca[A/C]agctgttatgtttttt |
| 03 | rs4268113 | 8 | q | q13.2 | C8orf34 | 69509456 | 3.04E-04 | 0.89 | 0.399 | 0.427 | G | (SEQ ID NO: 0709) gcaggatacccccttg[A/G]aacaagcagcgaagat |
| 03 | rs638853 | 8 | q | q13.2 | C8orf34 \| LOC100129096 | 70014344 | 5.33E-03 | 1.13 | 0.150 | 0.135 | A | (SEQ ID NO: 0710) cacctgtgtgtatcca[A/G]cagcaagaagactgaa |
| 03 | rs10957982 | 8 | q | q21.13 | ZBTB10 \| ZNF704 | 81455763 | 1.45E-04 | 1.16 | 0.202 | 0.179 | G | (SEQ ID NO: 0711) ggtttagagtaattca[A/G]tttagctgtcatttaa |
| 02 | exm710751 | 8 | q | q22.1 | INTS8 | 95878387 | 2.72E-17 | 9.20 | 0.012 | 0.001 | C | (SEQ ID NO: 0712) atttttgttttgtagg[A/C]gtgaactgattcttt |
| 03 | rs16896060 | 8 | q | q22.1 | MTDH | 98667777 | 4.96E-04 | 1.46 | 0.022 | 0.015 | A | (SEQ ID NO: 0713) gtcctggtggtcaaaa[A/G]ggcctggacaggcatc |
| 03 | rs2618137 | 8 | q | q22.1 | RUNX1T1 \| C8orf83 | 93567028 | 2.40E-03 | 0.78 | 0.039 | 0.050 | C | (SEQ ID NO: 0714) aaaagacttcttcaaa[A/C]gaaactgtgaagtctc |
| 03 | rs2704253 | 8 | q | q22.1 | SDC2 \| PGCP | 97651358 | 1.77E-04 | 1.18 | 0.148 | 0.128 | G | (SEQ ID NO: 0715) gaagaaagtttagtag[A/G]gctgaagtgtgcattt |
| 03 | rs4735529 | 8 | q | q22.2 | POP1 | 99139610 | 1.84E-03 | 0.91 | 0.459 | 0.483 | G | (SEQ ID NO: 0716) gtaggtagcacacaag[A/G]taatcatgtcaggatg |
| 03 | rs17476650 | 8 | q | q23.2 | KCNV1 \| CSMD3 | 111101361 | 1.92E-04 | 1.19 | 0.129 | 0.111 | A | (SEQ ID NO: 0717) taatagacaaatgttg[A/C]acaatagtcaaattct |
| 03 | rs7010965 | 8 | q | q23.3 | CSMD3 \| TRPS1 | 116299406 | 2.20E-02 | 1.14 | 0.084 | 0.075 | A | (SEQ ID NO: 0718) tgcacatcaatctctc[A/G]tattttgcatttaaac |
| 03 | rs16887231 | 8 | q | q23.3 | CSMD3 \| TRPS1 | 116253370 | 1.32E-02 | 1.15 | 0.084 | 0.074 | G | (SEQ ID NO: 0719) acctcaggaaaggatc[A/G]tggaacagggaggcct |
| 03 | rs4871240 | 8 | q | q24.13 | HAS2AS \| LOC100131552 | 123297701 | 1.02E-02 | 0.92 | 0.445 | 0.465 | G | (SEQ ID NO: 0720) caagtttgttgcttta[A/G]tactaccttgagtctg |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs13274301 | 8 | q | q24.21 | PVT1 | 128988045 | 7.96E-05 | 0.82 | 0.103 | 0.123 | C | (SEQ ID NO: 0721) gtttcctagcttgaaa[A/C]acgaagagaagaaaag |
| 03 | rs7826937 | 8 | q | 824.21 | PVT1 \| LOC100287906 | 129264171 | 1.01E-02 | 0.92 | 0.345 | 0.365 | G | (SEQ ID NO: 0722) tgactcaccatcagga[A/G]ggatctgctgcactgg |
| 03 | rs491614 | 8 | q | q24.22 | ADCY8 \| EFR3A | 132719817 | 1.19E-03 | 1.11 | 0.463 | 0.438 | G | (SEQ ID NO: 0723) tactgaaaaagagaat[A/G]aacaacataacagtca |
| 03 | rs581534 | 8 | q | q24.22 | ADCY8 \| EFR3A | 132711614 | 1.67E-02 | 1.15 | 0.085 | 0.075 | G | (SEQ ID NO: 0724) cttacttacctagagg[A/G]catatgtctgctactg |
| 02 | rs6999964 | 8 | q | q24.22 | ADCY8 \| EFR3A | 132862920 | 1.68E-05 | 1.14 | 0.216 | 0.195 | A | (SEQ ID NO: 0725) tataattaaggttaat[A/G]gtgagattgtttggct |
| 02 | rs4433159 | 8 | q | q24.22 | ASAP1 \| ADCY8 | 131571963 | 1.28E-03 | 1.17 | 0.320 | 0.287 | G | (SEQ ID NO: 0726) ttgacttatctatgga[G/A]tttttgactatttctg |
| 03 | rs16904553 | 8 | q | q24.22 | EFR3A | 132947786 | 2.70E-03 | 1.12 | 0.212 | 0.194 | A | (SEQ ID NO: 0727) taacataatagaaatt[A/G]actgacatatgtatgg |
| 03 | rs6985794 | 8 | q | q24.22 | LOC100129104 \| ZFAT | 134689013 | 9.73E-02 | 1.08 | 0.129 | 0.121 | G | (SEQ ID NO: 0728) atccatagaaacagac[A/G]ttaattaaataacaca |
| 03 | rs12548244 | 8 | q | q24.23 | KHDRBS3 \| FLJ45872 | 137112133 | 7.19E-04 | 0.90 | 0.368 | 0.395 | G | (SEQ ID NO: 0729) tttcatatcagaggca[A/G]cctctcaaccagatgt |
| 03 | rs2317547 | 8 | q | q24.23 | KHDRBS3 \| FLJ45872 | 136933622 | 3.97E-03 | 1.10 | 0.337 | 0.316 | C | (SEQ ID NO: 0730) tggccagaaagagaga[A/C]agagagacagagacag |
| 03 | rs10505647 | 8 | q | q24.23 | KHDRBS3 \| FLJ45872 | 137056293 | 1.23E-03 | 0.90 | 0.311 | 0.334 | A | (SEQ ID NO: 0731) aaataggacccttgac[A/G]cacaaaggaattttgg |
| 02 | exm728471 | 8 | q | q24.3 | EPPK1 | 144940658 | 3.25E-16 | Inf | 0.006 | 0.000 | A | (SEQ ID NO: 0732) tggaagggcgtgctgc[A/G]gcccggcacggccctg |
| 03 | rs903965 | 8 | q | q24.3 | FLJ43860 \| NCRNA00051 | 142698496 | 1.18E-03 | 1.44 | 0.020 | 0.014 | A | (SEQ ID NO: 0733) acacttggtacccttg[A/G]tacatttaatagtaaa |
| 03 | rs3819495 | 8 | q | q24.3 | GML | 143923250 | 1.12E-02 | 1.16 | 0.085 | 0.075 | A | (SEQ ID NO: 0734) ccacctgtgcgccagg[A/G]catacactggctgcac |
| 02 | rs10971957 | 9 | p | p13.3 | DCAF12 \| UBAP1 | 34151463 | 7.13E-03 | 1.13 | 0.415 | 0.386 | C | (SEQ ID NO: 0735) ctatcattatcgattc[C/T]acccagcaatttctct |
| 02 | rs10972684 | 9 | p | p13.3 | ORS2S \| RECK | 36003635 | 5.21E-03 | 0.85 | 0.167 | 0.190 | A | (SEQ ID NO: 0736) atctgctatacaacat[C/A]ctcagtccccctcatc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs12726 | 9 | p | p13.3 | UNC13B | 35404840 | 4.45E-04 | 1.13 | 0.263 | 0.240 | A | (SEQ ID NO: 0737) gttgaaggatccagga[A/G]tattttcttcttgggt |
| 03 | rs2383733 | 9 | p | p21.2 | C9orf72 \| LINGO2 | 27869510 | 7.13E-03 | 1.17 | 0.079 | 0.068 | A | (SEQ ID NO: 0738) tgtcactttcagtata[A/G]ataaaactctttagaa |
| 03 | rs10811800 | 9 | p | p21.3 | DMRTA1 \| LOC402360 | 22906729 | 2.19E-03 | 1.10 | 0.420 | 0.396 | A | (SEQ ID NO: 0739) ctacattataaattat[A/G]cttgataccagacatc |
| 03 | rs1381923 | 9 | p | p21.3 | DMRTA1 \| LOC402360 | 22909348 | 7.90E-03 | 0.92 | 0.448 | 0.469 | C | (SEQ ID NO: 0740) actgatatcattccct[A/C]cctgaaatatcccatg |
| 03 | rs10116397 | 9 | p | p21.3 | DMRTA1 \| LOC402360 | 23570688 | 3.01E-04 | 1.25 | 0.071 | 0.057 | G | (SEQ ID NO: 0741) ggcaaggagagcacca[A/G]tttaggaaatgttaga |
| 03 | rs2149913 | 9 | p | p21.3 | ELAVL2 \| TUSC1 | 24573717 | 6.46E-04 | 0.89 | 0.318 | 0.343 | A | (SEQ ID NO: 0742) gaataagaatactaac[A/G]tttatcccctgcattt |
| 03 | rs2026590 | 9 | p | p21.3 | ELAVL2 \| TUSC1 | 24833789 | 4.21E-04 | 1.14 | 0.240 | 0.217 | A | (SEQ ID NO: 0743) caatgggatttggtaa[A/C]tattttcttatctttg |
| 03 | rs11788362 | 9 | p | p21.3 | ELAVL2 \| TUSC1 | 24493958 | 1.79E-03 | 0.89 | 0.216 | 0.237 | A | (SEQ ID NO: 0744) aaaaaagtactaattc[A/G]gaaaagatataaaagt |
| 03 | rs10511626 | 9 | p | p22.2 | BNC2 | 16764989 | 3.61E-02 | 0.90 | 0.110 | 0.120 | A | (SEQ ID NO:0745) atcagagtatatgcca[A/C]agcgggtttcgtatcc |
| 02 | rs1442514 | 9 | p | p22.2 | CNTLN | 17419319 | 3.13E-05 | 1.25 | 0.094 | 0.076 | A | (SEQ ID NO: 0746) tactaagcattattct[A/G]tagatggaatatataa |
| 03 | rs2772695 | 9 | p | p22.2 | SH3GL2 \| ADAMTSL1 | 17985166 | 4.54E-03 | 1.13 | 0.166 | 0.150 | A | (SEQ ID NO: 0747) gagacttcactctgac[A/G]tctttctctttttgga |
| 03 | rs10810211 | 9 | p | p22.3 | ZDHHC21 | 14676870 | 1.30E-02 | 1.23 | 0.037 | 0.030 | G | (SEQ ID NO: 0748) caagtgctctctcaac[A/G]tgttcaatattactaa |
| 02 | rs12236892 | 9 | p | p24.1 | C9orf123 \| PTPRD | 7834442 | 5.91E-05 | 1.30 | 0.063 | 0.050 | G | (SEQ ID NO: 0749) gtttctaaatatgtca[A/G]agtagatattaaagaa |
| 02 | exm737779 | 9 | p | p24.1 | ERMP1 | 5832719 | 4.28E-24 | 4.87 | 0.028 | 0.006 | G | (SEQ ID NO: 0750) gcggggccgctggaca[C/G]cgcggggagttcgacg |
| 02 | rs10975519 | 9 | p | p24.1 | IL33 | 6253571 | 6.06E-07 | 1.18 | 0.338 | 0.302 | A | (SEQ ID NO: 0751) ggtgttgagactcata[A/G]taactcagtaacacct |
| 01 | rs1332290 | 9 | p | p24.1 | IL33 | 6255881 | 6.96E-07 | 1.17 | 0.391 | 0.354 | A | (SEQ ID NO: 0752) |

TABLE 1-continued

| TABLES (Based on build 37 or "GRCh37" as defined by the Genome Reference Consortium) | | | | | | | | | | | | |
|---|---|---|---|---|---|---|---|---|---|---|---|---|
| Set | Name | Chr | Arm | Cyto | Gene | Position | p-value | OR | Case MAF | Cont MAF | MA | Context Sequence |
| | | | | | | | | | | | | tggaaactaaagggga[A/C]tacttatttatgactt |
| 02 | rs10975516 | 9 | p | p24.1 | IL33 | 6247693 | 2.31E-05 | 1.15 | 0.335 | 0.304 | A | (SEQ ID NO: 0753)<br>ctttgaccccagtgga[A/G]tgctctctcctgcaaa |
| 01 | rs1048274 | 9 | p | p24.1 | IL33 | 6256292 | 3.99E-06 | 1.17 | 0.333 | 0.300 | A | (SEQ ID NO: 0754)<br>ttagcatgtgtggaat[A/G]ttttccatattatgta |
| 01 | rs1330383 | 9 | p | p24.1 | IL33 | 6251507 | 4.64E-06 | 1.17 | 0.333 | 0.300 | A | (SEQ ID NO: 0755)<br>accatgggattccaat[A/C]cattgcaagtatttca |
| 02 | rs10815398 | 9 | p | p24.1 | IL33 \| LOC645969 | 6272766 | 6.98E-06 | 1.16 | 0.393 | 0.359 | C | (SEQ ID NO: 0756)<br>gcagtctctcccttga[A/C]acatccttccccttcc |
| 02 | rs10815402 | 9 | p | p24.1 | LOC645969 \| TPD52L3 | 6293715 | 5.40E-06 | 1.17 | 0.305 | 0.273 | A | (SEQ ID NO: 0757)<br>tccagacacaagtcac[A/G]agttcaggggttcaca |
| 03 | rs10975539 | 9 | p | p24.1 | LOC645969 TPD52L3 | 6308729 | 9.21E-04 | 0.88 | 0.213 | 0.235 | A | (SEQ ID NO: 0758)<br>cccccaataacaggaa[A/G]gagattcctttgttcc |
| 03 | rs12551256 | 9 | p | p24.1 | RANBP6 \| IL33 | 6231239 | 1.64E-04 | 1.13 | 0.491 | 0.462 | G | (SEQ ID NO: 0759)<br>cttctttggcttctca[A/G]tgcactctgaatgaaa |
| 02 | rs1052335 | 9 | p | p24.1 | TPD52L3 | 6330380 | 2.74E-05 | 1.19 | 0.220 | 0.192 | C | (SEQ ID NO: 0760)<br>cactgcctgagataga[A/C]gtttgcatcttattgg |
| 03 | rs4741806 | 9 | p | p24.2 | KIAA0020 \| RFX3 | 3099009 | 1.23E-03 | 0.82 | 0.074 | 0.088 | C | (SEQ ID NO: 0761)<br>tttttcttattgattc[A/C]taggagttctttacat |
| 02 | rs7021672 | 9 | p | p24.2 | KIAA0020 \| RFX3 | 3097453 | 9.19E-05 | 0.86 | 0.205 | 0.231 | A | (SEQ ID NO: 0762)<br>tttattgatagtttac[A/G]ctgctggaaatataat |
| 03 | rs2986687 | 9 | p | p24.2 | RFX3 | 3301887 | 5.31E-05 | 1.19 | 0.124 | 0.106 | A | (SEQ ID NO: 0763)<br>agacctgaagagcagg[A/G]accctggtggattttt |
| 03 | rs3012708 | 9 | p | p24.2 | RFX3 | 3322283 | 1.71E-03 | 1.14 | 0.184 | 0.165 | G | (SEQ ID NO: 0764)<br>tcaagtttccttttgt[A/G]tccctggcgaacttta |
| 03 | rs7868484 | 9 | p | p24.3 | SMARCA2 | 2141357 | 7.19E-05 | 1.14 | 0.300 | 0.273 | A | (SEQ ID NO: 0765)<br>tatggtttttggattt[A/C]gcatttagttaatgac |
| 02 | rs10746847 | 9 | q | q21.12 | TRPM3 | 73170382 | 3.23E-05 | 0.89 | 0.416 | 0.446 | G | (SEQ ID NO: 0766)<br>tcctgtacaggtgcat[A/G]tggatgtgctatgtgt |
| 03 | rs10746850 | 9 | q | q21.12 | TRPM3 | 73183281 | 7.86E-05 | 0.90 | 0.443 | 0.469 | G | (SEQ ID NO: 0767)<br>aaattctatgccaagc[A/G]ctttcatatacaatat |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs3739776 | 9 | q | q21.12 | TRPM3 | 73151970 | 1.35E-05 | 0.88 | 0.414 | 0.445 | G | (SEQ ID NO: 0768) gccattctttctattc[A/G]gtcaatatgaaagaca |
| 02 | rs6560143 | 9 | q | q21.12 | TRPM3 | 73168680 | 4.19E-05 | 0.89 | 0.415 | 0.444 | G | (SEQ ID NO: 0769) cctgttgttaattccc[A/G]atcaatagtcccgaga |
| 03 | rs10119759 | 9 | q | q21.31 | PSAT1 \| TLE4 | 82018583 | 6.22E-02 | 0.94 | 0.305 | 0.319 | C | (SEQ ID NO: 0770) gctccagggctgggac[A/C]ctttctgagcctcctc |
| 03 | rs9314677 | 9 | q | q21.31 | PSAT1 \| TLE4 | 82018917 | 3.29E-03 | 1.10 | 0.347 | 0.325 | G | (SEQ ID NO: 0771) gatgtaggtaaccatc[A/G]ttatgggaccccagag |
| 03 | rs2378380 | 9 | q | q21.31 | PSAT1 \| TLE4 | 82032456 | 3.22E-02 | 0.93 | 0.300 | 0.316 | A | (SEQ ID NO: 0772) gcaacaggggtactag[A/G]gcatcatgaaattcac |
| 03 | rs3897745 | 9 | q | q21.32 | TLE1 | 84215944 | 1.22E-03 | 0.88 | 0.182 | 0.202 | A | (SEQ ID NO: 0773) ctacacagtcgtgtga[A/G]ccaatccctccaaata |
| 03 | rs9410282 | 9 | q | q22.1 | LOC286238 \| C9orf47 | 91318984 | 3.33E-04 | 0.89 | 0.418 | 0.446 | A | (SEQ ID NO: 0774) aggctctgtgatgggc[A/G]caggaacacactgagg |
| 02 | rs944485 | 9 | q | q22.1 | SHC3 | 91679818 | 4.83E-04 | 1.17 | 0.411 | 0.374 | T | (SEQ ID NO: 0775) ttgtgccgttattaat[T/G]ccatttgttatttcat |
| 02 | exm764237 | 9 | q | q22.32 | C9orf102 | 98684662 | 4.73E-08 | 18.90 | 0.004 | 0.000 | A | (SEQ ID NO: 0776) gcttgcagtagcgcga[A/C]atggttagctaccttc |
| 02 | exm768001 | 9 | q | q31.1 | GRIN3A | 104335619 | 4.40E-10 | 3.17 | 0.017 | 0.005 | G | (SEQ ID NO: 0777) gccttgcggaccacca[A/G]tgggaaagcagactcc |
| 03 | rs698459 | 9 | q | q31.1 | LOC347281 \| OR13F1 | 107234158 | 1.22E-03 | 0.89 | 0.282 | 0.306 | C | (SEQ ID NO: 0778) cttgatgtgtcaggac[A/C]attttgttgctgtagg |
| 03 | rs2808374 | 9 | q | q31.2 | LOC100128086 \| RAD23B | 109987079 | 4.12E-03 | 1.11 | 0.280 | 0.260 | G | (SEQ ID NO: 0779) ctcgctactgatggac[A/G]ttcacatttaaatttt |
| 03 | rs7864733 | 9 | q | q31.2 | LOC644620 | 109427261 | 9.34E-03 | 0.92 | 0.474 | 0.494 | C | (SEQ ID NO: 0780) actgaaatatagccag[A/C]aataaataatcatgct |
| 03 | rs16934033 | 9 | q | q33.1 | ASTN2 | 119657927 | 2.09E-04 | 1.55 | 0.019 | 0.012 | A | (SEQ ID NO: 0781) ctcctatattcaacag[A/G]acagcaaatgaagact |
| 03 | rs1990422 | 9 | q | q33.1 | DBC1 \| CDK5RAP2 | 122244046 | 5.73E-05 | 1.15 | 0.240 | 0.216 | G | (SEQ ID NO: 0782) atgaaaatataaaatc[A/G]attgtggtgatggttt |
| 02 | rs10513376 | 9 | q | q33.2 | DAB2IP | 124354826 | 3.47E-04 | 0.84 | 0.294 | 0.331 | C | (SEQ ID NO: 0783) agctcagaaaatctca[T/C]tggaacccttgaagta |

TABLE 1-continued

TABLES
(Based on build 37 or "GRCh37" as defined by the Genome Reference Consortium)

<table>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>02</td><td>rs10985200</td><td>9</td><td>q</td><td>q33.2</td><td>GSN</td><td>124043867</td><td>5.48E-05</td><td>1.14</td><td>0.497</td><td>0.465</td><td>A</td><td>(SEQ ID NO: 0784) cggggtttaagaggac[A/G]acaggtgtctgtattg</td></tr>
<tr><td>03</td><td>rs3810942</td><td>9</td><td>q</td><td>q33.2</td><td>GSN / LOC100128064</td><td>124044995</td><td>1.76E-04</td><td>1.13</td><td>0.490</td><td>0.461</td><td>A</td><td>(SEQ ID NO: 0785) atcagagccaagaccc[A/G]gccctcaagtcctcct</td></tr>
<tr><td>03</td><td>rs10156486</td><td>9</td><td>q</td><td>q33.2</td><td>LOC729012 | OR5C1</td><td>125538981</td><td>5.27E-03</td><td>0.65</td><td>0.010</td><td>0.016</td><td>C</td><td>(SEQ ID NO: 0786) tgtggaaggggaggtc[A/C]gtcagccagcattaag</td></tr>
<tr><td>02</td><td>rs4556152</td><td>9</td><td>q</td><td>q33.2</td><td>RAB14 | GSN</td><td>124016909</td><td>6.03E-05</td><td>1.14</td><td>0.503</td><td>0.471</td><td>A</td><td>(SEQ ID NO: 0787) gatttttctctcctct[A/G]aaagagcaattttctc</td></tr>
<tr><td>03</td><td>rs10760160</td><td>9</td><td>q</td><td>q33.2</td><td>RAB14 | GSN</td><td>124003326</td><td>3.42E-04</td><td>1.12</td><td>0.490</td><td>0.462</td><td>C</td><td>(SEQ ID NO: 0788) acaggaaacttcaacc[A/C]agtatcaagttactaa</td></tr>
<tr><td>03</td><td>rs10760159</td><td>9</td><td>q</td><td>q33.2</td><td>RAB14 | GSN</td><td>123998342</td><td>2.45E-04</td><td>1.12</td><td>0.489</td><td>0.460</td><td>A</td><td>(SEQ ID NO: 0789) cctcttcagagggaat[A/G]tggtcctgtggacacc</td></tr>
<tr><td>02</td><td>rs2239696</td><td>9</td><td>q</td><td>q33.2</td><td>RAB14 | GSN</td><td>124029155</td><td>2.82E-05</td><td>1.14</td><td>0.502</td><td>0.469</td><td>G</td><td>(SEQ ID NO: 0790) ggacccagggaatctc[A/G]ccctggctcttcctcc</td></tr>
<tr><td>01</td><td>rs34250136</td><td>9</td><td>q</td><td>q33.3</td><td>DENND1A | LHX2</td><td>126772954</td><td>3.07E-06</td><td>1.71</td><td>0.020</td><td>0.012</td><td>A</td><td>(SEQ ID NO: 0791) cactgatatcgaatgt[A/G]tcttggagtgagaaag</td></tr>
<tr><td>03</td><td>rs10217721</td><td>9</td><td>q</td><td>q33.3</td><td>PBX3 | FAM125B</td><td>128810846</td><td>2.46E-02</td><td>1.07</td><td>0.455</td><td>0.437</td><td>G</td><td>(SEQ ID NO: 0792) ggaattaacagccaca[A/G]tgcaagcttcttgctg</td></tr>
<tr><td>03</td><td>rs7861741</td><td>9</td><td>q</td><td>q33.3</td><td>PBX3 | FAM125B</td><td>128810469</td><td>1.28E-02</td><td>1.08</td><td>0.459</td><td>0.440</td><td>G</td><td>(SEQ ID NO: 0793) ggatccatggcctggc[A/G]attccaggtctgggtt</td></tr>
<tr><td>03</td><td>rs7023572</td><td>9</td><td>q</td><td>q34.13</td><td>C9orf171</td><td>135414981</td><td>5.87E-05</td><td>1.05</td><td>0.356</td><td>0.344</td><td>G</td><td>(SEQ ID NO: 0794) tgttctagggccaacc[A/G]ggggatcggaggagtc</td></tr>
<tr><td>02</td><td>rs10508855</td><td>10</td><td>p</td><td>p11.21</td><td>FZD8 | ANKRD30A</td><td>37070799</td><td>4.47E-06</td><td>1.30</td><td>0.050</td><td>0.039</td><td>A</td><td>(SEQ ID NO: 0795) gggcagagtacttatc[A/G]tatgtgcatactatat</td></tr>
<tr><td>03</td><td>rs17615892</td><td>10</td><td>p</td><td>p11.21</td><td>FZD8 | ANKRD30A</td><td>36635409</td><td>3.86E-03</td><td>0.89</td><td>0.172</td><td>0.190</td><td>G</td><td>(SEQ ID NO: 0796) ctcataacattttccc[A/G]ctagaaataatgtgtg</td></tr>
<tr><td>03</td><td>rs17627587</td><td>10</td><td>p</td><td>p11.21</td><td>FZD8 | ANKRD30A</td><td>36688414</td><td>1.64E-03</td><td>0.87</td><td>0.143</td><td>0.161</td><td>A</td><td>(SEQ ID NO: 0797) cttctattttgctgtt[A/G]ctgttttgcatttgag</td></tr>
<tr><td>03</td><td>rs3124188</td><td>10</td><td>p</td><td>p11.23</td><td>LOC645954</td><td>30955825</td><td>2.05E-03</td><td>0.89</td><td>0.232</td><td>0.253</td><td>G</td><td>(SEQ ID NO: 0798) atccagtgggaaagtc[A/G]gttgcatcctatgttt</td></tr>
<tr><td>03</td><td>rs17747622</td><td>10</td><td>p</td><td>p12.1</td><td>ABI1</td><td>27044752</td><td>2.15E-04</td><td>0.77</td><td>0.050</td><td>0.065</td><td>A</td><td>(SEQ ID NO: 0799)</td></tr>
</table>

TABLE 1-continued

TABLES
(Based on build 37 or "GRCh37" as defined by the Genome Reference Consortium)

tatgtttgtggtcctt[A/G]taactgacttctgctt

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10826406 | 10 | p | p12.1 | MPP7 | 28433708 | 4.41E-03 | 1.15 | 0.115 | 0.102 | A | (SEQ ID NO: 0800) |
| 03 | rs11006995 | 10 | p | p12.1 | MPP7 \| LOC100288110 | 28585496 | 2.13E-02 | 1.16 | 0.069 | 0.060 | A | tatggaaatgatatgg[A/G]atacataggaatggcg (SEQ ID NO: 0801) |
| 03 | rs16927305 | 10 | p | p12.1 | PDSS1 | 27023402 | 4.94E-03 | 1.16 | 0.096 | 0.083 | A | aatacatagcagttgc[A/G]atatccattttgggta (SEQ ID NO: 0802) |
| 03 | rs4748738 | 10 | p | p12.31 | NEBL | 21219406 | 2.28E-03 | 1.11 | 0.350 | 0.328 | A | tgcttagcagggcact[A/G]ggaaatgcacttcagt (SEQ ID NO: 0803) |
| 02 | rs11012384 | 10 | p | p12.31 | NEBL | 21198380 | 4.04E-02 | 1.10 | 0.397 | 0.375 | G | ttaatttgcattttca[A/G]aaagactaccttggct (SEQ ID NO: 0804) |
| 03 | rs17464580 | 10 | p | p12.33 | STAM | 17750968 | 9.33E-04 | 0.79 | 0.051 | 0.064 | C | tgcctctaagatattg[G/T]acacacaaatgaagca (SEQ ID NO: 0805) |
| 01 | rs11256106 | 10 | p | p14 | GATA3 \| SFTA1P | 9222228 | 1.98E-07 | 1.24 | 0.171 | 0.143 | C | actaactccaaacaag[A/C]atcaacagtaaaatta (SEQ ID NO: 0806) |
| 02 | rs1001019 | 10 | p | p14 | GATA3 \| SFTA1P | 9243785 | 9.54E-06 | 1.19 | 0.198 | 0.171 | A | tcacatatgatagatt[A/C]ggcaattgagttatat (SEQ ID NO: 0807) |
| 02 | rs7911451 | 10 | p | p14 | GATA3 \| SFTA1P | 9248331 | 1.56E-05 | 1.18 | 0.206 | 0.180 | A | gctgtttaaatgttta[A/C]ttgatgatggaatgtg (SEQ ID NO: 0808) |
| 03 | rs2387739 | 10 | p | p14 | LOC439949 \| SFMBT2 | 6813564 | 1.55E-04 | 1.16 | 0.214 | 0.191 | G | gtgtgtgtgaacaagc[A/G]caaagtccatatccag (SEQ ID NO: 0809) |
| 02 | rs11257215 | 10 | p | p14 | LOC439951 \| ECHDC3 | 11697403 | 3.79E-05 | 1.13 | 0.287 | 0.262 | G | agtaatgccaactaca[A/G]attatgaaatatttca (SEQ ID NO: 0810) |
| 03 | rs4881466 | 10 | p | p15.1 | CALML5 \| LOC100132159 | 5542109 | 2.16E-04 | 1.14 | 0.289 | 0.263 | A | ggagtttccctatccc[A/G]ggctgcagtgcaatgg (SEQ ID NO: 0811) |
| 03 | rs10904508 | 10 | p | p15.1 | NET1 \| CALML5 | 5503610 | 4.32E-04 | 0.89 | 0.298 | 0.324 | A | atggggctcactgcct[A/G]taacttcaaggaagca (SEQ ID NO: 0812) |
| 02 | rs11253141 | 10 | p | p15.1 | UCN3 \| TUBAL3 | 5422196 | 5.46E-05 | 0.88 | 0.361 | 0.392 | C | ataagaaaatatccag[A/C]actgagtgtatgttta (SEQ ID NO: 0813) |
| 03 | rs2279208 | 10 | p | p15.2 | PFKP | 3171043 | 1.52E-03 | 0.86 | 0.133 | 0.151 | A | tcaagtcatcagattg[A/C]atctccccacctgcca (SEQ ID NO: 0814) |

cgcccaccactgtgcc[A/G]gaatgtgatgcacaca

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2388558 | 10 | p | p15.2 | PITRM1 | 3180689 | 1.72E-03 | 0.89 | 0.240 | 0.262 | A | (SEQ ID NO: 0815) agagatcacaccccga[A/C]ctccagctcccacgtg |
| 03 | rs4881111 | 10 | p | p15.2 | PITRM1 | 3190265 | 4.38E-03 | 1.09 | 0.490 | 0.467 | A | (SEQ ID NO: 0816) gcacaccctgaaccaa[A/G]gaaaacacagaagaaa |
| 03 | rs9423709 | 10 | p | p15.2 | PITRM1 | 3202682 | 3.65E-03 | 0.89 | 0.211 | 0.230 | A | (SEQ ID NO: 0817) ggtccaaaaatatcac[A/G]gtacttcgagagacca |
| 03 | rs7898695 | 10 | p | p15.2 | PITRM1 | 3184507 | 3.61E-03 | 1.10 | 0.429 | 0.406 | A | (SEQ ID NO: 0818) cacctccccatctgtg[A/G]ccctctgtgacacacg |
| 03 | rs4881109 | 10 | p | p15.2 | PITRM1 | 3185237 | 1.42E-03 | 0.89 | 0.233 | 0.255 | G | (SEQ ID NO: 0819) acctaccatgtttatc[A/G]gaaatctcagcctaaa |
| 03 | rs4881110 | 10 | p | p15.2 | PITRM1 | 3185393 | 3.57E-03 | 0.90 | 0.244 | 0.264 | G | (SEQ ID NO: 0820) aatgactggctctaaa[A/G]ctgggtctctgttcac |
| 03 | rs12763675 | 10 | p | p15.3 | DIP2C \| LARP5 | 744591 | 6.79E-04 | 0.89 | 0.335 | 0.360 | A | (SEQ ID NO: 0821) gcaatgtttaaaaaca[A/G]cattttgggctgggcg |
| 03 | rs12572078 | 10 | p | p15.3 | NCRNA00168 \| ADARB2 | 1669110 | 5.49E-05 | 1.16 | 0.268 | 0.240 | A | (SEQ ID NO: 0822) ggtgggtgctgatgag[A/G]gaaggcaggagatgca |
| 03 | rs1875005 | 10 | p | p15.3 | NCRNA00168 \| ADARB2 | 1661398 | 8.56E-04 | 0.90 | 0.450 | 0.476 | A | (SEQ ID NO: 0823) tttatctaatctgatg[A/G]tctctgctattttat |
| 03 | rs2802477 | 10 | q | q11.21 | HNRNPA3P1 \| LOC100130539 | 44696034 | 1.83E-03 | 0.90 | 0.390 | 0.414 | G | (SEQ ID NO: 0824) cctgccgcctagggag[A/G]ttgtgctctgcccctc |
| 02 | rs11238956 | 10 | q | q11.21 | HNRNPA3P1 \| LOC100130539 | 44749854 | 1.09E-05 | 0.87 | 0.316 | 0.348 | G | (SEQ ID NO: 0825) ccactaaaattctaca[A/G]tcagaatgcttggcaa |
| 03 | rs268309 | 10 | q | q11.21 | HNRNPA3P1 \| LOC100130539 | 44611148 | 3.62E-03 | 1.28 | 0.035 | 0.028 | A | (SEQ ID NO: 0826) ctagaagccgaggaca[A/G]tgagatctcttcttct |
| 02 | rs2503853 | 10 | q | q11.21 | RASGEF1A \| FXYD4 | 43750260 | 2.57E-05 | 1.18 | 0.207 | 0.181 | A | (SEQ ID NO: 0827) ccctccctttagtcag[A/G]gattattctggggacc |
| 03 | rs3844600 | 10 | q | q11.22 | ARHGAP22 | 49683897 | 3.00E-02 | 1.09 | 0.224 | 0.211 | A | (SEQ ID NO: 0828) tgctaacagctctacc[A/G]tgatgacaaggccatt |
| 03 | rs1345107 | 10 | q | q11.22 | ARHGAP22 | 49794481 | 3.07E-04 | 1.15 | 0.204 | 0.182 | A | (SEQ ID NO: 0829) gggttactatggtgat[A/G]aggattaggataatgg |
| 03 | rs1806437 | 10 | q | q11.22 | ARHGAP22 | 49798463 | 4.29E-04 | 0.89 | 0.359 | 0.386 | A | (SEQ ID NO: 0830) tgcccccaccacaacc[A/G]aggacagtgtcttgcc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1881740 | 10 | q | q11.22 | FRMPD2 \| MAPK8 | 49551560 | 1.12E-03 | 0.88 | 0.212 | 0.233 | A | (SEQ ID NO: 0831) ggacccagtatcttca[A/G]ggtagcatttttgaac |
| 03 | rs7898026 | 10 | q | q11.22 | FRMPD2 \| MAPK8 | 49497934 | 5.13E-05 | 0.90 | 0.432 | 0.459 | G | (SEQ ID NO: 0832) ctgacagaaggactgc[A/G]gctgaatttcacattt |
| 02 | exm8220865 | 10 | q | q11.22 | GPRIN2 | 46999130 | 5.78E-20 | 79.75 | 0.008 | 0.000 | A | (SEQ ID NO: 0833) tggcctccagcactgg[A/G]tcgcgccttggggcca |
| 03 | rs10509234 | 10 | q | q21.3 | ANXA2P3 \| CTNNA3 | 67473973 | 7.69E-03 | 1.15 | 0.098 | 0.086 | A | (SEQ ID NO: 0834) ttttttcaatgctgac[A/G]cagagtgatttaaaaa |
| 03 | rs4370822 | 10 | q | q21.3 | CTNNA3 | 68072084 | 6.73E-04 | 0.86 | 0.138 | 0.157 | A | (SEQ ID NO: 0835) ccttgggtagctatca[A/G]gtacatgcctaacttg |
| 02 | exm8331707 | 10 | q | q22.1 | SPOCK2 | 73822855 | 1.96E-13 | 17.37 | 0.007 | 0.000 | A | (SEQ ID NO: 0836) gtgtgaccagagcagc[A/G]gtgactgctggtgtgt |
| 02 | exm829854 | 10 | q | q22.1 | SUPV3L1 | 70940052 | 1.26E-07 | Inf | 0.003 | 0.000 | A | (SEQ ID NO: 0837) tagggcacgggagaag[A/G]acatcgaggccgcagg |
| 02 | rs7081974 | 10 | q | q22.3 | LOC100132987 | 80215612 | 8.53E-05 | 0.74 | 0.044 | 0.059 | A | (SEQ ID NO: 0838) ggcagctagggactga[A/G]gcagcgtagcataaca |
| 03 | rs16935969 | 10 | q | q22.3 | LOC100132987 | 80220796 | 1.55E-04 | 0.75 | 0.043 | 0.056 | G | (SEQ ID NO: 0839) gttcgactgcaggaaa[A/G]ccctacaggttgctgg |
| 02 | rs12784427 | 10 | q | q22.3 | LOC100132987 | 80207497 | 4.87E-05 | 0.74 | 0.045 | 0.060 | C | (SEQ ID NO: 0840) ctttcctggggatgct[A/C]attgaggttggaaaga |
| 03 | rs4979997 | 10 | q | q22.3 | LOC100132987 \| LOC283050 | 80435887 | 1.49E-02 | 1.19 | 0.050 | 0.042 | G | (SEQ ID NO: 0841) ctggttttcctaatca[A/G]agaaagcttcaaagaa |
| 03 | rs288444 | 10 | q | q22.3 | LOC100132987 \| LOC283050 | 80348121 | 1.30E-03 | 0.85 | 0.103 | 0.119 | G | (SEQ ID NO: 0842) tattagcagactcacc[A/G]caaaaggatatgccag |
| 03 | rs288450 | 10 | q | q22.3 | LOC100132987 \| LOC283050 | 80356268 | 9.03E-03 | 0.87 | 0.102 | 0.115 | A | (SEQ ID NO: 0843) acagcacaagaggatg[A/G]tgagtgggtatatagt |
| 03 | rs288447 | 10 | q | q22.3 | LOC100132987 \| LOC283050 | 80359650 | 1.12E-02 | 0.88 | 0.103 | 0.116 | A | (SEQ ID NO: 0844) gaagcccaggatgaaa[A/C]agggttgttcaatgtc |
| 03 | rs288442 | 10 | q | q22.3 | LOC100132987 \| LOC283050 | 80348890 | 5.59E-03 | 0.87 | 0.100 | 0.114 | G | (SEQ ID NO: 0845) cacagacatgcaaatt[A/G]ggatgtggaaccactt |
| 02 | rs1249122 | 10 | q | q22.3 | RPS24 \| | 79949403 | 1.28E-02 | 0.89 | 0.367 | 0.393 | T | (SEQ ID NO: 0846) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | LOC283050 | | | | | | | gggaatagatgcagaa[C/T]tggcaaagaagcaaga |
| 03 | rs703990 | 10 | q | q22.3 | ZMIZ1 | 80930439 | 5.80E-04 | 1.14 | 0.224 | 0.202 | A | (SEQ ID NO: 0847) gcaggctttcatgtgt[A/G]ttaactattaaggctc |
| 03 | rs7906565 | 10 | q | q23.31 | LOC119358 \| HTR7 | 91922383 | 8.31E-03 | 0.78 | 0.027 | 0.035 | G | (SEQ ID NO: 0848) aacaaattccatatgt[A/G]attaggatgtacatgc |
| 02 | rs6583759 | 10 | q | q23.32 | NUDT9P1 \| PCGF5 | 92976570 | 7.20E-05 | 1.27 | 0.074 | 0.059 | C | (SEQ ID NO: 0849) tccccctaccattcat[A/C]catcattgattttagg |
| 03 | rs7894133 | 10 | q | q23.32 | NUDT9P1 \| PCGF5 | 92979176 | 8.65E-04 | 1.24 | 0.066 | 0.054 | A | (SEQ ID NO: 0850) ttgtggtatatataca[A/G]taatatcctccaatgc |
| 03 | rs1057971 | 10 | q | q23.32 | PCGF5 | 92987510 | 6.66E-04 | 1.24 | 0.067 | 0.054 | A | (SEQ ID NO: 0851) tggtaggggaggaagt[A/G]gtaggcagaaaccagt |
| 03 | rs7074612 | 10 | q | q23.32 | PCGF5 | 93041869 | 2.55E-03 | 1.22 | 0.064 | 0.053 | G | (SEQ ID NO: 0852) atataaatcccataga[A/G]tgaagtcttttctata |
| 03 | rs7082510 | 10 | q | q23.32 | PCGF5 | 93004825 | 9.19E-04 | 1.23 | 0.067 | 0.055 | A | (SEQ ID NO: 0853) ccttggtcctttactc[A/G]tgcctctctgtactca |
| 03 | rs10882232 | 10 | q | q23.33 | MYOF | 95189263 | 1.29E-02 | 1.08 | 0.416 | 0.397 | G | (SEQ ID NO: 0854) aagatggtataagtca[A/G]tgatttttctgccttc |
| 02 | rs2296580 | 10 | q | q24.32 | ACTR1A | 104241683 | 2.32E-05 | 0.88 | 0.265 | 0.292 | A | (SEQ ID NO: 0855) gcaccctgagaattga[A/C]ttgaagttctcctctt |
| 03 | rs7075281 | 10 | q | q24.32 | C10orf95 \| TMEM180 | 104220301 | 1.16E-03 | 0.89 | 0.282 | 0.305 | A | (SEQ ID NO: 0856) acagcctacattgagc[A/C]aaacaaaacttgattt |
| 03 | rs7475335 | 10 | q | q24.32 | SUFU | 104343428 | 1.27E-03 | 0.90 | 0.309 | 0.333 | A | (SEQ ID NO: 0857) tccagcctaaataaat[A/C]cccacccggtttgggg |
| 03 | rs2236211 | 10 | q | q24.33 | NEURL | 105349816 | 3.89E-03 | 1.10 | 0.421 | 0.399 | A | (SEQ ID NO: 0858) ggggacacaagaggcc[A/G]gggagctctcttcccg |
| 03 | rs7071247 | 10 | q | q24.33 | NEURL | 105257786 | 1.30E-04 | 1.19 | 0.151 | 0.130 | A | (SEQ ID NO: 0859) agatatacgctcaagc[A/C]cctccaagcctttact |
| 03 | rs7918186 | 10 | q | q24.33 | NEURL | 105350447 | 2.46E-03 | 1.10 | 0.420 | 0.397 | A | (SEQ ID NO: 0860) ctagaaacctgcctca[A/G]atggggaaagattagg |
| 03 | rs729952 | 10 | q | q24.33 | NEURL \| SH3PXD2A | 105352990 | 6.35E-03 | 1.09 | 0.417 | 0.396 | A | (SEQ ID NO: 0861) caacactgtgcctaga[A/C]cttggggccagtctgg |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs11191750 | 10 | q | q24.33 | SH3PXD2A | 105388286 | 2.73E-04 | 1.17 | 0.174 | 0.153 | A | (SEQ ID NO: 0862) ggtgcttgagccagta[A/G]ctcagaggtaacccct |
| 03 | rs7918134 | 10 | q | q24.33 | SH3PXD2A | 105391300 | 1.29E-03 | 1.14 | 0.183 | 0.164 | A | (SEQ ID NO: 0863) gtgattgttaggggtg[A/G]catcagcaaggactgt |
| 02 | rs11193561 | 10 | q | q25.1 | SORCS1 \| LOC100128304 | 109374384 | 2.91E-05 | 1.16 | 0.269 | 0.240 | A | (SEQ ID NO: 0864) gctgtaggcaaacagt[A/G]aatccaatttcctcca |
| 03 | rs11195815 | 10 | q | 825.2 | ADRA2A \| GPAM | 113859224 | 5.16E-03 | 1.30 | 0.029 | 0.022 | A | (SEQ ID NO: 0865) ctgtgctctaacactg[A/C]acattcatgtagcttt |
| 03 | rs17129504 | 10 | q | 825.2 | ADRA2A \| GPAM | 113855817 | 2.88E-03 | 1.37 | 0.023 | 0.017 | C | (SEQ ID NO: 0866) tccaggaattcagcac[A/C]ttccagccctggagac |
| 03 | rs6584993 | 10 | q | q25.2 | DUSP5 \| SMC3 | 112314670 | 3.83E-03 | 1.20 | 0.070 | 0.059 | A | (SEQ ID NO: 0867) agagaggaggggagag[A/G]taactgatacatgcta |
| 03 | rs1541466 | 10 | q | q25.3 | ATRNL1 | 117594744 | 3.71E-03 | 0.89 | 0.188 | 0.206 | G | (SEQ ID NO: 0868) cactgtccctgaatgc[A/G]aaataagggtgacctt |
| 03 | rs2024179 | 10 | q | q25.3 | ATRNL1 | 117591081 | 3.35E-03 | 0.89 | 0.188 | 0.207 | G | (SEQ ID NO: 0869) aagcaaaccaattgga[A/G]aggtgttccctgtatt |
| 03 | rs7099933 | 10 | q | q25.3 | LOC100286977 \| LOC100132839 | 115728772 | 6.95E-03 | 1.14 | 0.121 | 0.107 | A | (SEQ ID NO: 0870) ccgatagttggtgact[A/G]ttttatttctttgttg |
| 02 | rs2275111 | 10 | q | q26.11 | SFXN4 | 120917445 | 1.11E-06 | 1.14 | 0.527 | 0.494 | G | (SEQ ID NO: 0871) cagaggaaaacctgcc[A/G]agaggggcaaatggat |
| 02 | rs10749291 | 10 | q | q26.11 | SFXN4 | 120920588 | 3.61E-05 | 0.91 | 0.463 | 0.487 | G | (SEQ ID NO: 0872) tctcctttaagataca[A/G]gaagcttggaagcgga |
| 03 | rs12355817 | 10 | q | q26.12 | SEC23IP \| PPAPDC1A | 121838912 | 2.46E-03 | 1.18 | 0.092 | 0.079 | A | (SEQ ID NO: 0873) cccatctgtaaaatgg[A/G]cacctaccattgattc |
| 02 | rs2901297 | 10 | q | q26.13 | ATE1 | 123521484 | 3.23E-05 | 1.08 | 0.125 | 0.117 | A | (SEQ ID NO: 0874) gagggaatggccatta[A/G]gtaaatgctctttaga |
| 02 | rs1470996 | 10 | q | q26.13 | FAM53B | 126331555 | 2.39E-05 | 1.11 | 0.184 | 0.169 | A | (SEQ ID NO: 0875) caggtcccacgatacc[A/G]tcaggaatgtccgttt |
| 02 | rs7919338 | 10 | q | q26.2 | ADAM12 | 127731365 | 6.00E-02 | 1.10 | 0.276 | 0.258 | A | (SEQ ID NO: 0876) agttaagaaaagtgtc[A/G]caggctaaggaactgg |
| 03 | rs7076942 | 10 | q | q26.3 | GLRX3 \| TCERG1L | 132374743 | 2.51E-04 | 1.13 | 0.292 | 0.266 | C | (SEQ ID NO: 0877) attgtagacttgcacg[A/C]ggggctgtatgggctc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4880419 | 10 | q | q26.3 | INPP5A | 134456109 | 7.78E-03 | 0.92 | 0.411 | 0.432 | A | (SEQ ID NO: 0878) ggggacccctgctccc[A/G]gagtgacaggggagga |
| 03 | rs2814183 | 10 | q | q26.3 | JAKMIP3 | 133948347 | 4.01E-04 | 0.89 | 0.462 | 0.489 | G | (SEQ ID NO: 0879) cgcaaccgcgtgaggc[A/G]acagaaccgacgggca |
| 03 | rs12774814 | 10 | # N/A | # N/A | PITRM1 | 3182572 | 1.26E-03 | 0.89 | 0.241 | 0.264 | A | (SEQ ID NO: 0880) tttattacccacagtc[A/C]ccctcggtctgaaaat |
| 03 | rs11038044 | 11 | p | p11.2 | ALX4 \| CD82 | 44541295 | 5.37E-05 | 0.86 | 0.179 | 0.203 | G | (SEQ ID NO: 0881) tcaattttcgtccagc[A/G]ttctctgctacactgc |
| 01 | exm2264447 | 11 | p | p11.2 | C11orf49 | 46963196 | 1.45E-20 | 20.92 | 0.004 | 0.000 | A | (SEQ ID NO: 0882) cacgcctggccaacct[A/C]ttcaccctcaatctaa |
| 03 | rs6416127 | 11 | p | p11.2 | PRDM11 | 45239959 | 1.31E-03 | 1.15 | 0.169 | 0.151 | C | (SEQ ID NO: 0883) tcagcatcactaataa[A/C]agaaacacagcgtagt |
| 03 | rs4756204 | 11 | p | p13 | SLC1A2 | 35292312 | 4.58E-03 | 1.10 | 0.418 | 0.396 | A | (SEQ ID NO: 0884) gaaaatgagatagaga[A/G]aggaaagaaataatat |
| 03 | rs11030997 | 11 | p | p14.1 | KCNA4 \| FSHB | 30206532 | 2.43E-03 | 0.90 | 0.337 | 0.360 | G | (SEQ ID NO: 0885) ccctattgggctatta[A/G]tagattggcatttaaa |
| 03 | rs4074516 | 11 | p | p14.1 | LGR4 | 27465591 | 5.78E-05 | 1.10 | 0.441 | 0.418 | G | (SEQ ID NO: 0886) attgaaaaaagcctgt[A/G]ggggtgctttgtgcag |
| 02 | rs16916435 | 11 | p | p14.2 | FIBIN \| BBOX1 | 27030676 | 1.54E-05 | 1.09 | 0.095 | 0.088 | G | (SEQ ID NO: 0887) ctgttgattctaccct[A/G]tgaacagctgggctta |
| 03 | rs1602916 | 11 | p | p14.3 | LUZP2 \| ANO3 | 25696461 | 4.84E-03 | 1.09 | 0.447 | 0.425 | A | (SEQ ID NO: 0888) tcaagaccctgaattc[A/C]atttttttgaatatat |
| 02 | rs324204 | 11 | p | p14.3 | NELL1 \| ANO5 | 22001998 | 9.32E-06 | 1.17 | 0.265 | 0.235 | A | (SEQ ID NO: 0889) tccagtttttatggaa[A/G]ctaccatttactctgt |
| 02 | rs324172 | 11 | p | p14.3 | NELL1 \| ANO5 | 21952288 | 3.51E-05 | 1.15 | 0.326 | 0.296 | A | (SEQ ID NO: 0890) agactcatatcaaaac[A/G]caataagtgtgtggca |
| 02 | rs2009912 | 11 | p | p14.3 | NELL1 \| ANO5 | 21945004 | 5.97E-05 | 1.14 | 0.330 | 0.301 | G | (SEQ ID NO: 0891) tgcttctagttagctt[A/G]tctatagcttccctgt |
| 02 | rs10833683 | 11 | p | p14.3 | NELL1 \| ANO5 | 21984498 | 2.53E-05 | 0.87 | 0.429 | 0.462 | A | (SEQ ID NO: 0892) accctacatacacata[A/G]ctaaattttttttct |
| 03 | rs793283 | 11 | p | p15.1 | E2F8 \| NAV2 | 19264497 | 1.07E-03 | 0.88 | 0.205 | 0.226 | A | (SEQ ID NO: 0893) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs7924734 | 11 | p | p15.2 | ARNTL | 13350747 | 8.93E-03 | 1.10 | 0.270 | 0.252 | G | tgtggctcgcagattt[A/G]aaataaagcagaggtc (SEQ ID NO: 0894) |
| 03 | rs12290622 | 11 | p | p15.2 | ARNTL | 13314307 | 4.97E-03 | 1.10 | 0.310 | 0.290 | G | gagagtcacaggaagg[A/G]ccccttt acgtcggat (SEQ ID NO: 0895) |
| 03 | rs7949336 | 11 | p | p15.2 | ARNTL | 13319894 | 1.22E-02 | 1.09 | 0.273 | 0.255 | G | agtagatagtggtcca[A/G]gcctagtatttttaac (SEQ ID NO: 0896) |
| 03 | rs10766066 | 11 | p | p15.2 | RASSF10 \| ARNTL | 13278027 | 2.73E-02 | 1.08 | 0.296 | 0.280 | G | tcccccagaggtgtgt[A/G]tggctagttagctcac (SEQ ID NO: 0897) |
| 03 | rs11042937 | 11 | p | p15.3 | MRVI1 \| CTR9 | 10745394 | 3.79E-04 | 1.12 | 0.520 | 0.492 | A | attagtgtgcagttac[A/G]tagcttgggcccagac (SEQ ID NO: 0898) |
| 03 | rs10834648 | 11 | p | p15.4 | LOC650368 \| TRPC2 | 3645345 | 2.92E-03 | 1.11 | 0.325 | 0.303 | G | cagcacatgaatatgg[A/C]ggcctgctgtgtgcca (SEQ ID NO: 0899) |
| 03 | rs17403795 | 11 | p | p15.4 | LYVE1 | 10581217 | 2.51E-03 | 0.86 | 0.106 | 0.122 | A | ctagcctatacttaac[A/G]cataagtttcatccat (SEQ ID NO: 0900) |
| 03 | rs4910630 | 11 | p | p15.4 | OR52M1 \| C11orf40 | 4590639 | 2.59E-04 | 0.89 | 0.393 | 0.421 | A | aaaagattgggctgaa[A/G]ggaaagagatgagatg (SEQ ID NO: 0901) |
| 03 | rs12271195 | 11 | p | p15.4 | SYT9 | 7463443 | 2.27E-03 | 0.86 | 0.116 | 0.132 | A | ccctcctgctgccctc[A/G]gtttagggtttacaag (SEQ ID NO: 0902) |
| 02 | rs1908177 | 11 | p | p15.4 | TRIM68 \| OR51D1 | 4659419 | 6.34E-06 | 0.87 | 0.389 | 0.424 | A | ctcagtgaaaatggct[A/G]aggggaggagcttttc (SEQ ID NO: 0903) |
| 03 | rs1865558 | 11 | p | p15.4 | WEE1 \| SWAP70 | 9650585 | 1.83E-03 | 1.11 | 0.289 | 0.267 | A | tctcctctttcacccc[A/C]acatgcaattcaactt (SEQ ID NO: 0904) |
| 02 | rs885414 | 11 | p | p15.4 | ZNF195 \| ART5 | 3644307 | 1.01E-02 | 1.16 | 0.189 | 0.168 | C | tatatctccatgatat[A/G]taatccaagatatata (SEQ ID NO: 0905) |
| 02 | exm926722 | 11 | q | q13.1 | SCYL1 | 65305309 | 3.44E-14 | 9.50 | 0.010 | 0.001 | A | cttatttgtgagagaa[C/G]agaaacctccagggtg (SEQ ID NO: 0906) |
| 03 | rs10752564 | 11 | q | q13.3 | FGF19 \| FGF4 | 69540990 | 1.84E-04 | 1.13 | 0.322 | 0.295 | A | cggtgctccagtcgtc[A/C]tgctgggccagcacag (SEQ ID NO: 0907) |
| 02 | exm936578 | 11 | q | q13.3 | PPFIA1 | 70170536 | 1.14E-16 | 5.27 | 0.007 | 0.000 | G | ggaggaagcggctgtc[A/G]cagtggctgggcttag (SEQ ID NO: 0908) |
| | | | | | | | | | | | | cttactaaagaactca[A/G]tgtatgcagggaacag |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs11228498 | 11 | q | q13.3 | TPCN2 \| MYEOV | 68870298 | 9.14E-05 | 1.11 | 0.508 | 0.482 | A | (SEQ ID NO: 0909) ttgcatttgttttggg[A/G]actgtctgaggttaga |
| 02 | rs10751211 | 11 | q | q13.4 | ARAP1 | 72405223 | 3.03E-05 | 1.18 | 0.202 | 0.177 | A | (SEQ ID NO: 0910) tggcagcagtggagat[A/G]gacagagcagagagat |
| 02 | exm937263 | 11 | q | q13.4 | DHCR7 | 71155161 | 1.41E-08 | 35.86 | 0.004 | 0.000 | A | (SEQ ID NO: 0911) tgaccagtacagctgc[A/G]ccctgactggccctgt |
| 02 | rs6592850 | 11 | q | q14.1 | ODZ4 | 79226201 | 9.43E-05 | 1.19 | 0.407 | 0.366 | G | (SEQ ID NO: 0912) aataagcaataataaa[A/G]atgtgacttttacagc |
| 03 | rs10831309 | 11 | q | q21 | ENDOD1 \| SESN3 | 94881894 | 5.60E-03 | 0.91 | 0.449 | 0.471 | A | (SEQ ID NO: 0913) tcatataacttagcta[A/G]gtcattgtgaaatttt |
| 03 | rs16922232 | 11 | q | q21 | LOC100129203 \| FAM76B | 95304581 | 8.66E-03 | 1.26 | 0.033 | 0.026 | A | (SEQ ID NO: 0914) catggagaacaggtgt[A/G]acctaagtgcagagcc |
| 03 | rs2123325 | 11 | q | q22.1 | CNTN5 | 99959543 | 4.27E-04 | 0.88 | 0.279 | 0.305 | G | (SEQ ID NO: 0915) tctaccaaacatacaa[A/G]aaagagctgatatcaa |
| 03 | rs7128754 | 11 | q | q22.1 | JRKL \| CNTN5 | 97618161 | 1.23E-02 | 1.09 | 0.366 | 0.348 | A | (SEQ ID NO: 0916) aaatcctggtgaacac[A/C]tgtgccttttcacaga |
| 03 | rs11212569 | 11 | q | q22.1 | JRKL \| CNTN5 | 97623375 | 7.12E-04 | 1.12 | 0.351 | 0.326 | C | (SEQ ID NO: 0917) atggtgctttttcaa[A/C]catacccatgaccaat |
| 03 | rs12792912 | 11 | q | q22.2 | LOC100288111 \| MMP13 | 102801303 | 1.97E-02 | 0.93 | 0.414 | 0.432 | C | (SEQ ID NO: 0918) ctcacatttaaactga[A/C]ggaatcataaagtaac |
| 03 | rs12788925 | 11 | q | q22.2 | LOC100288111 \| MMP13 | 102801847 | 1.80E-02 | 0.93 | 0.413 | 0.431 | G | (SEQ ID NO: 0919) aaaagaaattctgggt[A/G]tctccagagagggaat |
| 02 | rs1784408 | 11 | q | q22.2 | MMP20 | 102469509 | 2.13E-02 | 1.11 | 0.367 | 0.343 | G | (SEQ ID NO: 0920) aaaagaagacctttaa[C/G]gctcaacaacatgcat |
| 02 | exm952255 | 11 | q | q22.3 | CASP12 | 104768141 | 5.64E-12 | 6.54 | 0.020 | 0.005 | A | (SEQ ID NO: 0921) aatgccatctagaaag[A/G]tcttgatcagcaactt |
| 03 | rs10891431 | 11 | q | q23.2 | LOC100132686 \| NCAM1 | 112641531 | 1.95E-02 | 0.92 | 0.240 | 0.256 | A | (SEQ ID NO: 0922) ccagccaatgggagag[A/G]tgaatgctagagggtt |
| 03 | rs2073848 | 11 | q | q23.2 | ZBTB16 | 114051904 | 7.66E-04 | 1.15 | 0.178 | 0.159 | G | (SEQ ID NO: 0923) agagctcccttcatgc[A/G]attaaagtatgactga |
| 03 | rs3782007 | 11 | q | q23.2 | ZBTB16 | 114066438 | 4.47E-04 | 1.15 | 0.207 | 0.186 | A | (SEQ ID NO: 0924) gataatctcaatatag[A/G]cctcgcatggagtaag |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs11215574 | 11 | q | q23.3 | CADM1 | 115363443 | 3.37E-02 | 0.93 | 0.245 | 0.260 | G | (SEQ ID NO: 0925) gttttcaccatgggag[A/G]aagaaaacacaaataa |
| 02 | exm960718 | 11 | q | q23.3 | PHLDB1 | 118516274 | 5.43E-15 | 33.17 | 0.007 | 0.000 | A | (SEQ ID NO: 0926) ggaggagggtgagcac[A/G]cctatgatacgctgag |
| 01 | rs11217801 | 11 | q | q23.3 | POU2F3 | 120165942 | 2.66E-06 | 1.25 | 0.132 | 0.109 | G | (SEQ ID NO: 0927) ctaacagatagcgccc[A/G]ggttggaggcaaagca |
| 03 | rs17671708 | 11 | q | q24.1 | LOC100128242 | 123306172 | 1.59E-02 | 1.11 | 0.147 | 0.134 | G | (SEQ ID NO: 0928) cctcttcatattttca[A/G]ctttgtgcagtgaaaa |
| 03 | rs10892895 | 11 | q | q24.1 | UBASH3B | 122630672 | 2.34E-02 | 1.14 | 0.086 | 0.076 | G | (SEQ ID NO: 0929) gtgttcactcctttgt[A/G]taattccctcccctca |
| 03 | rs1946091 | 11 | q | q24.2 | KIRREL3 | 126612903 | 3.20E-03 | 1.10 | 0.388 | 0.366 | G | (SEQ ID NO: 0930) tatctgagatgaggcc[A/G]tcagtgaggacctcct |
| 02 | exm968612 | 11 | q | q24.2 | RPUSD4 | 126081523 | 1.59E-08 | Inf | 0.003 | 0.000 | A | (SEQ ID NO: 0931) cgacgcgctccacctg[A/G]gcgccgccatcttaca |
| 03 | rs11221660 | 11 | q | q24.3 | RICS \| BARX2 | 129182778 | 1.35E-02 | 0.92 | 0.388 | 0.407 | A | (SEQ ID NO: 0932) ctgaggtttccgggat[A/G]aggagagggtgtggcg |
| 03 | rs7122696 | 11 | q | q25 | NTM | 132001390 | 1.81E-04 | 1.16 | 0.215 | 0.192 | A | (SEQ ID NO: 0933) acaaggctgcactttc[A/G]tagggttccatcataa |
| 03 | rs7310913 | 12 | p | p11.23 | ITPR2 | 26854487 | 1.45E-02 | 1.09 | 0.315 | 0.297 | C | (SEQ ID NO: 0934) ccagaccctatacata[A/C]gaataaaatgttacat |
| 03 | rs11048661 | 12 | p | p11.23 | ITPR2 | 26854124 | 1.31E-03 | 1.11 | 0.355 | 0.331 | C | (SEQ ID NO: 0935) ggcagtgaaagtcatg[A/C]ttgtaccgcaatcaat |
| 02 | rs11054439 | 12 | p | p13.2 | ETV6 | 11895308 | 7.91E-05 | 0.88 | 0.336 | 0.366 | A | (SEQ ID NO: 0936) atagggactcagaaaa[A/G]gcatcattcccttcat |
| 02 | rs2051525 | 12 | p | p13.2 | ETV6 | 11888423 | 7.12E-05 | 0.88 | 0.345 | 0.375 | A | (SEQ ID NO: 0937) ccctaataaacaaact[A/G]cttaattgaacagccc |
| 03 | rs17181375 | 12 | p | p13.31 | ANO2 | 5678868 | 6.25E-03 | 1.15 | 0.109 | 0.097 | A | (SEQ ID NO: 0938) gtctcaatcccagcca[A/G]gagtgaataatagatg |
| 03 | rs7296720 | 12 | p | p13.32 | TSPAN9 | 3374920 | 2.50E-04 | 1.19 | 0.128 | 0.110 | G | (SEQ ID NO: 0939) tagaaatttgtcgaac[A/G]tgtttgataaaatgga |
| 03 | rs2429166 | 12 | p | p13.33 | CACNA2D4 | 2025907 | 1.12E-03 | 0.88 | 0.181 | 0.201 | G | (SEQ ID NO: 0940) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10774066 | 12 | p | p13.33 | FKBP4 \| ITFG2 | 2920736 | 3.61E-04 | 1.18 | 0.144 | 0.125 | G | gtctcctggattgggc[A/G]tgaggagggctttggg (SEQ ID NO: 0941) |
| 03 | rs10848706 | 12 | p | p13.33 | FKBP4 \| ITFG2 | 2919701 | 3.45E-04 | 1.18 | 0.144 | 0.125 | G | aaaaaaaaatgattct[A/G]ccttatctgggatttt (SEQ ID NO: 0942) |
| 03 | rs2286601 | 12 | p | p13.33 | ITFG2 | 2932177 | 2.25E-04 | 1.18 | 0.148 | 0.128 | A | tgcagatatattctga[A/G]gctgaactgtgttaca (SEQ ID NO: 0943) |
| 03 | rs3759411 | 12 | p | p13.33 | LOC100288472 \| LOC728147 | 2901570 | 1.10E-04 | 1.19 | 0.145 | 0.124 | G | cacttccctttctgac[A/G]tatcccctgatgtaag (SEQ ID NO: 0944) |
| 03 | rs3814249 | 12 | p | p13.33 | NRIP2 | 2936276 | 1.57E-03 | 1.14 | 0.174 | 0.156 | G | catccaccttatctgt[A/G]ggtgactcctgctggg (SEQ ID NO: 0945) |
| 03 | rs3814250 | 12 | p | p13.33 | NRIP2 | 2936049 | 1.89E-04 | 1.18 | 0.147 | 0.127 | A | tggaagggcagacacc[A/G]tagtccccagctacct (SEQ ID NO: 0946) |
| 03 | rs11062376 | 12 | p | p13.33 | NRIP2 \| FOXM1 | 2950208 | 3.76E-04 | 1.17 | 0.146 | 0.127 | A | ctgcttgggctgggtc[A/G]aaggctctgctgactg (SEQ ID NO: 0947) |
| 02 | exm997545 | 12 | q | q13.11 | HDAC7 | 48187329 | 6.43E-21 | 12.71 | 0.013 | 0.001 | A | ttatgtccccaaaccc[A/G]cctggggcaagggggt (SEQ ID NO: 0948) |
| 03 | rs7488270 | 12 | q | q13.12 | SPATS2 | 49784365 | 1.05E-04 | 1.24 | 0.087 | 0.071 | A | tccccggtgctgcccc[A/G]ggggagccgcccagcc (SEQ ID NO: 0949) |
| 03 | rs7309610 | 12 | q | q13.12 | SPATS2 | 49783814 | 1.61E-04 | 1.24 | 0.087 | 0.071 | A | ttcatccttatttggc[A/G]ttaaagttaacacaaa (SEQ ID NO: 0950) |
| 03 | rs186231 | 12 | q | q13.13 | FIGNL2 | 52212489 | 9.30E-04 | 1.16 | 0.145 | 0.127 | A | atttcaacttgaacaa[A/G]aaaacaaaggcgttag (SEQ ID NO: 0951) |
| 03 | rs172559 | 12 | q | q13.13 | FLJ33996 | 52204246 | 7.90E-04 | 1.16 | 0.143 | 0.125 | A | tgcacaggaggctgag[A/G]tgggagagagaaaaag (SEQ ID NO: 0952) |
| 03 | rs3900362 | 12 | q | q13.13 | SCN8A | 52108030 | 2.18E-04 | 1.19 | 0.135 | 0.116 | G | taatatttggcaaagc[A/G]ttgccacttacccact (SEQ ID NO: 0953) |
| 03 | rs303808 | 12 | q | q13.13 | SCN8A | 52163789 | 2.88E-04 | 1.16 | 0.169 | 0.149 | G | ctgttatagtttccac[A/G]tcacaactaactgttt (SEQ ID NO: 0954) |
| 03 | rs303771 | 12 | q | q13.13 | SCN8A | 52152192 | 8.38E-04 | 1.17 | 0.131 | 0.114 | G | aaaggggatgaggagc[A/G]gatgggctggggacac (SEQ ID NO: 0955) |
| | | | | | | | | | | | | gttcgacattttgcaa[A/G]tctctttaatgtctgg |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2580807 | 12 | q | q13.13 | SCN8A | 52174231 | 6.32E-04 | 1.17 | 0.143 | 0.125 | A | (SEQ ID NO: 0956) cctttccttccaggtc[A/G]tttgagtcaagttgaa |
| 03 | rs715930 | 12 | q | q13.3 | B4GALNT1 | 58023981 | 1.85E-03 | 0.88 | 0.190 | 0.210 | A | (SEQ ID NO: 0957) ggctgctgtaagtgac[A/C]agttgtagttgcctgt |
| 03 | rs11173855 | 12 | q | q14.1 | LOC100289417 \| FAM19A2 | 61637441 | 1.33E-03 | 0.90 | 0.438 | 0.463 | A | (SEQ ID NO: 0958) tagactaaaattaata[A/C]agataagagttgaaac |
| 03 | rs10784186 | 12 | q | q14.1 | LOC100289417 \| FAM19A2 | 61604963 | 2.08E-03 | 0.91 | 0.425 | 0.449 | A | (SEQ ID NO: 0959) attatcatttcttctt[A/C]atttattcctagtctg |
| 02 | rs2270482 | 12 | q | q14.1 | PPM1H | 63087901 | 2.89E-05 | 0.82 | 0.131 | 0.155 | A | (SEQ ID NO: 0960) tccctataaaggaaga[A/G]gtagtcagtgtggtga |
| 03 | rs2711666 | 12 | q | q14.1 | SLC16A7 | 60132210 | 1.06E-02 | 0.92 | 0.437 | 0.457 | A | (SEQ ID NO: 0961) tgggctgctatttctc[A/G]tggaccaataacaaga |
| 03 | rs10431559 | 12 | q | q14.1 | SLC16A7 \| LOC100289417 | 60244639 | 7.38E-02 | 0.94 | 0.438 | 0.452 | A | (SEQ ID NO: 0962) attagtcttgggtcca[A/G]attaatttcatgatca |
| 03 | rs10437957 | 12 | q | q14.1 | SLC16A7 \| LOC100289417 | 60202218 | 3.19E-02 | 0.93 | 0.440 | 0.457 | A | (SEQ ID NO: 0963) ctaataatctccctag[A/G]ttttgtcctttgtcta |
| 03 | rs7307997 | 12 | q | q14.2 | AVPR1A \| DPY19L2 | 63557914 | 8.89E-03 | 0.92 | 0.414 | 0.434 | G | (SEQ ID NO: 0964) gaattcttgactgcct[A/G]tgtgttactcttcttc |
| 03 | rs6581482 | 12 | q | q14.2 | AVPR1A \| DPY19L2 | 63682898 | 1.85E-02 | 0.92 | 0.324 | 0.342 | A | (SEQ ID NO: 0965) gtaaagattgggaaaa[A/G]cttgcactaacttcca |
| 03 | rs11612942 | 12 | q | q14.2 | AVPR1A \| DPY19L2 | 63704363 | 1.38E-03 | 1.16 | 0.142 | 0.125 | A | (SEQ ID NO: 0966) ctggatgttggggaga[A/G]ttaacttgagttcaga |
| 02 | exm1020169 | 12 | q | q15 | CAND1 | 67706476 | 4.89E-10 | 40.96 | 0.004 | 0.000 | A | (SEQ ID NO: 0967) ctcttctctgcttctg[A/G]aatggttagcagtgct |
| 02 | rs1861933 | 12 | q | q15 | LOC100286998 \| LOC100288856 | 68842405 | 2.18E-05 | 1.16 | 0.214 | 0.190 | G | (SEQ ID NO: 0968) aagtaaaggaattata[A/G]actagctgctgcttca |
| 02 | rs7298169 | 12 | q | q15 | LOC100286998 \| LOC100288856 | 68854225 | 1.61E-05 | 1.21 | 0.129 | 0.109 | G | (SEQ ID NO: 0969) gccaaagctgtcagaa[A/G]acatcctacaatgcac |
| 02 | rs2216437 | 12 | q | q15 | LOC100286998 \| LOC100288856 | 68850924 | 4.99E-05 | 1.19 | 0.097 | 0.082 | G | (SEQ ID NO: 0970) acccccttgttgagcac[A/G]tggataccttttgaggt |
| 02 | rs3863373 | 12 | q | q15 | PTPRR | 71288396 | 3.63E-05 | 1.09 | 0.349 | 0.330 | A | (SEQ ID NO: 0971) tatttttagtaaaata[A/C]taaatacacaccttgt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2035151 | 12 | q | q21.2 | E2F7 | 77445086 | 8.84E-05 | 1.11 | 0.098 | 0.089 | G | (SEQ ID NO: 0972) tgtctcctcaacccac[A/G]tttgaaaggggctcca |
| 03 | rs12422952 | 12 | q | q21.2 | GLIPR1 | 75881018 | 3.38E-04 | 0.89 | 0.372 | 0.400 | A | (SEQ ID NO: 0973) ctggagttgcttttgg[A/G]gtctgcattttaacaa |
| 03 | rs7969930 | 12 | q | q21.2 | GLIPR1L2 \| GLIPR1 | 75867565 | 6.61E-04 | 0.90 | 0.375 | 0.401 | G | (SEQ ID NO: 0974) ttttgacagatagttg[A/G]caacagacatgtacag |
| 03 | rs11180540 | 12 | q | q21.2 | GLIPR1L2 \| GLIPR1 | 75873161 | 5.42E-04 | 0.89 | 0.375 | 0.402 | A | (SEQ ID NO: 0975) gctacaggtgtgcctg[A/G]aatgtttctttacttt |
| 03 | rs10785190 | 12 | q | q21.2 | GLIPR1L2 \| GLIPR1 | 75819844 | 7.57E-04 | 0.90 | 0.375 | 0.401 | G | (SEQ ID NO: 0976) aatacaactagagaga[A/G]atatatagatacttaa |
| 03 | rs733880 | 12 | q | q21.2 | KRR1 \| LOC100289143 | 75976164 | 7.43E-05 | 1.11 | 0.495 | 0.470 | G | (SEQ ID NO: 0977) taaaattgaccatttt[A/G]cagacataatggcaag |
| 03 | rs6582294 | 12 | q | q21.2 | KRR1 \| LOC100289143 | 76034992 | 7.29E-04 | 0.90 | 0.383 | 0.409 | A | (SEQ ID NO: 0978) gaatgaatcatcccca[A/G]tttgtttcttgctaca |
| 03 | rs12423804 | 12 | q | q21.31 | PPP1R12A \| C12orf64 | 80580111 | 7.63E-04 | 0.90 | 0.436 | 0.462 | A | (SEQ ID NO: 0979) acctgatgggagagac[A/G]cggctaagtaggaaag |
| 03 | rs4882448 | 12 | q | q21.31 | TMTC2 \| SLC6A15 | 83746599 | 1.24E-02 | 0.92 | 0.467 | 0.486 | G | (SEQ ID NO: 0980) tcctctgacatggatg[A/G]ttgtggcattagtaac |
| 03 | rs17790382 | 12 | q | q22 | EEA1 | 93230276 | 4.98E-03 | 0.85 | 0.087 | 0.100 | C | (SEQ ID NO: 0981) atgcttcatagcttac[A/C]aagttatttcagagat |
| 03 | rs11829776 | 12 | q | q22 | FGD6 | 95531442 | 2.93E-03 | 0.89 | 0.195 | 0.214 | G | (SEQ ID NO: 0982) ataggactgaacaaca[A/G]agaattgctgatatct |
| 03 | rs12579299 | 12 | q | q22 | NR2C1 | 95442242 | 1.10E-03 | 0.88 | 0.193 | 0.214 | G | (SEQ ID NO: 0983) cgcaataactgctatt[A/G]taactgacttaacagg |
| 02 | rs14121 | 12 | q | q22 | VEZT | 95694394 | 9.10E-06 | 0.85 | 0.262 | 0.294 | G | (SEQ ID NO: 0984) gaacagacttttggtg[A/G]tgaggaggaagaacaa |
| 01 | rs3596 | 12 | q | q22 | VEZT | 95696420 | 8.71E-08 | 1.16 | 0.508 | 0.471 | G | (SEQ ID NO: 0985) gaagtcagtggttctc[A/G]gttgtattagtggggt |
| 02 | rs10859856 | 12 | q | q22 | VEZT | 95631276 | 5.23E-07 | 1.15 | 0.505 | 0.470 | G | (SEQ ID NO: 0986) cctctggtttggtgat[A/G]tcagtggaggctgata |
| 02 | rs7959730 | 12 | q | q23.1 | NEDD1 \| RMST | 97495927 | 3.16E-05 | 1.09 | 0.347 | 0.328 | G | (SEQ ID NO: 0987) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs10861688 | 12 | q | q23.3 | CRY1 | 107394048 | 9.61E-05 | 0.85 | 0.169 | 0.193 | A | aatgcaaatgaaaaca[A/G]tatgagaagccactac (SEQ ID NO: 0988) |
| 03 | rs973724 | 12 | q | q23.3 | CRY1 \| BTBD11 | 107578877 | 4.68E-04 | 0.89 | 0.316 | 0.342 | G | tgtgctgcacaaggac[A/G]actgaaacaaaagaat (SEQ ID NO: 0989) |
| 03 | rs1896058 | 12 | q | q23.3 | LOC100287556 \| WSCD2 | 108405763 | 7.17E-04 | 1.11 | 0.436 | 0.410 | A | taacaagaatgaccca[A/G]tctatatgatcaactt (SEQ ID NO: 0990) |
| 03 | rs11068393 | 12 | q | q24.22 | FBXO21 | 117623136 | 3.08E-04 | 0.87 | 0.193 | 0.217 | G | catgaaagtgtcacta[A/G]aaaactctacctactg (SEQ ID NO: 0991) |
| 03 | rs1466852 | 12 | q | q24.22 | FBXO21 | 117591843 | 1.57E-04 | 0.86 | 0.192 | 0.216 | A | ggagagagaaatatct[A/G]tcagtggaacaactgt (SEQ ID NO: 0992) |
| 01 | rs10431397 | 12 | q | q24.23 | KSR2 | 118106194 | 1.38E-15 | 2.43 | 0.021 | 0.009 | A | atagacactggcccac[A/G]gtgttgttgaaaagaa (SEQ ID NO: 0993) |
| 03 | rs10846578 | 12 | q | q24.31 | DNAH10 | 124400278 | 7.08E-04 | 1.12 | 0.306 | 0.282 | A | cctatgatctggtgga[A/G]caccctccctcctgaa (SEQ ID NO: 0994) |
| 03 | rs7975815 | 12 | q | q24.31 | DNAH10 | 124388129 | 3.30E-03 | 0.72 | 0.019 | 0.026 | G | tgtctgttcatacacc[A/G]gaatatcattcagccc (SEQ ID NO: 0995) |
| 02 | exm1044289 | 12 | q | q24.31 | P2RX7 | 121622550 | 1.22E-10 | 6.57 | 0.009 | 0.001 | A | gtgagagtaggtcact[A/G]ttgaggcccccataca (SEQ ID NO: 0996) |
| 03 | rs4765052 | 12 | q | q24.32 | TMEM132B | 126043965 | 1.91E-03 | 0.87 | 0.140 | 0.158 | A | tgccgctggaggatcc[A/G]gaaagagtttccgaag (SEQ ID NO: 0997) |
| 03 | rs4765044 | 12 | q | q24.32 | TMEM132B | 125981136 | 9.73E-04 | 0.90 | 0.375 | 0.400 | A | atcacaaagccatact[A/G]caggtacagggtctga (SEQ ID NO: 0998) |
| 02 | exm1054045 | 12 | q | q24.33 | POLE | 133263886 | 1.21E-08 | 7.12 | 0.007 | 0.001 | C | ctcctgggttgccccc[A/G]tccttgagccaatgta (SEQ ID NO: 0999) |
| 02 | rs2012359 | 13 | q | q12.12 | PARP4 | 25078073 | 2.11E-02 | 1.16 | 0.135 | 0.119 | G | catgtctctgaggagc[C/G]gcgggcggcggcgcgc (SEQ ID NO: 1000) |
| 03 | rs3117849 | 13 | q | q12.13 | ATP8A2 | 26299179 | 4.22E-03 | 1.34 | 0.025 | 0.018 | A | cacatattgcaagcta[C/G]gatattattcaatttt (SEQ ID NO: 1001) |
| 03 | rs7328428 | 13 | q | q12.3 | HMGB1 \| USPL1 | 31083678 | 8.44E-04 | 1.24 | 0.062 | 0.051 | A | tgtcctcccagagtct[A/G]tcatctatcaggaagt (SEQ ID NO: 1002) aattaagaatattggg[A/G]cacggccaggcgtggt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1543660 | 13 | q | q12.3 | KIAA0774 | 29855650 | 6.01E-03 | 1.29 | 0.031 | 0.024 | G | (SEQ ID NO: 1003) ttaagtcactgcataa[A/G]tatctgtcacacaaat |
| 03 | rs9506012 | 13 | q | q12.3 | LOC100287487 \| POMP | 29135021 | 2.97E-04 | 1.16 | 0.183 | 0.161 | G | (SEQ ID NO: 1004) ccaaagctccctccac[A/G]gcagccaacacaccct |
| 03 | rs663528 | 13 | q | q12.3 | UBL3 \| KATNAL1 | 30607076 | 4.92E-04 | 0.90 | 0.464 | 0.492 | A | (SEQ ID NO: 1005) tctgaacaaagatgac[A/C]ggaggagctgccttgg |
| 03 | rs8002871 | 13 | q | q12.3 | UBL3 \| KATNAL1 | 30574667 | 4.74E-04 | 1.12 | 0.464 | 0.437 | G | (SEQ ID NO: 1006) tgtgctttggagtttg[A/G]gcggcagaaccgcgta |
| 02 | rs9595159 | 13 | q | q13.1 | FRY | 32798953 | 4.76E-05 | 1.16 | 0.230 | 0.204 | A | (SEQ ID NO: 1007) tatttcccccgaataa[A/G]agccttatataatgtt |
| 02 | rs394307 | 13 | q | q13.1 | LOC122038 \| KL | 33569834 | 3.37E-05 | 1.08 | 0.442 | 0.422 | G | (SEQ ID NO: 1008) actgagtagtcatcag[A/G]atatttggttgtgttg |
| 03 | rs1199994 | 13 | q | q13.3 | CSNK1A1L \| POSTN | 37694027 | 1.50E-03 | 1.23 | 0.063 | 0.052 | G | (SEQ ID NO: 1009) caagtactcaataaat[A/G]taaacaaacctgtcat |
| 03 | rs9315468 | 13 | q | q13.3 | FAM48A \| CSNK1A1L | 37667508 | 8.35E-04 | 0.90 | 0.416 | 0.442 | A | (SEQ ID NO: 1010) atgaaatagtaaatac[A/C]agccttacactttgaa |
| 03 | rs9603439 | 13 | q | q13.3 | FREM2 | 39402920 | 9.64E-03 | 1.20 | 0.055 | 0.046 | A | (SEQ ID NO: 1011) gagctgggtttatatg[A/C]attgacatgaaaagtt |
| 03 | rs9603442 | 13 | q | q13.3 | FREM2 | 39406629 | 5.34E-03 | 1.21 | 0.055 | 0.046 | A | (SEQ ID NO: 1012) aactggttatttccta[A/G]agctgagattgtgagg |
| 03 | rs2766484 | 13 | q | q14.13 | SIAH3 \| ZC3H13 | 46443060 | 1.56E-04 | 1.13 | 0.409 | 0.380 | C | (SEQ ID NO: 1013) attacaagtcagcagt[A/C]caagaaaggaacaggg |
| 03 | rs9567586 | 13 | q | q14.13 | SIAH3 \| ZC3H13 | 46431655 | 3.94E-04 | 1.12 | 0.409 | 0.382 | G | (SEQ ID NO: 1014) acaaagaatataaaca[A/G]agtacacagaagaagt |
| 02 | exm1068520 | 13 | q | q14.2 | CYSLTR2 | 49281785 | 5.84E-17 | 5.52 | 0.017 | 0.003 | T | (SEQ ID NO: 1015) agtctgtctttgcata[A/T]acccactttccatgtc |
| 03 | rs2765760 | 13 | q | q14.2 | FAM10A4 \| DLEU7 | 50851577 | 1.59E-04 | 0.83 | 0.123 | 0.145 | A | (SEQ ID NO: 1016) ggcacagtcacacgcc[A/C]acgaggccagccctgc |
| 03 | rs9591076 | 13 | q | q14.2 | HTR2A \| SUCLA2 | 48127371 | 1.44E-04 | 1.60 | 0.017 | 0.011 | A | (SEQ ID NO: 1017) ccttcagtttctccct[A/G]gggcttcattatggct |
| 03 | rs9596839 | 13 | q | q14.3 | OLFM4 \| LOC100287887 | 54264395 | 3.64E-02 | 0.93 | 0.283 | 0.298 | A | (SEQ ID NO: 1018) taattttaattgatcc[A/G]tcacctctactgtttg |

TABLE 1-continued

<table>
<tr><th colspan="13">TABLES<br>(Based on build 37 or "GRCh37" as defined by the Genome Reference Consortium)</th></tr>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>03</td><td>rs9563182</td><td>13</td><td>q</td><td>q14.3</td><td>OLFM4 | LOC100287887</td><td>54395310</td><td>1.71E-02</td><td>0.90</td><td>0.155</td><td>0.169</td><td>G</td><td>(SEQ ID NO: 1019) gtaattattaaattac[A/G]tggaagttccttgccc</td></tr>
<tr><td>03</td><td>rs9316660</td><td>13</td><td>q</td><td>q14.3</td><td>OLFM4 | LOC100287887</td><td>54353562</td><td>2.90E-03</td><td>0.88</td><td>0.146</td><td>0.163</td><td>G</td><td>(SEQ ID NO: 1020) tttacttacctcttac[A/G]tagtcctaagcacaat</td></tr>
<tr><td>03</td><td>rs9563183</td><td>13</td><td>q</td><td>q14.3</td><td>OLFM4 | LOC100287887</td><td>54396931</td><td>1.71E-02</td><td>0.90</td><td>0.155</td><td>0.169</td><td>C</td><td>(SEQ ID NO: 1021) gaggagagctagtgaa[A/C]taaaagcctaagtata</td></tr>
<tr><td>03</td><td>rs12860689</td><td>13</td><td>q</td><td>q14.3</td><td>OLFM4 | LOC100287887</td><td>54315805</td><td>2.89E-03</td><td>0.88</td><td>0.146</td><td>0.163</td><td>G</td><td>(SEQ ID NO: 1022) tttggggatatagcct[A/G]gaaatgtgtactttta</td></tr>
<tr><td>03</td><td>rs9568924</td><td>13</td><td>q</td><td>q14.3</td><td>OLFM4 | LOC100287887</td><td>54360952</td><td>3.94E-03</td><td>0.88</td><td>0.148</td><td>0.165</td><td>C</td><td>(SEQ ID NO: 1023) ctgtattacacattat[A/C]cataatctagaaatga</td></tr>
<tr><td>03</td><td>rs9568902</td><td>13</td><td>q</td><td>q14.3</td><td>OLFM4 | LOC100287887</td><td>54324954</td><td>3.15E-03</td><td>0.88</td><td>0.145</td><td>0.162</td><td>A</td><td>(SEQ ID NO: 1024) aaagctgtttgttttt[A/G]agaagttctatgctca</td></tr>
<tr><td>03</td><td>rs2806731</td><td>13</td><td>q</td><td>q14.3</td><td>OLFM4 | LOC100287887</td><td>54290333</td><td>3.33E-03</td><td>0.89</td><td>0.191</td><td>0.210</td><td>G</td><td>(SEQ ID NO: 1025) aacttctgtttttact[A/G]ttttctaggcaatgtc</td></tr>
<tr><td>03</td><td>rs9568919</td><td>13</td><td>q</td><td>q14.3</td><td>OLFM4 | LOC100287887</td><td>54352229</td><td>2.71E-03</td><td>0.88</td><td>0.146</td><td>0.163</td><td>C</td><td>(SEQ ID NO: 1026) tggtgtctagaactgc[A/C]tctagcaagtgggagg</td></tr>
<tr><td>02</td><td>rs2786266</td><td>13</td><td>q</td><td>q21.32</td><td>LOC730236 | KLHL1</td><td>68327766</td><td>2.37E-03</td><td>1.30</td><td>0.078</td><td>0.061</td><td>G</td><td>(SEQ ID NO: 1027) tgctggacaagtgtaa[A/G]gaatctggggtttaga</td></tr>
<tr><td>03</td><td>rs287548</td><td>13</td><td>q</td><td>822.1</td><td>KLF5 | LOC647281</td><td>73905783</td><td>1.15E-03</td><td>0.76</td><td>0.033</td><td>0.043</td><td>A</td><td>(SEQ ID NO: 1028) gagggtttggctttag[A/G]ctttgttagggcaagt</td></tr>
<tr><td>03</td><td>rs9543642</td><td>13</td><td>q</td><td>q22.1</td><td>LOC100288208 | LOC647288</td><td>75008312</td><td>2.48E-04</td><td>1.13</td><td>0.405</td><td>0.377</td><td>A</td><td>(SEQ ID NO: 1029) tagaagcacacctagc[A/G]tatttaaaacttggag</td></tr>
<tr><td>03</td><td>rs9543662</td><td>13</td><td>q</td><td>q22.1</td><td>LOC100288208 | LOC647288</td><td>75066010</td><td>1.30E-04</td><td>0.89</td><td>0.434</td><td>0.464</td><td>G</td><td>(SEQ ID NO: 1030) acggatgaatcaaaac[A/G]ttaagctctctaaaag</td></tr>
<tr><td>03</td><td>rs1337278</td><td>13</td><td>q</td><td>q31.1</td><td>SLITRK1 | SLITRK6</td><td>86316853</td><td>1.97E-02</td><td>1.08</td><td>0.406</td><td>0.388</td><td>G</td><td>(SEQ ID NO: 1031) aaataatccttgatac[A/G]gtactgaatattttgt</td></tr>
<tr><td>03</td><td>rs4344612</td><td>13</td><td>q</td><td>q31.1</td><td>SPRY2 | SLITRK1</td><td>81574866</td><td>3.11E-04</td><td>1.14</td><td>0.273</td><td>0.248</td><td>C</td><td>(SEQ ID NO: 1032) ttatctcaaaaaaaat[A/C]tgtaggtataaatttg</td></tr>
<tr><td>03</td><td>rs7336590</td><td>13</td><td>q</td><td>q31.1</td><td>SPRY2 | SLITRK1</td><td>81529694</td><td>3.80E-04</td><td>0.89</td><td>0.448</td><td>0.476</td><td>A</td><td>(SEQ ID NO: 1033) aatccatttgaaattg[A/G]cagtgtttttatattt</td></tr>
<tr><td>03</td><td>rs12865263</td><td>13</td><td>q</td><td>831.1</td><td>SPRY2 |</td><td>81362430</td><td>8.35E-04</td><td>1.15</td><td>0.174</td><td>0.154</td><td>A</td><td>(SEQ ID NO: 1034)</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | SLITRK1 | | | | | | | cttcagtcttcgtaca[A/G]aaacacttactttata |
| 03 | rs4536348 | 13 | q | 831.1 | SPRY2 \| SLITRK1 | 81562924 | 5.42E-03 | 1.13 | 0.165 | 0.149 | G | (SEQ ID NO: 1035) cctggtaatttgatca[A/G]tcattaagctatcctt |
| 03 | rs2348445 | 13 | q | q31.2 | LOC100287432 \| LOC144776 | 89846656 | 1.08E-03 | 1.15 | 0.156 | 0.138 | G | (SEQ ID NO: 1036) tgaagaatttactcac[A/G]tggggaaataaaggcc |
| 03 | rs11616543 | 13 | q | q31.2 | LOC100287432 \| LOC144776 | 89298757 | 3.61E-03 | 1.13 | 0.180 | 0.163 | A | (SEQ ID NO: 1037) tgtattctctagtcag[A/G]ttctctttccagcttg |
| 03 | rs11620369 | 13 | q | q31.3 | GPC5 \| GPC6 | 93873495 | 1.12E-03 | 0.82 | 0.068 | 0.082 | A | (SEQ ID NO: 1038) tagtattttaggtaac[A/G]atgagtaaatcttaag |
| 03 | rs9556267 | 13 | q | q31.3 | GPC5 \| GPC6 | 93839833 | 6.97E-04 | 0.81 | 0.067 | 0.082 | G | (SEQ ID NO: 1039) acagagtctggaaata[A/G]gaccgatgaaaccagg |
| 03 | rs7322277 | 13 | q | q31.3 | GPC6 | 94826895 | 7.99E-04 | 0.87 | 0.174 | 0.195 | G | (SEQ ID NO: 1040) agcacaaacttttgct[A/G]aatagcatgtcatcta |
| 03 | rs7329232 | 13 | q | q31.3 | GPC6 | 94828678 | 1.97E-03 | 0.86 | 0.113 | 0.130 | G | (SEQ ID NO: 1041) atatcggttctgctat[A/G]tctatgagttcctttc |
| 03 | rs9301082 | 13 | q | q33.2 | DAOA \| LOC728192 | 106586930 | 1.40E-03 | 1.12 | 0.302 | 0.279 | A | (SEQ ID NO: 1042) aatagatgaggaagtt[A/G]aagtccaaaaatagtc |
| 03 | rs9519858 | 13 | q | q33.2 | DAOA \| LOC728192 | 106583444 | 1.03E-03 | 1.12 | 0.304 | 0.280 | A | (SEQ ID NO: 1043) aaagtgaatgagaaca[A/G]tactgataataatagc |
| 02 | rs9583036 | 13 | q | q33.2 | DAOA \| LOC728192 | 106389385 | 8.28E-04 | 1.29 | 0.104 | 0.083 | G | (SEQ ID NO: 1044) tgcctgtgacacaata[T/G]tgaaatcttacttaaa |
| 02 | rs277836 | 13 | q | q33.3 | MYO16 | 109710600 | 2.10E-05 | 1.15 | 0.394 | 0.362 | G | (SEQ ID NO: 1045) atgttgaaagggtgcc[A/G]gtgccttggtgatcaa |
| 03 | rs12018760 | 13 | # N/A | # N/A | OLFM4 \| LOC100287887 | 54308253 | 3.67E-03 | 0.88 | 0.145 | 0.162 | A | (SEQ ID NO: 1046) ttgattcttaatctgg[A/G]ggtgtttatttcccta |
| 02 | exm1085390 | 14 | q | q11.2 | EDDM3A | 21216136 | 2.92E-12 | 9.13 | 0.008 | 0.001 | A | (SEQ ID NO: 1047) tggcgtagatggatat[A/G]ttgataacatagaaga |
| 02 | rs227865 | 14 | q | q11.2 | 0R4E2 \| DAD1 | 22953607 | 4.78E-05 | 1.27 | 0.076 | 0.061 | G | (SEQ ID NO: 1048) tcgtcaatgttttaaa[A/G]ggtaggagttgttaca |
| 03 | rs2233859 | 14 | q | q11.2 | RNASE3 | 21359808 | 9.05E-04 | 0.90 | 0.398 | 0.423 | A | (SEQ ID NO: 1049) ataaccgagaccggat[A/C]ggggagtagttacttc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2300850 | 14 | q | q12 | AKAP6 | 33271488 | 9.28E-05 | 1.18 | 0.131 | 0.113 | G | (SEQ ID NO: 1050) agttcataatcttcca[A/G]gcctccatagtctggt |
| 02 | exm-rs17111920 | 14 | q | q12 | NOVA1 \| LINC00645 | 27406892 | 6.53E-10 | 4.47 | 0.011 | 0.002 | A | (SEQ ID NO: 1051) tagactaatgcaagca[A/C]aaaatttccatttgct |
| 03 | rs8009605 | 14 | q | q12 | PRKD1 | 30254780 | 1.23E-04 | 0.86 | 0.208 | 0.233 | G | (SEQ ID NO: 1052) ggaagtcttattcgga[A/G]caatcagtcaagaaaa |
| 02 | rs17489969 | 14 | q | q12 | STXBP6 \| NOVA1 | 26642640 | 7.02E-04 | 1.36 | 0.073 | 0.055 | C | (SEQ ID NO: 1053) catgcaccgaaatctc[T/C]tcatgatggagaattt |
| 02 | rs17110902 | 14 | q | q12 | STXBP6 \| NOVA1 | 26673425 | 9.11E-07 | 1.12 | 0.169 | 0.153 | A | (SEQ ID NO: 1054) ggactgcaaggtaatc[A/G]tcaagggactcttaga |
| 02 | rs1012146 | 14 | q | q12 | STXBP6 \| NOVA1 | 26678953 | 6.04E-07 | 1.12 | 0.169 | 0.153 | A | (SEQ ID NO: 1055) ttcatttaattttaca[A/C]ggaagagtttaaaaaa |
| 03 | rs2899875 | 14 | q | q21.1 | CLEC14A \| LOC283547 | 39001144 | 8.58E-05 | 0.91 | 0.475 | 0.499 | G | (SEQ ID NO: 1056) tatcattgctatttcc[A/G]tgtttggtcaaggcat |
| 03 | rs8005701 | 14 | q | q21.2 | LOC644589 \| LOC100289583 | 46883709 | 7.79E-03 | 0.92 | 0.419 | 0.439 | A | (SEQ ID NO: 1057) aaattataacaaaaga[A/G]aattttactcttataa |
| 03 | rs10138214 | 14 | q | q21.2 | LOC644589 \| LOC100289583 | 46866809 | 1.36E-02 | 0.92 | 0.418 | 0.437 | A | (SEQ ID NO: 1058) agtgccagcattctga[A/G]ccataatttttgtgac |
| 03 | rs1669786 | 14 | q | q21.2 | LOC644589 \| LOC100289583 | 46894155 | 8.60E-03 | 0.92 | 0.420 | 0.440 | G | (SEQ ID NO: 1059) gggttcaacagtctat[A/G]tttttagcagactgtc |
| 03 | rs2415982 | 14 | q | q21.2 | LOC644589 \| LOC100289583 | 46865899 | 9.90E-03 | 0.92 | 0.417 | 0.437 | A | (SEQ ID NO: 1060) aggcctgcctgtgtat[A/G]actgtaaatattcatt |
| 03 | rs12883384 | 14 | q | q21.3 | MDGA2 | 47403684 | 6.84E-04 | 1.11 | 0.434 | 0.407 | A | (SEQ ID NO: 1061) tcttggcttgaactgc[A/C]aatcttaaaagttaat |
| 03 | rs11846126 | 14 | q | q21.3 | RPL10L \| MDGA2 | 47249450 | 2.32E-04 | 0.89 | 0.455 | 0.484 | G | (SEQ ID NO: 1062) tgaaatattgtaaatc[A/G]gtggttttgagtgtct |
| 03 | rs1253706 | 14 | q | q22.1 | GNG2 | 52400377 | 2.84E-04 | 1.12 | 0.456 | 0.427 | A | (SEQ ID NO: 1063) aaagaaaatgagagcc[A/G]ctgctcgagtgaaggg |
| 03 | rs4271525 | 14 | q | q22.1 | GNG2 | 52408987 | 5.65E-05 | 1.12 | 0.428 | 0.401 | A | (SEQ ID NO: 1064) ttttcatgatggcttt[A/G]tggctattttttttagg |
| 03 | rs10498440 | 14 | q | q22.1 | GNG2 | 52413573 | 8.43E-04 | 1.11 | 0.429 | 0.403 | G | (SEQ ID NO: 1065) aaagtactaggccagc[A/G]ttccaaagaagtgttt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1618825 | 14 | q | q22.1 | GNG2 | 52407340 | 1.32E-03 | 1.11 | 0.439 | 0.414 | A | (SEQ ID NO: 1066) tgattgggaaagagtg[A/G]ctgagtgtgcaaggtg |
| 03 | rs7157151 | 14 | q | q22.1 | NID2 \| PTGDR | 52571583 | 7.51E-04 | 1.12 | 0.311 | 0.287 | A | (SEQ ID NO: 1067) acgttactcatcaaat[A/G]tatacaatgtagctaa |
| 03 | rs941630 | 14 | q | q22.1 | NID2 \| PTGDR | 52557650 | 7.32E-03 | 1.10 | 0.236 | 0.218 | A | (SEQ ID NO: 1068) ttgtctatcagttgcc[A/G]tcttccattggccaag |
| 03 | rs34096981 | 14 | q | q22.3 | C14orf34 \| LOC100286940 | 56302744 | 6.76E-05 | 1.12 | 0.315 | 0.291 | A | (SEQ ID NO: 1069) ggcagagttacacctc[A/G]taaacaaactattcaa |
| 03 | rs2342595 | 14 | q | q22.3 | C14orf34 \| LOC100286940 | 56271486 | 8.48E-05 | 1.12 | 0.312 | 0.288 | A | (SEQ ID NO: 1070) agggccaagctgccaa[A/G]aacttcttgaggtctg |
| 02 | rs1953358 | 14 | q | q22.3 | C14orf34 \| LOC100286940 | 56295580 | 5.14E-05 | 0.88 | 0.458 | 0.489 | A | (SEQ ID NO: 1071) ggcagcatcaaagtca[A/G]atgactgacccaaggc |
| 02 | rs12896938 | 14 | q | q22.3 | TBPL2 \| C14orf33 | 55955102 | 3.40E-05 | 1.12 | 0.236 | 0.216 | G | (SEQ ID NO: 1072) ctatgctctggtttct[A/G]tatttctagaacttgt |
| 03 | rs12880763 | 14 | q | q22.3 | TBPL2 \| C14orf33 | 55970308 | 9.86E-05 | 1.12 | 0.225 | 0.206 | G | (SEQ ID NO: 1073) taatctttaaattgtt[A/G]catatttagcaagtgt |
| 03 | rs12884010 | 14 | q | q22.3 | TBPL2 \| C14orf33 | 55944612 | 1.96E-04 | 1.13 | 0.372 | 0.344 | G | (SEQ ID NO: 1074) gctgtgctcccagcca[A/G]cagccagaatcaactg |
| 02 | rs7156144 | 14 | q | q24.1 | TMEM229B | 67979713 | 5.74E-02 | 0.92 | 0.415 | 0.435 | A | (SEQ ID NO: 1075) taaatctgatacaacc[A/G]aaataaacacagtata |
| 03 | rs17104036 | 14 | q | q24.3 | C14orf179 \| C14orf118 | 76573554 | 1.38E-02 | 1.18 | 0.060 | 0.051 | A | (SEQ ID NO: 1076) cactctagaagaccct[A/G]caaatcagaaccagag |
| 02 | exm1114136 | 14 | q | q24.3 | COQ6 | 74427993 | 6.12E-12 | Inf | 0.004 | 0.000 | G | (SEQ ID NO: 1077) gcccccaagcgtagcc[A/G]gggtggatgccaaaag |
| 02 | exm1113959 | 14 | q | q24.3 | ZNF410 | 74388791 | 4.89E-10 | 40.96 | 0.004 | 0.000 | G | (SEQ ID NO: 1078) aagcctcttcaagcaa[A/G]ctactgcccattagtg |
| 03 | rs7148059 | 14 | q | q32.11 | KCNK13 \| PSMC1 | 90657405 | 8.80E-05 | 1.12 | 0.174 | 0.159 | A | (SEQ ID NO: 1079) gttgtcaatgctaaac[A/G]agaaagggtccctgga |
| 03 | rs1241719 | 14 | q | q32.12 | CPSF2 \| SLC24A4 | 92673710 | 3.01E-02 | 1.09 | 0.226 | 0.212 | A | (SEQ ID NO: 1080) tcaaaccagccctgcc[A/G]gtgcccttgtgtccct |
| 02 | rs1257415 | 14 | q | q32.2 | BCL11B | 99698931 | 3.94E-05 | 1.14 | 0.525 | 0.493 | C | (SEQ ID NO: 1081) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | cactccagggcccccca[A/C]gtggattcccccatcg |
| 02 | rs2614459 | 14 | q | q32.2 | BCL11B | 99691180 | 2.49E-06 | 1.15 | 0.314 | 0.285 | C | (SEQ ID NO: 1082) cattgtgggaagctct[A/C]gagatggggccatcct |
| 03 | rs2793321 | 14 | q | q32.2 | BCL11B | 99676623 | 1.04E-04 | 1.14 | 0.326 | 0.298 | A | (SEQ ID NO: 1083) ctgcagtgcttattct[A/G]tctcttttgtttgttt |
| 03 | rs756055 | 14 | q | q32.2 | DEGS2 \| YY1 | 100691178 | 6.05E-05 | 0.88 | 0.376 | 0.408 | G | (SEQ ID NO: 1084) atcaggggaaaagcat[A/G]aactcaaaatagatga |
| 03 | rs7153665 | 14 | q | q32.2 | YY1 | 100730920 | 8.62E-05 | 0.88 | 0.376 | 0.408 | A | (SEQ ID NO: 1085) aagggcgatgaatcct[A/G]ggccaggctgtgcaga |
| 02 | exm1134843 | 14 | q | q32.33 | PACS2 | 105858969 | 1.20E-07 | Inf | 0.003 | 0.000 | A | (SEQ ID NO: 1086) cagccagggtgtcggc[A/G]ccgagctgatggggct |
| 02 | rs8179187 | 15 | q | q11.2 | UBE3A | 25652326 | 2.69E-05 | 1.28 | 0.081 | 0.065 | C | (SEQ ID NO: 1087) gagggtcgcactttca[A/C]aaatgagtcagctggt |
| 03 | rs12437614 | 15 | q | q12 | GABRG3 | 27706661 | 2.08E-04 | 1.28 | 0.060 | 0.047 | A | (SEQ ID NO: 1088) cagcaagagttattgc[A/G]aagagaaacaacaaag |
| 03 | rs939981 | 15 | q | q13.1 | LOC727808 \| LOC100128435 | 30290306 | 3.19E-03 | 1.15 | 0.124 | 0.110 | A | (SEQ ID NO: 1089) ggtcctttctaaaaat[A/G]gtcaccccaatccatc |
| 03 | rs12905328 | 15 | q | q13.1 | LOC727808 \| LOC100128435 | 30239328 | 1.72E-03 | 0.88 | 0.202 | 0.222 | A | (SEQ ID NO: 1090) attaatattttatgtt[A/G]catgatttagatttat |
| 02 | rs12438794 | 15 | q | q14 | MEIS2 \| TMCO5A | 38146571 | 8.47E-07 | 1.08 | 0.076 | 0.071 | A | (SEQ ID NO: 1091) tcatggaactaaaagt[A/G]agcatctcaagagact |
| 02 | rs8041665 | 15 | q | q14 | MEIS2 \| TMCO5A | 38150179 | 2.56E-07 | 1.08 | 0.077 | 0.072 | A | (SEQ ID NO: 1092) agcgtatattatcttc[A/G]aagagcatttttattt |
| 02 | rs8037309 | 15 | q | q14 | MEIS2 \| TMCO5A | 38150438 | 2.77E-07 | 1.08 | 0.077 | 0.072 | A | (SEQ ID NO: 1093) gagcatccacatccat[A/G]aggctgctgaattcat |
| 03 | rs12907066 | 15 | q | q14 | RYR3 | 33990976 | 7.93E-04 | 1.12 | 0.319 | 0.295 | A | (SEQ ID NO: 1094) tctccagaagatccct[A/G]agcacatgtctggatg |
| 03 | rs7165303 | 15 | q | q14 | RYR3 | 33693677 | 2.31E-04 | 0.89 | 0.391 | 0.420 | G | (SEQ ID NO: 1095) ttcagcactattcagc[A/G]cctatcactgccagct |
| 03 | rs2279663 | 15 | q | q14 | RYR3 | 33952326 | 5.80E-03 | 1.13 | 0.157 | 0.142 | A | (SEQ ID NO: 1096) cccagacattttaacc[A/G]atatggccagtataaa |

TABLE 1-continued

<table>
<tr><th colspan="12">TABLES<br>(Based on build 37 or "GRCh37" as defined by the Genome Reference Consortium)</th></tr>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>01</td><td>exm1159600</td><td>15</td><td>q</td><td>q21.1</td><td>DUT</td><td>48623812</td><td>4.41E-08</td><td>1.65</td><td>0.010</td><td>0.000</td><td>A</td><td>(SEQ ID NO: 1097)<br>cgcacggcagagggcc[A/G]aagccgcggtactctc</td></tr>
<tr><td>03</td><td>rs17645290</td><td>15</td><td>q</td><td>q21.2</td><td>USP8</td><td>50787955</td><td>1.92E-02</td><td>1.10</td><td>0.191</td><td>0.177</td><td>G</td><td>(SEQ ID NO: 1098)<br>tacaaacacttgccag[A/G]tttagaaacacctgta</td></tr>
<tr><td>02</td><td>rs16940167</td><td>15</td><td>q</td><td>q21.3</td><td>AQP9 | LIPC</td><td>58683697</td><td>7.99E-05</td><td>1.18</td><td>0.176</td><td>0.154</td><td>G</td><td>(SEQ ID NO: 1099)<br>ttatgggcccagaatg[A/G]ttccagatcagaattt</td></tr>
<tr><td>03</td><td>rs1280415</td><td>15</td><td>q</td><td>q21.3</td><td>CGNL1</td><td>57749193</td><td>4.60E-02</td><td>1.12</td><td>0.082</td><td>0.074</td><td>G</td><td>(SEQ ID NO: 1100)<br>tattgaacattctaca[A/G]atttttataaaaaagg</td></tr>
<tr><td>03</td><td>rs1280416</td><td>15</td><td>q</td><td>q21.3</td><td>CGNL1</td><td>57749300</td><td>2.10E-03</td><td>1.24</td><td>0.055</td><td>0.045</td><td>A</td><td>(SEQ ID NO: 1101)<br>ttctttgtcagctacc[A/G]ttgctataaaaccttt</td></tr>
<tr><td>03</td><td>rs2017176</td><td>15</td><td>q</td><td>q21.3</td><td>KIAA1370 |<br>ONECUT1</td><td>53006147</td><td>6.68E-05</td><td>0.89</td><td>0.440</td><td>0.469</td><td>A</td><td>(SEQ ID NO: 1102)<br>tgactaattacactgg[A/G]gagtccatcaacatct</td></tr>
<tr><td>02</td><td>rs17543144</td><td>15</td><td>q</td><td>q21.3</td><td>KIAA1370 |<br>ONECUT1</td><td>53008923</td><td>2.07E-05</td><td>0.88</td><td>0.438</td><td>0.468</td><td>A</td><td>(SEQ ID NO: 1103)<br>tggttggaacatagcc[A/G]tgacagctagccaaca</td></tr>
<tr><td>03</td><td>rs2414407</td><td>15</td><td>q</td><td>q21.3</td><td>RAB27A</td><td>55556228</td><td>4.27E-03</td><td>1.14</td><td>0.131</td><td>0.117</td><td>A</td><td>(SEQ ID NO: 1104)<br>caaacaaacagaaaaa[A/G]taaccctggctatagt</td></tr>
<tr><td>03</td><td>rs1991574</td><td>15</td><td>q</td><td>q21.3</td><td>UNC13C</td><td>54484950</td><td>6.41E-04</td><td>0.87</td><td>0.200</td><td>0.223</td><td>A</td><td>(SEQ ID NO: 1105)<br>gaaggcccagtgggaa[A/G]ccgagtagtgctacag</td></tr>
<tr><td>03</td><td>rs12440360</td><td>15</td><td>q</td><td>q21.3</td><td>UNC13C</td><td>54491059</td><td>1.01E-03</td><td>0.90</td><td>0.450</td><td>0.476</td><td>C</td><td>(SEQ ID NO: 1106)<br>atccaaatcaagaaaa[A/C]aatctctgaattgcca</td></tr>
<tr><td>03</td><td>rs16950635</td><td>15</td><td>q</td><td>q22.33</td><td>SMAD3</td><td>67418205</td><td>7.50E-04</td><td>1.27</td><td>0.052</td><td>0.041</td><td>A</td><td>(SEQ ID NO: 1107)<br>ggggtaatttattgcc[A/G]ccgctcgcttcaccag</td></tr>
<tr><td>03</td><td>rs16951541</td><td>15</td><td>q</td><td>q23</td><td>LOC100286942 |<br>PIAS1</td><td>68276895</td><td>2.17E-04</td><td>1.23</td><td>0.090</td><td>0.074</td><td>A</td><td>(SEQ ID NO: 1108)<br>attctgcagacacaca[A/G]tcctttttgcctacaa</td></tr>
<tr><td>02</td><td>exm1173822</td><td>15</td><td>q</td><td>q23</td><td>THSD4</td><td>72023502</td><td>9.46E-11</td><td>17.87</td><td>0.006</td><td>0.000</td><td>A</td><td>(SEQ ID NO: 1109)<br>cgtgcactacgagtac[A/G]tgatcatggggaccaa</td></tr>
<tr><td>03</td><td>rs1130741</td><td>15</td><td>q</td><td>q24.1</td><td>MPI</td><td>75189930</td><td>1.47E-04</td><td>1.13</td><td>0.477</td><td>0.448</td><td>A</td><td>(SEQ ID NO: 1110)<br>tggtacaggggacagt[A/G]atagccagcacaccca</td></tr>
<tr><td>03</td><td>rs2415251</td><td>15</td><td>q</td><td>q24.2</td><td>COX5A | RPP25</td><td>75242155</td><td>2.06E-04</td><td>1.12</td><td>0.502</td><td>0.473</td><td>A</td><td>(SEQ ID NO: 1111)<br>atctgagcccttgggt[A/G]cccctgcctttggaga</td></tr>
<tr><td>03</td><td>rs11855944</td><td>15</td><td>q</td><td>q24.3</td><td>LINGO1 |<br>LOC645752</td><td>78088127</td><td>8.41E-03</td><td>1.11</td><td>0.195</td><td>0.179</td><td>C</td><td>(SEQ ID NO: 1112)<br>tgccacttgctgccag[A/C]cctggctgaagcaggg</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs4075024 | 15 | q | q24.3 | LINGO1 \| LOC645752 | 78093898 | 1.18E-02 | 1.10 | 0.198 | 0.183 | G | (SEQ ID NO: 1113) ttgtttttctgattac[A/G]acagaagacccaacaa |
| 03 | rs15939 | 15 | q | q24.3 | RCN2 | 77241542 | 2.36E-02 | 0.89 | 0.105 | 0.117 | G | (SEQ ID NO: 1114) gctcatcatgatagaa[A/G]tagtcatcatggagct |
| 02 | exm1181151 | 15 | q | q25.1 | ADAMTS7 | 79089098 | 2.26E-09 | Inf | 0.003 | 0.000 | A | (SEQ ID NO: 1115) gagtctcgacgggagc[A/G]ttgggagcagcggcag |
| 02 | exm1182536 | 15 | q | q25.1 | IL16 | 81572094 | 1.94E-08 | 34.64 | 0.004 | 0.000 | A | (SEQ ID NO: 1116) caattacagaatcatg[A/G]tggaggtttctctgca |
| 03 | rs12905510 | 15 | q | q25.3 | AGBL1 \| NCRNA00052 | 87944954 | 1.60E-04 | 1.13 | 0.353 | 0.325 | G | (SEQ ID NO: 1117) tgataagctggacttc[A/G]taaaaactatacacat |
| 03 | rs2016517 | 15 | q | q25.3 | AKAP13 | 86229618 | 1.28E-03 | 1.12 | 0.275 | 0.253 | A | (SEQ ID NO: 1118) catggtaaaatacttt[A/G]gctatatttccatcag |
| 03 | rs11630274 | 15 | q | q25.3 | AKAP13 | 86288387 | 9.24E-04 | 1.12 | 0.288 | 0.265 | A | (SEQ ID NO: 1119) tgaccagacgcctggt[A/G]cagactgggccttctt |
| 03 | rs1978391 | 15 | q | q25.3 | KLHL25 | 86311695 | 9.49E-04 | 1.12 | 0.288 | 0.264 | A | (SEQ ID NO: 1120) ggatgctggttcctcc[A/G]aaaacaaagagcttca |
| 03 | rs3743332 | 15 | q | q25.3 | LOC100288896 | 86303751 | 1.33E-02 | 1.09 | 0.288 | 0.270 | G | (SEQ ID NO: 1121) accagaaaggtgacca[A/G]gacagattttttaagg |
| 03 | rs11634975 | 15 | q | q25.3 | PDE8A | 85606478 | 3.07E-03 | 1.11 | 0.309 | 0.288 | G | (SEQ ID NO: 1122) aacagtgacctattct[A/G]gtaaacacattacgaa |
| 03 | rs11629962 | 15 | q | q25.3 | PDE8A | 85530028 | 1.18E-03 | 1.12 | 0.268 | 0.246 | A | (SEQ ID NO: 1123) agcaagatctcgtctc[A/G]acaaaaaaaaagttta |
| 03 | rs6496766 | 15 | q | q25.3 | PDE8A \| LOC728121 | 85702375 | 1.06E-03 | 1.11 | 0.400 | 0.375 | C | (SEQ ID NO: 1124) atgaaccaactatatg[A/C]tgtctacaagaaacac |
| 03 | rs12905479 | 15 | q | q26.1 | LOC390638 \| SV2B | 91711209 | 1.44E-02 | 0.93 | 0.431 | 0.450 | A | (SEQ ID NO: 1125) cggcctttgtggtgct[A/G]tttggtttcatcccca |
| 02 | exm1190729 | 15 | q | q26.1 | UNC45A | 91486258 | 1.72E-08 | Inf | 0.003 | 0.000 | A | (SEQ ID NO: 1126) tccttgagagacttcc[A/G]gggcaccgctttaatc |
| 03 | rs896070 | 15 | q | q26.2 | LOC145820 \| NR2F2 | 96428860 | 1.06E-04 | 1.17 | 0.198 | 0.175 | A | (SEQ ID NO: 1127) aaggctctgaggtttt[A/G]gtaccccagaaagatt |
| 03 | rs1025833 | 15 | q | 826.2 | SPATA8 \| | 98224547 | 2.07E-04 | 1.25 | 0.073 | 0.059 | A | (SEQ ID NO: 1128) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | LOC91948 | | | | | | | tattaccatgaacttt[A/G]gtaaaagttacaaata |
| 02 | rs8024630 | 15 | q | 826.2 | SPATA8 \| LOC91948 | 98034118 | 4.66E-05 | 1.14 | 0.526 | 0.494 | A | (SEQ ID NO: 1129) ttagaaaatctataac[A/G]gtaaaaagtacattag |
| 03 | rs12910816 | 15 | q | 826.2 | SPATA8 \| LOC91948 | 98249133 | 2.76E-04 | 1.26 | 0.065 | 0.052 | C | (SEQ ID NO: 1130) aaaacctctcacatga[A/C]taagcttacaaaatag |
| 03 | rs8041786 | 15 | q | q26.2 | SPATA8 \| LOC91948 | 97896453 | 8.59E-04 | 1.18 | 0.112 | 0.096 | G | (SEQ ID NO: 1131) ttctatagcagacatt[A/G]gtctctgaacttgggt |
| 02 | exm1193980 | 15 | q | q26.3 | LRRK1 | 101567912 | 8.37E-13 | Inf | 0.005 | 0.000 | A | (SEQ ID NO: 1132) ccgcagccgggacgac[A/G]acgtgcagtacctgac |
| 02 | rs7173796 | 15 | q | q26.3 | PCSK6 \| TM2D3 | 102148666 | 1.66E-05 | 1.22 | 0.134 | 0.113 | A | (SEQ ID NO: 1133) ggcaggcagggaacag[A/G]tgattagtaaccaaag |
| 01 | exm1194576 | 15 | q | q26.3 | TM2D3 | 102192537 | 1.63E-21 | 46.41 | 0.013 | 0.000 | C | (SEQ ID NO: 1134) ggtgctcccgctgagg[C/G]gcctccgcgccttgtg |
| 03 | rs1132812 | 16 | p | p11.2 | CORO1A | 30198151 | 2.94E-04 | 0.89 | 0.438 | 0.466 | A | (SEQ ID NO: 1135) aggtgtgggagatccc[A/G]gatgggggcctgatgc |
| 03 | rs11859842 | 16 | p | p11.2 | SLC7A5P1 \| SPN | 29661217 | 1.65E-04 | 1.13 | 0.497 | 0.467 | A | (SEQ ID NO: 1136) cagcaaagtctgacca[A/G]tctaaagtaaccactc |
| 02 | rs12447415 | 16 | p | p11.2 | SPN \| QPRT | 29682945 | 5.03E-06 | 1.11 | 0.412 | 0.386 | A | (SEQ ID NO: 1137) agggacccttctaaaa[A/G]gtcactgtgggctggg |
| 02 | rs2343605 | 16 | p | p12.1 | TNRC6A \| SLC5A11 | 24848663 | 1.33E-05 | 0.91 | 0.369 | 0.392 | G | (SEQ ID NO: 1138) gagaccagcctacgca[A/G]catagaacctgtctct |
| 03 | rs7200734 | 16 | p | p12.3 | XYLT1 | 17443547 | 1.00E-02 | 1.08 | 0.495 | 0.475 | A | (SEQ ID NO: 1139) agtaatacttcccata[A/C]gagatagttgtgaaat |
| 02 | exm1219737 | 16 | p | p13.11 | KIAA0430 | 15729650 | 1.26E-07 | Inf | 0.003 | 0.000 | A | (SEQ ID NO: 1140) ttctgatttcacaagc[A/G]gggctccagggcattt |
| 03 | rs1541702 | 16 | p | p13.13 | C16orf75 | 11445552 | 2.32E-02 | 1.11 | 0.140 | 0.128 | G | (SEQ ID NO: 1141) tctacaaccatgtcag[A/G]acacaatctaactcct |
| 03 | rs434762 | 16 | p | p13.13 | GSPT1 | 12009781 | 4.81E-04 | 1.24 | 0.069 | 0.056 | G | (SEQ ID NO: 1142) cagaggcggcggcggc[A/G]gcagctcaaccctcct |
| 03 | rs7204004 | 16 | p | p13.2 | C16orf72 \| GRIN2A | 9332745 | 2.64E-04 | 0.86 | 0.168 | 0.190 | A | (SEQ ID NO: 1143) ctcccctgacccaggt[A/G]aggcagtgagtacccc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs12443943 | 16 | p | p13.2 | GRIN2A \| LOC100287628 | 10428747 | 2.59E-05 | 1.15 | 0.236 | 0.212 | G | (SEQ ID NO: 1144) atgtcctctggagcac[A/G]ccccacagcaagttgg |
| 02 | exm1215795 | 16 | p | p13.3 | ALG1 | 5122041 | 2.22E-15 | 16.45 | 0.008 | 0.001 | A | (SEQ ID NO: 1145) cacggcttctcggtga[A/C]cctcctggggttctgc |
| 02 | exm1207746 | 16 | p | p13.3 | C16orf59 | 2512728 | 1.48E-14 | Inf | 0.005 | 0.000 | A | (SEQ ID NO: 1146) aggctgcaggagctgc[A/G]tgcaggtgagaccccg |
| 02 | rs2171226 | 16 | p | p13.3 | LOC650177 \| A2BP1 | 5588451 | 1.22E-06 | 0.88 | 0.427 | 0.458 | A | (SEQ ID NO: 1147) atcctcctcatttttc[A/G]tctaaaagccttagtc |
| 03 | rs2294619 | 16 | p | p13.3 | MAPK8IP3 | 1814440 | 1.89E-03 | 1.13 | 0.200 | 0.181 | G | (SEQ ID NO: 1148) gcccaagagcgcccac[A/G]cgtctcccgagaagaa |
| 03 | rs3211995 | 16 | p | p13.3 | SLC9A3R2 | 2089006 | 4.89E-04 | 1.15 | 0.187 | 0.166 | A | (SEQ ID NO: 1149) gcatgcgcgctctcag[A/G]ataaacaggccctgcc |
| 02 | exm1211849 | 16 | p | p13.3 | SLX4 | 3640815 | 8.05E-11 | 43.93 | 0.005 | 0.000 | C | (SEQ ID NO: 1150) aggggcacggggagca[C/G]aggcccctgagcagga |
| 03 | rs13334798 | 16 | q | q12.1 | ABCC11 | 48244717 | 5.74E-05 | 1.18 | 0.080 | 0.069 | G | (SEQ ID NO: 1151) aaaattcaaatttttc[A/G]tggagggcaaacacag |
| 03 | rs7194667 | 16 | q | q12.1 | ABCC11 | 48242898 | 5.35E-05 | 1.18 | 0.080 | 0.068 | C | (SEQ ID NO: 1152) cccatcccctcagctt[A/C]tattctgagctcaatg |
| 03 | rs3910446 | 16 | q | q12.1 | LOC388276 \| TOX3 | 52196841 | 1.68E-03 | 1.11 | 0.369 | 0.345 | A | (SEQ ID NO: 1153) gagtcacagtgatggc[A/G]acccggtattctcagc |
| 03 | rs8052698 | 16 | q | q12.2 | TOX3 \| CHD9 | 52967995 | 3.62E-04 | 1.12 | 0.474 | 0.446 | A | (SEQ ID NO: 1154) tgcgccatcatgccct[A/G]cgcatttcatttaaat |
| 03 | rs4784181 | 16 | q | q21 | CDH8 \| CDH11 | 62346479 | 8.70E-03 | 0.92 | 0.410 | 0.431 | A | (SEQ ID NO: 1155) atgagcatgtgatcca[A/G]tgatagtcaatgaaat |
| 03 | rs11861466 | 16 | q | q21 | GOT2 \| LOC644649 | 59495475 | 7.02E-03 | 1.09 | 0.434 | 0.413 | A | (SEQ ID NO: 1156) gtcaaaaaaagcatca[A/G]taaataagtagagagt |
| 03 | rs1582600 | 16 | q | q21 | GOT2 \| LOC644649 | 59314789 | 1.09E-02 | 1.09 | 0.397 | 0.378 | C | (SEQ ID NO: 1157) taaatgtagtcatggc[A/C]gaaagctgagtgggtg |
| 03 | rs1364204 | 16 | q | q21 | GOT2 \| LOC644649 | 59411217 | 1.77E-02 | 1.08 | 0.385 | 0.367 | A | (SEQ ID NO: 1158) tgatcaggttttgggc[A/G]agggtctgcttttttg |
| 02 | rs7193968 | 16 | q | q22.1 | IL34 | 70672952 | 4.90E-03 | 0.88 | 0.443 | 0.474 | C | (SEQ ID NO: 1159) tgccagctttacaagc[C/G]acagaatcaccaaaac |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs4149499 | 16 | q | q22.2 | CHST4 | 71570413 | 5.95E-06 | 1.36 | 0.057 | 0.042 | A | (SEQ ID NO: 1160) caacaatggcaccagt[A/C]cttctccaaatcattt |
| 03 | rs150617 | 16 | q | q22.2 | DHX38 | 72139396 | 1.82E-04 | 1.20 | 0.124 | 0.106 | A | (SEQ ID NO: 1161) gagcaggacatacagg[A/G]agggaaaaatgagtcc |
| 03 | rs4788591 | 16 | q | q22.2 | PKD1L3 | 72020323 | 1.51E-02 | 1.09 | 0.233 | 0.218 | A | (SEQ ID NO: 1162) tgtgatgtgatacttg[A/G]tagtactgaaggaaac |
| 03 | rs152828 | 16 | q | q22.2 | TXNL4B | 72123886 | 1.93E-04 | 1.20 | 0.123 | 0.105 | A | (SEQ ID NO: 1163) tctaccctcagtcata[A/G]gcaggaggaaatacca |
| 02 | exm1257256 | 16 | q | q22.2 | ZFHX3 | 72821344 | 2.06E-15 | 5.63 | 0.015 | 0.003 | A | (SEQ ID NO: 1164) gacttcctggaggcgt[A/G]gggggaagcggaggag |
| 03 | rs12102460 | 16 | q | q23.1 | WWOX | 79093317 | 6.10E-03 | 1.30 | 0.028 | 0.022 | G | (SEQ ID NO: 1165) tgagatgtagagcttg[A/G]cacctgcatataaagt |
| 02 | rs9923563 | 16 | q | q23.1 | WWOX | 78615460 | 3.64E-05 | 1.16 | 0.262 | 0.234 | G | (SEQ ID NO: 1166) ttcctagaggttcaca[A/G]taaatctaaaaagatc |
| 02 | rs12598440 | 16 | q | q23.1 | WWOX | 78576107 | 1.74E-05 | 1.14 | 0.508 | 0.474 | G | (SEQ ID NO: 1167) tccggcagtgtttacg[A/G]agggctggagatacac |
| 02 | rs11150085 | 16 | q | q23.1 | WWOX | 78567094 | 1.50E-05 | 1.22 | 0.117 | 0.098 | A | (SEQ ID NO: 1168) caggtcagccagttgg[A/G]aacagagttgacggag |
| 03 | rs2943768 | 16 | q | q23.1 | WWOX | 78612914 | 1.77E-03 | 1.13 | 0.206 | 0.187 | C | (SEQ ID NO: 1169) ttacattatacatctt[A/C]ggcatttttttccttt |
| 01 | rs4319778 | 16 | q | q23.1 | WWOX | 78552954 | 1.99E-06 | 1.16 | 0.423 | 0.387 | A | (SEQ ID NO: 1170) tttctaatttaatctt[A/G]tacatgagacagctat |
| 02 | rs2978632 | 16 | q | q23.1 | WWOX | 78559880 | 7.70E-05 | 1.14 | 0.341 | 0.312 | A | (SEQ ID NO: 1171) gcagataggatgatac[A/G]tgtgctctgcaaccat |
| 03 | rs16947885 | 16 | q | q23.1 | WWOX | 78551317 | 3.56E-04 | 1.24 | 0.077 | 0.064 | G | (SEQ ID NO: 1172) caccagaactgaaatt[A/G]tttccagctatgttta |
| 03 | rs30405 | 16 | q | q23.2 | LOC729251 \| MAF | 79621818 | 9.13E-04 | 0.87 | 0.181 | 0.202 | G | (SEQ ID NO: 1173) gaacacagaaactgca[A/G]tggcttttggacgcta |
| 01 | rs30428 | 16 | q | q23.2 | LOC729251 \| MAF | 79598399 | 2.68E-06 | 0.86 | 0.349 | 0.384 | G | (SEQ ID NO: 1174) cttcttccatcaggga[A/G]gttatcaggctcaaag |
| 03 | rs3784925 | 16 | q | q23.2 | LOC729251 \| | 79605583 | 2.50E-04 | 1.16 | 0.189 | 0.167 | A | (SEQ ID NO: 1175) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | MAF | | | | | | | atcctctgctctccta[A/G]gttcaggcaggataga |
| 03 | rs173645 | 16 | q | q23.2 | LOC729251 \| MAF | 79594409 | 5.42E-04 | 0.88 | 0.243 | 0.267 | G | (SEQ ID NO: 1176) caaaccattgcatcat[A/G]ttttggactgatagtt |
| 03 | rs7206458 | 16 | q | q23.3 | CDH13 | 83446995 | 3.30E-04 | 1.13 | 0.284 | 0.259 | A | (SEQ ID NO: 1177) ttccccaattattatc[A/C]gtcactcctcctccat |
| 02 | rs1013465 | 16 | q | q23.3 | CDH13 | 83412113 | 2.31E-05 | 1.14 | 0.406 | 0.375 | A | (SEQ ID NO: 1178) tggccaatccaactga[A/C]ggggaccccttttattg |
| 02 | exm1263172 | 16 | q | q23.3 | SGIN1 | 83999431 | 1.18E-07 | Inf | 0.003 | 0.000 | G | (SEQ ID NO: 1179) gcagtggatcctgacc[A/G]gccgctgagcgccaag |
| 03 | rs13521 | 16 | q | q24.1 | COTL1 | 84599970 | 5.86E-04 | 0.88 | 0.263 | 0.287 | A | (SEQ ID NO: 1180) gccaggagctgtgccc[A/G]gtgcctgcagccttca |
| 03 | rs11641616 | 16 | q | q24.1 | FOXL1 \| LOC100288525 | 86638543 | 6.76E-04 | 1.24 | 0.070 | 0.057 | A | (SEQ ID NO: 1181) ttaatcaaatatcggg[A/G]ttaaagaatgtatcaa |
| 03 | rs7202350 | 16 | q | q24.1 | FOXL1 \| LOC100288525 | 86642680 | 1.37E-03 | 1.22 | 0.070 | 0.058 | G | (SEQ ID NO: 1182) gcagccccagcaggaa[A/G]gacacgataatcgatt |
| 03 | rs11642168 | 16 | q | q24.1 | LOC732275 \| FOXF1 | 86520474 | 4.54E-03 | 1.13 | 0.152 | 0.136 | A | (SEQ ID NO: 1183) aaggggaaacggagcc[A/G]gccaaggacaggtgaa |
| 03 | rs7186320 | 16 | q | q24.1 | TMEM148 \| KIAA0182 | 85577092 | 9.13E-05 | 0.79 | 0.052 | 0.065 | A | (SEQ ID NO: 1184) acatggggaatggggt[A/G]tggactctatggggtg |
| 03 | rs2274892 | 17 | p | p11.2 | TNFRSF13B | 16852027 | 1.23E-04 | 1.13 | 0.400 | 0.370 | C | (SEQ ID NO: 1185) cccaaggcaaacctgc[A/C]tggtgtcacgcagggt |
| 03 | rs17793572 | 17 | p | p11.2 | TNFRSF13B | 16843992 | 5.67E-01 | 1.02 | 0.292 | 0.288 | A | (SEQ ID NO: 1186) tgctctctggatcctg[A/G]aggaagttgatccact |
| 03 | rs4792801 | 17 | p | p11.2 | TNFRSF13B | 16845467 | 6.12E-05 | 1.11 | 0.438 | 0.412 | G | (SEQ ID NO: 1187) caggtcctcaaaaaac[A/G]aaacagagctattatg |
| 03 | rs8072293 | 17 | p | p11.2 | TNFRSF13B | 16855878 | 1.02E-03 | 1.12 | 0.278 | 0.255 | G | (SEQ ID NO: 1188) cacagggcctgtggac[A/G]gggtggctatgagat |
| 02 | rs7223652 | 17 | p | p11.2 | TNFRSF13B | 16864559 | 3.60E-05 | 1.22 | 0.325 | 0.283 | G | (SEQ ID NO: 1189) gttcttttggatgttt[G/A]cttaggagtggaatta |
| 03 | rs7504096 | 17 | p | p11.2 | TNFRSF13B \| MPRIP | 16877083 | 2.25E-04 | 1.15 | 0.216 | 0.192 | A | (SEQ ID NO: 1190) caggccagagccagga[A/G]tctattgcacagttaa |

TABLE 1-continued

<table>
<tr><th colspan="13">TABLES<br>(Based on build 37 or "GRCh37" as defined by the Genome Reference Consortium)</th></tr>
<tr><th>Set</th><th>Name</th><th>Chr</th><th>Arm</th><th>Cyto</th><th>Gene</th><th>Position</th><th>p-value</th><th>OR</th><th>Case MAF</th><th>Cont MAF</th><th>MA</th><th>Context Sequence</th></tr>
<tr><td>02</td><td>rs4441330</td><td>17</td><td>p</td><td>p11.2</td><td>ZNF286B</td><td>18562720</td><td>1.22E-05</td><td>1.12</td><td>0.513</td><td>0.485</td><td>G</td><td>(SEQ ID NO: 1191)<br>cattcatcaagaagtc[A/G]gataaagggtttaaac</td></tr>
<tr><td>02</td><td>rs11078211</td><td>17</td><td>p</td><td>p12</td><td>HS3ST3A1 | CDRT15P</td><td>13836036</td><td>7.83E-05</td><td>1.15</td><td>0.297</td><td>0.270</td><td>A</td><td>(SEQ ID NO: 1192)<br>ttaactcctttcaaac[A/G]atttcctttgtatctt</td></tr>
<tr><td>03</td><td>rs10852926</td><td>17</td><td>p</td><td>p12</td><td>PIRT | FLJ45455</td><td>10778976</td><td>2.25E-01</td><td>1.04</td><td>0.494</td><td>0.484</td><td>A</td><td>(SEQ ID NO: 1193)<br>aaatagagacacagcc[A/G]gagtgctggctatgac</td></tr>
<tr><td>02</td><td>rs179521</td><td>17</td><td>p</td><td>p12</td><td>PMP22 | TEKT3</td><td>15173221</td><td>9.82E-05</td><td>1.13</td><td>0.387</td><td>0.357</td><td>A</td><td>(SEQ ID NO: 1194)<br>catctctgagttcctg[A/C]accacttatcaagtgt</td></tr>
<tr><td>02</td><td>rs8068414</td><td>17</td><td>p</td><td>p12</td><td>TEKT3 | LOC100287829</td><td>15248449</td><td>9.77E-05</td><td>1.15</td><td>0.289</td><td>0.262</td><td>A</td><td>(SEQ ID NO: 1195)<br>gggagtgtggacacgg[A/G]gctgcactgccaggct</td></tr>
<tr><td>02</td><td>rs11078672</td><td>17</td><td>p</td><td>p13.1</td><td>EIF5A</td><td>7215142</td><td>5.26E-05</td><td>0.87</td><td>0.306</td><td>0.336</td><td>A</td><td>(SEQ ID NO: 1196)<br>ctctctcctacctagg[A/G]tggcggtggtggcagc</td></tr>
<tr><td>03</td><td>rs8072788</td><td>17</td><td>p</td><td>p13.2</td><td>NLRP1 | WSCD1</td><td>5594285</td><td>8.70E-03</td><td>1.11</td><td>0.200</td><td>0.184</td><td>A</td><td>(SEQ ID NO: 1197)<br>aaataaaggcctgtgg[A/G]cctcagtttcctgtgt</td></tr>
<tr><td>02</td><td>rs17804008</td><td>17</td><td>p</td><td>p13.2</td><td>PITPNM3</td><td>6433659</td><td>6.08E-06</td><td>1.12</td><td>0.369</td><td>0.344</td><td>G</td><td>(SEQ ID NO: 1198)<br>ctgaccctgactttga[A/G]atttcgtctgtaaaat</td></tr>
<tr><td>03</td><td>rs907941</td><td>17</td><td>p</td><td>p13.2</td><td>PITPNM3</td><td>6362387</td><td>3.70E-04</td><td>0.89</td><td>0.433</td><td>0.461</td><td>G</td><td>(SEQ ID NO: 1199)<br>ggagcagcccctcttc[A/G]tctggcccttccacct</td></tr>
<tr><td>03</td><td>rs11078612</td><td>17</td><td>p</td><td>p13.2</td><td>WSCD1 | AIPL1</td><td>6067298</td><td>8.12E-03</td><td>0.87</td><td>0.101</td><td>0.114</td><td>G</td><td>(SEQ ID NO: 1200)<br>tattgctcattttttt[A/G]tagatgaggaaactgc</td></tr>
<tr><td>03</td><td>rs9894371</td><td>17</td><td>p</td><td>p13.2</td><td>WSCD1 | AIPL1</td><td>6212579</td><td>1.92E-03</td><td>0.91</td><td>0.475</td><td>0.499</td><td>G</td><td>(SEQ ID NO: 1201)<br>ccttgtcttagttcca[A/G]acgtctccctctgtga</td></tr>
<tr><td>03</td><td>rs8078781</td><td>17</td><td>p</td><td>p13.3</td><td>OR1D2 | OR1G1</td><td>3008882</td><td>8.67E-05</td><td>1.16</td><td>0.082</td><td>0.072</td><td>A</td><td>(SEQ ID NO: 1202)<br>aacaccatacagcaat[A/G]agcatgaacaacctac</td></tr>
<tr><td>03</td><td>rs9902340</td><td>17</td><td>q</td><td>q11.2</td><td>CCDC55</td><td>28476458</td><td>3.06E-02</td><td>1.07</td><td>0.503</td><td>0.486</td><td>C</td><td>(SEQ ID NO: 1203)<br>gcaatcttactcctct[A/C]tgataacaaatagatc</td></tr>
<tr><td>03</td><td>rs11080118</td><td>17</td><td>q</td><td>q11.2</td><td>CCDC55</td><td>28475379</td><td>3.31E-02</td><td>1.07</td><td>0.502</td><td>0.486</td><td>A</td><td>(SEQ ID NO: 1204)<br>ctatgtctataagtgg[A/G]aaaggctttgtttatt</td></tr>
<tr><td>03</td><td>rs9896012</td><td>17</td><td>q</td><td>q11.2</td><td>CCDC55</td><td>28470091</td><td>3.12E-02</td><td>1.07</td><td>0.503</td><td>0.486</td><td>G</td><td>(SEQ ID NO: 1205)<br>gaagcagatgtgtatg[A/G]ttttggagaaacagaa</td></tr>
<tr><td>03</td><td>rs9897794</td><td>17</td><td>q</td><td>q11.2</td><td>EFCAB5</td><td>28296327</td><td>2.57E-02</td><td>1.07</td><td>0.507</td><td>0.489</td><td>C</td><td>(SEQ ID NO: 1206)<br>gtgacttctttcatca[A/C]cctctggtaaccagac</td></tr>
</table>

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs3102555 | 17 | q | q11.2 | SSH2 | 28044101 | 5.26E-03 | 0.92 | 0.464 | 0.486 | G | (SEQ ID NO: 1207) tctctgttttaagggc[A/G]gtggatagggtagggt |
| 03 | rs10445384 | 17 | q | q11.2 | SSH2 \| EFCAB5 | 28182685 | 1.59E-02 | 1.08 | 0.503 | 0.484 | G | (SEQ ID NO: 1208) tccttagttggatcag[A/G]cacagactatgaaatt |
| 03 | rs10445400 | 17 | q | q11.2 | SSH2 \| EFCAB5 | 28183059 | 1.33E-02 | 1.08 | 0.504 | 0.485 | G | (SEQ ID NO: 1209) gatgaggtctgtgcat[A/G]ctcctttccccatcaa |
| 03 | rs7219163 | 17 | q | q11.2 | SSH2 \| EFCAB5 | 28210703 | 1.11E-02 | 0.92 | 0.466 | 0.486 | A | (SEQ ID NO: 1210) ttaattctcttcctgg[A/C]cagcctaacttctcct |
| 03 | rs9914342 | 17 | q | q12 | FLJ43826 | 37190141 | 5.71E-04 | 0.88 | 0.238 | 0.262 | G | (SEQ ID NO: 1211) gtaaggactttatcca[A/G]aatcacttatgtgtct |
| 03 | rs8070269 | 17 | q | q12 | MRM1 \| LHX1 | 35134033 | 3.98E-03 | 1.14 | 0.146 | 0.130 | A | (SEQ ID NO: 1212) tgatagccatcaccca[A/G]ggagaatggtgaaaga |
| 02 | rs3744474 | 17 | q | q21.31 | CIQL1 \| DCAKD | 43100070 | 2.70E-05 | 1.12 | 0.219 | 0.199 | G | (SEQ ID NO: 1213) ggatgtgtaagaccct[A/G]tagttaacataacact |
| 03 | rs4793598 | 17 | q | q21.32 | HOXB9 \| PRAC | 46743914 | 7.15E-05 | 1.11 | 0.387 | 0.362 | G | (SEQ ID NO: 1214) tgctgaactttgtcct[A/G]gcatataattagttac |
| 02 | rs12453356 | 17 | q | q22 | TMEM100 | 53808950 | 4.16E-05 | 1.50 | 0.027 | 0.018 | C | (SEQ ID NO: 1215) tagctaacactactac[A/C]caagctaccagaacag |
| 03 | rs10512502 | 17 | q | q23.3 | DDX5 | 62495009 | 2.05E-03 | 1.21 | 0.071 | 0.059 | A | (SEQ ID NO: 1216) taatgactaatcagga[A/G]gcaacgtaaccaaaag |
| 02 | exm1345526 | 17 | q | q23.3 | SCN4A | 62028920 | 7.02E-18 | 9.29 | 0.033 | 0.002 | C | (SEQ ID NO: 1217) gacggccccccatcca[C/G]cctcgagctggaccac |
| 02 | exm1345636 | 17 | q | q23.3 | SCN4A | 62049749 | 1.33E-12 | 5.07 | 0.013 | 0.003 | A | (SEQ ID NO: 1218) gctgagccccttcagc[A/G]tagtcaggcgcggggc |
| 03 | rs7218921 | 17 | q | q24.1 | GNA13 \| RGS9 | 63068976 | 3.64E-04 | 0.89 | 0.461 | 0.489 | A | (SEQ ID NO: 1219) tcatgtcctaaccaac[A/G]gaatcaccctggttcc |
| 03 | rs2907373 | 17 | q | q24.2 | FAM20A | 66533655 | 1.19E-04 | 1.13 | 0.372 | 0.343 | A | (SEQ ID NO: 1220) gccagagtctggggcc[A/G]actgttccactgggcc |
| 02 | rs8076465 | 17 | q | q24.2 | PRKAR1A | 66513025 | 3.83E-05 | 1.13 | 0.372 | 0.343 | A | (SEQ ID NO: 1221) ttttgaagtcaagtgc[A/G]ttcctggagatccggt |
| 02 | rs8080306 | 17 | q | q24.2 | PRKAR1A | 66508243 | 1.62E-05 | 1.16 | 0.314 | 0.284 | C | (SEQ ID NO: 1222) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | gagagcgaagagcagg[A/C]ggaggaacaaaggcag |
| 03 | rs2952275 | 17 | q | q24.2 | PRKAR1A | 66518663 | 1.33E-04 | 1.13 | 0.372 | 0.344 | A | (SEQ ID NO: 1223)<br>atggcttgtactaatg[A/G]cttttgcccattaata |
| 02 | rs2302782 | 17 | q | q24.2 | WIPI1 | 66446803 | 8.10E-05 | 1.14 | 0.334 | 0.306 | G | (SEQ ID NO: 1224)<br>aaacaaaaagatggac[A/G]tctttcaagatcaatg |
| 03 | rs2952291 | 17 | q | q24.2 | WIPI1 \|<br>PRKAR1A | 66460984 | 1.20E-04 | 1.14 | 0.327 | 0.299 | G | (SEQ ID NO: 1225)<br>ctattatgaaattctg[A/G]gtctaaagacattgca |
| 03 | rs16969749 | 17 | q | q25.2 | SEC14L1 | 75192907 | 2.88E-03 | 0.87 | 0.127 | 0.143 | A | (SEQ ID NO: 1226)<br>ctaattctgtcagcct[A/G]cttactagaaaccaaa |
| 03 | rs4969170 | 17 | q | q25.3 | SOCS3 \| PGS1 | 76360538 | 7.40E-03 | 1.09 | 0.358 | 0.338 | A | (SEQ ID NO: 1227)<br>gtttttagagaccaca[A/G]cctgctttcttctaga |
| 02 | rs9957245 | 18 | p | p11.21 | LOC100131500 \|<br>LOC644669 | 15102421 | 1.26E-03 | 1.21 | 0.188 | 0.161 | A | (SEQ ID NO: 1228)<br>tcctaaaaggtttcac[G/A]tcaagcataagtttct |
| 03 | rs1852893 | 18 | p | p11.21 | LOC100131500 \|<br>LOC644669 | 15082789 | 1.12E-04 | 1.14 | 0.282 | 0.256 | G | (SEQ ID NO: 1229)<br>attatctggagtcagg[A/G]ttcttctttagcagtg |
| 02 | rs1893187 | 18 | p | p11.22 | VAPA \|<br>APCDD1 | 10295300 | 2.33E-06 | 1.20 | 0.170 | 0.146 | A | (SEQ ID NO: 1230)<br>actcaccttgtcatca[A/G]aagagaaaggaccatg |
| 03 | rs206475 | 18 | p | p11.22 | VAPA \|<br>APCDD1 | 10295284 | 4.30E-04 | 0.89 | 0.444 | 0.472 | A | (SEQ ID NO: 1231)<br>gggcactaggtgccac[A/G]ctcaccttgtcatcag |
| 03 | rs206470 | 18 | p | p11.22 | VAPA \|<br>APCDD1 | 10296623 | 5.55E-04 | 0.89 | 0.316 | 0.341 | A | (SEQ ID NO: 1232)<br>cattactcagaattat[A/G]tctggagcaaataaca |
| 02 | rs189982 | 18 | p | p11.22 | VAPA \|<br>APCDD1 | 10302384 | 1.52E-05 | 1.20 | 0.157 | 0.135 | A | (SEQ ID NO: 1233)<br>cttacaccatgtttct[A/G]tcagtatcaaacaaag |
| 02 | rs11080401 | 18 | p | p11.22 | VAPA \|<br>APCDD1 | 10304345 | 2.69E-06 | 1.20 | 0.177 | 0.153 | A | (SEQ ID NO: 1234)<br>ggtttggagtctgatc[A/G]cttggattctggcagg |
| 03 | rs475001 | 18 | p | p11.32 | C18orf2 \|<br>METTL4 | 2192946 | 8.65E-03 | 1.15 | 0.102 | 0.090 | A | (SEQ ID NO: 1235)<br>ttcatttgaatgaaac[A/G]ggtcactttaaaaatt |
| 03 | rs1507732 | 18 | p | p11.32 | C18orf2 \|<br>METTL4 | 1464859 | 1.29E-03 | 1.14 | 0.181 | 0.162 | A | (SEQ ID NO: 1236)<br>ctgcaaagttccatta[A/G]aaagatggtggacaaa |
| 03 | rs561312 | 18 | p | p11.32 | C18orf2 \|<br>METTL4 | 2194248 | 7.75E-03 | 1.15 | 0.103 | 0.091 | A | (SEQ ID NO: 1237)<br>cctgtgcctgagatga[A/G]gcaggaatctccaggg |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2419027 | 18 | q | q12.1 | CDH2 \| DSC3 | 27785716 | 4.67E-03 | 1.09 | 0.493 | 0.470 | A | (SEQ ID NO: 1238) tttacttttggcctcc[A/G]ttgacccagatgggga |
| 03 | rs954640 | 18 | q | q12.1 | CDH2 \| DSC3 | 27688654 | 1.89E-03 | 1.10 | 0.475 | 0.451 | A | (SEQ ID NO: 1239) tttacagatactgact[A/G]cataaaacaacaatcc |
| 03 | rs9967020 | 18 | q | q12.1 | CDH2 \| DSC3 | 27681568 | 5.95E-03 | 1.09 | 0.492 | 0.471 | A | (SEQ ID NO: 1240) caaaaggacgtactgc[A/G]tgatgctaatttataa |
| 03 | rs8090231 | 18 | q | q12.1 | CDH2 \| DSC3 | 27755950 | 3.86E-03 | 1.10 | 0.468 | 0.446 | A | (SEQ ID NO: 1241) acagacttaagtgaag[A/G]cccgcattcctacttt |
| 03 | rs12456839 | 18 | q | q12.1 | CDH2 \| DSC3 | 25895735 | 2.66E-03 | 0.89 | 0.218 | 0.238 | A | (SEQ ID NO: 1242) aagctaggagcatttt[A/G]aatatgtatactgga |
| 03 | rs11564361 | 18 | q | q12.1 | CDH2 \| DSC3 | 25904868 | 2.12E-03 | 0.89 | 0.217 | 0.238 | G | (SEQ ID NO: 1243) aacactagttgagtaa[A/G]tggatacaattgaggt |
| 03 | rs9952363 | 18 | q | q12.1 | CDH2 \| DSC3 | 27690198 | 6.81E-04 | 1.11 | 0.479 | 0.452 | A | (SEQ ID NO: 1244) ctagacctactgccat[A/G]agttttgtaagacaca |
| 03 | rs12967345 | 18 | q | q12.1 | CDH2 \| DSC3 | 27758155 | 2.29E-03 | 1.12 | 0.221 | 0.202 | G | (SEQ ID NO: 1245) caggacaggcaacaca[A/G]taacttgatacaaaag |
| 03 | rs8094149 | 18 | q | q12.2 | BRUNOL4 | 34979873 | 2.11E-04 | 0.89 | 0.365 | 0.394 | C | (SEQ ID NO: 1246) agtgaggctcatctgc[A/C]tgggtgagaagcgaaa |
| 03 | rs1511938 | 18 | q | q12.2 | BRUNOL4 \| LOC647946 | 35967920 | 8.63E-04 | 0.90 | 0.461 | 0.488 | G | (SEQ ID NO: 1247) atgctgtagccacttg[A/G]taacatctttcttgaa |
| 03 | rs12604671 | 18 | q | q12.2 | BRUNOL4 \| LOC647946 | 36039666 | 4.68E-04 | 1.12 | 0.343 | 0.318 | A | (SEQ ID NO: 1248) aacgacttggaaatag[A/G]ctataaatgtagaagg |
| 03 | rs2625068 | 18 | q | q12.2 | LOC647946 | 37172774 | 1.34E-04 | 0.88 | 0.337 | 0.366 | A | (SEQ ID NO: 1249) tttaatttaaaataat[A/C]acattctggggtgcca |
| 02 | rs10502725 | 18 | q | q12.2 | LOC647946 | 37111762 | 4.65E-05 | 0.88 | 0.365 | 0.396 | A | (SEQ ID NO: 1250) ccaatgacataatatc[A/C]gaccttaaaaaaatga |
| 03 | rs2852346 | 18 | q | q12.2 | LOC647946 | 37194499 | 7.92E-04 | 0.90 | 0.475 | 0.501 | A | (SEQ ID NO: 1251) caggtcttatttcttc[A/G]tttacgttatgtgaaa |
| 03 | rs2255757 | 18 | q | q12.3 | LOC100131669 \| SLC14A2 | 42958392 | 1.63E-03 | 1.11 | 0.416 | 0.392 | C | (SEQ ID NO: 1252) gccatcccctatctct[A/C]ttgaaaactgacttca |
| 03 | rs2726262 | 18 | q | q12.3 | LOC647946 | 37200183 | 1.99E-04 | 0.89 | 0.351 | 0.379 | A | (SEQ ID NO: 1253) cctctcccatgatcca[A/G]tcatctctccccaggc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2726267 | 18 | q | q12.3 | LOC647946 | 37208969 | 2.06E-04 | 0.88 | 0.338 | 0.366 | C | (SEQ ID NO: 1254) gtattcaaatcttggc[A/C]aatatccaactagcaa |
| 03 | rs2726232 | 18 | q | q12.3 | LOC647946 | 37212167 | 3.33E-04 | 0.89 | 0.465 | 0.493 | G | (SEQ ID NO: 1255) gaagaatgaatgtctt[A/G]ggatacaattaagtga |
| 02 | rs10163756 | 18 | q | q12.3 | LOC647946 \| KC6 | 38325874 | 7.90E-05 | 1.18 | 0.171 | 0.148 | C | (SEQ ID NO: 1256) aaaccattacataggt[A/C]tcaaaatccaaatatt |
| 03 | rs981500 | 18 | q | q12.3 | LOC647946 \| KC6 | 38024748 | 5.32E-04 | 1.17 | 0.151 | 0.133 | C | (SEQ ID NO: 1257) aaacattttccagagt[A/C]aagaaagagtagaaaa |
| 03 | rs16973432 | 18 | q | q12.3 | LOC647946 \| KC6 | 38041069 | 5.69E-04 | 1.16 | 0.151 | 0.133 | C | (SEQ ID NO: 1258) gtcattttatgagtga[A/C]aaaaagaaacaaatgg |
| 03 | rs4799515 | 18 | q | q12.3 | LOC647946 \| KC6 | 37387509 | 9.04E-04 | 0.90 | 0.429 | 0.455 | A | (SEQ ID NO: 1259) aagcaatcctagctgg[A/G]gtagagctggcatttt |
| 03 | rs12455503 | 18 | q | q12.3 | LOC647946 \| KC6 | 37373687 | 4.31E-04 | 0.89 | 0.340 | 0.367 | G | (SEQ ID NO: 1260) aacacaatggggttga[A/G]catcacctcatattca |
| 03 | rs10502850 | 18 | q | q12.3 | SETBP1 | 42589714 | 1.87E-04 | 1.28 | 0.060 | 0.048 | A | (SEQ ID NO: 1261) acctgttctgtttgat[A/G]tgcagactgaggctca |
| 02 | exm1386239 | 18 | q | q21.1 | C18ORF32 | 47008746 | 1.26E-07 | Inf | 0.003 | 0.000 | A | (SEQ ID NO: 1262) atcacagatttctgtt[A/G]gtccttttgttggtaa |
| 03 | rs16949181 | 18 | q | q21.1 | LOC647055 | 45945536 | 1.16E-03 | 0.90 | 0.444 | 0.470 | G | (SEQ ID NO: 1263) ttccaggtcccctttc[A/G]cttcctgtgctgttgc |
| 03 | rs1377016 | 18 | q | q21.1 | LOXHD1 | 44063598 | 1.14E-02 | 0.92 | 0.314 | 0.333 | A | (SEQ ID NO: 1264) ggtcttgacatgccag[A/G]caagttctctcttggg |
| 03 | rs10502876 | 18 | q | q21.1 | LOXHD1 \| ST8SIA5 | 44257422 | 4.14E-04 | 0.73 | 0.032 | 0.043 | A | (SEQ ID NO: 1265) agggaaagtgcttaac[A/G]tagcttgataaatgct |
| 03 | rs17681615 | 18 | q | q21.2 | DCC | 50124619 | 2.09E-03 | 0.90 | 0.316 | 0.339 | A | (SEQ ID NO: 1266) cattatactaaatacc[A/G]aggttaagagaataaa |
| 03 | rs9964201 | 18 | q | q21.2 | DCC | 50600552 | 1.82E-02 | 1.14 | 0.092 | 0.082 | A | (SEQ ID NO: 1267) agttactatgatttaa[A/C]tgtttcattgtgttta |
| 03 | rs12327270 | 18 | q | q21.2 | TCF4 | 53168073 | 5.79E-05 | 1.11 | 0.065 | 0.058 | G | (SEQ ID NO: 1268) gcttcattatatcaca[A/G]agaatgagctcaaata |
| 03 | rs1506647 | 18 | q | q21.31 | TCF4 \| TXNL1 | 54136314 | 1.01E-03 | 1.28 | 0.047 | 0.037 | A | (SEQ ID NO: 1269) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | rs1469488 | 18 | q | q21.32 | CCBE1 | 57228450 | 6.44E-05 | 1.26 | 0.085 | 0.069 | A | ctacctttaagaaaca[A/G]gataaaaaataatgat (SEQ ID NO: 1270) |
| 02 | rs2332079 | 18 | q | q21.32 | LOC728111 \| CDH20 | 58594189 | 4.68E-05 | 0.90 | 0.416 | 0.443 | G | gcttttgggtacacag[A/G]cccattacatacatga (SEQ ID NO: 1271) |
| 02 | rs17609410 | 18 | q | q21.32 | LOC728111 \| CDH20 | 58563363 | 1.11E-05 | 0.90 | 0.386 | 0.412 | A | ccaatttcctttaaaa[A/G]agaggcttctgaaatt (SEQ ID NO: 1272) |
| 02 | rs1979787 | 18 | q | q21.32 | LOC728111 \| CDH20 | 58684971 | 2.68E-05 | 0.88 | 0.407 | 0.438 | G | atagcacctctttctg[A/C]agctctcgggactctt (SEQ ID NO: 1273) |
| 02 | rs2332197 | 18 | q | q21.32 | LOC728111 \| CDH20 | 58717342 | 1.65E-05 | 0.88 | 0.406 | 0.436 | A | tcctaactgtctaact[A/G]tatgaattccaaaagt (SEQ ID NO: 1274) |
| 03 | rs2850768 | 18 | q | q21.33 | KDSR | 61001410 | 6.16E-03 | 0.90 | 0.190 | 0.208 | G | ttaaggcagaacaatc[A/G]tcatatctgttcagga (SEQ ID NO: 1275) |
| 03 | rs12969516 | 18 | q | q22.2 | SOCS6 \| CBLN2 | 68518485 | 6.27E-03 | 0.92 | 0.445 | 0.466 | G | tacattacagaatgaa[A/G]agaaaagagggcttgg (SEQ ID NO: 1276) |
| 03 | rs7235677 | 18 | q | q22.2 | SOCS6 \| CBLN2 | 68552596 | 1.23E-03 | 1.14 | 0.200 | 0.181 | G | gcttgagctctctttt[A/G]aggattcatctttgac (SEQ ID NO: 1277) |
| 03 | rs4555235 | 18 | q | q22.3 | LOC100289370 \| FBXO15 | 71071370 | 6.68E-03 | 1.09 | 0.504 | 0.483 | A | agaggttgcaagcaca[A/G]gtatttgacacactgt (SEQ ID NO: 1278) |
| 02 | exm1392554 | 18 | q | q22.3 | TIMM21 | 71816278 | 3.44E-17 | 3.66 | 0.026 | 0.007 | A | tctctggctttaaaca[A/G]aaagatgactaaaact (SEQ ID NO: 1279) |
| 03 | rs8084536 | 18 | q | q23 | FLJ44313 \| LOC284276 | 74227791 | 1.30E-03 | 1.11 | 0.417 | 0.392 | G | aaaagcaaaggaggat[A/G]gcagcaaacaagtgtc (SEQ ID NO: 1280) |
| 03 | rs4891030 | 18 | q | q23 | LOC284276 \| FLJ44881 | 74295607 | 3.91E-03 | 0.89 | 0.196 | 0.214 | G | cccaccagcagtatac[A/G]aggcttctcatttcac (SEQ ID NO: 1281) |
| 03 | rs11874114 | 18 | q | q23 | MBP | 74699134 | 1.41E-03 | 1.23 | 0.062 | 0.051 | A | agagaaataagtggat[A/G]taacagagtggatctg (SEQ ID NO: 1282) |
| 03 | rs8086634 | 18 | q | q23 | MBP | 74701192 | 2.52E-04 | 1.23 | 0.087 | 0.072 | A | agtggactttggggcc[A/G]tcgtgccggatcctcc (SEQ ID NO: 1283) |
| 03 | rs11669407 | 19 | p | p13.11 | CHERP \| SLC35E1 | 16654444 | 2.29E-02 | 0.90 | 0.142 | 0.155 | A | cgctactcctagcccc[A/G]gaaagggctcacggtg (SEQ ID NO: 1284) aggaggcaagatcaag[A/G]atttttttttttctaa |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 02 | exm1442461 | 19 | p | p13.11 | SLC27A1 | 17597661 | 2.51E-20 | 7.24 | 0.017 | 0.002 | A | (SEQ ID NO: 1285) agcagcgcggcctcca[A/T]gcccgccttggccagg |
| 03 | rs794084 | 19 | p | p13.2 | XAB2 | 7692058 | 4.63E-04 | 1.12 | 0.422 | 0.395 | G | (SEQ ID NO: 1286) ctgggtgacatcctac[A/G]cggagctagtgtcaca |
| 02 | exm1400852 | 19 | p | p13.3 | APC2 | 1468696 | 1.17E-07 | Inf | 0.003 | 0.000 | A | (SEQ ID NO: 1287) ctgggcacggggtgcc[A/G]ggctggggacgtagat |
| 02 | rs313784 | 19 | p | p13.3 | BRUNOL5 | 3293593 | 1.27E-05 | 0.90 | 0.232 | 0.252 | A | (SEQ ID NO: 1288) ggtggggtgatgcttc[A/G]agaggctacaagaaac |
| 03 | rs1610045 | 19 | p | p13.3 | BTBD2 | 1997363 | 1.61E-04 | 0.88 | 0.300 | 0.328 | G | (SEQ ID NO: 1289) gcagtgcgaggaaggc[A/G]gcgggttccacgtcgg |
| 03 | rs12976454 | 19 | p | p13.3 | C19orf28 | 3544971 | 5.02E-04 | 1.13 | 0.312 | 0.288 | A | (SEQ ID NO: 1290) cggggggtggtaccc[A/G]cggtgcctactcatcc |
| 03 | rs3916080 | 19 | p | p13.3 | FUT6 | 5832899 | 2.02E-03 | 0.90 | 0.345 | 0.369 | A | (SEQ ID NO: 1291) ccttttctggtgtgtc[A/C]ccagactcttcctcaa |
| 03 | rs11878982 | 19 | p | p13.3 | KDM4B | 5041049 | 1.37E-04 | 1.15 | 0.252 | 0.227 | A | (SEQ ID NO: 1292) cacccatgaaagaggc[A/G]ggaggggctctgctcc |
| 02 | rs33938520 | 19 | p | p13.3 | KDM4B | 4984588 | 4.40E-05 | 1.15 | 0.292 | 0.264 | A | (SEQ ID NO: 1293) acctgacgaggcgtac[A/G]gaacaggccggaacag |
| 03 | rs4805077 | 19 | q | q13.11 | LSM14A \| KIAA0355 | 34742705 | 2.08E-02 | 1.08 | 0.381 | 0.363 | G | (SEQ ID NO: 1294) ttccagtgtgaacatg[A/G]catcaaagaagaggca |
| 03 | rs6510478 | 19 | q | q13.12 | CD22 | 35834621 | 2.20E-04 | 0.87 | 0.234 | 0.260 | G | (SEQ ID NO: 1295) cccacacctcatagca[A/G]gatctcatctctacaa |
| 03 | rs7251526 | 19 | q | q13.12 | CD22 | 35829513 | 4.64E-03 | 0.90 | 0.263 | 0.283 | A | (SEQ ID NO: 1296) aaaacaagcatctacc[A/G]agcaccctccatgagc |
| 02 | rs4806152 | 19 | q | q13.12 | FFAR3 \| LOC100128682 | 35886660 | 5.27E-06 | 0.84 | 0.204 | 0.235 | C | (SEQ ID NO: 1297) caagtgagagcagata[A/C]ggcagcacagggattc |
| 03 | rs11669734 | 19 | q | q13.12 | MAG | 35794775 | 1.41E-03 | 0.89 | 0.233 | 0.254 | A | (SEQ ID NO: 1298) cgatattccagaggga[A/G]ttgcttaaggaagggg |
| 02 | exm1458802 | 19 | q | q13.12 | WDR62 | 36546015 | 8.28E-18 | 5.91 | 0.017 | 0.003 | A | (SEQ ID NO: 1299) tcggaggccgtcgaga[A/G]tcgcgtccgccgccgt |
| 03 | rs234341 | 19 | q | q13.2 | PSMC4 | 40486136 | 1.29E-02 | 1.25 | 0.034 | 0.027 | A | (SEQ ID NO: 1300) ctaaggggtggttatc[A/G]tgacaggaaggaggta |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs17289513 | 19 | q | q13.32 | AP2S1 \| GRLF1 | 47412622 | 3.06E-03 | 0.85 | 0.087 | 0.101 | A | (SEQ ID NO: 1301) cagtagactttcaagg[A/G]ctagtaactcgcatgc |
| 02 | exm1493646 | 19 | q | q13.33 | MYH14 | 50747534 | 4.61E-24 | 95.05 | 0.010 | 0.000 | A | (SEQ ID NO: 1302) ttcaaggcaatgttgc[A/C]aaactggagaactgct |
| 03 | rs10403102 | 19 | q | q13.33 | TPRX1 \| CRX | 48317892 | 4.87E-03 | 0.91 | 0.452 | 0.474 | A | (SEQ ID NO: 1303) aggtgtctgatcaacg[A/C]cctcagagatgacctg |
| 03 | rs11881877 | 19 | q | q13.41 | ZNF320 \| LOC388559 | 53401760 | 1.11E-04 | 0.89 | 0.446 | 0.476 | A | (SEQ ID NO: 1304) gatttttaaaaaaagc[A/G]ttgacattgtaacagt |
| 03 | rs6080719 | 20 | p | p12.1 | BFSP1 | 17477592 | 5.89E-03 | 1.11 | 0.254 | 0.236 | A | (SEQ ID NO: 1305) tctcagcactggatcc[A/G]gtgggaaaggtaacgc |
| 03 | rs1333400 | 20 | p | p12.1 | BTBD3 \| LOC100289040 | 12693139 | 6.20E-04 | 1.11 | 0.522 | 0.495 | G | (SEQ ID NO: 1306) catgcccagagtatgg[A/G]tatattggggaatca |
| 02 | rs1333383 | 20 | p | p12.1 | BTBD3 \| LOC100289040 | 12710164 | 5.83E-05 | 0.88 | 0.384 | 0.415 | A | (SEQ ID NO: 1307) attgaactgtaactta[A/C]acagagcaaacattgt |
| 03 | rs4814155 | 20 | p | p12.1 | BTBD3 \| LOC100289040 | 12708838 | 1.08E-04 | 0.88 | 0.374 | 0.403 | G | (SEQ ID NO: 1308) gcctactaacagcaag[A/G]gcctttattaatattt |
| 02 | rs6111020 | 20 | p | p12.1 | KIF16B | 16273832 | 7.40E-05 | 1.14 | 0.364 | 0.334 | A | (SEQ ID NO: 1309) acccatgggttctatc[A/G]atttctgccatatcct |
| 03 | rs7263619 | 20 | p | p12.1 | KIF16B | 16447367 | 1.08E-02 | 0.91 | 0.204 | 0.220 | A | (SEQ ID NO: 1310) gtgtccacctgtatta[A/G]agtgttttcatgtgct |
| 03 | rs7273594 | 20 | p | p12.1 | KIF16B | 16302535 | 3.12E-03 | 1.14 | 0.143 | 0.128 | A | (SEQ ID NO: 1311) cacagttttcccataa[A/G]agctcaaatatctttg |
| 03 | rs6111005 | 20 | p | p12.1 | KIF16B | 16256912 | 1.64E-03 | 0.86 | 0.113 | 0.129 | G | (SEQ ID NO: 1312) gcctaaagggtataat[A/G]agaagagaagtaaaag |
| 03 | rs6043962 | 20 | p | p12.1 | KIF16B | 16438733 | 6.11E-04 | 1.13 | 0.286 | 0.262 | C | (SEQ ID NO: 1313) ggctcacagcaaaact[A/C]taccgttttgatctgg |
| 03 | rs8120353 | 20 | p | p12.1 | KIF16B | 16412764 | 1.15E-02 | 0.90 | 0.158 | 0.173 | A | (SEQ ID NO: 1314) gtcagatgggcctgat[A/G]tcaagataaggcctac |
| 03 | rs1028539 | 20 | p | p12.1 | KIF16B | 16445463 | 3.42E-04 | 1.14 | 0.244 | 0.221 | A | (SEQ ID NO: 1315) tacttgcatcccaacc[A/G]cctaaaagtgttggtt |
| 03 | rs8116503 | 20 | p | p12.1 | KIF16B | 16359650 | 8.91E-03 | 0.90 | 0.184 | 0.201 | A | (SEQ ID NO: 1316) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | | | | | | | | tggagtccagagagaa[A/G]cagcagagagaggcgc |
| 03 | rs6085463 | 20 | p | p12.3 | FERMT1 \| BMP2 | 6252538 | 1.46E-02 | 0.92 | 0.388 | 0.407 | A | (SEQ ID NO: 1317)<br>cttcaacctcatgtta[A/G]atcagtacttataagc |
| 02 | exm1519568 | 20 | p | p13 | TGM3 | 2297721 | 4.47E-11 | Inf | 0.004 | 0.000 | A | (SEQ ID NO: 1318)<br>tctgcccagatcaata[A/G]caatgatgacaatggt |
| 03 | rs4911107 | 20 | q | q11.21 | DNMT3B | 31374991 | 3.21E-03 | 0.91 | 0.378 | 0.401 | A | (SEQ ID NO: 1319)<br>ttggtctctggtcacc[A/G]acatcctttgctctgg |
| 02 | exm1534977 | 20 | q | q11.22 | EIF2S2 | 32685262 | 1.32E-35 | Inf | 0.023 | 0.000 | A | (SEQ ID NO: 1320)<br>tgagcctgcccaagca[A/G]ggcctgtctgattact |
| 03 | rs8050 | 20 | q | q11.22 | RBM12 | 34237224 | 3.52E-03 | 0.73 | 0.021 | 0.028 | A | (SEQ ID NO: 1321)<br>ccatacctgtacacaa[A/C]cacagactccagtaaa |
| 02 | rs16988087 | 20 | q | q12 | LOC339568 \| MAFB | 38087936 | 3.89E-05 | 1.21 | 0.136 | 0.115 | A | (SEQ ID NO: 1322)<br>ctaaatcaaatgacaa[A/G]gagaaaagttagcttt |
| 03 | rs7263998 | 20 | q | q12 | LOC339568 \| MAFB | 38022796 | 1.65E-04 | 1.19 | 0.135 | 0.116 | A | (SEQ ID NO: 1323)<br>tctcttccccccacaa[A/G]gtcattttcttaattc |
| 03 | rs6028507 | 20 | q | q12 | LOC339568 \| MAFB | 38181661 | 9.17E-04 | 1.14 | 0.187 | 0.168 | G | (SEQ ID NO: 1324)<br>ccaagaaaaagtgccc[A/G]caagaaaaccaaaaca |
| 03 | rs11697337 | 20 | q | q12 | LOC339568 \| MAFB | 38236027 | 1.06E-02 | 1.25 | 0.035 | 0.028 | A | (SEQ ID NO: 1325)<br>cacagttactcaagtc[A/G]agaggcaaaaaaaaaa |
| 03 | rs6101558 | 20 | q | q12 | LOC339568 \| MAFB | 38090963 | 8.72E-05 | 1.16 | 0.174 | 0.154 | G | (SEQ ID NO: 1326)<br>tgtgactaaaccactc[A/G]tctgtttcccccactc |
| 02 | rs13044948 | 20 | q | q12 | LOC339568 \| MAFB | 38062804 | 1.20E-05 | 1.23 | 0.132 | 0.110 | A | (SEQ ID NO: 1327)<br>attaaatatatttttc[A/G]taataacccagctaga |
| 03 | rs2207799 | 20 | q | q12 | LOC339568 \| MAFB | 38195894 | 1.99E-04 | 1.26 | 0.069 | 0.055 | A | (SEQ ID NO: 1328)<br>tattaacattcataaa[A/C]cattcagacaattgct |
| 02 | rs13036738 | 20 | q | q12 | LOC339568 \| MAFB | 38078988 | 1.64E-05 | 1.22 | 0.132 | 0.110 | C | (SEQ ID NO: 1329)<br>tgcctatttctaaact[A/C]tgctggggaaagcagg |
| 02 | rs13044925 | 20 | q | q12 | LOC339568 \| MAFB | 38085378 | 1.81E-05 | 1.22 | 0.133 | 0.111 | G | (SEQ ID NO: 1330)<br>aggagattagggtgtt[A/G]attttcccgttctttc |
| 03 | rs2143216 | 20 | q | q12 | LOC339568 \| MAFB | 38066525 | 1.62E-04 | 1.17 | 0.183 | 0.161 | A | (SEQ ID NO: 1331)<br>ataaacttgccttact[A/G]tatacacacacatgca |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs8119002 | 20 | q | q12 | PTPRT | 41072290 | 1.06E-02 | 0.89 | 0.145 | 0.160 | A | (SEQ ID NO: 1332) ccagggctatgaaacc[A/G]tctcattctgcagcag |
| 03 | rs6090639 | 20 | q | q13.12 | EYA2 \| ZMYND8 | 45835008 | 2.30E-04 | 1.16 | 0.180 | 0.159 | G | (SEQ ID NO: 1333) ttttaggggtgtgat[A/G]tctgctatgtggacac |
| 02 | exm2264714 | 20 | q | q13.13 | B4GALT5 \| SLC9A8 | 48383467 | 3.26E-10 | Inf | 0.005 | 0.000 | C | (SEQ ID NO: 1334) ggattacaggcatgag[A/C]caccacatgctgccat |
| 03 | rs13041253 | 20 | q | q13.13 | LOC100130589 \| LOC284749 | 46773023 | 3.39E-04 | 1.14 | 0.227 | 0.205 | G | (SEQ ID NO: 1335) atgagttggaagaggt[A/G]ttagagtccccatcgt |
| 03 | rs162076 | 20 | q | q13.13 | LOC100130589 \| LOC284749 | 46785499 | 1.17E-04 | 1.13 | 0.461 | 0.431 | G | (SEQ ID NO: 1336) ggttttcaggaatgca[A/G]aagtctgagaagacac |
| 03 | rs927478 | 20 | q | q13.13 | LOC100130589 \| LOC284749 | 46761590 | 2.66E-04 | 1.15 | 0.227 | 0.203 | A | (SEQ ID NO: 1337) taagacaaagataagg[A/G]tctaatttcattcttt |
| 03 | rs852353 | 20 | q | q13.13 | LOC100130589 \| LOC284749 | 46833654 | 2.34E-04 | 1.12 | 0.453 | 0.425 | A | (SEQ ID NO: 1338) aatttttccttagaag[A/C]ctcaacctcagcatac |
| 03 | rs852373 | 20 | q | q13.13 | LOC100130589 \| LOC284749 | 46841297 | 4.67E-03 | 0.90 | 0.212 | 0.231 | G | (SEQ ID NO: 1339) ggggtcccttccctgc[A/G]ctctcataagctcccc |
| 02 | rs162079 | 20 | q | q13.13 | LOC100130589 \| LOC284749 | 46784745 | 8.36E-05 | 1.16 | 0.239 | 0.214 | A | (SEQ ID NO: 1340) tcgagggctagagagt[A/G]atgagagtgggtgggg |
| 03 | rs6023407 | 20 | q | q13.2 | DOK5 | 53221238 | 9.11E-05 | 0.93 | 0.329 | 0.346 | G | (SEQ ID NO: 1341) atgtatatttaaggta[A/G]gcttttctttttccct |
| 03 | rs6064102 | 20 | q | q13.2 | DOK5 \| CBLN4 | 53283735 | 7.76E-03 | 0.88 | 0.123 | 0.137 | A | (SEQ ID NO: 1342) tgacatccctcctatc[A/G]ggtctttgagggagaa |
| 02 | exm1550638 | 20 | q | q13.2 | SALL4 | 50408481 | 1.26E-07 | Inf | 0.003 | 0.000 | A | (SEQ ID NO: 1343) agtggccaacactaat[A/G]tgaccttgcaggcact |
| 02 | rs6013748 | 20 | q | q13.2 | ZNF217 \| SUMO1P1 | 52275163 | 1.44E-05 | 1.17 | 0.177 | 0.156 | A | (SEQ ID NO: 1344) agcatatttggcctcc[A/G]taatgccgcttaaggt |
| 03 | rs6025739 | 20 | q | q13.31 | PMEPA1 \| LOC100129869 | 56294313 | 1.40E-03 | 1.18 | 0.100 | 0.086 | G | (SEQ ID NO: 1345) taaatggcaattgttc[A/G]tgcaataaagaacaat |
| 03 | rs170602 | 20 | q | q13.31 | RBM38 \| HMGB1L1 | 56019162 | 2.24E-03 | 0.89 | 0.222 | 0.242 | G | (SEQ ID NO: 1346) ctcatctcttctagcc[A/G]gctttccccttacagg |
| 03 | rs6129089 | 20 | q | q13.33 | CDH4 | 59850852 | 2.39E-03 | 1.11 | 0.270 | 0.249 | A | (SEQ ID NO: 1347) ttccacccccagtgat[A/G]ctcagaatccaggatc |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs2427021 | 20 | q | q13.33 | CDH4 | 59845250 | 1.52E-03 | 1.15 | 0.157 | 0.140 | A | (SEQ ID NO: 1348) ataaataacgatagcc[A/G]gtaacttacgttcact |
| 03 | rs6010784 | 20 | q | q13.33 | DIDO1 | 61540319 | 1.25E-03 | 0.90 | 0.474 | 0.500 | A | (SEQ ID NO: 1349) ctcatgctgcgctgct[A/G]tcagaggccacatctg |
| 01 | JBL0001 | 20 | q | q13.33 | LAMA5 | 60892450 | 5.28E-12 | 3.959 | 0.020 | 0.010 | T | (SEQ ID NO: 1350) tgtgcgtgggcctcgg[C/T]ggcctccactagacgc |
| 03 | rs6015653 | 20 | q | q13.33 | LOC729296 \| CDH4 | 58692731 | 4.54E-04 | 1.21 | 0.095 | 0.080 | A | (SEQ ID NO: 1351) actgggttttgtggac[A/C]ctttgcagaggtcggg |
| 03 | rs2426990 | 20 | q | q13.33 | LOC729296 \| CDH4 | 59788003 | 9.56E-03 | 1.09 | 0.356 | 0.337 | G | (SEQ ID NO: 1352) gtgccttttaatatat[A/G]gaccacaagctcagag |
| 03 | rs2426983 | 20 | q | q13.33 | LOC729296 \| CDH4 | 59777873 | 1.43E-02 | 1.08 | 0.424 | 0.405 | C | (SEQ ID NO: 1353) cattgacacactggca[A/C]actcaatactgtgcac |
| 03 | rs6028076 | 20 | q | q13.33 | LOC729296 \| CDH4 | 59801421 | 2.54E-02 | 1.08 | 0.359 | 0.343 | G | (SEQ ID NO: 1354) cccaaaaggaaaccct[A/G]aacccaataagcagtc |
| 03 | rs2426986 | 20 | q | q13.33 | LOC729296 \| CDH4 | 59786367 | 1.33E-02 | 1.11 | 0.167 | 0.153 | G | (SEQ ID NO: 1355) tgttactgaggtatgc[A/G]atgccatgatttccac |
| 03 | rs6028080 | 20 | q | q13.33 | LOC729296 \| CDH4 | 59804478 | 8.27E-04 | 1.15 | 0.168 | 0.149 | G | (SEQ ID NO: 1356) tgtaaatcaccacctc[A/G]ttttgttcctagagct |
| 03 | rs2427000 | 20 | q | q13.33 | LOC729296 \| CDH4 | 59802749 | 2.07E-02 | 1.09 | 0.269 | 0.254 | A | (SEQ ID NO: 1357) cccttgccataaattg[A/G]aatccagagctgtaag |
| 03 | rs2426993 | 20 | q | q13.33 | LOC729296 \| CDH4 | 59798418 | 1.03E-02 | 1.12 | 0.167 | 0.153 | G | (SEQ ID NO: 1358) acttctactcagcata[A/G]aatgggccgttgccaa |
| 03 | rs6027379 | 20 | q | q13.33 | LOC729296 \| CDH4 | 58747589 | 9.67E-05 | 0.89 | 0.445 | 0.474 | G | (SEQ ID NO: 1359) ccataaaaggccggct[A/G]tagactcacatgtttt |
| 02 | rs1023361 | 21 | q | q21.1 | NCAM2 \| NCRNA00158 | 23344282 | 3.08E-05 | 1.13 | 0.049 | 0.044 | A | (SEQ ID NO: 1360) gtttaaatgaaataaa[A/G]catcctctgtttgcgg |
| 03 | rs390955 | 21 | q | q21.3 | ADAMTS1 \| ADAMTS5 | 28218457 | 8.60E-04 | 0.89 | 0.283 | 0.307 | C | (SEQ ID NO: 1361) cgcacgccacctcttc[A/C]ccagagacgactttgt |
| 03 | rs10482984 | 21 | q | q21.3 | LOC100288252 \| NCRNA00113 | 28820729 | 7.34E-04 | 1.22 | 0.075 | 0.062 | G | (SEQ ID NO: 1362) tggaagaagaggtaag[A/G]tatctccagagccgct |
| 03 | rs12482697 | 21 | q | q22.11 | ATP5O \| | 35293199 | 2.60E-04 | 0.81 | 0.081 | 0.098 | C | (SEQ ID NO: 1363) |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| | | | | | FLJ46020 | | | | | | | gtttctccctttgccc[A/C]caccactaaaatacag |
| 03 | rs11701963 | 21 | q | q22.11 | ATP5O \| FLJ46020 | 35323657 | 1.08E-03 | 0.80 | 0.055 | 0.068 | A | (SEQ ID NO: 1364) agtccaagcagcacct[A/G]gtaattaaactgagtc |
| 03 | rs2032314 | 21 | q | q22.11 | FLJ46020 \| MRPS6 | 35354523 | 2.40E-03 | 0.82 | 0.063 | 0.075 | A | (SEQ ID NO: 1365) gcaaatctatacagac[A/G]gacacagattcatggt |
| 03 | rs2070371 | 21 | q | q22.11 | HUNK | 33368188 | 6.19E-04 | 1.13 | 0.246 | 0.223 | A | (SEQ ID NO: 1366) tctgaatctgtgtcat[A/G]agcgagcctgagggct |
| 03 | rs198914 | 21 | q | q22.11 | KRTAP6-2 \| KRTAP22-1 | 31973405 | 7.04E-04 | 0.89 | 0.275 | 0.299 | A | (SEQ ID NO: 1367) ctcagttgtatagcag[A/G]atcagattctagagtt |
| 03 | rs2834889 | 21 | q | q22.12 | RUNX1 \| SETD4 | 36675294 | 4.79E-04 | 0.90 | 0.437 | 0.464 | C | (SEQ ID NO: 1368) agaaaccagccatttg[A/C]atgcgctcaatggaat |
| 03 | rs6517494 | 21 | q | q22.2 | FLJ45139 \| LOC100289305 | 40330767 | 6.46E-03 | 1.10 | 0.314 | 0.295 | A | (SEQ ID NO: 1369) aaaaagctacgcccac[A/C]tcctaaccctcggact |
| 02 | exm1571045 | 21 | q | q22.2 | LCA5L | 40778182 | 2.87E-10 | 1.47 | 0.127 | 0.090 | A | (SEQ ID NO: 1370) ggggccagccaatgcc[A/G]gcaacatgaggtacag |
| 02 | rs9981939 | 21 | q | q22.3 | C21orf121 \| UMODL1 | 43473602 | 2.00E-05 | 1.13 | 0.259 | 0.236 | C | (SEQ ID NO: 1371) tataaccttccaaaaa[A/C]ttcaacatcatcttcc |
| 02 | rs467997 | 21 | q | q22.3 | C21orf121 \| UMODL1 | 43488016 | 3.66E-05 | 1.16 | 0.279 | 0.251 | A | (SEQ ID NO: 1372) aaaggaaaagtcattc[A/G]ggctgtgataagaaag |
| 02 | rs2839452 | 21 | q | q22.3 | C21orf121 \| UMODL1 | 43466047 | 1.88E-05 | 1.13 | 0.289 | 0.265 | G | (SEQ ID NO: 1373) taccactaattccaat[A/G]ctcaagaagagctgac |
| 03 | rs220263 | 21 | q | q22.3 | C21orf121 \| UMODL1 | 43482161 | 5.74E-05 | 1.13 | 0.471 | 0.440 | G | (SEQ ID NO: 1374) ccccacgtgaactcgc[A/G]gcaggcagagaatcta |
| 03 | rs762395 | 21 | q | q22.3 | C21orf136 \| FLJ41733 | 44769676 | 5.57E-03 | 1.10 | 0.361 | 0.340 | A | (SEQ ID NO: 1375) gggctcgtttcagaat[A/G]cggttgggcaagtttg |
| 03 | rs9978582 | 21 | q | q22.3 | COL6A1 \| COL6A2 | 47488387 | 2.34E-03 | 0.91 | 0.417 | 0.441 | C | (SEQ ID NO: 1376) tccgtctacagccacc[A/C]agttaaataacagcgg |
| 03 | rs2282527 | 21 | q | q22.3 | RRP1B | 45081426 | 3.72E-03 | 1.10 | 0.357 | 0.336 | A | (SEQ ID NO: 1377) gttcacctcctgatga[A/C]ataaattcttgaccgt |
| 03 | rs3814903 | 21 | q | q22.3 | TMPRSS3 \| UBASH3A | 43817117 | 3.43E-04 | 1.12 | 0.363 | 0.336 | A | (SEQ ID NO: 1378) gggctatttgataggc[A/C]cacggcagcttgggtt |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs5992034 | 22 | q | q11.1 | CECR1 \| CECR2 | 17852805 | 1.63E-03 | 1.15 | 0.144 | 0.128 | A | (SEQ ID NO: 1379) aatccatgagttcagc[A/C]tggtgagatctttccc |
| 03 | rs1296795 | 22 | q | q11.21 | CECR2 | 18021760 | 1.19E-04 | 0.87 | 0.235 | 0.262 | G | (SEQ ID NO: 1380) cattgcgtcctttccc[A/G]aagagtctgttcccat |
| 03 | rs714027 | 22 | q | q12.2 | HORMAD2 \| LIF | 30577771 | 4.03E-03 | 1.09 | 0.475 | 0.453 | A | (SEQ ID NO: 1381) aaagaattttccccca[A/G]tgctctagcaaattgc |
| 03 | rs1049536 | 22 | q | q12.2 | THOC5 | 29904354 | 5.88E-03 | 1.11 | 0.245 | 0.227 | A | (SEQ ID NO: 1382) ggctggtgtctttgga[A/G]aatatcaagagtcaca |
| 03 | rs2016485 | 22 | q | q12.3 | LARGE | 34086416 | 7.28E-03 | 0.92 | 0.442 | 0.463 | A | (SEQ ID NO: 1383) gtcattcagccctccc[A/G]gcaaccccagaaatag |
| 03 | rs739166 | 22 | q | q13.1 | ELFN2 \| MFNG | 37863459 | 9.09E-05 | 1.12 | 0.267 | 0.244 | G | (SEQ ID NO: 1384) gaagtgacccatctgg[A/G]ccccagaggcaggggc |
| 02 | rs1005522 | 22 | q | q13.1 | MAP3K7IP1 \| MGAT3 | 39845898 | 7.35E-05 | 1.15 | 0.271 | 0.244 | C | (SEQ ID NO: 1385) cctgcagcacccctgg[A/C]cctcatggggcacttc |
| 02 | exm1609618 | 22 | q | q13.1 | PDGFB | 39621819 | 2.38E-08 | 4.42 | 0.009 | 0.002 | A | (SEQ ID NO: 1386) ccggcggactcgcacc[A/G]tccgaatggtcacccg |
| 03 | rs2187793 | 22 | q | q13.31 | LOC100289420 \| FAM19A5 | 47688003 | 2.72E-04 | 0.89 | 0.330 | 0.357 | A | (SEQ ID NO: 1387) tgcaaaatgcttctga[A/G]atgggtcaaccagaag |
| 03 | rs16993202 | 22 | q | q13.31 | PHF21B | 45353413 | 1.02E-03 | 0.84 | 0.097 | 0.113 | G | (SEQ ID NO: 1388) aaagagagggctgact[A/G]ttgattctgtgcatac |
| 03 | rs736490 | 22 | q | q13.31 | PHF21B | 45338213 | 4.34E-04 | 0.82 | 0.078 | 0.094 | A | (SEQ ID NO: 1389) agagggtgcccccagg[A/G]tcctactgtggatcag |
| 03 | rs138850 | 22 | q | q13.33 | BRD1 | 50193337 | 1.71E-03 | 1.12 | 0.241 | 0.220 | G | (SEQ ID NO: 1390) gaagggagcaggtgct[A/G]tcaatggaaatgggac |
| 03 | rs138843 | 22 | q | q13.33 | BRD1 | 50183162 | 3.97E-04 | 1.14 | 0.251 | 0.228 | A | (SEQ ID NO: 1391) gaatgtcgtaatcagg[A/G]cgagagctcggggcgg |
| 03 | rs5769373 | 22 | q | q13.33 | LOC100128946 \| LOC100287247 | 49411595 | 7.63E-02 | 1.06 | 0.413 | 0.399 | A | (SEQ ID NO: 1392) caagtctctcagtgac[A/G]gggccgacacttggtc |
| 03 | rs5769807 | 22 | q | q13.33 | LOC100128946 \| LOC100287247 | 49415539 | 1.58E-02 | 1.09 | 0.303 | 0.285 | G | (SEQ ID NO: 1393) aactttctgtaaagca[A/G]tgggagttagggcaac |
| 03 | rs2064542 | 22 | q | q13.33 | LOC100128946 \| LOC100287247 | 49430916 | 5.02E-02 | 1.07 | 0.399 | 0.384 | C | (SEQ ID NO: 1394) ctgcctctaaacccga[A/C]gtcttcaagcctgact |

TABLE 1-continued

TABLES
(Based on build 37 or "GRCh37" as defined by the Genome Reference Consortium)

| Set | Name | Chr | Arm | Cyto | Gene | Position | p-value | OR | Case MAF | Cont MAF | MA | Context Sequence |
|---|---|---|---|---|---|---|---|---|---|---|---|---|
| 03 | rs1548245 | 22 | q | q13.33 | LOC100128946 \| LOC100287247 | 49412197 | 5.13E-02 | 1.07 | 0.249 | 0.236 | A | (SEQ ID NO: 1395) gtgtcgtggcagatac[A/C]aggtctcacggaagtc |
| 03 | rs4823969 | 22 | q | q13.33 | LOC100128946 \| LOC100287247 | 49416063 | 6.92E-03 | 1.11 | 0.207 | 0.190 | G | (SEQ ID NO: 1396) gtgagctgcacatcct[A/G]cctagaagggacatct |
| 03 | rs5770992 | 22 | q | q13.33 | SHANK3 | 51146139 | 1.21E-04 | 0.81 | 0.092 | 0.111 | G | (SEQ ID NO: 1397) tagctattccaaataa[A/G]ataaaacccaaagaaa |
| 02 | rs1007461 | X | p | p22.2 | CLCN4 \| MID1 | 10297210 | 1.36E-04 | 1.19 | 0.466 | 0.423 | A | (SEQ ID NO: 1398) ccaatgtatgtgaagt[G/A]gctcaaatgaattttg |

The invention claimed is:

1. A method comprising applying an endometriosis altered risk therapeutic to a patient having at least one endometriosis increased risk associated biomarker defining the minor allele of a biomarker of table 1 having an OR of greater than 1.0 in the DNA of said patient.

2. The method of claim 1, wherein said at least one endometriosis increased risk associated biomarker defines the minor allele of a SNP.

3. The method of claim 1, wherein said at least one endometriosis increased risk associated biomarker defines a plurality of endometriosis increased risk associated biomarkers, each endometriosis increased risk associated biomarker defining the minor allele of a biomarker of table 1 having an OR of greater than 1.0.

4. The method of claim 1, wherein said endometriosis increased risk therapeutic defines administering a hormonal treatment.

5. The method of claim 4, wherein said hormonal treatment defines at least one of administering a composition in an amount effective to alter the hormone level of said patient, performing a surgical procedure, and a combination thereof.

6. The method of claim 1, wherein said endometriosis increased risk therapeutic defines administering an Oral Contraceptive Pill (OCP).

7. The method of claim 1, wherein said patient defines an endometriosis asymptomatic human female.

8. The method of claim 1, wherein said applying step is preceded by the step of obtaining clinical data (CD) of said patient.

9. The method of claim 1, wherein said applying step is preceded by the steps of:

identifying an endometriosis asymptomatic human female subject, obtaining clinical data (CD) and a biological sample of said subject, said CD defining the answers to the questions of "menarche after age 14 (Y/N)", "dysmenorrhea (Y/N)", and "previous pregnancy (Y/N)", assigning a raw clinical probability value (RCPV) to said CD, assaying said sample, detecting in said sample a plurality of endometriosis increased risk associated biomarkers, each endometriosis increased risk associated biomarker defining the minor allele of a biomarker of table 1 having an OR of greater than 1.0 resulting in endometriosis increased risk associated biomarker data, and performing a statistical analysis using said RCPV and said endometriosis increased risk associated biomarker data to result in an endometriosis condition prognosis of said subject of at least one of an increased risk of endometriosis existence and an increased risk of endometriosis predisposition.

10. A method comprising applying an endometriosis altered risk therapeutic to a patient having at least one endometriosis decreased risk associated biomarker defining the minor allele of a biomarker of table 1 having an OR of less than 1.0 in the DNA of said patient.

11. The method of claim 10, wherein said at least one endometriosis decreased risk associated biomarker defines the minor allele of a SNP.

12. The method of claim 10, wherein said at least one endometriosis decreased risk associated biomarker defines a plurality of endometriosis decreased risk associated biomarkers, each endometriosis decreased risk associated biomarker defining the minor allele of a biomarker of table 1 having an OR of less than 1.0.

13. The method of claim 10, wherein said endometriosis decreased risk therapeutic defines canceling a contemplated hormonal treatment.

14. The method of claim 13, wherein said hormonal treatment defines at least one of administering a composition in an amount effective to alter the hormone level of said patient, performing a surgical procedure, and a combination thereof.

15. The method of claim 10, wherein said endometriosis decreased risk therapeutic defines canceling a contemplated administration of an Oral Contraceptive Pill (OCP).

16. The method of claim 10, wherein said patient defines an endometriosis asymptomatic human female.

17. The method of claim 10, wherein said applying step is preceded by the step of obtaining clinical data (CD) of said patient.

18. The method of claim 10, wherein said applying step is preceded by the steps of:

identifying an endometriosis asymptomatic human female subject, obtaining clinical data (CD) and a biological sample of said subject, said CD defining the answers to the questions of "menarche after age 14 (Y/N)", "dysmenorrhea (Y/N)", and "previous pregnancy (Y/N)", assigning a raw clinical probability value (RCPV) to said CD, assaying said sample, detecting in said sample a plurality of endometriosis decreased risk associated biomarkers, each endometriosis decreased risk associated biomarker defining the minor allele of a biomarker of table 1 having an OR of less than 1.0 resulting in endometriosis decreased risk associated biomarker data, and performing a statistical analysis using said RCPV and said endometriosis decreased risk associated biomarker data to result in an endometriosis condition prognosis of said subject of at least one of a decreased risk of endometriosis existence and a decreased risk of endometriosis predisposition.

19. A method comprising applying an endometriosis altered risk therapeutic to a patient having at least one endometriosis altered risk associated biomarker defining the minor allele of a biomarker of table 1 in the DNA of said patient.

20. The method of claim 19, wherein said at least one endometriosis altered risk associated biomarker defines the minor allele of a SNP.

21. The method of claim 19, wherein said endometriosis altered risk defines at least one of an endometriosis increased risk as compared to a control subject and an endometriosis decreased risk as compared to a control subject, and wherein said endometriosis altered risk therapeutic defines at least one of an endometriosis increased risk therapeutic and an endometriosis decreased risk therapeutic.

22. The method of claim 21, wherein said at least one endometriosis increased risk associated biomarker defines the minor allele of a biomarker of table 1 having an OR of greater than 1.0, and wherein said at least one endometriosis decreased risk associated biomarker defines the minor allele of a biomarker of table 1 having an OR of less than 1.0.

23. The method of claim 21, wherein said at least one endometriosis increased risk associated biomarker defines a plurality of endometriosis increased risk associated biomarkers, each endometriosis increased risk associated biomarker defining the minor allele of a biomarker of table 1 having an OR of greater than 1.0, and wherein said at least one endometriosis decreased risk associated biomarker defines a plurality of endometriosis decreased risk associated biomarkers, each endometriosis decreased risk associated biomarker defining the minor allele of a biomarker of table 1 having an OR of less than 1.0.

24. The method of claim 21, wherein said endometriosis increased risk therapeutic defines administering a hormonal treatment, and wherein said endometriosis decreased risk therapeutic defines canceling a contemplated hormonal treatment.

25. The method of claim 24, wherein said hormonal treatment defines at least one of administering a composition in an amount effective to alter the hormone level of said subject, performing a surgical procedure, and a combination thereof.

26. The method of claim 21, wherein said endometriosis increased risk therapeutic defines administering an Oral Contraceptive Pill (OCP), and wherein said endometriosis decreased risk therapeutic defines canceling a contemplated administration of an OCP.

27. The method of claim 19, wherein said patient defines an endometriosis asymptomatic human female.

28. The method of claim 19, wherein said applying step is preceded by the step of obtaining clinical data (CD) of said patient.

29. The method of claim 19, wherein said applying step is preceded by the steps of:

identifying an endometriosis asymptomatic human female subject, obtaining clinical data (CD) and a biological sample of said subject, said CD defining the answers to the questions of "menarche after age 14 (Y/N)", "dysmenorrhea (Y/N)", and "previous pregnancy (Y/N)", assigning a raw clinical probability value (RCPV) to said CD, assaying said sample, detecting in said sample at least one of a plurality of endometriosis increased risk associated biomarkers, each endometriosis increased risk associated biomarker defining the minor allele of a biomarker of table 1 having an OR of greater than 1.0 resulting in endometriosis increased risk associated biomarker data and a plurality of endometriosis decreased risk associated biomarkers, each endometriosis decreased risk associated biomarker defining the minor allele of a biomarker of table 1 having an OR of less than 1.0 resulting in endometriosis decreased risk associated biomarker data, and performing at least one of a statistical analysis using said RCPV and said endometriosis increased risk associated biomarker data to result in an endometriosis condition prognosis of said subject of at least one of an increased risk of endometriosis existence and an increased risk of endometriosis predisposition and a statistical analysis using said RCPV and said endometriosis decreased risk associated biomarker data to result in an endometriosis condition prognosis of said subject of at least one of a decreased risk of endometriosis existence and a decreased risk of endometriosis predisposition.

* * * * *